US011542558B2

(12) United States Patent
Sudo et al.

(10) Patent No.: US 11,542,558 B2
(45) Date of Patent: Jan. 3, 2023

(54) ESOPHAGEAL CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Hiroko Sudo, Kamakura (JP); Hitoshi Nobumasa, Kamakura (JP); Satoko Kozono, Kamakura (JP); Satoshi Kondou, Kamakura (JP); Junpei Kawauchi, Kamakura (JP); Atsushi Ochiai, Kashiwa (JP); Motohiro Kojima, Kashiwa (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 140 days.

(21) Appl. No.: 16/803,390

(22) Filed: Feb. 27, 2020

(65) Prior Publication Data
US 2020/0318199 A1  Oct. 8, 2020

Related U.S. Application Data

(62) Division of application No. 15/317,857, filed as application No. PCT/JP2015/067580 on Jun. 18, 2015, now Pat. No. 10,619,212.

(30) Foreign Application Priority Data

Jun. 18, 2014 (JP) ................. 2014-125036
Mar. 30, 2015 (JP) ................. 2015-070379

(51) Int. Cl.
| | | |
|---|---|---|
| *C12Q 1/68* | (2018.01) | |
| *C12P 19/34* | (2006.01) | |
| *C12Q 1/6886* | (2018.01) | |
| *C12N 15/09* | (2006.01) | |
| *G01N 33/574* | (2006.01) | |
| *G01N 33/53* | (2006.01) | |

(52) U.S. Cl.
CPC .......... *C12Q 1/6886* (2013.01); *C12N 15/09* (2013.01); *C12Q 1/68* (2013.01); *G01N 33/53* (2013.01); *G01N 33/574* (2013.01); *C12Q 2600/158* (2013.01); *C12Q 2600/178* (2013.01)

(58) Field of Classification Search
CPC .. C12Q 1/68; C12Q 1/6886; C12Q 2600/158; C12Q 2600/178; C12Q 1/6837
See application file for complete search history.

(56) References Cited

U.S. PATENT DOCUMENTS

2010/0285471 A1  11/2010 Croce et al.
2014/0031246 A1  1/2014 Meltzer et al.

FOREIGN PATENT DOCUMENTS

| CN | 101316935 A | 12/2008 |
|---|---|---|
| CN | 101861401 A | 10/2010 |
| JP | 2010-510769 A | 4/2010 |
| JP | 2011-501943 A | 1/2011 |
| WO | WO 2008/064519 A1 | 6/2008 |
| WO | WO 2009/049129 A1 | 4/2009 |

OTHER PUBLICATIONS

Qiagen Prodcut sheet for "miScript™ miRNA PCR Array (384-well, 384HC) Human miRBase Profiler HC Plate 7" from https://b2b.qiagen.com/~/media/genetable/mi/hs/34/mihs-3407a, document 1073798, Aug. 2012 (Year: 2012).*
American Cancer Society, "Esophagus Cancer", 2014, pp. 2-8, 19-20, and 29-41.
Cheung et al., "Natural variation in human gene expression assessed in lymphoblastoid cells", Nature Genetics, vol. 33, Mar. 2003, pp. 422-425.
Chinese Office Action and Search Report for Chinese Application No. 201580031909.6, dated Jul. 30, 2018.
Cobb et al., "Sepsis gene expression profiling: Murine splenic compared with hepatic responses determined by using complementary DNA microarrays", Critical Care Medicine, vol. 30, No. 12, 2002, pp. 2711-2721.
Cui et al., "Growth inhibition of hepatocellular carcinoma tumor endothelial cells by miR-204-3p and underlying mechanism," World Journal of Gastroenterology, vol. 20, No. 18, May 14, 2014, pp. 5493-5504 (13 pages total).
Eto et al., "Prospect of microRNA toward laboratory medicine Gastrointestinal Cancer and microRNA", Clinical Chemistry, 2014, vol. 43, No. 2, pp. 99-105.
Gen Bank Locus N R_029621 (2013) obtained from https://www.ncbi.nlm.nih.gov/nuccore/262206275?sat=18&satkey=2740935 on Aug. 7, 2019; three pages.
Hoshikawa et al., "Hypoxia induces different genes in the lungs of rats compared with mice", Physiological Genomics, vol. 12, 2003, pp. 209-219.
International Search Report, issued in PCT/JP2015/067580, PCT/ISA/210, dated Sep. 15, 2015.
Ito et al., "Cancer and MicroRNA as a Diagnostic and Therapeutic Market", Yamaguchi Medical Journal, 2013, vol. 62, No. 4, pp. 191-197.
Japanese Office Action dated May 28, 2019 for Application No. 2016-529504.
Kitaya, "Reproductive Immuno-Dysfunctional Diseases", American Journal of Reproductive Immunology, vol. 70, No. 1, 2013, pp. 21-27.

(Continued)

*Primary Examiner* — Stephen T Kapushoc
(74) *Attorney, Agent, or Firm* — Birch, Stewart, Kolasch & Birch, LLP

(57) ABSTRACT

It is intended to provide a kit or a device for the detection of esophageal cancer and a method for detecting esophageal cancer. The present invention provides a kit or a device for the detection of esophageal cancer, comprising nucleic acid(s) capable of specifically binding to miRNA(s) in a sample f a subject, and a method for detecting esophageal cancer, comprising measuring the miRNA in vitro.

6 Claims, 4 Drawing Sheets

Specification includes a Sequence Listing.

(56) References Cited

OTHER PUBLICATIONS

MiScript™ miRNA PCR Array (384-well, 384HC) Human miRBase Profiler HC Plate 5, Qiagen, 2012, 10 pages.

NCBI GEO Accession Display for Platform GPL7766, public on May 14, 2009. Kyoto Univ. 3D-Gene Human miRNA Oligo chip v11.0. Obtained from https://www.ncbi.nlm.nih.gov/geo/query/acc.cgi?acc=GPL7766 on Aug. 22, 2018. Including full Data Table. 2009, 12 pages.

Partial Supplementary European Search Report for European Application No. 15809775.8, dated Dec. 15, 2017.

Sakai et al., "A review of the current understanding and clinical utility of miRNAs in esophageal cancer", Seminars in Cancer Biology, 2013, vol. 23P, pp. 512-521.

Shen et al., "Exploration of Genome-Wide Circulating MicroRNA in Hepatocellular Carcinoma: MiR-483-5p as a Potential Biomarker", Cancer Epidemiology, Biomarkers and Prevention, vol. 22, No. 12, Dec. 2013, pp. 2364-2373.

Sobin et al., "TNM Classification of Malignant Tumours, the 7th edition, Japanese version", 2009, p. 63-68.

Terada et al., "Epstein-Barr virus associated lymphoepithelial carcinoma of the esophagus", International Journal of Clinical and Experimental Medicine, 2013, vol. 6, No. 3, pp. 219-226.

Written Opinion of the International Searching Authority, issued in PCT/JP2015/067580, PCT/ISA/237, dated Sep. 15, 2015.

International Publication No. WO2008064519A1; Publication Date: Jun. 5, 2008; International Application No. PCT/CN2006/003195; Title: Methods and compositions for diagnosis of esophageal cancer and prognosis and improvement of patient survial.

Berillo et al., "Binding of intronic miRNAs to the mRNAs of host genes encoding intronic miRNAs and proteins that participate in tumourigenesis," Computers in Biology and Medicine (2013), Vo. 43, pp. 1374-1381.

Partial European Search Report dated Mar. 5, 2021, in European Patent Application No. 20207038.9.

Office Action dated Sep. 24, 2021, in Korean Patent Application No. 10-2017-7000803.

Xie et al., "Salivary MicroRNAs as Promising Biomarkers for Detection of Esophageal Cancer," PLOS ONE (2013), vol. 8, Issue 4, e57502, pp. 1-12.

Kano et al., "miR-145, miR-133a and miR-133b: tumor-suppressive miRNAs target FSCN1 in esophageal squamous cell carcinoma," Int. J. Cancer (2010), vol. 127, pp. 2804-2814.

Office Action dated Mar. 22, 2022, in Republic of Korea Patent Application No. 10-2017-7000803.

\* cited by examiner

ESOPHAGEAL CANCER DETECTION KIT OR DEVICE, AND DETECTION METHOD

CROSS-REFERENCE TO RELATED APPLICATIONS

This application is a Divisional of application Ser. No. 15/317,857, filed on Dec. 9, 2016, which is the National Phase under 35 U.S.C. § 371 of International Application No. PCT/JP2015/067580, filed on Jun. 18, 2015, and under 35 U.S.C. § 119(a) to Patent Application No. 2014-125036, filed in Japan on Jun. 18, 2014 and to Patent Application No. 2015-070379, filed in Japan on Mar. 30, 2015, all of which are hereby expressly incorporated by reference into the present application.

TECHNICAL FIELD

The present invention relates to a kit or a device for the detection of esophageal cancer, comprising a nucleic acid capable of specifically binding to a particular miRNA, which is used for examining the presence or absence of esophageal cancer in a subject, and a method for detecting esophageal cancer, comprising measuring an expression level of the miRNA using the nucleic acid.

BACKGROUND ART

The esophagus is a tubular organ that conveys food from the mouth to the stomach, and is positioned between the trachea and the backbone. The wall of the esophagus is divided into 4 layers: mucosa, submucosa, proper muscular layer, and outer membrane from inside toward outside. These layers have their respective functions of conveying food from the mouth to the stomach (Non-Patent Literature 1). According to the 2012 statistics of cancer type in Japan disclosed by the Center for Cancer Control and Information Services, National Cancer Center, the number of esophageal cancer deaths climbed to 11,592 people, and esophageal cancer is the 10th leading cause of cancer type-specific mortality. Japanese men have 5.6 times higher risk of mortality due to esophageal cancer than women, and smoking and alcohol intake are reported risk factors for esophageal cancer (Non-Patent Literature 1). Also, it is estimated that one out of 125 American men and one out of 435 American women experience esophageal cancer. The estimated number of individuals affected by esophageal cancer in 2014 climbed to 18,170 people, among which approximately 15,450 people reportedly died (Non-Patent Literature 1).

The progressed stages of esophageal cancer are defined in Non-Patent Literature 2 and classified into stage 0 (Tis/N0/M0), stage IA (T1/N0/M0), stage IB (T2/N0/M0), stage IIA (T3/N/M), stage IIB (T1 to T2/N1/M0s), stage IIIA (T4a/N0/M0, T3/N1/M0, and T1 to T2/N2/M), stage IIIB (T3/N2/M0), stage IIIC (T4a/N1 to N2/M0, T4b/M0, and N3/M0), and stage IV (M1) according to tumor size (Tis, T1 to T3, and T4a to T4b), lymph node metastasis (N1 to N3), distant metastasis (M0 to M1), etc.

The 5-year relative survival rate of esophageal cancer largely depends on the stages of cancer progression and is reportedly 39% for tumors limited to esophageal tissues, 21% for tumors limited to esophageal and adjacent tissues, and 4% for tumors that have metastasized distantly (Non-Patent Literature 1). Thus, the early detection of esophageal cancer leads to drastic improvement in the survival rate. Therefore, the provision of an approach that permits the early detection is strongly desired.

The method for treating esophageal cancer is determined in view of the stages of cancer progression and general conditions and mainly includes endoscopic therapy, surgery, radiotherapy, and anticancer agents. Esophageal cancer that has progressed to some extent is treated by multimodality therapy which combines these treatment methods to exert synergistic effects by exploiting their respective features (Non-Patent Literature 1). Early esophageal cancer at stage 0, 1, or the like may be adaptable to endoscopic therapy or photo dynamic therapy, which places less burden on patients (Non-Patent Literature 1).

According to Non-Patent Literature 1, initial diagnostic tests of esophageal cancer are X-ray esophagography and endoscopy. In addition, CT scan, MRI scan, endosonography, ultrasonography, or the like is performed in order to examine the degree of cancer spread. When there are findings on suspected esophageal cancer by these initial tests, pathological examination which involves inserting a needle into a lesion and collecting cells or tissues to be examined under a microscope is carried out as a secondary test. For example, CEA and SCC are known as tumor markers in blood for the detection of esophageal cancer (Non-Patent Literature 3).

As shown in Patent Literature 1, there is a report, albeit at a research stage, on the detection of esophageal cancer using the expression levels of microRNAs (miRNAs) or combinations of the expression levels of miRNAs and the expression levels of additional protein markers in biological samples including blood.

Patent Literature 1 discloses a method for detecting esophageal cancer by measuring miRNAs such as miR-663a, miR-92a-3p, and miR-575 in serum.

CITATION LIST

Patent Literature

Patent Literature 1: Published U.S. Patent Application No. 2014/031246

Non-Patent Literature

Non-Patent Literature 1: American Cancer Society, "Esophagus Cancer", 2014, p. 2 to 8, 19 to 20, and 29 to 41

Non-Patent Literature 2: Sobin, L. et al., "TNM Classification of Malignant Tumours, the 7th edition, Japanese version", 2009, p. 63 to 68

Non-Patent Literature 3: Terada, T. et al., 2013, International Journal of Clinical and Experimental Medicine, Vol. 6 (3), p. 219-26

SUMMARY OF INVENTION

Technical Problem

An object of the present invention is to find a novel tumor marker for esophageal cancer and to provide a method that can effectively detect esophageal cancer using a nucleic acid capable of specifically binding to the marker.

As described in Non-Patent Literature 1, general tests of esophageal cancer are X-ray esophagography and endoscopy. However, ordinary medical checkup places emphasis on stomach cancer screening and often insufficiently observes the esophagus. Although these tests are now popularized, the number of esophageal cancer deaths in Japan is still increasing. Thus, such diagnostic imaging cannot always serve as a deterrent against esophageal cancer. In addition, CT scan or MRI scan is capable of detecting esophageal cancer with high performance, but requires a special apparatus and high examination costs. Therefore, these tests are not suitable for widely used as primary tests for esophageal cancer.

For example, CEA and SCC are known as tumor markers in blood for the detection of esophageal cancer (Non-Patent Literature 3). These markers, however, present problems associated with accuracy in such a way that the markers also elevate in cancers other than esophageal cancer. Therefore, their usefulness has not yet been established. If use of these markers causes false diagnosis of other cancers as esophageal cancer, this wastes appropriate therapeutic opportunity or places unnecessary economical and physical burdens on patients due to the application of wrong medicine. Hence, the esophageal cancer guidebook provided by the American Cancer Society makes no mention about these markers (Non-Patent Literature 1).

As described below, there is a report, albeit at a research stage, on the determination of esophageal cancer using the expression levels of microRNAs (miRNAs) in biological samples including blood, none of which, however, have yet to be brought into the practical use.

Patent Literature 1 discloses a method for detecting esophageal cancer by measuring miRNAs such as miR-663a, miR-92a-3p, and miR-575 in serum. Specifically, this literature shows a list of miRNAs that vary in serum in 16 esophageal cancer patients compared with 12 healthy subjects, and the presence or absence of esophageal cancer is determined by measuring the expression levels of these miRNAs. This detection method, however, includes few Examples or statements regarding specific detection performance such as accuracy, sensitivity, or specificity for determining esophageal cancer, and is thus industrially less practical. hsa-miR-345, which was only one miRNA validated therein, had AUC of 0.814 and is difficult to use alone for determining esophageal cancer according to the description.

As mentioned above, the existing tumor markers exhibit low performance in the detection of esophageal cancer, or neither performance nor detection methods are specifically shown as to the markers at a research stage. Therefore, use of these markers might lead to carrying out needless extra examination due to the false detection of healthy subjects as being esophageal cancer patients, or might waste therapeutic opportunity because of overlooking esophageal cancer patients. In addition, the measurement of dozens of miRNAs increases examination costs and is therefore difficult to use in large-scale screening such as medical checkup. Furthermore, the collection of esophageal tissues for measuring the tumor markers is highly invasive to patients and is not favorable. Hence, there is a demand for a highly accurate esophageal cancer marker that is detectable from blood, which can be collected with limited invasiveness, and is capable of correctly identifying an esophageal cancer patient as an esophageal cancer patient and a healthy subject as a healthy subject. Particularly, the early detection and treatment of esophageal cancer can drastically improve survival rates. In addition, endoscopic therapy or photo dynamic therapy which places less burden on patients can be applied as a therapeutic choice. Therefore, a highly sensitive esophageal cancer marker capable of detecting esophageal cancer even at an early progressed stage is desired.

Solution to Problem

The present inventors have conducted diligent studies to attain the object and consequently completed the present invention by finding multiple genes usable as markers for the detection of esophageal cancer from blood and finding that esophageal cancer can be significantly detected by using nucleic acids capable of specifically binding to any of these markers.

SUMMARY OF INVENTION

The present invention has the following features:
(1) A kit for the detection of esophageal cancer, comprising nucleic acid(s) capable of specifically binding to at least one polynucleotide selected from the group consisting of the following esophageal cancer markers: miR-204-3p, miR-1247-3p, miR-6875-5p, miR-6857-5p, miR-6726-5p, miR-3188, miR-8069, miR-4257, miR-1343-3p, miR-7108-5p, miR-6825-5p, miR-7641, miR-3185, miR-4746-3p, miR-6791-5p, miR-6893-5p, miR-4433b-3p, miR-3135b, miR-6781-5p, miR-1908-5p, miR-4792, miR-7845-5p, miR-4417, miR-3184-5p, miR-1225-5p, miR-1231, miR-1225-3p, miR-150-3p, miR-4433-3p, miR-6125, miR-4513, miR-6787-5p, miR-6784-5p, miR-615-5p, miR-6765-3p, miR-5572, miR-6842-5p, miR-8063, miR-6780b-5p, miR-187-5p, miR-128-1-5p, miR-6729-5p, miR-6741-5p, miR-6757-5p, miR-7110-5p, miR-7975, miR-1233-5p, miR-6845-5p, miR-3937, miR-4467, miR-7109-5p, miR-6088, miR-6782-5p, miR-5195-3p, miR-4454, miR-6724-5p, miR-8072, miR-4516, miR-6756-5p, miR-4665-3p, miR-6826-5p, miR-6820-5p, miR-6887-5p, miR-3679-5p, miR-7847-3p, miR-6721-5p, miR-3622a-5p, miR-939-5p, miR-602, miR-7977, miR-6749-5p, miR-1914-3p, miR-4651, miR-4695-5p, miR-6848-5p, miR-1228-3p, miR-642b-3p, miR-6746-5p, miR-3620-5p, miR-3131, miR-6732-5p, miR-7113-3p, miR-23a-3p, miR-3154, miR-4723-5p, miR-3663-3p, miR-4734, miR-6816-5p, miR-4442, miR-4476, miR-423-5p, miR-1249, miR-6515-3p, miR-887-3p, miR-4741, miR-6766-3p, miR-4673, miR-6779-5p, miR-4706, miR-1268b, miR-4632-5p, miR-3197, miR-6798-5p, miR-711, miR-6840-3p, miR-6763-5p, miR-6727-5p, miR-371a-5p, miR-6824-5p, miR-4648, miR-1227-5p, miR-564, miR-3679-3p, miR-2861, miR-6737-5p, miR-4725-3p, miR-6716-5p, miR-4675, miR-1915-3p, miR-671-5p, miR-3656, miR-6722-3p, miR-4707-5p, miR-4449, miR-1202, miR-4649-5p, miR-744-5p, miR-642a-3p, miR-451a, miR-6870-5p, miR-4443, miR-6808-5p, miR-4728-5p, miR-937-5p, miR-135a-3p, miR-663b, miR-1343-5p, miR-6822-5p, miR-6803-5p, miR-6805-3p, miR-128-2-5p, miR-4640-5p, miR-1469, miR-92a-2-5p, miR-3940-5p, miR-4281, miR-1260b, miR-4758-5p, miR-1915-5p, miR-5001-5p, miR-4286, miR-6126, miR-6789-5p, miR-4459, miR-1268a, miR-6752-5p, miR-6131, miR-6800-5p, miR-4532, miR-6872-3p, miR-718, miR-6769a-5p, miR-4707-3p, miR-6765-5p, miR-4739, miR-4525, miR-4270, miR-4534, miR-6785-5p, miR-6850-5p, miR-4697-5p, miR-1260a, miR-4486, miR-6880-5p, miR-6802-5p, miR-6861-5p, miR-92b-5p, miR-1238-5p, miR-6851-5p, miR-7704, miR-149-3p, miR-4689, miR-4688, miR-125a-3p, miR-23b-3p, miR-614, miR-1913, miR-16-5p, miR-6717-5p, miR-3648, miR-3162-5p, miR-1909-3p, miR-8073, miR-6769b-5p, miR-6836-3p, miR-4484, miR-6819-5p and miR-6794-5p.

(2) The kit according to (1), wherein miR-204-3p is hsa-miR-204-3p, miR-1247-3p is hsa-miR-1247-3p, miR-6875-5p is hsa-miR-6875-5p, miR-6857-5p is hsa-miR-6857-5p, miR-6726-5p is hsa-miR-6726-5p, miR-3188 is hsa-miR-3188, miR-8069 is hsa-miR-8069, miR-4257 is hsa-miR-4257, miR-1343-3p is hsa-miR-1343-3p, miR-7108-5p is hsa-miR-7108-5p, miR-6825-5p is hsa-miR-6825-5p, miR-7641 is hsa-miR-7641, miR-3185 is hsa-miR-3185, miR-4746-3p is hsa-miR-4746-3p, miR-6791-5p is hsa-miR-6791-5p, miR-6893-5p is hsa-miR-6893-5p, miR-4433b-3p is hsa-miR-4433b-3p, miR-3135b is hsa-miR-3135b, miR-6781-5p is hsa-miR-6781-5p, miR-1908-5p is hsa-miR-1908-5p, miR-4792 is hsa-miR-4792, miR-7845-5p is hsa-miR-7845-5p, miR-4417 is hsa-miR-4417, miR-3184-5p is hsa-miR-3184-5p, miR-1225-5p is hsa-miR-1225-5p, miR-1231 is hsa-miR-1231, miR-1225-3p is hsa-miR-1225-3p, miR-150-3p is hsa-miR-150-3p, miR-4433-3p is hsa-miR-4433-3p, miR-6125 is hsa-miR-6125, miR-4513 is hsa-miR-4513, miR-6787-5p is hsa-miR-6787-5p, miR-6784-5p is hsa-miR-6784-5p, miR-615-5p is hsa-miR-615-5p, miR-6765-3p is hsa-miR-6765-3p, miR-5572 is hsa-miR-5572, miR-6842-5p is hsa-miR-6842-5p, miR-8063 is hsa-miR-8063, miR-6780b-5p is hsa-miR-6780b-5p, miR-187-5p is hsa-miR-187-5p, miR-128-1-5p is hsa-miR-128-1-5p, miR-6729-5p is hsa-miR-6729-5p, miR-6741-5p is hsa-miR-6741-5p, miR-6757-5p is hsa-miR-6757-5p, miR-7110-5p is hsa-miR-7110-5p, miR-7975 is hsa-miR-7975, miR-1233-5p is hsa-miR-1233-5p, miR-6845-5p is hsa-miR-6845-5p, miR-3937 is hsa-miR-3937, miR-4467 is hsa-miR-4467, miR-7109-5p is hsa-miR-7109-5p, miR-6088 is hsa-miR-6088, miR-6782-5p is hsa-miR-6782-5p, miR-5195-3p is hsa-miR-5195-3p, miR-4454 is hsa-miR-4454, miR-6724-5p is hsa-miR-6724-5p, miR-8072 is hsa-miR-8072, miR-4516 is hsa-miR-4516, miR-6756-5p is hsa-miR-6756-5p, miR-4665-3p is hsa-miR-4665-3p, miR-6826-5p is hsa-miR-6826-5p, miR-6820-5p is hsa-miR-6820-5p, miR-6887-5p is hsa-miR-6887-5p, miR-3679-5p is hsa-miR-3679-5p, miR-7847-3p is hsa-miR-7847-3p, miR-6721-5p is hsa-miR-6721-5p, miR-3622a-5p is hsa-miR-3622a-5p, miR-939-5p is hsa-miR-939-5p, miR-602 is hsa-miR-602, miR-7977 is hsa-miR-7977, miR-6749-5p is hsa-miR-6749-5p, miR-1914-3p is hsa-miR-1914-3p, miR-4651 is hsa-miR-4651, miR-4695-5p is hsa-miR-4695-5p, miR-6848-5p is hsa-miR-6848-5p, miR-1228-3p is hsa-miR-1228-3p, miR-642b-3p is hsa-miR-642b-3p, miR-6746-5p is hsa-miR-6746-5p, miR-3620-5p is hsa-miR-3620-5p, miR-3131 is hsa-miR-3131, miR-6732-5p is hsa-miR-6732-5p, miR-7113-3p is hsa-miR-7113-3p, miR-23a-3p is hsa-miR-23a-3p, miR-3154 is hsa-miR-3154, miR-4723-5p is hsa-miR-4723-5p, miR-3663-3p is hsa-miR-3663-3p, miR-4734 is hsa-miR-4734, miR-6816-5p is hsa-miR-6816-5p, miR-4442 is hsa-miR-4442, miR-4476 is hsa-miR-4476, miR-423-5p is hsa-miR-423-5p, miR-1249 is hsa-miR-1249, miR-6515-3p is hsa-miR-6515-3p, miR-887-3p is hsa-miR-887-3p, miR-4741 is hsa-miR-4741, miR-6766-3p is hsa-miR-6766-3p, miR-4673 is hsa-miR-4673, miR-6779-5p is hsa-miR-6779-5p, miR-4706 is hsa-miR-4706, miR-1268b is hsa-miR-1268b, miR-4632-5p is hsa-miR-4632-5p, miR-3197 is hsa-miR-3197, miR-6798-5p is hsa-miR-6798-5p, miR-711 is hsa-miR-711, miR-6840-3p is hsa-miR-6840-3p, miR-6763-5p is hsa-miR-6763-5p, miR-6727-5p is hsa-miR-6727-5p, miR-371a-5p is hsa-miR-371a-5p, miR-6824-5p is hsa-miR-6824-5p, miR-4648 is hsa-miR-4648, miR-1227-5p is hsa-miR-1227-5p, miR-564 is hsa-miR-564, miR-3679-3p is hsa-miR-3679-3p, miR-2861 is hsa-miR-2861, miR-6737-5p is hsa-miR-6737-5p, miR-4725-3p is hsa-miR-4725-3p, miR-6716-5p is hsa-miR-6716-5p, miR-4675 is hsa-miR-4675, miR-1915-3p is hsa-miR-1915-3p, miR-671-5p is hsa-miR-671-5p, miR-3656 is hsa-miR-3656, miR-6722-3p is hsa-miR-6722-3p, miR-4707-5p is hsa-miR-4707-5p, miR-4449 is hsa-miR-4449, miR-1202 is hsa-miR-1202, miR-4649-5p is hsa-miR-4649-5p, miR-744-5p is hsa-miR-744-5p, miR-642a-3p is hsa-miR-642a-3p, miR-451a is hsa-miR-451a, miR-6870-5p is hsa-miR-6870-5p, miR-4443 is hsa-miR-4443, miR-6808-5p is hsa-miR-6808-5p, miR-4728-5p is hsa-miR-4728-5p, miR-937-5p is hsa-miR-937-5p, miR-135a-3p is hsa-miR-135a-3p, miR-663b is hsa-miR-663b, miR-1343-5p is hsa-miR-1343-5p, miR-6822-5p is hsa-miR-6822-5p, miR-6803-5p is hsa-miR-6803-5p, miR-6805-3p is hsa-miR-6805-3p, miR-128-2-5p is hsa-miR-128-2-5p, miR-4640-5p is hsa-miR-4640-5p, miR-1469 is hsa-miR-1469, miR-92a-2-5p is hsa-miR-92a-2-5p, miR-3940-5p is hsa-miR-3940-5p, miR-4281 is hsa-miR-4281, miR-1260b is hsa-miR-1260b, miR-4758-5p is hsa-miR-4758-5p, miR-1915-5p is hsa-miR-1915-5p, miR-5001-5p is hsa-miR-5001-5p, miR-4286 is hsa-miR-4286, miR-6126 is hsa-miR-6126, miR-6789-5p is hsa-miR-6789-5p, miR-4459 is hsa-miR-4459, miR-1268a is hsa-miR-1268a, miR-6752-5p is hsa-miR-6752-5p, miR-6131 is hsa-miR-6131, miR-6800-5p is hsa-miR-6800-5p, miR-4532 is hsa-miR-4532, miR-6872-3p is hsa-miR-6872-3p, miR-718 is hsa-miR-718, miR-6769a-5p is hsa-miR-6769a-5p, miR-4707-3p is hsa-miR-4707-3p, miR-6765-5p is hsa-miR-6765-5p, miR-4739 is hsa-miR-4739, miR-4525 is hsa-miR-4525, miR-4270 is hsa-miR-4270, miR-4534 is hsa-miR-4534, miR-6785-5p is hsa-miR-6785-5p, miR-6850-5p is hsa-miR-6850-5p, miR-4697-5p is hsa-miR-4697-5p, miR-1260a is hsa-miR-1260a, miR-4486 is hsa-miR-4486, miR-6880-5p is hsa-miR-6880-5p, miR-6802-5p is hsa-miR-6802-5p, miR-6861-5p is hsa-miR-6861-5p, miR-92b-5p is hsa-miR-92b-5p, miR-1238-5p is hsa-miR-1238-5p, miR-6851-5p is hsa-miR-6851-5p, miR-7704 is hsa-miR-7704, miR-149-3p is hsa-miR-149-3p, miR-4689 is hsa-miR-4689, miR-4688 is hsa-miR-4688, miR-125a-3p is hsa-miR-125a-3p, miR-23b-3p is hsa-miR-23b-3p, miR-614 is hsa-miR-614, miR-1913 is hsa-miR-1913, miR-16-5p is hsa-miR-16-5p, miR-6717-5p is hsa-miR-6717-5p, miR-3648 is hsa-miR-3648, miR-3162-5p is hsa-miR-3162-5p, miR-1909-3p is hsa-miR-1909-3p, miR-8073 is hsa-miR-8073, miR-6769b-5p is hsa-miR-6769b-5p, miR-6836-3p is hsa-miR-6836-3p, miR-4484 is hsa-miR-4484, miR-6819-5p is hsa-miR-6819-5p, and miR-6794-5p is hsa-miR-6794-5p.

(3) The kit according to (1) or (2), wherein the nucleic acid(s) is/are polynucleotide(s) selected from the group consisting of the following polynucleotides (a) to (e):
(a) a polynucleotide consisting of a nucleotide sequence represented by any of SEQ ID NOs: 1 to 115, 117 to 189, and 666 to 675 or a nucleotide sequence from the nucleotide sequence by the replacement of u with t, a variant thereof, a derivative thereof, or a fragment thereof comprising 15 or more consecutive nucleotides,
(b) a polynucleotide comprising a nucleotide sequence represented by any of SEQ ID NOs: 1 to 115, 117 to 189, and 666 to 675,
(c) a polynucleotide consisting of a nucleotide sequence complementary to a nucleotide sequence represented by any of SEQ ID NOs: 1 to 115, 117 to 189, and 666 to 675 or a nucleotide sequence from the nucleotide sequence by the replacement of u with t, a variant thereof, a derivative thereof, or a fragment thereof comprising 15 or more consecutive nucleotides,
(d) a polynucleotide comprising a nucleotide sequence complementary to a nucleotide sequence represented by any of SEQ ID NOs: 1 to 115, 117 to 189, and 666 to 675 or a nucleotide sequence from the nucleotide sequence by the replacement of u with t, and (e) a polynucleotide hybridizing under stringent conditions to any of the polynucleotides (a) to (d).

(4) The kit according to any of (1) to (3), wherein the kit further comprises a nucleic acid capable of specifically binding to polynucleotide(s) selected from other esophageal cancer markers miR-575 and miR-24-3p.

(5) The kit according to (4), wherein miR-575 is hsa-miR-575, and miR-24-3p is hsa-miR-24-3p.

(6) The kit according to (4) or (5), wherein the nucleic acid(s) is/are polynucleotide(s) selected from the group consisting of the following polynucleotides (f) to (j):

(f) a polynucleotide consisting of a nucleotide sequence represented by any of SEQ ID NOs: 116 and 676 or a nucleotide sequence from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 116 and 676, (h) a polynucleotide consisting of a nucleotide sequence complementary to a nucleotide sequence represented by any of SEQ ID NOs: 116 and 676 or a nucleotide sequence from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 116 and 676 or a nucleotide sequence from the nucleotide sequence by the replacement of u with t, and (j) a polynucleotide hybridizing under stringent conditions to any of the polynucleotides (f) to (i).

(7) The kit according to any of (1) to (6), wherein the kit further comprises a nucleic acid capable of specifically binding to at least one polynucleotide selected from the group consisting of the following other esophageal cancer markers: miR-675-5p, miR-486-3p, miR-6777-5p, miR-4497, miR-296-3p, miR-6738-5p, miR-4731-5p, miR-6889-5p, miR-6786-5p, miR-92a-3p, miR-4294, miR-4763-3p, miR-6076, miR-663a, miR-760, miR-4667-5p, miR-6090, miR-4730, miR-7106-5p, miR-3196, miR-5698, miR-6087, miR-4665-5p, miR-8059 and miR-6879-5p.

(8) The kit according to (7), wherein miR-675-5p is hsa-miR-675-5p, miR-486-3p is hsa-miR-486-3p, miR-6777-5p is hsa-miR-6777-5p, miR-4497 is hsa-miR-4497, miR-296-3p is hsa-miR-296-3p, miR-6738-5p is hsa-miR-6738-5p, miR-4731-5p is hsa-miR-4731-5p, miR-6889-5p is hsa-miR-6889-5p, miR-6786-5p is hsa-miR-6786-5p, miR-92a-3p is hsa-miR-92a-3p, miR-4294 is hsa-miR-4294, miR-4763-3p is hsa-miR-4763-3p, miR-6076 is hsa-miR-6076, miR-663a is hsa-miR-663a, miR-760 is hsa-miR-760, miR-4667-5p is hsa-miR-4667-5p, miR-6090 is hsa-miR-6090, miR-4730 is hsa-miR-4730, miR-7106-5p is hsa-miR-7106-5p, miR-3196 is hsa-miR-3196, miR-5698 is hsa-miR-5698, miR-6087 is hsa-miR-6087, miR-4665-5p is hsa-miR-4665-5p, miR-8059 is hsa-miR-8059, and miR-6879-5p is hsa-miR-6879-5p.

(9) The kit according to (7) or (8), wherein the nucleic acid(s) is/are polynucleotide(s) selected from the group consisting of the following polynucleotides (k) to (o):

(k) a polynucleotide consisting of a nucleotide sequence represented by any of SEQ ID NOs: 190 to 214 or a nucleotide sequence from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 190 to 214, (m) a polynucleotide consisting of a nucleotide sequence complementary to a nucleotide sequence represented by any of SEQ ID NOs: 190 to 214 or a nucleotide sequence from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 190 to 214 or a nucleotide sequence from the nucleotide sequence by the replacement of u with t, and (o) a polynucleotide hybridizing under stringent conditions to any of the polynucleotides (k) to (n).

(10) The kit according to any of (1) to (9), wherein the kit comprises at least two nucleic acids capable of specifically binding to at least two polynucleotides, respectively, selected from all of the esophageal cancer markers according to (1) or (2).

(11) A device for the detection of esophageal cancer, comprising nucleic acid(s) capable of specifically binding to at least one polynucleotide selected from the group consisting of the following esophageal cancer markers: miR-204-3p, miR-1247-3p, miR-6875-5p, miR-6857-5p, miR-6726-5p, miR-3188, miR-8069, miR-4257, miR-1343-3p, miR-7108-5p, miR-6825-5p, miR-7641, miR-3185, miR-4746-3p, miR-6791-5p, miR-6893-5p, miR-4433b-3p, miR-3135b, miR-6781-5p, miR-1908-5p, miR-4792, miR-7845-5p, miR-4417, miR-3184-5p, miR-1225-5p, miR-1231, miR-1225-3p, miR-150-3p, miR-4433-3p, miR-6125, miR-4513, miR-6787-5p, miR-6784-5p, miR-615-5p, miR-6765-3p, miR-5572, miR-6842-5p, miR-8063, miR-6780b-5p, miR-187-5p, miR-128-1-5p, miR-6729-5p, miR-6741-5p, miR-6757-5p, miR-7110-5p, miR-7975, miR-1233-5p, miR-6845-5p, miR-3937, miR-4467, miR-7109-5p, miR-6088, miR-6782-5p, miR-5195-3p, miR-4454, miR-6724-5p, miR-8072, miR-4516, miR-6756-5p, miR-4665-3p, miR-6826-5p, miR-6820-5p, miR-6887-5p, miR-3679-5p, miR-7847-3p, miR-6721-5p, miR-3622a-5p, miR-939-5p, miR-602, miR-7977, miR-6749-5p, miR-1914-3p, miR-4651, miR-4695-5p, miR-6848-5p, miR-1228-3p, miR-642b-3p, miR-6746-5p, miR-3620-5p, miR-3131, miR-6732-5p, miR-7113-3p, miR-23a-3p, miR-3154, miR-4723-5p, miR-3663-3p, miR-4734, miR-6816-5p, miR-4442, miR-4476, miR-423-5p, miR-1249, miR-6515-3p, miR-887-3p, miR-4741, miR-6766-3p, miR-4673, miR-6779-5p, miR-4706, miR-1268b, miR-4632-5p, miR-3197, miR-6798-5p, miR-711, miR-6840-3p, miR-6763-5p, miR-6727-5p, miR-371a-5p, miR-6824-5p, miR-4648, miR-1227-5p, miR-564, miR-3679-3p, miR-2861, miR-6737-5p, miR-4725-3p, miR-6716-5p, miR-4675, miR-1915-3p, miR-671-5p, miR-3656, miR-6722-3p, miR-4707-5p, miR-4449, miR-1202, miR-4649-5p, miR-744-5p, miR-642a-3p, miR-451a, miR-6870-5p, miR-4443, miR-6808-5p, miR-4728-5p, miR-937-5p, miR-135a-3p, miR-663b, miR-1343-5p, miR-6822-5p, miR-6803-5p, miR-6805-3p, miR-128-2-5p, miR-4640-5p, miR-1469, miR-92a-2-5p, miR-3940-5p, miR-4281, miR-1260b, miR-4758-5p, miR-1915-5p, miR-5001-5p, miR-4286, miR-6126, miR-6789-5p, miR-4459, miR-1268a, miR-6752-5p, miR-6131, miR-6800-5p, miR-4532, miR-6872-3p, miR-718, miR-6769a-5p, miR-4707-3p, miR-6765-5p, miR-4739, miR-4525, miR-4270, miR-4534, miR-6785-5p, miR-6850-5p, miR-4697-5p, miR-1260a, miR-4486, miR-6880-5p, miR-6802-5p, miR-6861-

5p, miR-92b-5p, miR-1238-5p, miR-6851-5p, miR-7704, miR-149-3p, miR-4689, miR-4688, miR-125a-3p, miR-23b-3p, miR-614, miR-1913, miR-16-5p, miR-6717-5p, miR-3648, miR-3162-5p, miR-1909-3p, miR-8073, miR-6769b-5p, miR-6836-3p, miR-4484, miR-6819-5p and miR-6794-5p.

(12) The device according to (11), wherein miR-204-3p is hsa-miR-204-3p, miR-1247-3p is hsa-miR-1247-3p, miR-6875-5p is hsa-miR-6875-5p, miR-6857-5p is hsa-miR-6857-5p, miR-6726-5p is hsa-miR-6726-5p, miR-3188 is hsa-miR-3188, miR-8069 is hsa-miR-8069, miR-4257 is hsa-miR-4257, miR-1343-3p is hsa-miR-1343-3p, miR-7108-5p is hsa-miR-7108-5p, miR-6825-5p is hsa-miR-6825-5p, miR-7641 is hsa-miR-7641, miR-3185 is hsa-miR-3185, miR-4746-3p is hsa-miR-4746-3p, miR-6791-5p is hsa-miR-6791-5p, miR-6893-5p is hsa-miR-6893-5p, miR-4433b-3p is hsa-miR-4433b-3p, miR-3135b is hsa-miR-3135b, miR-6781-5p is hsa-miR-6781-5p, miR-1908-5p is hsa-miR-1908-5p, miR-4792 is hsa-miR-4792, miR-7845-5p is hsa-miR-7845-5p, miR-4417 is hsa-miR-4417, miR-3184-5p is hsa-miR-3184-5p, miR-1225-5p is hsa-miR-1225-5p, miR-1231 is hsa-miR-1231, miR-1225-3p is hsa-miR-1225-3p, miR-150-3p is hsa-miR-150-3p, miR-4433-3p is hsa-miR-4433-3p, miR-6125 is hsa-miR-6125, miR-4513 is hsa-miR-4513, miR-6787-5p is hsa-miR-6787-5p, miR-6784-5p is hsa-miR-6784-5p, miR-615-5p is hsa-miR-615-5p, miR-6765-3p is hsa-miR-6765-3p, miR-5572 is hsa-miR-5572, miR-6842-5p is hsa-miR-6842-5p, miR-8063 is hsa-miR-8063, miR-6780b-5p is hsa-miR-6780b-5p, miR-187-5p is hsa-miR-187-5p, miR-128-1-5p is hsa-miR-128-1-5p, miR-6729-5p is hsa-miR-6729-5p, miR-6741-5p is hsa-miR-6741-5p, miR-6757-5p is hsa-miR-6757-5p, miR-7110-5p is hsa-miR-7110-5p, miR-7975 is hsa-miR-7975, miR-1233-5p is hsa-miR-1233-5p, miR-6845-5p is hsa-miR-6845-5p, miR-3937 is hsa-miR-3937, miR-4467 is hsa-miR-4467, miR-7109-5p is hsa-miR-7109-5p, miR-6088 is hsa-miR-6088, miR-6782-5p is hsa-miR-6782-5p, miR-5195-3p is hsa-miR-5195-3p, miR-4454 is hsa-miR-4454, miR-6724-5p is hsa-miR-6724-5p, miR-8072 is hsa-miR-8072, miR-4516 is hsa-miR-4516, miR-6756-5p is hsa-miR-6756-5p, miR-4665-3p is hsa-miR-4665-3p, miR-6826-5p is hsa-miR-6826-5p, miR-6820-5p is hsa-miR-6820-5p, miR-6887-5p is hsa-miR-6887-5p, miR-3679-5p is hsa-miR-3679-5p, miR-7847-3p is hsa-miR-7847-3p, miR-6721-5p is hsa-miR-6721-5p, miR-3622a-5p is hsa-miR-3622a-5p, miR-939-5p is hsa-miR-939-5p, miR-602 is hsa-miR-602, miR-7977 is hsa-miR-7977, miR-6749-5p is hsa-miR-6749-5p, miR-1914-3p is hsa-miR-1914-3p, miR-4651 is hsa-miR-4651, miR-4695-5p is hsa-miR-4695-5p, miR-6848-5p is hsa-miR-6848-5p, miR-1228-3p is hsa-miR-1228-3p, miR-642b-3p is hsa-miR-642b-3p, miR-6746-5p is hsa-miR-6746-5p, miR-3620-5p is hsa-miR-3620-5p, miR-3131 is hsa-miR-3131, miR-6732-5p is hsa-miR-6732-5p, miR-7113-3p is hsa-miR-7113-3p, miR-23a-3p is hsa-miR-23a-3p, miR-3154 is hsa-miR-3154, miR-4723-5p is hsa-miR-4723-5p, miR-3663-3p is hsa-miR-3663-3p, miR-4734 is hsa-miR-4734, miR-6816-5p is hsa-miR-6816-5p, miR-4442 is hsa-miR-4442, miR-4476 is hsa-miR-4476, miR-423-5p is hsa-miR-423-5p, miR-1249 is hsa-miR-1249, miR-6515-3p is hsa-miR-6515-3p, miR-887-3p is hsa-miR-887-3p, miR-4741 is hsa-miR-4741, miR-6766-3p is hsa-miR-6766-3p, miR-4673 is hsa-miR-4673, miR-6779-5p is hsa-miR-6779-5p, miR-4706 is hsa-miR-4706, miR-1268b is hsa-miR-1268b, miR-4632-5p is hsa-miR-4632-5p, miR-3197 is hsa-miR-3197, miR-6798-5p is hsa-miR-6798-5p, miR-711 is hsa-miR-711, miR-6840-3p is hsa-miR-6840-3p, miR-6763-5p is hsa-miR-6763-5p, miR-6727-5p is hsa-miR-6727-5p, miR-371a-5p is hsa-miR-371a-5p, miR-6824-5p is hsa-miR-6824-5p, miR-4648 is hsa-miR-4648, miR-1227-5p is hsa-miR-1227-5p, miR-564 is hsa-miR-564, miR-3679-3p is hsa-miR-3679-3p, miR-2861 is hsa-miR-2861, miR-6737-5p is hsa-miR-6737-5p, miR-4725-3p is hsa-miR-4725-3p, miR-6716-5p is hsa-miR-6716-5p, miR-4675 is hsa-miR-4675, miR-1915-3p is hsa-miR-1915-3p, miR-671-5p is hsa-miR-671-5p, miR-3656 is hsa-miR-3656, miR-6722-3p is hsa-miR-6722-3p, miR-4707-5p is hsa-miR-4707-5p, miR-4449 is hsa-miR-4449, miR-1202 is hsa-miR-1202, miR-4649-5p is hsa-miR-4649-5p, miR-744-5p is hsa-miR-744-5p, miR-642a-3p is hsa-miR-642a-3p, miR-451a is hsa-miR-451a, miR-6870-5p is hsa-miR-6870-5p, miR-4443 is hsa-miR-4443, miR-6808-5p is hsa-miR-6808-5p, miR-4728-5p is hsa-miR-4728-5p, miR-937-5p is hsa-miR-937-5p, miR-135a-3p is hsa-miR-135a-3p, miR-663b is hsa-miR-663b, miR-1343-5p is hsa-miR-1343-5p, miR-6822-5p is hsa-miR-6822-5p, miR-6803-5p is hsa-miR-6803-5p, miR-6805-3p is hsa-miR-6805-3p, miR-128-2-5p is hsa-miR-128-2-5p, miR-4640-5p is hsa-miR-4640-5p, miR-1469 is hsa-miR-1469, miR-92a-2-5p is hsa-miR-92a-2-5p, miR-3940-5p is hsa-miR-3940-5p, miR-4281 is hsa-miR-4281, miR-1260b is hsa-miR-1260b, miR-4758-5p is hsa-miR-4758-5p, miR-1915-5p is hsa-miR-1915-5p, miR-5001-5p is hsa-miR-5001-5p, miR-4286 is hsa-miR-4286, miR-6126 is hsa-miR-6126, miR-6789-5p is hsa-miR-6789-5p, miR-4459 is hsa-miR-4459, miR-1268a is hsa-miR-1268a, miR-6752-5p is hsa-miR-6752-5p, miR-6131 is hsa-miR-6131, miR-6800-5p is hsa-miR-6800-5p, miR-4532 is hsa-miR-4532, miR-6872-3p is hsa-miR-6872-3p, miR-718 is hsa-miR-718, miR-6769a-5p is hsa-miR-6769a-5p, miR-4707-3p is hsa-miR-4707-3p, miR-6765-5p is hsa-miR-6765-5p, miR-4739 is hsa-miR-4739, miR-4525 is hsa-miR-4525, miR-4270 is hsa-miR-4270, miR-4534 is hsa-miR-4534, miR-6785-5p is hsa-miR-6785-5p, miR-6850-5p is hsa-miR-6850-5p, miR-4697-5p is hsa-miR-4697-5p, miR-1260a is hsa-miR-1260a, miR-4486 is hsa-miR-4486, miR-6880-5p is hsa-miR-6880-5p, miR-6802-5p is hsa-miR-6802-5p, miR-6861-5p is hsa-miR-6861-5p, miR-92b-5p is hsa-miR-92b-5p, miR-1238-5p is hsa-miR-1238-5p, miR-6851-5p is hsa-miR-6851-5p, miR-7704 is hsa-miR-7704, miR-149-3p is hsa-miR-149-3p, miR-4689 is hsa-miR-4689, miR-4688 is hsa-miR-4688, miR-125a-3p is hsa-miR-125a-3p, miR-23b-3p is hsa-miR-23b-3p, miR-614 is hsa-miR-614, miR-1913 is hsa-miR-1913, miR-16-5p is hsa-miR-16-5p, miR-6717-5p is hsa-miR-6717-5p, miR-3648 is hsa-miR-3648, miR-3162-5p is hsa-miR-3162-5p, miR-1909-3p is hsa-miR-1909-3p, miR-8073 is hsa-miR-8073, miR-6769b-5p is hsa-miR-6769b-5p, miR-6836-3p is hsa-miR-6836-3p, miR-4484 is hsa-miR-4484, miR-6819-5p is hsa-miR-6819-5p, and miR-6794-5p is hsa-miR-6794-5p.

(13) The device according to (11) or (12), wherein the nucleic acid(s) is/are polynucleotide(s) selected from the group consisting of the following polynucleotides (a) to (e):
(a) a polynucleotide consisting of a nucleotide sequence represented by any of SEQ ID NOs: 1 to 115, 117 to 189, and 666 to 675 or a nucleotide sequence from the nucleotide sequence by the replacement of u with t, a variant thereof, a derivative thereof, or a fragment thereof comprising 15 or more consecutive nucleotides,
(b) a polynucleotide comprising a nucleotide sequence represented by any of SEQ ID NOs: 1 to 115, 117 to 189, and 666 to 675,
(c) a polynucleotide consisting of a nucleotide sequence complementary to a nucleotide sequence represented by any of SEQ ID NOs: 1 to 115, 117 to 189, and 666 to 675 or a nucleotide sequence from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 115, 117 to 189, and 666 to 675 or a nucleotide sequence from the nucleotide sequence by the replacement of u with t, and (e) a polynucleotide hybridizing under stringent conditions to any of the polynucleotides (a) to (d).

(14) The device according to any of (11) to (13), wherein the device further comprises nucleic acid(s) capable of specifically binding to polynucleotide(s) selected from other esophageal cancer markers miR-575 and miR-24-3p.

(15) The device according to (14), wherein miR-575 is hsa-miR-575, and miR-24-3p is hsa-miR-24-3p.

(16) The device according to (14) or (15), wherein the nucleic acid(s) is/are polynucleotide(s) selected from the group consisting of the following polynucleotides (f) to (j):

(f) a polynucleotide consisting of a nucleotide sequence represented by any of SEQ ID NOs: 116 and 676 or a nucleotide sequence from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 116 and 676, (h) a polynucleotide consisting of a nucleotide sequence complementary to a nucleotide sequence represented by any of SEQ ID NOs: 116 and 676 or a nucleotide sequence from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 116 and 676 or a nucleotide sequence from the nucleotide sequence by the replacement of u with t, and (j) a polynucleotide hybridizing under stringent conditions to any of the polynucleotides (f) to (i).

(17) The device according to any of (11) to (16), wherein the device further comprises a nucleic acid capable of specifically binding to at least one polynucleotide selected from the group consisting of the following other esophageal cancer markers: miR-675-5p, miR-486-3p, miR-6777-5p, miR-4497, miR-296-3p, miR-6738-5p, miR-4731-5p, miR-6889-5p, miR-6786-5p, miR-92a-3p, miR-4294, miR-4763-3p, miR-6076, miR-663a, miR-760, miR-4667-5p, miR-6090, miR-4730, miR-7106-5p, miR-3196, miR-5698, miR-6087, miR-4665-5p, miR-8059, and miR-6879-5p.

(18) The device according to (17), wherein miR-675-5p is hsa-miR-675-5p, miR-486-3p is hsa-miR-486-3p, miR-6777-5p is hsa-miR-6777-5p, miR-4497 is hsa-miR-4497, miR-296-3p is hsa-miR-296-3p, miR-6738-5p is hsa-miR-6738-5p, miR-4731-5p is hsa-miR-4731-5p, miR-6889-5p is hsa-miR-6889-5p, miR-6786-5p is hsa-miR-6786-5p, miR-92a-3p is hsa-miR-92a-3p, miR-4294 is hsa-miR-4294, miR-4763-3p is hsa-miR-4763-3p, miR-6076 is hsa-miR-6076, miR-663a is hsa-miR-663a, miR-760 is hsa-miR-760, miR-4667-5p is hsa-miR-4667-5p, miR-6090 is hsa-miR-6090, miR-4730 is hsa-miR-4730, miR-7106-5p is hsa-miR-7106-5p, miR-3196 is hsa-miR-3196, miR-5698 is hsa-miR-5698, miR-6087 is hsa-miR-6087, miR-4665-5p is hsa-miR-4665-5p, miR-8059 is hsa-miR-8059, and miR-6879-5p is hsa-miR-6879-5p.

(19) The device according to (17) or (18), wherein the nucleic acid is a polynucleotide selected from the group consisting of the following polynucleotides (k) to (o):

(k) a polynucleotide consisting of a nucleotide sequence represented by any of SEQ ID NOs: 190 to 214 or a nucleotide sequence from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 190 to 214, (m) a polynucleotide consisting of a nucleotide sequence complementary to a nucleotide sequence represented by any of SEQ ID NOs: 190 to 214 or a nucleotide sequence from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 190 to 214 or a nucleotide sequence from the nucleotide sequence by the replacement of u with t, and (o) a polynucleotide hybridizing under stringent conditions to any of the polynucleotides (k) to (n).

(20) The device according to any one of (11) to (19), wherein the device is for measurement based on a hybridization technique.

(21) The device according to (20), wherein the hybridization technique is a nucleic acid array technique.

(22) The device according to any of (11) to (21), wherein the device comprises at least two nucleic acids capable of specifically binding to at least two polynucleotides, respectively, selected from all of the esophageal cancer markers according to (11) or (12).

(23) A method for detecting esophageal cancer, comprising measuring an expression level of a target nucleic acid in a sample of a subject using a kit according to any of (1) to (10) or a device according to any of (11) to (22), and evaluating the subject in vitro as having esophageal cancer or having no esophageal cancer using the measured expression level and a control expression level of a healthy subject measured in the same way as above.

(24) The method according to (23), wherein the subject is a human.

(25) The method according to (23) or (24), wherein the sample is blood, serum, or plasma.

Definition of Term

The terms used herein are defined as follows.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein refers to a nucleic acid including any of RNA, DNA, and RNA/DNA (chimera). The DNA includes any of cDNA, genomic DNA, and synthetic DNA. The aforementioned RNA includes any of total RNA, mRNA, rRNA, miRNA, siRNA, snoRNA, snRNA, non-coding RNA and synthetic RNA. Here, the "synthetic DNA" and the "synthetic RNA" refer to DNA and RNA artificially prepared using, for example, an automatic nucleic acid synthesizer, on the basis of predetermined nucleotide sequences (which may be any of natural and non-natural sequences). The "non-natural sequence" used herein is intended to be used in a broad sense and includes, for example, a sequence comprising substitution, deletion, insertion, and/or addition of one or more nucleotide(s) (i.e., a variant sequence) and a sequence comprising one or more modified nucleotide(s) (i.e., a modified sequence), which are different from the natural sequence. The term "polynucleotide" used herein is used interchangeably with the term "nucleic acid".

The term "fragment" used herein is a polynucleotide having a nucleotide sequence that consists of a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but also each single-stranded DNA such as a plus (+) strand (or a sense strand) or a complementary strand (or an antisense strand) that constitutes a duplex. The gene is not particularly limited by its length. Thus, the "gene" used herein includes any of double-stranded DNA including human genomic DNA, single-stranded DNA (plus strand), single-stranded DNA having a sequence complementary to the plus strand (complementary strand) including cDNA, microRNA (miRNA), and their fragments, and their transcripts, unless otherwise specified. The "gene" includes not only a "gene" represented by a particular nucleotide sequence (or SEQ ID NO) but also "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 700 or a nucleotide sequence from the nucleotide sequence by the replacement of u with t. Regardless whether or not there is a difference in functional region, the "gene" can comprise, for example, expression regulatory regions, coding regions, exons, or introns. The "gene" may be contained in a cell or may exist alone after being released from a cell. Alternatively, the "gene" may be in a state enclosed in a vesicle called exosome.

The term "exosome" used herein is a vesicle that is encapsulated by lipid bilayer and secreted from a cell. The exosome is derived from a multivesicular endosome and may incorporate biomaterials such as "genes" (e.g., RNA or DNA) or proteins when released into an extracellular environment. The exosome is known to be contained in a body fluid such as blood, serum, plasma or lymph.

The term "transcript" used herein refers to an RNA synthesized from the DNA sequence of a gene as a template. RNA polymerase binds to a site called a promoter located upstream of the gene and adds ribonucleotides complementary to the nucleotide sequence of the DNA to the 3' end to synthesize RNA. This RNA contains not only the gene itself but also the whole sequence from a transcription initiation site to the end of a polyA sequence, including expression regulatory regions, coding regions, exons, or introns.

Unless otherwise specified, the term "microRNA (miRNA)" used herein is intended to mean a 15- to 25-nucleotide non-coding RNA that is involved in the suppression of translation of mRNA, and that transcribed as an RNA precursor having a hairpin-like structure, cleaved by a dsRNA-cleaving enzyme which has RNase III cleavage activity, and integrated into a protein complex called RISC.

The term "miRNA" used herein includes not only a "miRNA" represented by a particular nucleotide sequence (or SEQ ID NO) but also a precursor of the "miRNA" (pre-miRNA or pri-miRNA), and miRNAs that have biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 700. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting RNA resulting from the expression of a gene or a polynucleotide from the RNA, and/or a polynucleotide complementary thereto.

The term "primer" used herein includes a polynucleotide that specifically recognizes and amplifies an RNA resulting from the expression of a gene or a polynucleotide from the RNA, and/or a polynucleotide complementary thereto. In this context, the complementary polynucleotide (complementary strand or reverse strand) means a polynucleotide in a complementary relationship of-A:T (U) and G:C base pairs with the full-length sequence of a polynucleotide consisting of a nucleotide sequence defined by any of SEQ ID NOs: 1 to 700 or a nucleotide sequence from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a larger extent (e.g., a measurement value equal to or larger than "(a mean of background measurement values)+(a standard deviation of the background measurement values)×2") than that for other sequences. The stringent conditions are dependent on a sequence and differ depending on an environment where hybridization is performed. A target sequence that is 100% complementary to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1 or 2 or more nucleotides in a nucleotide sequence represented by any of SEQ ID NOs: 1 to 700 or a nucleotide sequence from the nucleotide sequence by the replacement of u with t, or a partial sequence thereof, a variant that exhibits identity of approximately 90% or higher, approximately 95% or higher, approximately 97% or higher, approximately 98% or higher, approximately 99% or higher to each of these nucleotide sequences or the partial sequence thereof; or a nucleic acid hybridizing under the stringent conditions defined above to a polynucleotide or an oligonucleotide comprising each of these nucleotide sequences or the partial sequence thereof.

The term "several" or "plurality" used herein means an integer of approximately 10, 9, 8, 7, 6, 5, 4, 3, or 2.

The variant used herein can be prepared by use of a well-known technique such as site-directed mutagenesis or PCR-based mutagenesis.

The term "identity" used herein can be determined with or without an introduced gap, using a protein or gene search system based on BLAST or FASTA (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A, Vol. 85, p. 2444-2448).

The term "derivative" used herein is meant to include a unlimitedly modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404) n.

The "nucleic acid" used herein capable of specifically binding to a polynucleotide selected from the esophageal cancer marker miRNAs described above is a synthesized or prepared nucleic acid and specifically includes a "nucleic acid probe" or a "primer". The "nucleic acid" is utilized directly or indirectly for detecting the presence or absence of esophageal cancer in a subject, for diagnosing the presence or absence of esophageal cancer the severity of esophageal cancer, the presence or absence of amelioration or the degree of amelioration of esophageal cancer, or the therapeutic sensitivity of esophageal cancer, or for screening for a candidate substance useful in the prevention, amelioration, or treatment of esophageal cancer. The "nucleic acid" includes a nucleotide, an oligonucleotide, and a polynucleotide capable of specifically recognizing and binding to a transcript represented by any of SEQ ID NOs: 1 to 700 or a synthetic cDNA nucleic acid thereof in vivo, particularly, in a sample such as a body fluid (e.g., blood or urine), in relation to the development of esophageal cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "detection", or "decision support". The term "evaluation" used herein is meant to include diagnosing or evaluation-supporting on the basis of examination results or measurement results.

The term "subject" used herein means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected, i.e., esophageal cancer.

The term "P" or "P value" used herein refers to a probability at which a more extreme statistic than that actually calculated from data under null hypothesis is observed in a statistical test. Thus, smaller "P" or "P value" s regarded as being a more significant difference between subjects to be compared.

The term "sensitivity" used herein means a value of (the number of true positives)/(the number of true positives+the number of false negatives). High sensitivity allows esophageal cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being esophageal cancer patients, leading to reduction in burden on patients and reduction in medical expense.

The term "accuracy" used herein means a value of (the number of true positives+the number of true negatives)/(the total number of cases). The accuracy indicates the ratio of samples that identified correctly in the discriminant results to all samples and serves as a primary index for evaluating detection performance.

The "sample" used herein that is subjected to determination, detection, or diagnosis refers to a tissue and a biological material in which the expression of the gene of the present invention varies as esophageal cancer develops, as esophageal cancer progresses, or as therapeutic effects on esophageal cancer are exerted. Specifically, the "sample" refers to an esophageal tissue, a periesophageal vascular channel, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-204-3p gene" or "hsa-miR-204-3p" used herein includes the hsa-miR-204-3p gene (miRBase Accession No. MIMAT0022693) consisting of the nucleotide sequence represented by SEQ ID NO: 1, a homolog or an ortholog of a different organism species, and the like. The hsa-miR-204-3p gene can be obtained by a method described in Lim L P et al., 2003, Science, Vol. 299, p. 1540. Also, "hsa-mir-204" (miRBase Accession No. MI0000284, SEQ ID NO: 215) having a hairpin-like structure is known as a precursor of "hsa-miR-204-3p".

The term "hsa-miR-1247-3p gene" or "hsa-miR-1247-3p" used herein includes the hsa-miR-1247-3p gene (miRBase Accession No. MIMAT0022721) consisting of the nucleotide sequence represented by SEQ ID NO: 2, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. MI0006382, SEQ ID NO: 216) having a hairpin-like structure is known as a precursor of "hsa-miR-1247-3p".

The term "hsa-miR-6875-5p gene" or "hsa-miR-6875-5p" used herein includes the hsa-miR-6875-5p gene (miRBase Accession No. MIMAT0027650) consisting of the nucleotide sequence represented by SEQ ID NO: 3, a homolog or an ortholog of a different organism species, and the like. The hsa-miR-6875-5p gene can be obtained by a method described in Ladewig E et al., 2012, Genome Res, Vol. 22, p. 1634-1645. Also, "hsa-mir-6875" (miRBase Accession No. MI0022722, SEQ ID NO: 217) having a hairpin-like structure is known as a precursor of "hsa-miR-6875-5p".

The term "hsa-miR-6857-5p gene" or "hsa-miR-6857-5p" used herein includes the hsa-miR-6857-5p gene (miRBase Accession No. MIMAT0027614) consisting of the nucleotide sequence represented by SEQ ID NO: 4, a homolog or an ortholog of a different organism species, and the like. The hsa-miR-6857-5p gene can be obtained by a method described in Ladewig E et al., 2012, Genome Res, Vol. 22, p. 1634-1645. Also, "hsa-mir-6857" (miRBase Accession No. MI0022703, SEQ ID NO: 218) having a hairpin-like structure is known as a precursor of "hsa-miR-6857-5p."

The term "hsa-miR-6726-5p gene" or "hsa-miR-6726-5p" used herein includes the hsa-miR-6726-5p gene (miRBase Accession No. MIMAT0027353) consisting of the nucleotide sequence represented by SEQ ID NO: 5, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 219) having a hairpin-like structure is known as a precursor of "hsa-miR-6726-5p".

The term "hsa-miR-3188 gene" or "hsa-miR-3188" used herein includes the hsa-miR-3188 gene (miRBase Accession No. MIMAT0015070) consisting of the nucleotide sequence represented by SEQ ID NO: 6, a homolog or an ortholog of a different organism species, and the like. The hsa-miR-3188 gene can be obtained by a method described in Stark M S et al., 2010, PLoS One, Vol. 5, e9685. Also, "hsa-mir-3188" (miRBase Accession No. MI0014232, SEQ ID NO: 220) having a hairpin-like structure is known as a precursor of "hsa-miR-3188".

The term "hsa-miR-8069 gene" or "hsa-miR-8069" used herein includes the hsa-miR-8069 gene (miRBase Accession No. MIMAT0030996) consisting of the nucleotide sequence represented by SEQ ID NO: 7, a homolog or an ortholog of a different organism species, and the like. The hsa-miR-8069 gene can be obtained by a method described in Wang H J et al., 2013, Shock, Vol. 39, p. 480-487. Also, "hsa-mir-8069" (miRBase Accession No. MI0025905, SEQ ID NO: 221) having a hairpin-like structure is known as a precursor of "hsa-miR-8069".

The term "hsa-miR-4257 gene" or "hsa-miR-4257" used herein includes the hsa-miR-4257 gene (miRBase Accession No. MIMAT0016878) consisting of the nucleotide sequence represented by SEQ ID NO: 8, a homolog or an ortholog of a different organism species, and the like. The hsa-miR-4257 gene can be obtained by a method described in Goff L A et al., 2009, PLoS One, Vol. 4, e7192. Also, "hsa-mir-4257" (miRBase Accession No. MI0015856, SEQ ID NO: 222) having a hairpin-like structure is known as a precursor of "hsa-miR-4257".

The term "hsa-miR-1343-3p gene" or "hsa-miR-1343-3p" used herein includes the hsa-miR-1343-3p gene (miRBase Accession No. MIMAT0019776) consisting of the nucleotide sequence represented by SEQ ID NO: 9, a homolog or an ortholog of a different organism species, and the like. The hsa-miR-1343-3p gene can be obtained by a method described in Persson H et al., 2011, Cancer Res, Vol. 71, p. 78-86. Also, "hsa-mir-1343" (miRBase Accession No. MI0017320, SEQ ID NO: 223) having a hairpin-like structure is known as a precursor of "hsa-miR-1343-3p".

The term "hsa-miR-7108-5p gene" or "hsa-miR-7108-5p" used herein includes the hsa-miR-7108-5p gene (miRBase Accession No. MIMAT0028113) consisting of the nucleotide sequence represented by SEQ ID NO: 10, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. MI0022959, SEQ ID NO: 224) having a hairpin-like structure is known as a precursor of "hsa-miR-7108-5p".

The term "hsa-miR-6825-5p gene" or "hsa-miR-6825-5p" used herein includes the hsa-miR-6825-5p gene (miRBase Accession No. MIMAT0027550) consisting of the nucleotide sequence represented by SEQ ID NO: 11, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825" (miRBase Accession No. MI0022670, SEQ ID NO: 225) having a hairpin-like structure is known as a precursor of "hsa-miR-6825-5p".

The term "hsa-miR-7641 gene" or "hsa-miR-7641" used herein includes the hsa-miR-7641 gene (miRBase Accession No. MIMAT0029782) consisting of the nucleotide sequence represented by SEQ ID NO: 12, a homolog or an ortholog of a different organism species, and the like. The hsa-miR-7641 gene can be obtained by a method described in Yoo J K et al., 2013, Arch Pharm Res, Vol. 36, p. 353-358. Also, "hsa-mir-7641-1 and hsa-mir-7641-2" (miRBase Accession Nos. MI0024975 and MI0024976, SEQ ID NOs: 226 and 227) having a hairpin-like structure are known as precursors of "hsa-miR-7641".

The term "hsa-miR-3185 gene" or "hsa-miR-3185" used herein includes the hsa-miR-3185 gene (miRBase Accession No. MIMAT0015065) consisting of the nucleotide sequence represented by SEQ ID NO: 13, a homolog or an ortholog of a different organism species, and the like. The hsa-miR-3185 gene can be obtained by a method described in Stark M S et al., 2010, PLoS One, Vol. 5, e9685. Also, "hsa-mir-3185" (miRBase Accession No. MI0014227, SEQ ID NO: 228) having a hairpin-like structure is known as a precursor of "hsa-miR-3185".

The term "hsa-miR-4746-3p gene" or "hsa-miR-4746-3p" used herein includes the hsa-miR-4746-3p gene (miRBase Accession No. MIMAT0019881) consisting of the nucleotide sequence represented by SEQ ID NO: 14, a homolog or an ortholog of a different organism species, and the like. The hsa-miR-4746-3p gene can be obtained by a method described in Persson H et al., 2011, Cancer Res, Vol. 71, p. 78-86. Also, "hsa-mir-4746" (miRBase Accession No. MI0017385, SEQ ID NO: 229) having a hairpin-like structure is known as a precursor of "hsa-miR-4746-3p".

The term "hsa-miR-6791-5p gene" or "hsa-miR-6791-5p" used herein includes the hsa-miR-6791-5p gene (miRBase Accession No. MIMAT0027482) consisting of the nucleotide sequence represented by SEQ ID NO: 15, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 230) having a hairpin-like structure is known as a precursor of "hsa-miR-6791-5p".

The term "hsa-miR-6893-5p gene" or "hsa-miR-6893-5p" used herein includes the hsa-miR-6893-5p gene (miRBase Accession No. MIMAT0027686) consisting of the nucleotide sequence represented by SEQ ID NO: 16, a homolog or an ortholog of a different organism species, and the like. The hsa-miR-6893-5p gene can be obtained by a method described in Ladewig E et al., 2012, Genome Res, Vol. 22, p. 1634-1645. Also, "hsa-mir-6893" (miRBase Accession No. MI0022740, SEQ ID NO: 231) having a hairpin-like structure is known as a precursor of "hsa-miR-6893-5p".

The term "hsa-miR-4433b-3p gene" or "hsa-miR-4433b-3p" used herein includes the hsa-miR-4433b-3p gene (miRBase Accession No. MIMAT0030414) consisting of the nucleotide sequence represented by SEQ ID NO: 17, a homolog or an ortholog of a different organism species, and the like. The hsa-miR-4433b-3p gene can be obtained by a method described in Ple H et al., 2012, PLoS One, Vol. 7, e50746. Also, "hsa-mir-4433b" (miRBase Accession No. MI0025511, SEQ ID NO: 232) having a hairpin-like structure is known as a precursor of "hsa-miR-4433b-3p".

The term "hsa-miR-3135b gene" or "hsa-miR-3135b" used herein includes the hsa-miR-3135b gene (miRBase Accession No. MIMAT0018985) consisting of the nucleotide sequence represented by SEQ ID NO: 18, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 233) having a hairpin-like structure is known as a precursor of "hsa-miR-3135b".

The term "hsa-miR-6781-5p gene" or "hsa-miR-6781-5p" used herein includes the hsa-miR-6781-5p gene (miRBase Accession No. MIMAT0027462) consisting of the nucleotide sequence represented by SEQ ID NO: 19, a homolog or an ortholog of a different organism species, and the like. The hsa-miR-6781-5p gene can be obtained by a method described in Ladewig E et al., 2012, Genome Res, Vol. 22, p. 1634-1645. Also, "hsa-mir-6781" (miRBase Accession No. MI0022626, SEQ ID NO: 234) having a hairpin-like structure is known as a precursor of "hsa-miR-6781-5p."

The term "hsa-miR-1908-5p gene" or "hsa-miR-1908-5p" used herein includes the hsa-miR-1908-5p gene (miRBase Accession No. MIMAT0007881) consisting of the nucleotide sequence represented by SEQ ID NO: 20, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI0008329, SEQ ID NO: 235) having a hairpin-like structure is known as a precursor of "hsa-miR-1908-5p".

The term "hsa-miR-4792 gene" or "hsa-miR-4792" used herein includes the hsa-miR-4792 gene (miRBase Accession No. MIMAT0019964) consisting of the nucleotide sequence represented by SEQ ID NO: 21, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 236) having a hairpin-like structure is known as a precursor of "hsa-miR-4792".

The term "hsa-miR-7845-5p gene" or "hsa-miR-7845-5p" used herein includes the hsa-miR-7845-5p gene (miRBase Accession No. MIMAT0030420) consisting of the nucleotide sequence represented by SEQ ID NO: 22, a homolog or an ortholog of a different organism species, and the like. The hsa-miR-7845-5p gene can be obtained by a method described in Ple H et al., 2012, PLoS One, Vol. 7, e50746. Also, "hsa-mir-7845" (miRBase Accession No. MI0025515, SEQ ID NO: 237) having a hairpin-like structure is known as a precursor of "hsa-miR-7845-5p".

The term "hsa-miR-4417 gene" or "hsa-miR-4417" used herein includes the hsa-miR-4417 gene (miRBase Accession No. MIMAT0018929) consisting of the nucleotide sequence represented by SEQ ID NO: 23, a homolog or an ortholog of a different organism species, and the like. The hsa-miR-4417 gene can be obtained by a method described in Jima D D et al., 2010, Blood, Vol. 116, e118-e127. Also, "hsa-mir-4417" (miRBase Accession No. MI0016753, SEQ ID NO: 238) having a hairpin-like structure is known as a precursor of "hsa-miR-4417".

The term "hsa-miR-3184-5p gene" or "hsa-miR-3184-5p" used herein includes the hsa-miR-3184-5p gene (miRBase Accession No. MIMAT0015064) consisting of the nucleotide sequence represented by SEQ ID NO: 24, a homolog or an ortholog of a different organism species, and the like. The hsa-miR-3184-5p gene can be obtained by a method described in Stark M S et al., 2010, PLoS One, Vol. 5, e9685. Also, "hsa-mir-3184" (miRBase Accession No. MI0014226, SEQ ID NO: 239) having a hairpin-like structure is known as a precursor of "hsa-miR-3184-5p".

The term "hsa-miR-1225-5p gene" or "hsa-miR-1225-5p" used herein includes the hsa-miR-1225-5p gene (miRBase Accession No. MIMAT0005572) consisting of the nucleotide sequence represented by SEQ ID NO: 25, a homolog or an ortholog of a different organism species, and the like. The hsa-miR-1225-5p gene can be obtained by a method described in Berezikov E et al., 2007, Mol Cell, Vol. 28, p. 328-336. Also, "hsa-mir-1225" (miRBase Accession No. MI0006311, SEQ ID NO: 240) having a hairpin-like structure is known as a precursor of "hsa-miR-1225-5p".

The term "hsa-miR-1231 gene" or "hsa-miR-1231" used herein includes the hsa-miR-1231 gene (miRBase Accession No. MIMAT0005586) consisting of the nucleotide sequence represented by SEQ ID NO: 26, a homolog or an ortholog of a different organism species, and the like. The hsa-miR-1231 gene can be obtained by a method described in Berezikov E et al., 2007, Mol Cell, Vol. 28, p. 328-336. Also, "hsa-mir-1231" (miRBase Accession No. MI0006321, SEQ ID NO: 241) having a hairpin-like structure is known as a precursor of "hsa-miR-1231".

The term "hsa-miR-1225-3p gene" or "hsa-miR-1225-3p" used herein includes the hsa-miR-1225-3p gene (miRBase Accession No. MIMAT0005573) consisting of the nucleotide sequence represented by SEQ ID NO: 27, a homolog or an ortholog of a different organism species, and the like. The hsa-miR-1225-3p gene can be obtained by a method described in Berezikov E et al., 2007, Mol Cell, Vol. 28, p. 328-336. Also, "hsa-mir-1225" (miRBase Accession No. MI0006311, SEQ ID NO: 240) having a hairpin-like structure is known as a precursor of "hsa-miR-1225-3p".

The term "hsa-miR-150-3p gene" or "hsa-miR-150-3p" used herein includes the hsa-miR-150-3p gene (miRBase Accession No. MIMAT0004610) consisting of the nucleotide sequence represented by SEQ ID NO: 28, a homolog or an ortholog of a different organism species, and the like. The hsa-miR-150-3p gene can be obtained by a method described in Lagos-Quintana M et al., 2002, Curr Biol, Vol. 12, p. 735-739. Also, "hsa-mir-150" (miRBase Accession No. MI0000479, SEQ ID NO: 242) having a hairpin-like structure is known as a precursor of "hsa-miR-150-3p".

The term "hsa-miR-4433-3p gene" or "hsa-miR-4433-3p" used herein includes the hsa-miR-4433-3p gene (miRBase Accession No. MIMAT0018949) consisting of the nucleotide sequence represented by SEQ ID NO: 29, a homolog or an ortholog of a different organism species, and the like. The hsa-miR-4433-3p gene can be obtained by a method described in Jima D D et al., 2010, Blood, Vol. 116, e118-e127. Also, "hsa-mir-4433" (miRBase Accession No. MI0016773, SEQ ID NO: 243) having a hairpin-like structure is known as a precursor of "hsa-miR-4433-3p".

The term "hsa-miR-6125 gene" or "hsa-miR-6125" used herein includes the hsa-miR-6125 gene (miRBase Accession No. MIMAT0024598) consisting of the nucleotide sequence represented by SEQ ID NO: 30, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 244) having a hairpin-like structure is known as a precursor of "hsa-miR-6125".

The term "hsa-miR-4513 gene" or "hsa-miR-4513" used herein includes the hsa-miR-4513 gene (miRBase Accession No. MIMAT0019050) consisting of the nucleotide sequence represented by SEQ ID NO: 31, a homolog or an ortholog of a different organism species, and the like. The hsa-miR-4513 gene can be obtained by a method described in Jima D D et al., 2010, Blood, Vol. 116, e118-e127. Also, "hsa-mir-4513" (miRBase Accession No. MI0016879, SEQ ID NO: 245) having a hairpin-like structure is known as a precursor of "hsa-miR-4513".

The term "hsa-miR-6787-5p gene" or "hsa-miR-6787-5p" used herein includes the hsa-miR-6787-5p gene (miRBase Accession No. MIMAT0027474) consisting of the nucleotide sequence represented by SEQ ID NO: 32, a homolog or an ortholog of a different organism species, and the like. The hsa-miR-6787-5p gene can be obtained by a method described in Ladewig E et al., 2012, Genome Res, Vol. 22, p. 1634-1645. Also, "hsa-mir-6787" (miRBase Accession No. MI0022632, SEQ ID NO: 246) having a hairpin-like structure is known as a precursor of "hsa-miR-6787-5p".

The term "hsa-miR-6784-5p gene" or "hsa-miR-6784-5p" used herein includes the hsa-miR-6784-5p gene (miRBase Accession No. MIMAT0027468) consisting of the nucleotide sequence represented by SEQ ID NO: 33, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. MI0022629, SEQ ID NO: 247) having a hairpin-like structure is known as a precursor of "hsa-miR-6784-5p".

The term "hsa-miR-615-5p gene" or "hsa-miR-615-5p" used herein includes the hsa-miR-615-5p gene (miRBase Accession No. MIMAT0004804) consisting of the nucleotide sequence represented by SEQ ID NO: 34, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. MI0003628, SEQ ID NO: 248) having a hairpin-like structure is known as a precursor of "hsa-miR-615-5p".

The term "hsa-miR-6765-3p gene" or "hsa-miR-6765-3p" used herein includes the hsa-miR-6765-3p gene (miRBase Accession No. MIMAT0027431) consisting of the nucleotide sequence represented by SEQ ID NO: 35, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 249) having a hairpin-like structure is known as a precursor of "hsa-miR-6765-3p".

The term "hsa-miR-5572 gene" or "hsa-miR-5572" used herein includes the hsa-miR-5572 gene (miRBase Accession No. MIMAT0022260) consisting of the nucleotide sequence represented by SEQ ID NO: 36, a homolog or an ortholog of a different organism species, and the like. The hsa-miR-5572 gene can be obtained by a method described in Tandon M et al., 2012, Oral Dis, Vol. 18, p. 127-131. Also, "hsa-mir-5572" (miRBase Accession No. MI0019117, SEQ ID NO: 250) having a hairpin-like structure is known as a precursor of "hsa-miR-5572".

The term "hsa-miR-6842-5p gene" or "hsa-miR-6842-5p" used herein includes the hsa-miR-6842-5p gene (miRBase Accession No. MIMAT0027586) consisting of the nucleotide sequence represented by SEQ ID NO: 37, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688, SEQ ID NO: 251) having a hairpin-like structure is known as a precursor of "hsa-miR-6842-5p."

The term "hsa-miR-8063 gene" or "hsa-miR-8063" used herein includes the hsa-miR-8063 gene (miRBase Accession No. MIMAT0030990) consisting of the nucleotide sequence represented by SEQ ID NO: 38, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 252) having a hairpin-like structure is known as a precursor of "hsa-miR-8063".

The term "hsa-miR-6780b-5p gene" or "hsa-miR-6780b-5p" used herein includes the hsa-miR-6780b-5p gene (miRBase Accession No. MIMAT0027572) consisting of the nucleotide sequence represented by SEQ ID NO: 39, a homolog or an ortholog of a different organism species, and the like. The hsa-miR-6780b-5p gene can be obtained by a method described in Ladewig E et al., 2012, Genome Res, Vol. 22, p. 1634-1645. Also, "hsa-mir-6780b" (miRBase Accession No. MI0022681, SEQ ID NO: 253) having a hairpin-like structure is known as a precursor of "hsa-miR-6780b-5p".

The term "hsa-miR-187-5p gene" or "hsa-miR-187-5p" used herein includes the hsa-miR-187-5p gene (miRBase Accession No. MIMAT0004561) consisting of the nucleotide sequence represented by SEQ ID NO: 40, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274, SEQ ID NO: 254) having a hairpin-like structure is known as a precursor of "hsa-miR-187-5p".

The term "hsa-miR-128-1-5p gene" or "hsa-miR-128-1-5p" used herein includes the hsa-miR-128-1-5p gene (miRBase Accession No. MIMAT0026477) consisting of the nucleotide sequence represented by SEQ ID NO: 41, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. MI0000447, SEQ ID NO: 255) having a hairpin-like structure is known as a precursor of "hsa-miR-128-1-5p".

The term "hsa-miR-6729-5p gene" or "hsa-miR-6729-5p" used herein includes the hsa-miR-6729-5p gene (miRBase Accession No. MIMAT0027359) consisting of the nucleotide sequence represented by SEQ ID NO: 42, a homolog or an ortholog of a different organism species, and the like. The hsa-miR-6729-5p gene can be obtained by a method described in Ladewig E et al., 2012, Genome Res, Vol. 22, p. 1634-1645. Also, "hsa-mir-6729" (miRBase Accession No. MI0022574, SEQ ID NO: 256) having a hairpin-like structure is known as a precursor of "hsa-miR-6729-5p".

The term "hsa-miR-6741-5p gene" or "hsa-miR-6741-5p" used herein includes the hsa-miR-6741-5p gene (miRBase Accession No. MIMAT0027383) consisting of the nucleotide sequence represented by SEQ ID NO: 43, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. MI0022586, SEQ ID NO: 257) having a hairpin-like structure is known as a precursor of "hsa-miR-6741-5p".

The term "hsa-miR-6757-5p gene" or "hsa-miR-6757-5p" used herein includes the hsa-miR-6757-5p gene (miRBase Accession No. MIMAT0027414) consisting of the nucleotide sequence represented by SEQ ID NO: 44, a homolog or an ortholog of a different organism species, and the like. The hsa-miR-6757-5p gene can be obtained by a method described in Ladewig E et al., 2012, Genome Res, Vol. 22, p. 1634-1645. Also, "hsa-mir-6757" (miRBase Accession No. MI0022602, SEQ ID NO: 258) having a hairpin-like structure is known as a precursor of "hsa-miR-6757-5p".

The term "hsa-miR-7110-5p gene" or "hsa-miR-7110-5p" used herein includes the hsa-miR-7110-5p gene (miRBase Accession No. MIMAT0028117) consisting of the nucleotide sequence represented by SEQ ID NO: 45, a homolog or an ortholog of a different organism species, and the like. The hsa-miR-7110-5p gene can be obtained by a method described in Ladewig E et al., 2012, Genome Res, Vol. 22, p. 1634-1645. Also, "hsa-mir-7110" (miRBase Accession No. MI0022961, SEQ ID NO: 259) having a hairpin-like structure is known as a precursor of "hsa-miR-7110-5p".

The term "hsa-miR-7975 gene" or "hsa-miR-7975" used herein includes the hsa-miR-7975 gene (miRBase Accession No. MIMAT0031178) consisting of the nucleotide sequence represented by SEQ ID NO: 46, a homolog or an ortholog of a different organism species, and the like. The hsa-miR-7975 gene can be obtained by a method described in Velthut-Meikas A et al., 2013, Mol Endocrinol, online. Also, "hsa-mir-7975" (miRBase Accession No. MI0025751, SEQ ID NO: 260) having a hairpin-like structure is known as a precursor of "hsa-miR-7975".

The term "hsa-miR-1233-5p gene" or "hsa-miR-1233-5p" used herein includes the hsa-miR-1233-5p gene (miRBase Accession No. MIMAT0022943) consisting of the nucleotide sequence represented by SEQ ID NO: 47, a homolog or an ortholog of a different organism species, and the like. The hsa-miR-1233-5p gene can be obtained by a method described in Berezikov E et al., 2007, Mol Cell, Vol. 28, p. 328-336. Also, "hsa-mir-1233-1 and hsa-mir-1233-2" (miRBase Accession Nos. MI0006323 and MI0015973, SEQ ID NOs: 261 and 262) having a hairpin-like structure are known as precursors of "hsa-miR-1233-5p".

The term "hsa-miR-6845-5p gene" or "hsa-miR-6845-5p" used herein includes the hsa-miR-6845-5p gene (miRBase Accession No. MIMAT0027590) consisting of the nucleotide sequence represented by SEQ ID NO: 48, a homolog or an ortholog of a different organism species, and the like. The hsa-miR-6845-5p gene can be obtained by a method described in Ladewig E et al., 2012, Genome Res, Vol. 22, p. 1634-1645. Also, "hsa-mir-6845" (miRBase Accession No. MI0022691, SEQ ID NO: 263) having a hairpin-like structure is known as a precursor of "hsa-miR-6845-5p."

The term "hsa-miR-3937 gene" or "hsa-miR-3937" used herein includes the hsa-miR-3937 gene (miRBase Accession No. MIMAT0018352) consisting of the nucleotide sequence represented by SEQ ID NO: 49, a homolog or an ortholog of a different organism species, and the like. The hsa-miR-3937 gene can be obtained by a method described in Liao J Y et al., 2010, PLoS One, Vol. 5, e10563. Also, "hsa-mir-3937" (miRBase Accession No. MI0016593, SEQ ID NO: 264) having a hairpin-like structure is known as a precursor of "hsa-miR-3937".

The term "hsa-miR-4467 gene" or "hsa-miR-4467" used herein includes the hsa-miR-4467 gene (miRBase Accession No. MIMAT0018994) consisting of the nucleotide sequence represented by SEQ ID NO: 50, a homolog or an ortholog of a different organism species, and the like. The hsa-miR-4467 gene can be obtained by a method described in Jima D D et al., 2010, Blood, Vol. 116, e118-e127. Also, "hsa-mir-4467" (miRBase Accession No. MI0016818, SEQ ID NO: 265) having a hairpin-like structure is known as a precursor of "hsa-miR-4467".

The term "hsa-miR-7109-5p gene" or "hsa-miR-7109-5p" used herein includes the hsa-miR-7109-5p gene (miRBase Accession No. MIMAT0028115) consisting of the nucleotide sequence represented by SEQ ID NO: 51, a homolog or an ortholog of a different organism species, and the like. The hsa-miR-7109-5p gene can be obtained by a method described in Ladewig E et al., 2012, Genome Res, Vol. 22, p. 1634-1645. Also, "hsa-mir-7109" (miRBase Accession No. MI0022960, SEQ ID NO: 266) having a hairpin-like structure is known as a precursor of "hsa-miR-7109-5p".

The term "hsa-miR-6088 gene" or "hsa-miR-6088" used herein includes the hsa-miR-6088 gene (miRBase Accession No. MIMAT0023713) consisting of the nucleotide sequence represented by SEQ ID NO: 52, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 267) having a hairpin-like structure is known as a precursor of "hsa-miR-6088".

The term "hsa-miR-6782-5p gene" or "hsa-miR-6782-5p" used herein includes the hsa-miR-6782-5p gene (miRBase Accession No. MIMAT0027464) consisting of the nucleotide sequence represented by SEQ ID NO: 53, a homolog or an ortholog of a different organism species, and the like. The hsa-miR-6782-5p gene can be obtained by a method described in Ladewig E et al., 2012, Genome Res, Vol. 22, p. 1634-1645. Also, "hsa-mir-6782" (miRBase Accession No. MI0022627, SEQ ID NO: 268) having a hairpin-like structure is known as a precursor of "hsa-miR-6782-5p".

The term "hsa-miR-5195-3p gene" or "hsa-miR-5195-3p" used herein includes the hsa-miR-5195-3p gene (miRBase Accession No. MIMAT0021127) consisting of the nucleotide sequence represented by SEQ ID NO: 54, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 269) having a hairpin-like structure is known as a precursor of "hsa-miR-5195-3p".

The term "hsa-miR-4454 gene" or "hsa-miR-4454" used herein includes the hsa-miR-4454 gene (miRBase Accession No. MIMAT0018976) consisting of the nucleotide sequence represented by SEQ ID NO: 55, a homolog or an ortholog of a different organism species, and the like. The hsa-miR-4454 gene can be obtained by a method described in Jima D D et al., 2010, Blood, Vol. 116, e118-e127. Also, "hsa-mir-4454" (miRBase Accession No. MI0016800, SEQ ID NO: 270) having a hairpin-like structure is known as a precursor of "hsa-miR-4454".

The term "hsa-miR-6724-5p gene" or "hsa-miR-6724-5p" used herein includes the hsa-miR-6724-5p gene (miRBase Accession No. MIMAT0025856) consisting of the nucleotide sequence represented by SEQ ID NO: 56, a homolog or an ortholog of a different organism species, and the like. The hsa-miR-6724-5p gene can be obtained by a method described in Li Y et al., 2012, Gene, Vol. 497, p. 330-335. Also, "hsa-mir-6724" (miRBase Accession No. MI0022559, SEQ ID NO: 271) having a hairpin-like structure is known as a precursor of "hsa-miR-6724-5p".

The term "hsa-miR-8072 gene" or "hsa-miR-8072" used herein includes the hsa-miR-8072 gene (miRBase Accession No. MIMAT0030999) consisting of the nucleotide sequence represented by SEQ ID NO: 57, a homolog or an ortholog of a different organism species, and the like. The hsa-miR-8072 gene can be obtained by a method described in Wang H J et al., 2013, Shock, Vol. 39, p. 480-487. Also, "hsa-mir-8072" (miRBase Accession No. MI0025908, SEQ ID NO: 272) having a hairpin-like structure is known as a precursor of "hsa-miR-8072".

The term "hsa-miR-4516 gene" or "hsa-miR-4516" used herein includes the hsa-miR-4516 gene (miRBase Accession No. MIMAT0019053) consisting of the nucleotide sequence represented by SEQ ID NO: 58, a homolog or an ortholog of a different organism species, and the like. The hsa-miR-4516 gene can be obtained by a method described in Jima D D et al., 2010, Blood, Vol. 116, e118-e127. Also, "hsa-mir-4516" (miRBase Accession No. MI0016882, SEQ ID NO: 273) having a hairpin-like structure is known as a precursor of "hsa-miR-4516".

The term "hsa-miR-6756-5p gene" or "hsa-miR-6756-5p" used herein includes the hsa-miR-6756-5p gene (miRBase Accession No. MIMAT0027412) consisting of the nucleotide sequence represented by SEQ ID NO: 59, a homolog or an ortholog of a different organism species, and the like. The hsa-miR-6756-5p gene can be obtained by a method described in Ladewig E et al., 2012, Genome Res, Vol. 22, p. 1634-1645. Also, "hsa-mir-6756" (miRBase Accession No. MI0022601, SEQ ID NO: 274) having a hairpin-like structure is known as a precursor of "hsa-miR-6756-5p."

The term "hsa-miR-4665-3p gene" or "hsa-miR-4665-3p" used herein includes the hsa-miR-4665-3p gene (miRBase Accession No. MIMAT0019740) consisting of the nucleotide sequence represented by SEQ ID NO: 60, a homolog or an ortholog of a different organism species, and the like. The hsa-miR-4665-3p gene can be obtained by a method described in Persson H et al., 2011, Cancer Res, Vol. 71, p. 78-86. Also, "hsa-mir-4665" (miRBase Accession No. MI0017295, SEQ ID NO: 275) having a hairpin-like structure is known as a precursor of "hsa-miR-4665-3p".

The term "hsa-miR-6826-5p gene" or "hsa-miR-6826-5p" used herein includes the hsa-miR-6826-5p gene (miRBase Accession No. MIMAT0027552) consisting of the nucleotide sequence represented by SEQ ID NO: 61, a homolog or an ortholog of a different organism species, and the like. The hsa-miR-6826-5p gene can be obtained by a method described in Ladewig E et al., 2012, Genome Res, Vol. 22, p. 1634-1645. Also, "hsa-mir-6826" (miRBase Accession No. MI0022671, SEQ ID NO: 276) having a hairpin-like structure is known as a precursor of "hsa-miR-6826-5p".

The term "hsa-miR-6820-5p gene" or "hsa-miR-6820-5p" used herein includes the hsa-miR-6820-5p gene (miRBase Accession No. MIMAT0027540) consisting of the nucleotide sequence represented by SEQ ID NO: 62, a homolog or an ortholog of a different organism species, and the like. The hsa-miR-6820-5p gene can be obtained by a method described in Ladewig E et al., 2012, Genome Res, Vol. 22, p. 1634-1645. Also, "hsa-mir-6820" (miRBase Accession No. MI0022665, SEQ ID NO: 277) having a hairpin-like structure is known as a precursor of "hsa-miR-6820-5p".

The term "hsa-miR-6887-5p gene" or "hsa-miR-6887-5p" used herein includes the hsa-miR-6887-5p gene (miRBase Accession No. MIMAT0027674) consisting of the nucleotide sequence represented by SEQ ID NO: 63, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887" (miRBase Accession No. MI0022734, SEQ ID NO: 278) having a hairpin-like structure is known as a precursor of "hsa-miR-6887-5p".

The term "hsa-miR-3679-5p gene" or "hsa-miR-3679-5p" used herein includes the hsa-miR-3679-5p gene (miRBase Accession No. MIMAT0018104) consisting of the nucleotide sequence represented by SEQ ID NO: 64, a homolog or an ortholog of a different organism species, and the like. The hsa-miR-3679-5p gene can be obtained by a method described in Creighton C J et al., 2010, PLoS One, Vol. 5, e9637. Also, "hsa-mir-3679" (miRBase Accession No. MI0016080, SEQ ID NO: 279) having a hairpin-like structure is known as a precursor of "hsa-miR-3679-5p".

The term "hsa-miR-7847-3p gene" or "hsa-miR-7847-3p" used herein includes the hsa-miR-7847-3p gene (miRBase Accession No. MIMAT0030422) consisting of the nucleotide sequence represented by SEQ ID NO: 65, a homolog or an ortholog of a different organism species, and the like. The hsa-miR-7847-3p gene can be obtained by a method described in Ple H et al., 2012, PLoS One, Vol. 7, e50746. Also, "hsa-mir-7847" (miRBase Accession No. MI0025517, SEQ ID NO: 280) having a hairpin-like structure is known as a precursor of "hsa-miR-7847-3p".

The term "hsa-miR-6721-5p gene" or "hsa-miR-6721-5p" used herein includes the hsa-miR-6721-5p gene (miRBase Accession No. MIMAT0025852) consisting of the nucleotide sequence represented by SEQ ID NO: 66, a homolog or an ortholog of a different organism species, and the like. The hsa-miR-6721-5p gene can be obtained by a method described in Li Y et al., 2012, Gene, Vol. 497, p. 330-335. Also, "hsa-mir-6721" (miRBase Accession No. MI0022556, SEQ ID NO: 281) having a hairpin-like structure is known as a precursor of "hsa-miR-6721-5p".

The term "hsa-miR-3622a-5p gene" or "hsa-miR-3622a-5p" used herein includes the hsa-miR-3622a-5p gene (miRBase Accession No. MIMAT0018003) consisting of the nucleotide sequence represented by SEQ ID NO: 67, a homolog or an ortholog of a different organism species, and the like. The hsa-miR-3622a-5p gene can be obtained by a method described in Witten D et al., 2010, BMC Biol, Vol. 8, p. 58. Also, "hsa-mir-3622a" (miRBase Accession No. MI0016013, SEQ ID NO: 282) having a hairpin-like structure is known as a precursor of "hsa-miR-3622a-5p".

The term "hsa-miR-939-5p gene" or "hsa-miR-939-5p" used herein includes the hsa-miR-939-5p gene (miRBase Accession No. MIMAT0004982) consisting of the nucleotide sequence represented by SEQ ID NO: 68, a homolog or an ortholog of a different organism species, and the like. The hsa-miR-939-5p gene can be obtained by a method described in Lui W O et al., 2007, Cancer Res, Vol. 67, p. 6031-6043. Also, "hsa-mir-939" (miRBase Accession No. MI0005761, SEQ ID NO: 283) having a hairpin-like structure is known as a precursor of "hsa-miR-939-5p".

The term "hsa-miR-602 gene" or "hsa-miR-602" used herein includes the hsa-miR-602 gene (miRBase Accession No. MIMAT0003270) consisting of the nucleotide sequence represented by SEQ ID NO: 69, a homolog or an ortholog of a different organism species, and the like. The hsa-miR-602 gene can be obtained by a method described in Cummins J M et al., 2006, Proc Natl Acad Sci USA, Vol. 103, p. 3687-3692. Also, "hsa-mir-602" (miRBase Accession No. MI0003615, SEQ ID NO: 284) having a hairpin-like structure is known as a precursor of "hsa-miR-602".

The term "hsa-miR-7977 gene" or "hsa-miR-7977" used herein includes the hsa-miR-7977 gene (miRBase Accession No. MIMAT0031180) consisting of the nucleotide sequence represented by SEQ ID NO: 70, a homolog or an ortholog of a different organism species, and the like. The hsa-miR-7977 gene can be obtained by a method described in Velthut-Meikas A et al., 2013, Mol Endocrinol, online. Also, "hsa-mir-7977" (miRBase Accession No. MI0025753, SEQ ID NO: 285) having a hairpin-like structure is known as a precursor of "hsa-miR-7977".

The term "hsa-miR-6749-5p gene" or "hsa-miR-6749-5p" used herein includes the hsa-miR-6749-5p gene (miRBase Accession No. MIMAT0027398) consisting of the nucleotide sequence represented by SEQ ID NO: 71, a homolog or an ortholog of a different organism species, and the like. The hsa-miR-6749-5p gene can be obtained by a method described in Ladewig E et al., 2012, Genome Res, Vol. 22, p. 1634-1645. Also, "hsa-mir-6749" (miRBase Accession No. MI0022594, SEQ ID NO: 286) having a hairpin-like structure is known as a precursor of "hsa-miR-6749-5p".

The term "hsa-miR-1914-3p gene" or "hsa-miR-1914-3p" used herein includes the hsa-miR-1914-3p gene (miRBase Accession No. MIMAT0007890) consisting of the nucleotide sequence represented by SEQ ID NO: 72, a homolog or an ortholog of a different organism species, and the like. The hsa-miR-1914-3p gene can be obtained by a method described in Bar M et al., 2008, Stem Cells, Vol. 26, p. 2496-2505. Also, "hsa-mir-1914" (miRBase Accession No. MI0008335, SEQ ID NO: 287) having a hairpin-like structure is known as a precursor of "hsa-miR-1914-3p".

The term "hsa-miR-4651 gene" or "hsa-miR-4651" used herein includes the hsa-miR-4651 gene (miRBase Accession No. MIMAT0019715) consisting of the nucleotide sequence represented by SEQ ID NO: 73, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 288) having a hairpin-like structure is known as a precursor of "hsa-miR-4651".

The term "hsa-miR-4695-5p gene" or "hsa-miR-4695-5p" used herein includes the hsa-miR-4695-5p gene (miRBase Accession No. MIMAT0019788) consisting of the nucleotide sequence represented by SEQ ID NO: 74, a homolog or an ortholog of a different organism species, and the like. The hsa-miR-4695-5p gene can be obtained by a method described in Persson H et al., 2011, Cancer Res, Vol. 71, p. 78-86. Also, "hsa-mir-4695" (miRBase Accession No. MI0017328, SEQ ID NO: 289) having a hairpin-like structure is known as a precursor of "hsa-miR-4695-5p".

The term "hsa-miR-6848-5p gene" or "hsa-miR-6848-5p" used herein includes the hsa-miR-6848-5p gene (miRBase Accession No. MIMAT0027596) consisting of the nucleotide sequence represented by SEQ ID NO: 75, a homolog or an ortholog of a different organism species, and the like. The hsa-miR-6848-5p gene can be obtained by a method described in Ladewig E et al., 2012, Genome Res, Vol. 22, p. 1634-1645. Also, "hsa-mir-6848" (miRBase Accession No. MI0022694, SEQ ID NO: 290) having a hairpin-like structure is known as a precursor of "hsa-miR-6848-5p".

The term "hsa-miR-1228-3p gene" or "hsa-miR-1228-3p" used herein includes the hsa-miR-1228-3p gene (miRBase Accession No. MIMAT0005583) consisting of the nucleotide sequence represented by SEQ ID NO: 76, a homolog or an ortholog of a different organism species, and the like. The hsa-miR-1228-3p gene can be obtained by a method described in Berezikov E et al., 2007, Mol Cell, Vol. 28, p. 328-336. Also, "hsa-mir-1228" (miRBase Accession No. MI0006318, SEQ ID NO: 291) having a hairpin-like structure is known as a precursor of "hsa-miR-1228-3p".

The term "hsa-miR-642b-3p gene" or "hsa-miR-642b-3p" used herein includes the hsa-miR-642b-3p gene (miRBase Accession No. MIMAT0018444) consisting of the nucleotide sequence represented by SEQ ID NO: 77, a homolog or an ortholog of a different organism species, and the like. The hsa-miR-642b-3p gene can be obtained by a method described in Witten D et al., 2010, BMC Biol, Vol. 8, p. 58. Also, "hsa-mir-642b" (miRBase Accession No. MI0016685, SEQ ID NO: 292) having a hairpin-like structure is known as a precursor of "hsa-miR-642b-3p".

The term "hsa-miR-6746-5p gene" or "hsa-miR-6746-5p" used herein includes the hsa-miR-6746-5p gene (miRBase Accession No. MIMAT0027392) consisting of the nucleotide sequence represented by SEQ ID NO: 78, a homolog or an ortholog of a different organism species, and the like. The hsa-miR-6746-5p gene can be obtained by a method described in Ladewig E et al., 2012, Genome Res, Vol. 22, p. 1634-1645. Also, "hsa-mir-6746" (miRBase Accession No. MI0022591, SEQ ID NO: 293) having a hairpin-like structure is known as a precursor of "hsa-miR-6746-5p".

The term "hsa-miR-3620-5p gene" or "hsa-miR-3620-5p" used herein includes the hsa-miR-3620-5p gene (miRBase Accession No. MIMAT0022967) consisting of the nucleotide sequence represented by SEQ ID NO: 79, a homolog or an ortholog of a different organism species, and the like. The hsa-miR-3620-5p gene can be obtained by a method described in Witten D et al., 2010, BMC Biol, Vol. 8, p. 58. Also, "hsa-mir-3620" (miRBase Accession No. MI0016011, SEQ ID NO: 294) having a hairpin-like structure is known as a precursor of "hsa-miR-3620-5p".

The term "hsa-miR-3131 gene" or "hsa-miR-3131" used herein includes the hsa-miR-3131 gene (miRBase Accession No. MIMAT0014996) consisting of the nucleotide sequence represented by SEQ ID NO: 80, a homolog or an ortholog of a different organism species, and the like. The hsa-miR-3131 gene can be obtained by a method described in Stark M S et al., 2010, PLoS One, Vol. 5, e9685. Also, "hsa-mir-3131" (miRBase Accession No. MI0014151, SEQ ID NO: 295) having a hairpin-like structure is known as a precursor of "hsa-miR-3131".

The term "hsa-miR-6732-5p gene" or "hsa-miR-6732-5p" used herein includes the hsa-miR-6732-5p gene (miRBase Accession No. MIMAT0027365) consisting of the nucleotide sequence represented by SEQ ID NO: 81, a homolog or an ortholog of a different organism species, and the like. The hsa-miR-6732-5p gene can be obtained by a method described in Ladewig E et al., 2012, Genome Res, Vol. 22, p. 1634-1645. Also, "hsa-mir-6732" (miRBase Accession No. MI0022577, SEQ ID NO: 296) having a hairpin-like structure is known as a precursor of "hsa-miR-6732-5p".

The term "hsa-miR-7113-3p gene" or "hsa-miR-7113-3p" used herein includes the hsa-miR-7113-3p gene (miRBase Accession No. MIMAT0028124) consisting of the nucleotide sequence represented by SEQ ID NO: 82, a homolog or an ortholog of a different organism species, and the like. The hsa-miR-7113-3p gene can be obtained by a method described in Ladewig E et al., 2012, Genome Res, Vol. 22, p. 1634-1645. Also, "hsa-mir-7113" (miRBase Accession No. MI0022964, SEQ ID NO: 297) having a hairpin-like structure is known as a precursor of "hsa-miR-7113-3p".

The term "hsa-miR-23a-3p gene" or "hsa-miR-23a-3p" used herein includes the hsa-miR-23a-3p gene (miRBase Accession No. MIMAT0000078) consisting of the nucleotide sequence represented by SEQ ID NO: 83, a homolog or an ortholog of a different organism species, and the like. The hsa-miR-23a-3p gene can be obtained by a method described in Lagos-Quintana M et al., 2001, Science, Vol. 294, p. 853-858. Also, "hsa-mir-23a" (miRBase Accession No. MI0000079, SEQ ID NO: 298) having a hairpin-like structure is known as a precursor of "hsa-miR-23a-3p".

The term "hsa-miR-3154 gene" or "hsa-miR-3154" used herein includes the hsa-miR-3154 gene (miRBase Accession No. MIMAT0015028) consisting of the nucleotide sequence represented by SEQ ID NO: 84, a homolog or an ortholog of a different organism species, and the like. The hsa-miR-3154 gene can be obtained by a method described in Berezikov E et al., 2006, Genome Res, Vol. 16, p. 1289-1298. Also, "hsa-mir-3154" (miRBase Accession No. MI0014182, SEQ ID NO: 299) having a hairpin-like structure is known as a precursor of "hsa-miR-3154".

The term "hsa-miR-4723-5p gene" or "hsa-miR-4723-5p" used herein includes the hsa-miR-4723-5p gene (miRBase Accession No. MIMAT0019838) consisting of the nucleotide sequence represented by SEQ ID NO: 85, a homolog or an ortholog of a different organism species, and the like. The hsa-miR-4723-5p gene can be obtained by a method described in Persson H et al., 2011, Cancer Res, Vol. 71, p. 78-86. Also, "hsa-mir-4723" (miRBase Accession No. MI0017359, SEQ ID NO: 300) having a hairpin-like structure is known as a precursor of "hsa-miR-4723-5p".

The term "hsa-miR-3663-3p gene" or "hsa-miR-3663-3p" used herein includes the hsa-miR-3663-3p gene (miRBase Accession No. MIMAT0018085) consisting of the nucleotide sequence represented by SEQ ID NO: 86, a homolog or an ortholog of a different organism species, and the like. The hsa-miR-3663-3p gene can be obtained by a method described in Liao J Y et al., 2010, PLoS One, Vol. 5, e10563. Also, "hsa-mir-3663" (miRBase Accession No. MI0016064, SEQ ID NO: 301) having a hairpin-like structure is known as a precursor of "hsa-miR-3663-3p".

The term "hsa-miR-4734 gene" or "hsa-miR-4734" used herein includes the hsa-miR-4734 gene (miRBase Accession No. MIMAT0019859) consisting of the nucleotide sequence represented by SEQ ID NO: 87, a homolog or an ortholog of a different organism species, and the like. The hsa-miR-4734 gene can be obtained by a method described in Persson H et al., 2011, Cancer Res, Vol. 71, p. 78-86. Also, "hsa-mir-4734" (miRBase Accession No. MI0017371, SEQ ID NO: 302) having a hairpin-like structure is known as a precursor of "hsa-miR-4734".

The term "hsa-miR-6816-5p gene" or "hsa-miR-6816-5p" used herein includes the hsa-miR-6816-5p gene (miRBase Accession No. MIMAT0027532) consisting of the nucleotide sequence represented by SEQ ID NO: 88, a homolog or an ortholog of a different organism species, and the like. The hsa-miR-6816-5p gene can be obtained by a method described in Ladewig E et al., 2012, Genome Res, Vol. 22, p. 1634-1645. Also, "hsa-mir-6816" (miRBase Accession No. MI0022661, SEQ ID NO: 303) having a hairpin-like structure is known as a precursor of "hsa-miR-6816-5p."

The term "hsa-miR-4442 gene" or "hsa-miR-4442" used herein includes the hsa-miR-4442 gene (miRBase Accession No. MIMAT0018960) consisting of the nucleotide sequence represented by SEQ ID NO: 89, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. MI0016785, SEQ ID NO: 304) having a hairpin-like structure is known as a precursor of "hsa-miR-4442".

The term "hsa-miR-4476 gene" or "hsa-miR-4476" used herein includes the hsa-miR-4476 gene (miRBase Accession No. MIMAT0019003) consisting of the nucleotide sequence represented by SEQ ID NO: 90, a homolog or an ortholog of a different organism species, and the like. The hsa-miR-4476 gene can be obtained by a method described in Jima D D et al., 2010, Blood, Vol. 116, e118-e127. Also, "hsa-mir-4476" (miRBase Accession No. MI0016828, SEQ ID NO: 305) having a hairpin-like structure is known as a precursor of "hsa-miR-4476".

The term "hsa-miR-423-5p gene" or "hsa-miR-423-5p" used herein includes the hsa-miR-423-5p gene (miRBase Accession No. MIMAT0004748) consisting of the nucleotide sequence represented by SEQ ID NO: 91, a homolog or an ortholog of a different organism species, and the like. The hsa-miR-423-5p gene can be obtained by a method described in Kasashima K et al., 2004, Biochem Biophys Res Commun, Vol. 322, p. 403-410. Also, "hsa-mir-423" (miRBase Accession No. MI0001445, SEQ ID NO: 306) having a hairpin-like structure is known as a precursor of "hsa-miR-423-5p".

The term "hsa-miR-1249 gene" or "hsa-miR-1249" used herein includes the hsa-miR-1249 gene (miRBase Accession No. MIMAT0005901) consisting of the nucleotide sequence represented by SEQ ID NO: 92, a homolog or an ortholog of a different organism species, and the like. The hsa-miR-1249 gene can be obtained by a method described in Morin R D et al., 2008, Genome Res, Vol. 18, p. 610-621. Also, "hsa-mir-1249" (miRBase Accession No. MI0006384, SEQ ID NO: 307) having a hairpin-like structure is known as a precursor of "hsa-miR-1249".

The term "hsa-miR-6515-3p gene" or "hsa-miR-6515-3p" used herein includes the hsa-miR-6515-3p gene (miRBase Accession No. MIMAT0025487) consisting of the nucleotide sequence represented by SEQ ID NO: 93, a homolog or an ortholog of a different organism species, and the like. The hsa-miR-6515-3p gene can be obtained by a method described in Joyce C E et al., 2011, Hum Mol Genet, Vol. 20, p. 4025-4040. Also, "hsa-mir-6515" (miRBase Accession No. MI0022227, SEQ ID NO: 308) having a hairpin-like structure is known as a precursor of "hsa-miR-6515-3p".

The term "hsa-miR-887-3p gene" or "hsa-miR-887-3p" used herein includes the hsa-miR-887-3p gene (miRBase Accession No. MIMAT0004951) consisting of the nucleotide sequence represented by SEQ ID NO: 94, a homolog or an ortholog of a different organism species, and the like. The hsa-miR-887-3p gene can be obtained by a method described in Berezikov E et al., 2006, Genome Res, Vol. 16, p. 1289-1298. Also, "hsa-mir-887" (miRBase Accession No. MI0005562, SEQ ID NO: 309) having a hairpin-like structure is known as a precursor of "hsa-miR-887-3p".

The term "hsa-miR-4741 gene" or "hsa-miR-4741" used herein includes the hsa-miR-4741 gene (miRBase Accession No. MIMAT0019871) consisting of the nucleotide sequence represented by SEQ ID NO: 95, a homolog or an ortholog of a different organism species, and the like. The hsa-miR-4741 gene can be obtained by a method described in Persson H et al., 2011, Cancer Res, Vol. 71, p. 78-86. Also, "hsa-mir-4741" (miRBase Accession No. MI0017379, SEQ ID NO: 310) having a hairpin-like structure is known as a precursor of "hsa-miR-4741".

The term "hsa-miR-6766-3p gene" or "hsa-miR-6766-3p" used herein includes the hsa-miR-6766-3p gene (miRBase Accession No. MIMAT0027433) consisting of the nucleotide sequence represented by SEQ ID NO: 96, a homolog or an ortholog of a different organism species, and the like. The hsa-miR-6766-3p gene can be obtained by a method described in Ladewig E et al., 2012, Genome Res, Vol. 22, p. 1634-1645. Also, "hsa-mir-6766" (miRBase Accession No. MI0022611, SEQ ID NO: 311) having a hairpin-like structure is known as a precursor of "hsa-miR-6766-3p".

The term "hsa-miR-4673 gene" or "hsa-miR-4673" used herein includes the hsa-miR-4673 gene (miRBase Accession No. MIMAT0019755) consisting of the nucleotide sequence represented by SEQ ID NO: 97, a homolog or an ortholog of a different organism species, and the like. The hsa-miR-4673 gene can be obtained by a method described in Persson H et al., 2011, Cancer Res, Vol. 71, p. 78-86. Also, "hsa-mir-4673" (miRBase Accession No. MI0017304, SEQ ID NO: 312) having a hairpin-like structure is known as a precursor of "hsa-miR-4673".

The term "hsa-miR-6779-5p gene" or "hsa-miR-6779-5p" used herein includes the hsa-miR-6779-5p gene (miRBase Accession No. MIMAT0027458) consisting of the nucleotide sequence represented by SEQ ID NO: 98, a homolog or an ortholog of a different organism species, and the like. The hsa-miR-6779-5p gene can be obtained by a method described in Ladewig E et al., 2012, Genome Res, Vol. 22, p. 1634-1645. Also, "hsa-mir-6779" (miRBase Accession No. MI0022624, SEQ ID NO: 313) having a hairpin-like structure is known as a precursor of "hsa-miR-6779-5p".

The term "hsa-miR-4706 gene" or "hsa-miR-4706" used herein includes the hsa-miR-4706 gene (miRBase Accession No. MIMAT0019806) consisting of the nucleotide sequence represented by SEQ ID NO: 99, a homolog or an ortholog of a different organism species, and the like. The hsa-miR-4706 gene can be obtained by a method described in Persson H et al., 2011, Cancer Res, Vol. 71, p. 78-86. Also, "hsa-mir-4706" (miRBase Accession No. MI0017339, SEQ ID NO: 314) having a hairpin-like structure is known as a precursor of "hsa-miR-4706".

The term "hsa-miR-1268b gene" or "hsa-miR-1268b" used herein includes the hsa-miR-1268b gene (miRBase Accession No. MIMAT0018925) consisting of the nucleotide sequence represented by SEQ ID NO: 100, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 315) having a hairpin-like structure is known as a precursor of "hsa-miR-1268b".

The term "hsa-miR-4632-5p gene" or "hsa-miR-4632-5p" used herein includes the hsa-miR-4632-5p gene (miRBase Accession No. MIMAT0022977) consisting of the nucleotide sequence represented by SEQ ID NO: 101, a homolog or an ortholog of a different organism species, and the like. The hsa-miR-4632-5p gene can be obtained by a method described in Persson H et al., 2011, Cancer Res, Vol. 71, p. 78-86. Also, "hsa-mir-4632" (miRBase Accession No. MI0017259, SEQ ID NO: 316) having a hairpin-like structure is known as a precursor of "hsa-miR-4632-5p".

The term "hsa-miR-3197 gene" or "hsa-miR-3197" used herein includes the hsa-miR-3197 gene (miRBase Accession No. MIMAT0015082) consisting of the nucleotide sequence represented by SEQ ID NO: 102, a homolog or an ortholog of a different organism species, and the like. The hsa-miR-3197 gene can be obtained by a method described in Stark M S et al., 2010, PLoS One, Vol. 5, e9685. Also, "hsa-mir-3197" (miRBase Accession No. MI0014245, SEQ ID NO: 317) having a hairpin-like structure is known as a precursor of "hsa-miR-3197".

The term "hsa-miR-6798-5p gene" or "hsa-miR-6798-5p" used herein includes the hsa-miR-6798-5p gene (miRBase Accession No. MIMAT0027496) consisting of the nucleotide sequence represented by SEQ ID NO: 103, a homolog or an ortholog of a different organism species, and the like. The hsa-miR-6798-5p gene can be obtained by a method described in Ladewig E et al., 2012, Genome Res, Vol. 22, p. 1634-1645. Also, "hsa-mir-6798" (miRBase Accession No. MI0022643, SEQ ID NO: 318) having a hairpin-like structure is known as a precursor of "hsa-miR-6798-5p".

The term "hsa-miR-711 gene" or "hsa-miR-711" used herein includes the hsa-miR-711 gene (miRBase Accession No. MIMAT0012734) consisting of the nucleotide sequence represented by SEQ ID NO: 104, a homolog or an ortholog of a different organism species, and the like. The hsa-miR-711 gene can be obtained by a method described in Artzi S et al., 2008, BMC Bioinformatics, Vol. 9, p. 39. Also, "hsa-mir-711" (miRBase Accession No. MI0012488, SEQ ID NO: 319) having a hairpin-like structure is known as a precursor of "hsa-miR-711".

The term "hsa-miR-6840-3p gene" or "hsa-miR-6840-3p" used herein includes the hsa-miR-6840-3p gene (miRBase Accession No. MIMAT0027583) consisting of the nucleotide sequence represented by SEQ ID NO: 105, a homolog or an ortholog of a different organism species, and the like. The hsa-miR-6840-3p gene can be obtained by a method described in Ladewig E et al., 2012, Genome Res, Vol. 22, p. 1634-1645. Also, "hsa-mir-6840" (miRBase Accession No. MI0022686, SEQ ID NO: 320) having a hairpin-like structure is known as a precursor of "hsa-miR-6840-3p".

The term "hsa-miR-6763-5p gene" or "hsa-miR-6763-5p" used herein includes the hsa-miR-6763-5p gene (miRBase Accession No. MIMAT0027426) consisting of the nucleotide sequence represented by SEQ ID NO: 106, a homolog or an ortholog of a different organism species, and the like. The hsa-miR-6763-5p gene can be obtained by a method described in Ladewig E et al., 2012, Genome Res, Vol. 22, p. 1634-1645. Also, "hsa-mir-6763" (miRBase Accession No. MI0022608, SEQ ID NO: 321) having a hairpin-like structure is known as a precursor of "hsa-miR-6763-5p."

The term "hsa-miR-6727-5p gene" or "hsa-miR-6727-5p" used herein includes the hsa-miR-6727-5p gene (miRBase Accession No. MIMAT0027355) consisting of the nucleotide sequence represented by SEQ ID NO: 107, a homolog or an ortholog of a different organism species, and the like. The hsa-miR-6727-5p gene can be obtained by a method described in Ladewig E et al., 2012, Genome Res, Vol. 22, p. 1634-1645. Also, "hsa-mir-6727" (miRBase Accession No. MI0022572, SEQ ID NO: 322) having a hairpin-like structure is known as a precursor of "hsa-miR-6727-5p".

The term "hsa-miR-371a-5p gene" or "hsa-miR-371a-5p" used herein includes the hsa-miR-371a-5p gene (miRBase Accession No. MIMAT0004687) consisting of the nucleotide sequence represented by SEQ ID NO: 108, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 323) having a hairpin-like structure is known as a precursor of "hsa-miR-371a-5p".

The term "hsa-miR-6824-5p gene" or "hsa-miR-6824-5p" used herein includes the hsa-miR-6824-5p gene (miRBase Accession No. MIMAT0027548) consisting of the nucleotide sequence represented by SEQ ID NO: 109, a homolog or an ortholog of a different organism species, and the like. The hsa-miR-6824-5p gene can be obtained by a method described in Ladewig E et al., 2012, Genome Res, Vol. 22, p. 1634-1645. Also, "hsa-mir-6824" (miRBase Accession No. MI0022669, SEQ ID NO: 324) having a hairpin-like structure is known as a precursor of "hsa-miR-6824-5p".

The term "hsa-miR-4648 gene" or "hsa-miR-4648" used herein includes the hsa-miR-4648 gene (miRBase Accession No. MIMAT0019710) consisting of the nucleotide sequence represented by SEQ ID NO: 110, a homolog or an ortholog of a different organism species, and the like. The hsa-miR-4648 gene can be obtained by a method described in Persson H et al., 2011, Cancer Res, Vol. 71, p. 78-86. Also, "hsamir-4648" (miRBase Accession No. MI0017275, SEQ ID NO: 325) having a hairpin-like structure is known as a precursor of "hsa-miR-4648".

The term "hsa-miR-1227-5p gene" or "hsa-miR-1227-5p" used herein includes the hsa-miR-1227-5p gene (miRBase Accession No. MIMAT0022941) consisting of the nucleotide sequence represented by SEQ ID NO: 111, a homolog or an ortholog of a different organism species, and the like. The hsa-miR-1227-5p gene can be obtained by a method described in Berezikov E et al., 2007, Mol Cell, Vol. 28, p. 328-336. Also, "hsa-mir-1227" (miRBase Accession No. MI0006316, SEQ ID NO: 326) having a hairpin-like structure is known as a precursor of "hsa-miR-1227-5p".

The term "hsa-miR-564 gene" or "hsa-miR-564" used herein includes the hsa-miR-564 gene (miRBase Accession No. MIMAT0003228) consisting of the nucleotide sequence represented by SEQ ID NO: 112, a homolog or an ortholog of a different organism species, and the like. The hsa-miR-564 gene can be obtained by a method described in Cummins J M et al., 2006, Proc Natl Acad Sci USA, Vol. 103, p. 3687-3692. Also, "hsa-mir-564" (miRBase Accession No. MI0003570, SEQ ID NO: 327) having a hairpin-like structure is known as a precursor of "hsa-miR-564".

The term "hsa-miR-3679-3p gene" or "hsa-miR-3679-3p" used herein includes the hsa-miR-3679-3p gene (miRBase Accession No. MIMAT0018105) consisting of the nucleotide sequence represented by SEQ ID NO: 113, a homolog or an ortholog of a different organism species, and the like. The hsa-miR-3679-3p gene can be obtained by a method described in Creighton C J et al., 2010, PLoS One, Vol. 5, e9637. Also, "hsa-mir-3679" (miRBase Accession No. MI0016080, SEQ ID NO: 279) having a hairpin-like structure is known as a precursor of "hsa-miR-3679-3p".

The term "hsa-miR-2861 gene" or "hsa-miR-2861" used herein includes the hsa-miR-2861 gene (miRBase Accession No. MIMAT0013802) consisting of the nucleotide sequence represented by SEQ ID NO: 114, a homolog or an ortholog of a different organism species, and the like. The hsa-miR-2861 gene can be obtained by a method described in Li H et al., 2009, J Clin Invest, Vol. 119, p. 3666-3677. Also, "hsa-mir-2861" (miRBase Accession No. MI0013006, SEQ ID NO: 328) having a hairpin-like structure is known as a precursor of "hsa-miR-2861".

The term "hsa-miR-6737-5p gene" or "hsa-miR-6737-5p" used herein includes the hsa-miR-6737-5p gene (miRBase Accession No. MIMAT0027375) consisting of the nucleotide sequence represented by SEQ ID NO: 115, a homolog or an ortholog of a different organism species, and the like. The hsa-miR-6737-5p gene can be obtained by a method described in Ladewig E et al., 2012, Genome Res, Vol. 22, p. 1634-1645. Also, "hsa-mir-6737" (miRBase Accession No. MI0022582, SEQ ID NO: 329) having a hairpin-like structure is known as a precursor of "hsa-miR-6737-5p".

The term "hsa-miR-575 gene" or "hsa-miR-575" used herein includes the hsa-miR-575 gene (miRBase Accession No. MIMAT0003240) consisting of the nucleotide sequence represented by SEQ ID NO: 116, a homolog or an ortholog of a different organism species, and the like. The hsa-miR-575 gene can be obtained by a method described in Cummins J M et al., 2006, Proc Natl Acad Sci USA, Vol. 103, p. 3687-3692. Also, "hsa-mir-575" (miRBase Accession No. MI0003582, SEQ ID NO: 330) having a hairpin-like structure is known as a precursor of "hsa-miR-575".

The term "hsa-miR-4725-3p gene" or "hsa-miR-4725-3p" used herein includes the hsa-miR-4725-3p gene (miRBase Accession No. MIMAT0019844) consisting of the nucleotide sequence represented by SEQ ID NO: 117, a homolog or an ortholog of a different organism species, and the like. The hsa-miR-4725-3p gene can be obtained by a method described in Persson H et al., 2011, Cancer Res, Vol. 71, p. 78-86. Also, "hsa-mir-4725" (miRBase Accession No. MI0017362, SEQ ID NO: 331) having a hairpin-like structure is known as a precursor of "hsa-miR-4725-3p".

The term "hsa-miR-6716-5p gene" or "hsa-miR-6716-5p" used herein includes the hsa-miR-6716-5p gene (miRBase Accession No. MIMAT0025844) consisting of the nucleotide sequence represented by SEQ ID NO: 118, a homolog or an ortholog of a different organism species, and the like. The hsa-miR-6716-5p gene can be obtained by a method described in Li Y et al., 2012, Gene, Vol. 497, p. 330-335. Also, "hsa-mir-6716" (miRBase Accession No. MI0022550, SEQ ID NO: 332) having a hairpin-like structure is known as a precursor of "hsa-miR-6716-5p".

The term "hsa-miR-4675 gene" or "hsa-miR-4675" used herein includes the hsa-miR-4675 gene (miRBase Accession No. MIMAT0019757) consisting of the nucleotide sequence represented by SEQ ID NO: 119, a homolog or an ortholog of a different organism species, and the like. The hsa-miR-4675 gene can be obtained by a method described in Persson H et al., 2011, Cancer Res, Vol. 71, p. 78-86. Also, "hsa-mir-4675" (miRBase Accession No. MI0017306, SEQ ID NO: 333) having a hairpin-like structure is known as a precursor of "hsa-miR-4675".

The term "hsa-miR-1915-3p gene" or "hsa-miR-1915-3p" used herein includes the hsa-miR-1915-3p gene (miRBase Accession No. MIMAT0007892) consisting of the nucleotide sequence represented by SEQ ID NO: 120, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 334) having a hairpin-like structure is known as a precursor of "hsa-miR-1915-3p".

The term "hsa-miR-671-5p gene" or "hsa-miR-671-5p" used herein includes the hsa-miR-671-5p gene (miRBase Accession No. MIMAT0003880) consisting of the nucleotide sequence represented by SEQ ID NO: 121, a homolog or an ortholog of a different organism species, and the like. The hsa-miR-671-5p gene can be obtained by a method described in Berezikov E et al., 2006, Genome Res, Vol. 16, p. 1289-1298. Also, "hsa-mir-671" (miRBase Accession No. MI0003760, SEQ ID NO: 335) having a hairpin-like structure is known as a precursor of "hsa-miR-671-5p".

The term "hsa-miR-3656 gene" or "hsa-miR-3656" used herein includes the hsa-miR-3656 gene (miRBase Accession No. MIMAT0018076) consisting of the nucleotide sequence represented by SEQ ID NO: 122, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 336) having a hairpin-like structure is known as a precursor of "hsa-miR-3656".

The term "hsa-miR-6722-3p gene" or "hsa-miR-6722-3p" used herein includes the hsa-miR-6722-3p gene (miRBase Accession No. MIMAT0025854) consisting of the nucleotide sequence represented by SEQ ID NO: 123, a homolog or an ortholog of a different organism species, and the like. The hsa-miR-6722-3p gene can be obtained by a method described in Li Y et al., 2012, Gene, Vol. 497, p. 330-335. Also, "hsa-mir-6722" (miRBase Accession No. MI0022557, SEQ ID NO: 337) having a hairpin-like structure is known as a precursor of "hsa-miR-6722-3p".

The term "hsa-miR-4707-5p gene" or "hsa-miR-4707-5p" used herein includes the hsa-miR-4707-5p gene (miRBase Accession No. MIMAT0019807) consisting of the nucleotide sequence represented by SEQ ID NO: 124, a homolog or an ortholog of a different organism species, and the like. The hsa-miR-4707-5p gene can be obtained by a method described in Persson H et al., 2011, Cancer Res, Vol. 71, p. 78-86. Also, "hsa-mir-4707" (miRBase Accession No. MI0017340, SEQ ID NO: 338) having a hairpin-like structure is known as a precursor of "hsa-miR-4707-5p."

The term "hsa-miR-4449 gene" or "hsa-miR-4449" used herein includes the hsa-miR-4449 gene (miRBase Accession No. MIMAT0018968) consisting of the nucleotide sequence represented by SEQ ID NO: 125, a homolog or an ortholog of a different organism species, and the like. The hsa-miR-4449 gene can be obtained by a method described in Jima D D et al., 2010, Blood, Vol. 116, e118-e127. Also, "hsa-mir-4449" (miRBase Accession No. MI0016792, SEQ ID NO: 339) having a hairpin-like structure is known as a precursor of "hsa-miR-4449".

The term "hsa-miR-1202 gene" or "hsa-miR-1202" used herein includes the hsa-miR-1202 gene (miRBase Accession No. MIMAT0005865) consisting of the nucleotide sequence represented by SEQ ID NO: 126, a homolog or an ortholog of a different organism species, and the like. The hsa-miR-1202 gene can be obtained by a method described in Marton S et al., 2008, Leukemia, Vol. 22, p. 330-338. Also, "hsa-mir-1202" (miRBase Accession No. MI0006334, SEQ ID NO: 340) having a hairpin-like structure is known as a precursor of "hsa-miR-1202".

The term "hsa-miR-4649-5p gene" or "hsa-miR-4649-5p" used herein includes the hsa-miR-4649-5p gene (miRBase Accession No. MIMAT0019711) consisting of the nucleotide sequence represented by SEQ ID NO: 127, a homolog or an ortholog of a different organism species, and the like. The hsa-miR-4649-5p gene can be obtained by a method described in Persson H et al., 2011, Cancer Res, Vol. 71, p. 78-86. Also, "hsa-mir-4649" (miRBase Accession No. MI0017276, SEQ ID NO: 341) having a hairpin-like structure is known as a precursor of "hsa-miR-4649-5p".

The term "hsa-miR-744-5p gene" or "hsa-miR-744-5p" used herein includes the hsa-miR-744-5p gene (miRBase Accession No. MIMAT0004945) consisting of the nucleotide sequence represented by SEQ ID NO: 128, a homolog or an ortholog of a different organism species, and the like. The hsa-miR-744-5p gene can be obtained by a method described in Berezikov E et al., 2006, Genome Res, Vol. 16, p. 1289-1298. Also, "hsa-mir-744" (miRBase Accession No. MI0005559, SEQ ID NO: 342) having a hairpin-like structure is known as a precursor of "hsa-miR-744-5p".

The term "hsa-miR-642a-3p gene" or "hsa-miR-642a-3p" used herein includes the hsa-miR-642a-3p gene (miRBase Accession No. MIMAT0020924) consisting of the nucleotide sequence represented by SEQ ID NO: 129, a homolog or an ortholog of a different organism species, and the like. The hsa-miR-642a-3p gene can be obtained by a method described in Cummins J M et al., 2006, Proc Natl Acad Sci USA, Vol. 103, p. 3687-3692. Also, "hsa-mir-642a" (miRBase Accession No. MI0003657, SEQ ID NO: 343) having a hairpin-like structure is known as a precursor of "hsa-miR-642a-3p".

The term "hsa-miR-451a gene" or "hsa-miR-451a" used herein includes the hsa-miR-451a gene (miRBase Accession No. MIMAT0001631) consisting of the nucleotide sequence represented by SEQ ID NO: 130, a homolog or an ortholog of a different organism species, and the like. The hsa-miR-451a gene can be obtained by a method described in Altuvia Y et al., 2005, Nucleic Acids Res, Vol. 33, p. 2697-2706. Also, "hsa-mir-451a" (miRBase Accession No. MI0001729, SEQ ID NO: 344) having a hairpin-like structure is known as a precursor of "hsa-miR-451a".

The term "hsa-miR-6870-5p gene" or "hsa-miR-6870-5p" used herein includes the hsa-miR-6870-5p gene (miRBase Accession No. MIMAT0027640) consisting of the nucleotide sequence represented by SEQ ID NO: 131, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. MI0022717, SEQ ID NO: 345) having a hairpin-like structure is known as a precursor of "hsa-miR-6870-5p".

The term "hsa-miR-4443 gene" or "hsa-miR-4443" used herein includes the hsa-miR-4443 gene (miRBase Accession No. MIMAT0018961) consisting of the nucleotide sequence represented by SEQ ID NO: 132, a homolog or an ortholog of a different organism species, and the like. The hsa-miR-4443 gene can be obtained by a method described in Jima D D et al., 2010, Blood, Vol. 116, e118-e127. Also, "hsa-mir-4443" (miRBase Accession No. MI0016786, SEQ ID NO: 346) having a hairpin-like structure is known as a precursor of "hsa-miR-4443".

The term "hsa-miR-6808-5p gene" or "hsa-miR-6808-5p" used herein includes the hsa-miR-6808-5p gene (miRBase Accession No. MIMAT0027516) consisting of the nucleotide sequence represented by SEQ ID NO: 133, a homolog or an ortholog of a different organism species, and the like. The hsa-miR-6808-5p gene can be obtained by a method described in Ladewig E et al., 2012, Genome Res, Vol. 22, p. 1634-1645. Also, "hsa-mir-6808" (miRBase Accession No. MI0022653, SEQ ID NO: 347) having a hairpin-like structure is known as a precursor of "hsa-miR-6808-5p".

The term "hsa-miR-4728-5p gene" or "hsa-miR-4728-5p" used herein includes the hsa-miR-4728-5p gene (miRBase Accession No. MIMAT0019849) consisting of the nucleotide sequence represented by SEQ ID NO: 134, a homolog or an ortholog of a different organism species, and the like. The hsa-miR-4728-5p gene can be obtained by a method described in Persson H et al., 2011, Cancer Res, Vol. 71, p. 78-86. Also, "hsa-mir-4728" (miRBase Accession No. MI0017365, SEQ ID NO: 348) having a hairpin-like structure is known as a precursor of "hsa-miR-4728-5p".

The term "hsa-miR-937-5p gene" or "hsa-miR-937-5p" used herein includes the hsa-miR-937-5p gene (miRBase Accession No. MIMAT0022938) consisting of the nucleotide sequence represented by SEQ ID NO: 135, a homolog or an ortholog of a different organism species, and the like. The hsa-miR-937-5p gene can be obtained by a method described in Lui W O et al., 2007, Cancer Res, Vol. 67, p. 6031-6043. Also, "hsa-mir-937" (miRBase Accession No. MI0005759, SEQ ID NO: 349) having a hairpin-like structure is known as a precursor of "hsa-miR-937-5p".

The term "hsa-miR-135a-3p gene" or "hsa-miR-135a-3p" used herein includes the hsa-miR-135a-3p gene (miRBase Accession No. MIMAT0004595) consisting of the nucleotide sequence represented by SEQ ID NO: 136, a homolog or an ortholog of a different organism species, and the like. The hsa-miR-135a-3p gene can be obtained by a method described in Lagos-Quintana M et al., 2002, Curr Biol, Vol. 12, p. 735-739. Also, "hsa-mir-135a-1" (miRBase Accession No. MI0000452, SEQ ID NO: 350) having a hairpin-like structure is known as a precursor of "hsa-miR-135a-3p".

The term "hsa-miR-663b gene" or "hsa-miR-663b" used herein includes the hsa-miR-663b gene (miRBase Accession No. MIMAT0005867) consisting of the nucleotide sequence represented by SEQ ID NO: 137, a homolog or an ortholog of a different organism species, and the like. The hsa-miR-663b gene can be obtained by a method described in Takada S et al., 2008, Leukemia, Vol. 22, p. 1274-1278. Also, "hsa-mir-663b" (miRBase Accession No. MI0006336, SEQ ID NO: 351) having a hairpin-like structure is known as a precursor of "hsa-miR-663b".

The term "hsa-miR-1343-5p gene" or "hsa-miR-1343-5p" used herein includes the hsa-miR-1343-5p gene (miRBase Accession No. MIMAT0027038) consisting of the nucleotide sequence represented by SEQ ID NO: 138, a homolog or an ortholog of a different organism species, and the like. The hsa-miR-1343-5p gene can be obtained by a method described in Persson H et al., 2011, Cancer Res, Vol. 71, p. 78-86. Also, "hsa-mir-1343" (miRBase Accession No. MI0017320, SEQ ID NO: 223) having a hairpin-like structure is known as a precursor of "hsa-miR-1343-5p".

The term "hsa-miR-6822-5p gene" or "hsa-miR-6822-5p" used herein includes the hsa-miR-6822-5p gene (miRBase Accession No. MIMAT0027544) consisting of the nucleotide sequence represented by SEQ ID NO: 139, a homolog or an ortholog of a different organism species, and the like. The hsa-miR-6822-5p gene can be obtained by a method described in Ladewig E et al., 2012, Genome Res, Vol. 22, p. 1634-1645. Also, "hsa-mir-6822" (miRBase Accession No. MI0022667, SEQ ID NO: 352) having a hairpin-like structure is known as a precursor of "hsa-miR-6822-5p".

The term "hsa-miR-6803-5p gene" or "hsa-miR-6803-5p" used herein includes the hsa-miR-6803-5p gene (miRBase Accession No. MIMAT0027506) consisting of the nucleotide sequence represented by SEQ ID NO: 140, a homolog or an ortholog of a different organism species, and the like. The hsa-miR-6803-5p gene can be obtained by a method described in Ladewig E et al., 2012, Genome Res, Vol. 22, p. 1634-1645. Also, "hsa-mir-6803" (miRBase Accession No. MI0022648, SEQ ID NO: 353) having a hairpin-like structure is known as a precursor of "hsa-miR-6803-5p".

The term "hsa-miR-6805-3p gene" or "hsa-miR-6805-3p" used herein includes the hsa-miR-6805-3p gene (miRBase Accession No. MIMAT0027511) consisting of the nucleotide sequence represented by SEQ ID NO: 141, a homolog or an ortholog of a different organism species, and the like. The hsa-miR-6805-3p gene can be obtained by a method described in Ladewig E et al., 2012, Genome Res, Vol. 22, p. 1634-1645. Also, "hsa-mir-6805" (miRBase Accession No. MI0022650, SEQ ID NO: 354) having a hairpin-like structure is known as a precursor of "hsa-miR-6805-3p".

The term "hsa-miR-128-2-5p gene" or "hsa-miR-128-2-5p" used herein includes the hsa-miR-128-2-5p gene (miRBase Accession No. MIMAT0031095) consisting of the nucleotide sequence represented by SEQ ID NO: 142, a homolog or an ortholog of a different organism species, and the like. The hsa-miR-128-2-5p gene can be obtained by a method described in Lagos-Quintana M et al., 2002, Curr Biol, Vol. 12, p. 735-739. Also, "hsa-mir-128-2" (miRBase Accession No. MI0000727, SEQ ID NO: 355) having a hairpin-like structure is known as a precursor of "hsa-miR-128-2-5p".

The term "hsa-miR-4640-5p gene" or "hsa-miR-4640-5p" used herein includes the hsa-miR-4640-5p gene (miRBase Accession No. MIMAT0019699) consisting of the nucleotide sequence represented by SEQ ID NO: 143, a homolog or an ortholog of a different organism species, and the like. The hsa-miR-4640-5p gene can be obtained by a method described in Persson H et al., 2011, Cancer Res, Vol. 71, p. 78-86. Also, "hsa-mir-4640" (miRBase Accession No. MI0017267, SEQ ID NO: 356) having a hairpin-like structure is known as a precursor of "hsa-miR-4640-5p".

The term "hsa-miR-1469 gene" or "hsa-miR-1469" used herein includes the hsa-miR-1469 gene (miRBase Accession No. MIMAT0007347) consisting of the nucleotide sequence represented by SEQ ID NO: 144, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 357) having a hairpin-like structure is known as a precursor of "hsa-miR-1469".

The term "hsa-miR-92a-2-5p gene" or "hsa-miR-92a-2-5p" used herein includes the hsa-miR-92a-2-5p gene (miRBase Accession No. MIMAT0004508) consisting of the nucleotide sequence represented by SEQ ID NO: 145, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 358) having a hairpin-like structure is known as a precursor of "hsa-miR-92a-2-5p".

The term "hsa-miR-3940-5p gene" or "hsa-miR-3940-5p" used herein includes the hsa-miR-3940-5p gene (miRBase Accession No. MIMAT0019229) consisting of the nucleotide sequence represented by SEQ ID NO: 146, a homolog or an ortholog of a different organism species, and the like. The hsa-miR-3940-5p gene can be obtained by a method described in Liao J Y et al., 2010, PLoS One, Vol. 5, e10563. Also, "hsa-mir-3940" (miRBase Accession No. MI0016597, SEQ ID NO: 359) having a hairpin-like structure is known as a precursor of "hsa-miR-3940-5p".

The term "hsa-miR-4281 gene" or "hsa-miR-4281" used herein includes the hsa-miR-4281 gene (miRBase Accession No. MIMAT0016907) consisting of the nucleotide sequence represented by SEQ ID NO: 147, a homolog or an ortholog of a different organism species, and the like. The hsa-miR-4281 gene can be obtained by a method described in Goff L A et al., 2009, PLoS One, Vol. 4, e7192. Also, "hsa-mir-4281" (miRBase Accession No. MI0015885, SEQ ID NO: 360) having a hairpin-like structure is known as a precursor of "hsa-miR-4281".

The term "hsa-miR-1260b gene" or "hsa-miR-1260b" used herein includes the hsa-miR-1260b gene (miRBase Accession No. MIMAT0015041) consisting of the nucleotide sequence represented by SEQ ID NO: 148, a homolog or an ortholog of a different organism species, and the like. The hsa-miR-1260b gene can be obtained by a method described in Stark M S et al., 2010, PLoS One, Vol. 5, e9685. Also, "hsa-mir-1260b" (miRBase Accession No. MI0014197, SEQ ID NO: 361) having a hairpin-like structure is known as a precursor of "hsa-miR-1260b".

The term "hsa-miR-4758-5p gene" or "hsa-miR-4758-5p" used herein includes the hsa-miR-4758-5p gene (miRBase Accession No. MIMAT0019903) consisting of the nucleotide sequence represented by SEQ ID NO: 149, a homolog or an ortholog of a different organism species, and the like. The hsa-miR-4758-5p gene can be obtained by a method described in Persson H et al., 2011, Cancer Res, Vol. 71, p. 78-86. Also, "hsa-mir-4758" (miRBase Accession No. MI0017399, SEQ ID NO: 362) having a hairpin-like structure is known as a precursor of "hsa-miR-4758-5p".

The term "hsa-miR-1915-5p gene" or "hsa-miR-1915-5p" used herein includes the hsa-miR-1915-5p gene (miRBase Accession No. MIMAT0007891) consisting of the nucleotide sequence represented by SEQ ID NO: 150, a homolog or an ortholog of a different organism species, and the like. The hsa-miR-1915-5p gene can be obtained by a method described in Bar M et al., 2008, Stem Cells, Vol. 26, p. 2496-2505. Also, "hsa-mir-1915" (miRBase Accession No. MI0008336, SEQ ID NO: 334) having a hairpin-like structure is known as a precursor of "hsa-miR-1915-5p".

The term "hsa-miR-5001-5p gene" or "hsa-miR-5001-5p" used herein includes the hsa-miR-5001-5p gene (miRBase Accession No. MIMAT0021021) consisting of the nucleotide sequence represented by SEQ ID NO: 151, a homolog or an ortholog of a different organism species, and the like. The hsa-miR-5001-5p gene can be obtained by a method described in Hansen T B et al., 2011, RNA Biol, Vol. 8, p. 378-383. Also, "hsa-mir-5001" (miRBase Accession No. MI0017867, SEQ ID NO: 363) having a hairpin-like structure is known as a precursor of "hsa-miR-5001-5p".

The term "hsa-miR-4286 gene" or "hsa-miR-4286" used herein includes the hsa-miR-4286 gene (miRBase Accession No. MIMAT0016916) consisting of the nucleotide sequence represented by SEQ ID NO: 152, a homolog or an ortholog of a different organism species, and the like. The hsa-miR-4286 gene can be obtained by a method described in Goff L A et al., 2009, PLoS One, Vol. 4, e7192. Also, "hsa-mir-4286" (miRBase Accession No. MI0015894, SEQ ID NO: 364) having a hairpin-like structure is known as a precursor of "hsa-miR-4286".

The term "hsa-miR-6126 gene" or "hsa-miR-6126" used herein includes the hsa-miR-6126 gene (miRBase Accession No. MIMAT0024599) consisting of the nucleotide sequence represented by SEQ ID NO: 153, a homolog or an ortholog of a different organism species, and the like. The hsa-miR-6126 gene can be obtained by a method described in Smith J L et al., 2012, J Virol, Vol. 86, p. 5278-5287. Also, "hsa-mir-6126" (miRBase Accession No. MI0021260, SEQ ID NO: 365) having a hairpin-like structure is known as a precursor of "hsa-miR-6126".

The term "hsa-miR-6789-5p gene" or "hsa-miR-6789-5p" used herein includes the hsa-miR-6789-5p gene (miRBase Accession No. MIMAT0027478) consisting of the nucleotide sequence represented by SEQ ID NO: 154, a homolog or an ortholog of a different organism species, and the like. The hsa-miR-6789-5p gene can be obtained by a method described in Ladewig E et al., 2012, Genome Res, Vol. 22, p. 1634-1645. Also, "hsa-mir-6789" (miRBase Accession No. MI0022634, SEQ ID NO: 366) having a hairpin-like structure is known as a precursor of "hsa-miR-6789-5p".

The term "hsa-miR-4459 gene" or "hsa-miR-4459" used herein includes the hsa-miR-4459 gene (miRBase Accession No. MIMAT0018981) consisting of the nucleotide sequence represented by SEQ ID NO: 155, a homolog or an ortholog of a different organism species, and the like. The hsa-miR-4459 gene can be obtained by a method described in Jima D D et al., 2010, Blood, Vol. 116, e118-e127. Also, "hsa-mir-4459" (miRBase Accession No. MI0016805, SEQ ID NO: 367) having a hairpin-like structure is known as a precursor of "hsa-miR-4459".

The term "hsa-miR-1268a gene" or "hsa-miR-1268a" used herein includes the hsa-miR-1268a gene (miRBase Accession No. MIMAT0005922) consisting of the nucleotide sequence represented by SEQ ID NO: 156, a homolog or an ortholog of a different organism species, and the like. The hsa-miR-1268a gene can be obtained by a method described in Morin R D et al., 2008, Genome Res, Vol. 18, p. 610-621. Also, "hsa-mir-1268a" (miRBase Accession No. MI0006405, SEQ ID NO: 368) having a hairpin-like structure is known as a precursor of "hsa-miR-1268a".

The term "hsa-miR-6752-5p gene" or "hsa-miR-6752-5p" used herein includes the hsa-miR-6752-5p gene (miRBase Accession No. MIMAT0027404) consisting of the nucleotide sequence represented by SEQ ID NO: 157, a homolog or an ortholog of a different organism species, and the like. The hsa-miR-6752-5p gene can be obtained by a method described in Ladewig E et al., 2012, Genome Res, Vol. 22, p. 1634-1645. Also, "hsa-mir-6752" (miRBase Accession No. MI0022597, SEQ ID NO: 369) having a hairpin-like structure is known as a precursor of "hsa-miR-6752-5p."

The term "hsa-miR-6131 gene" or "hsa-miR-6131" used herein includes the hsa-miR-6131 gene (miRBase Accession No. MIMAT0024615) consisting of the nucleotide sequence represented by SEQ ID NO: 158, a homolog or an ortholog of a different organism species, and the like. The hsa-miR-6131 gene can be obtained by a method described in Dannemann M et al., 2012, Genome Biol Evol, Vol. 4, p. 552-564. Also, "hsa-mir-6131" (miRBase Accession No. MI0021276, SEQ ID NO: 370) having a hairpin-like structure is known as a precursor of "hsa-miR-6131".

The term "hsa-miR-6800-5p gene" or "hsa-miR-6800-5p" used herein includes the hsa-miR-6800-5p gene (miRBase Accession No. MIMAT0027500) consisting of the nucleotide sequence represented by SEQ ID NO: 159, a homolog or an ortholog of a different organism species, and the like. The hsa-miR-6800-5p gene can be obtained by a method described in Ladewig E et al., 2012, Genome Res, Vol. 22, p. 1634-1645. Also, "hsa-mir-6800" (miRBase Accession No. MI0022645, SEQ ID NO: 371) having a hairpin-like structure is known as a precursor of "hsa-miR-6800-5p".

The term "hsa-miR-4532 gene" or "hsa-miR-4532" used herein includes the hsa-miR-4532 gene (miRBase Accession No. MIMAT0019071) consisting of the nucleotide sequence represented by SEQ ID NO: 160, a homolog or an ortholog of a different organism species, and the like. The hsa-miR-4532 gene can be obtained by a method described in Jima D D et al., 2010, Blood, Vol. 116, e118-e127. Also, "hsa-mir-4532" (miRBase Accession No. MI0016899, SEQ ID NO: 372) having a hairpin-like structure is known as a precursor of "hsa-miR-4532".

The term "hsa-miR-6872-3p gene" or "hsa-miR-6872-3p" used herein includes the hsa-miR-6872-3p gene (miRBase Accession No. MIMAT0027645) consisting of the nucleotide sequence represented by SEQ ID NO: 161, a homolog or an ortholog of a different organism species, and the like. The hsa-miR-6872-3p gene can be obtained by a method described in Ladewig E et al., 2012, Genome Res, Vol. 22, p. 1634-1645. Also, "hsa-mir-6872" (miRBase Accession No. MI0022719, SEQ ID NO: 373) having a hairpin-like structure is known as a precursor of "hsa-miR-6872-3p".

The term "hsa-miR-718 gene" or "hsa-miR-718" used herein includes the hsa-miR-718 gene (miRBase Accession No. MIMAT0012735) consisting of the nucleotide sequence represented by SEQ ID NO: 162, a homolog or an ortholog of a different organism species, and the like. The hsa-miR-718 gene can be obtained by a method described in Artzi S et al., 2008, BMC Bioinformatics, Vol. 9, p. 39. Also, "hsa-mir-718" (miRBase Accession No. MI0012489, SEQ ID NO: 374) having a hairpin-like structure is known as a precursor of "hsa-miR-718".

The term "hsa-miR-6769a-5p gene" or "hsa-miR-6769a-5p" used herein includes the hsa-miR-6769a-5p gene (miRBase Accession No. MIMAT0027438) consisting of the nucleotide sequence represented by SEQ ID NO: 163, a homolog or an ortholog of a different organism species, and the like. The hsa-miR-6769a-5p gene can be obtained by a method described in Ladewig E et al., 2012, Genome Res, Vol. 22, p. 1634-1645. Also, "hsa-mir-6769a" (miRBase Accession No. MI0022614, SEQ ID NO: 375) having a hairpin-like structure is known as a precursor of "hsa-miR-6769a-5p".

The term "hsa-miR-4707-3p gene" or "hsa-miR-4707-3p" used herein includes the hsa-miR-4707-3p gene (miRBase Accession No. MIMAT0019808) consisting of the nucleotide sequence represented by SEQ ID NO: 164, a homolog or an ortholog of a different organism species, and the like. The hsa-miR-4707-3p gene can be obtained by a method described in Persson H et al., 2011, Cancer Res, Vol. 71, p. 78-86. Also, "hsa-mir-4707" (miRBase Accession No. MI0017340, SEQ ID NO: 338) having a hairpin-like structure is known as a precursor of "hsa-miR-4707-3p".

The term "hsa-miR-6765-5p gene" or "hsa-miR-6765-5p" used herein includes the hsa-miR-6765-5p gene (miRBase Accession No. MIMAT0027430) consisting of the nucleotide sequence represented by SEQ ID NO: 165, a homolog or an ortholog of a different organism species, and the like. The hsa-miR-6765-5p gene can be obtained by a method described in Ladewig E et al., 2012, Genome Res, Vol. 22, p. 1634-1645. Also, "hsa-mir-6765" (miRBase Accession No. MI0022610, SEQ ID NO: 249) having a hairpin-like structure is known as a precursor of "hsa-miR-6765-5p".

The term "hsa-miR-4739 gene" or "hsa-miR-4739" used herein includes the hsa-miR-4739 gene (miRBase Accession No. MIMAT0019868) consisting of the nucleotide sequence represented by SEQ ID NO: 166, a homolog or an ortholog of a different organism species, and the like. The hsa-miR-4739 gene can be obtained by a method described in Persson H et al., 2011, Cancer Res, Vol. 71, p. 78-86. Also, "hsa-mir-4739" (miRBase Accession No. MI0017377, SEQ ID NO: 376) having a hairpin-like structure is known as a precursor of "hsa-miR-4739".

The term "hsa-miR-4525 gene" or "hsa-miR-4525" used herein includes the hsa-miR-4525 gene (miRBase Accession No. MIMAT0019064) consisting of the nucleotide sequence represented by SEQ ID NO: 167, a homolog or an ortholog of a different organism species, and the like. The hsa-miR-4525 gene can be obtained by a method described in Jima D D et al., 2010, Blood, Vol. 116, e118-e127. Also, "hsa-mir-4525" (miRBase Accession No. MI0016892, SEQ ID NO: 377) having a hairpin-like structure is known as a precursor of "hsa-miR-4525".

The term "hsa-miR-4270 gene" or "hsa-miR-4270" used herein includes the hsa-miR-4270 gene (miRBase Accession No. MIMAT0016900) consisting of the nucleotide sequence represented by SEQ ID NO: 168, a homolog or an ortholog of a different organism species, and the like. The hsa-miR-4270 gene can be obtained by a method described in Goff L A et al., 2009, PLoS One, Vol. 4, e7192. Also, "hsa-mir-4270" (miRBase Accession No. MI0015878, SEQ ID NO: 378) having a hairpin-like structure is known as a precursor of "hsa-miR-4270".

The term "hsa-miR-4534 gene" or "hsa-miR-4534" used herein includes the hsa-miR-4534 gene (miRBase Accession No. MIMAT0019073) consisting of the nucleotide sequence represented by SEQ ID NO: 169, a homolog or an ortholog of a different organism species, and the like. The hsa-miR-4534 gene can be obtained by a method described in Jima D D et al., 2010, Blood, Vol. 116, e118-e127. Also, "hsa-mir-4534" (miRBase Accession No. MI0016901, SEQ ID NO: 379) having a hairpin-like structure is known as a precursor of "hsa-miR-4534".

The term "hsa-miR-6785-5p gene" or "hsa-miR-6785-5p" used herein includes the hsa-miR-6785-5p gene (miRBase Accession No. MIMAT0027470) consisting of the nucleotide sequence represented by SEQ ID NO: 170, a homolog or an ortholog of a different organism species, and the like. The hsa-miR-6785-5p gene can be obtained by a method described in Ladewig E et al., 2012, Genome Res, Vol. 22, p. 1634-1645. Also, "hsa-mir-6785" (miRBase Accession No. MI0022630, SEQ ID NO: 380) having a hairpin-like structure is known as a precursor of "hsa-miR-6785-5p".

The term "hsa-miR-6850-5p gene" or "hsa-miR-6850-5p" used herein includes the hsa-miR-6850-5p gene (miRBase Accession No. MIMAT0027600) consisting of the nucleotide sequence represented by SEQ ID NO: 171, a homolog or an ortholog of a different organism species, and the like. The hsa-miR-6850-5p gene can be obtained by a method described in Ladewig E et al., 2012, Genome Res, Vol. 22, p. 1634-1645. Also, "hsa-mir-6850" (miRBase Accession No. MI0022696, SEQ ID NO: 381) having a hairpin-like structure is known as a precursor of "hsa-miR-6850-5p".

The term "hsa-miR-4697-5p gene" or "hsa-miR-4697-5p" used herein includes the hsa-miR-4697-5p gene (miRBase Accession No. MIMAT0019791) consisting of the nucleotide sequence represented by SEQ ID NO: 172, a homolog or an ortholog of a different organism species, and the like. The hsa-miR-4697-5p gene can be obtained by a method described in Persson H et al., 2011, Cancer Res, Vol. 71, p. 78-86. Also, "hsa-mir-4697" (miRBase Accession No. MI0017330, SEQ ID NO: 382) having a hairpin-like structure is known as a precursor of "hsa-miR-4697-5p".

The term "hsa-miR-1260a gene" or "hsa-miR-1260a" used herein includes the hsa-miR-1260a gene (miRBase Accession No. MIMAT0005911) consisting of the nucleotide sequence represented by SEQ ID NO: 173, a homolog or an ortholog of a different organism species, and the like. The hsa-miR-1260a gene can be obtained by a method described in Morin R D et al., 2008, Genome Res, Vol. 18, p. 610-621. Also, "hsa-mir-1260a" (miRBase Accession No. MI0006394, SEQ ID NO: 383) having a hairpin-like structure is known as a precursor of "hsa-miR-1260a".

The term "hsa-miR-4486 gene" or "hsa-miR-4486" used herein includes the hsa-miR-4486 gene (miRBase Accession No. MIMAT0019020) consisting of the nucleotide sequence represented by SEQ ID NO: 174, a homolog or an ortholog of a different organism species, and the like. The hsa-miR-4486 gene can be obtained by a method described in Jima D D et al., 2010, Blood, Vol. 116, e118-e127. Also, "hsa-mir-4486" (miRBase Accession No. MI0016847, SEQ ID NO: 384) having a hairpin-like structure is known as a precursor of "hsa-miR-4486".

The term "hsa-miR-6880-5p gene" or "hsa-miR-6880-5p" used herein includes the hsa-miR-6880-5p gene (miRBase Accession No. MIMAT0027660) consisting of the nucleotide sequence represented by SEQ ID NO: 175, a homolog or an ortholog of a different organism species, and the like. The hsa-miR-6880-5p gene can be obtained by a method described in Ladewig E et al., 2012, Genome Res, Vol. 22, p. 1634-1645. Also, "hsa-mir-6880" (miRBase Accession No. MI0022727, SEQ ID NO: 385) having a hairpin-like structure is known as a precursor of "hsa-miR-6880-5p".

The term "hsa-miR-6802-5p gene" or "hsa-miR-6802-5p" used herein includes the hsa-miR-6802-5p gene (miRBase Accession No. MIMAT0027504) consisting of the nucleotide sequence represented by SEQ ID NO: 176, a homolog or an ortholog of a different organism species, and the like. The hsa-miR-6802-5p gene can be obtained by a method described in Ladewig E et al., 2012, Genome Res, Vol. 22, p. 1634-1645. Also, "hsa-mir-6802" (miRBase Accession No. MI0022647, SEQ ID NO: 386) having a hairpin-like structure is known as a precursor of "hsa-miR-6802-5p".

The term "hsa-miR-6861-5p gene" or "hsa-miR-6861-5p" used herein includes the hsa-miR-6861-5p gene (miRBase Accession No. MIMAT0027623) consisting of the nucleotide sequence represented by SEQ ID NO: 177, a homolog or an ortholog of a different organism species, and the like. The hsa-miR-6861-5p gene can be obtained by a method described in Ladewig E et al., 2012, Genome Res, Vol. 22, p. 1634-1645. Also, "hsa-mir-6861" (miRBase Accession No. MI0022708, SEQ ID NO: 387) having a hairpin-like structure is known as a precursor of "hsa-miR-6861-5p".

The term "hsa-miR-92b-5p gene" or "hsa-miR-92b-5p" used herein includes the hsa-miR-92b-5p gene (miRBase Accession No. MIMAT0004792) consisting of the nucleotide sequence represented by SEQ ID NO: 178, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 388) having a hairpin-like structure is known as a precursor of "hsa-miR-92b-5p".

The term "hsa-miR-1238-5p gene" or "hsa-miR-1238-5p" used herein includes the hsa-miR-1238-5p gene (miRBase Accession No. MIMAT0022947) consisting of the nucleotide sequence represented by SEQ ID NO: 179, a homolog or an ortholog of a different organism species, and the like. The hsa-miR-1238-5p gene can be obtained by a method described in Berezikov E et al., 2007, Mol Cell, Vol. 28, p. 328-336. Also, "hsa-mir-1238" (miRBase Accession No. MI0006328, SEQ ID NO: 389) having a hairpin-like structure is known as a precursor of "hsa-miR-1238-5p."

The term "hsa-miR-6851-5p gene" or "hsa-miR-6851-5p" used herein includes the hsa-miR-6851-5p gene (miRBase Accession No. MIMAT0027602) consisting of the nucleotide sequence represented by SEQ ID NO: 180, a homolog or an ortholog of a different organism species, and the like. The hsa-miR-6851-5p gene can be obtained by a method described in Ladewig E et al., 2012, Genome Res, Vol. 22, p. 1634-1645. Also, "hsa-mir-6851" (miRBase Accession No. MI0022697, SEQ ID NO: 390) having a hairpin-like structure is known as a precursor of "hsa-miR-6851-5p".

The term "hsa-miR-7704 gene" or "hsa-miR-7704" used herein includes the hsa-miR-7704 gene (miRBase Accession No. MIMAT0030019) consisting of the nucleotide sequence represented by SEQ ID NO: 181, a homolog or an ortholog of a different organism species, and the like. The hsa-miR-7704 gene can be obtained by a method described in Swaminathan S et al., 2013, Biochem Biophys Res Commun, Vol. 434, p. 228-234. Also, "hsa-mir-7704" (miRBase Accession No. MI0025240, SEQ ID NO: 391) having a hairpin-like structure is known as a precursor of "hsa-miR-7704".

The term "hsa-miR-149-3p gene" or "hsa-miR-149-3p" used herein includes the hsa-miR-149-3p gene (miRBase Accession No. MIMAT0004609) consisting of the nucleotide sequence represented by SEQ ID NO: 182, a homolog or an ortholog of a different organism species, and the like. The hsa-miR-149-3p gene can be obtained by a method described in Lagos-Quintana M et al., 2002, Curr Biol, Vol. 12, p. 735-739. Also, "hsa-mir-149" (miRBase Accession No. MI0000478, SEQ ID NO: 392) having a hairpin-like structure is known as a precursor of "hsa-miR-149-3p".

The term "hsa-miR-4689 gene" or "hsa-miR-4689" used herein includes the hsa-miR-4689 gene (miRBase Accession No. MIMAT0019778) consisting of the nucleotide sequence represented by SEQ ID NO: 183, a homolog or an ortholog of a different organism species, and the like. The hsa-miR-4689 gene can be obtained by a method described in Persson H et al., 2011, Cancer Res, Vol. 71, p. 78-86. Also, "hsa-mir-4689" (miRBase Accession No. MI0017322, SEQ ID NO: 393) having a hairpin-like structure is known as a precursor of "hsa-miR-4689".

The term "hsa-miR-4688 gene" or "hsa-miR-4688" used herein includes the hsa-miR-4688 gene (miRBase Accession No. MIMAT0019777) consisting of the nucleotide sequence represented by SEQ ID NO: 184, a homolog or an ortholog of a different organism species, and the like. The hsa-miR-4688 gene can be obtained by a method described in Persson H et al., 2011, Cancer Res, Vol. 71, p. 78-86. Also, "hsa-mir-4688" (miRBase Accession No. MI0017321, SEQ ID NO: 394) having a hairpin-like structure is known as a precursor of "hsa-miR-4688".

The term "hsa-miR-125a-3p gene" or "hsa-miR-125a-3p" used herein includes the hsa-miR-125a-3p gene (miRBase Accession No. MIMAT0004602) consisting of the nucleotide sequence represented by SEQ ID NO: 185, a homolog or an ortholog of a different organism species, and the like. The hsa-miR-125a-3p gene can be obtained by a method described in Lagos-Quintana M et al., 2002, Curr Biol, Vol. 12, p. 735-739. Also, "hsa-mir-125a" (miRBase Accession No. MI0000469, SEQ ID NO: 395) having a hairpin-like structure is known as a precursor of "hsa-miR-125a-3p".

The term "hsa-miR-23b-3p gene" or "hsa-miR-23b-3p" used herein includes the hsa-miR-23b-3p gene (miRBase Accession No. MIMAT0000418) consisting of the nucleotide sequence represented by SEQ ID NO: 186, a homolog or an ortholog of a different organism species, and the like. The hsa-miR-23b-3p gene can be obtained by a method described in Lagos-Quintana M et al., 2002, Curr Biol, Vol. 12, p. 735-739. Also, "hsa-mir-23b" (miRBase Accession No. MI0000439, SEQ ID NO: 396) having a hairpin-like structure is known as a precursor of "hsa-miR-23b-3p".

The term "hsa-miR-614 gene" or "hsa-miR-614" used herein includes the hsa-miR-614 gene (miRBase Accession No. MIMAT0003282) consisting of the nucleotide sequence represented by SEQ ID NO: 187, a homolog or an ortholog of a different organism species, and the like. The hsa-miR-614 gene can be obtained by a method described in Cummins J M et al., 2006, Proc Natl Acad Sci USA, Vol. 103, p. 3687-3692. Also, "hsa-mir-614" (miRBase Accession No. MI0003627, SEQ ID NO: 397) having a hairpin-like structure is known as a precursor of "hsa-miR-614".

The term "hsa-miR-1913 gene" or "hsa-miR-1913" used herein includes the hsa-miR-1913 gene (miRBase Accession No. MIMAT0007888) consisting of the nucleotide sequence represented by SEQ ID NO: 188, a homolog or an ortholog of a different organism species, and the like. The hsa-miR-1913 gene can be obtained by a method described in Bar M et al., 2008, Stem Cells, Vol. 26, p. 2496-2505. Also, "hsa-mir-1913" (miRBase Accession No. MI0008334, SEQ ID NO: 398) having a hairpin-like structure is known as a precursor of "hsa-miR-1913".

The term "hsa-miR-16-5p gene" or "hsa-miR-16-5p" used herein includes the hsa-miR-16-5p gene (miRBase Accession No. MIMAT0000069) consisting of the nucleotide sequence represented by SEQ ID NO: 189, a homolog or an ortholog of a different organism species, and the like. The hsa-miR-16-5p gene can be obtained by a method described in Lagos-Quintana M et al., 2001, Science, Vol. 294, p. 853-858. Also, "hsa-mir-16-1 and hsa-mir-16-2" (miRBase Accession Nos. MI0000070 and MI0000115, SEQ ID NOs: 399 and 400) having a hairpin-like structure are known as precursors of "hsa-miR-16-5p".

The term "hsa-miR-675-5p gene" or "hsa-miR-675-5p" used herein includes the hsa-miR-675-5p gene (miRBase Accession No. MIMAT0004284) consisting of the nucleotide sequence represented by SEQ ID NO: 190, a homolog or an ortholog of a different organism species, and the like. The hsa-miR-675-5p gene can be obtained by a method described in Cai X et al., 2007, RNA, Vol. 13, p. 313-316. Also, "hsa-mir-675" (miRBase Accession No. MI0005416, SEQ ID NO: 401) having a hairpin-like structure is known as a precursor of "hsa-miR-675-5p".

The term "hsa-miR-486-3p gene" or "hsa-miR-486-3p" used herein includes the hsa-miR-486-3p gene (miRBase Accession No. MIMAT0004762) consisting of the nucleotide sequence represented by SEQ ID NO: 191, a homolog or an ortholog of a different organism species, and the like. The hsa-miR-486-3p gene can be obtained by a method described in Fu H et al., 2005, FEBS Lett, Vol. 579, p. 3849-3854. Also, "hsa-mir-486 and hsa-mir-486-2" (miRBase Accession Nos. MI0002470 and MI0023622, SEQ ID NOs: 402 and 403) having a hairpin-like structure are known as precursors of "hsa-miR-486-3p".

The term "hsa-miR-6777-5p gene" or "hsa-miR-6777-5p" used herein includes the hsa-miR-6777-5p gene (miRBase Accession No. MIMAT0027454) consisting of the nucleotide sequence represented by SEQ ID NO: 192, a homolog or an ortholog of a different organism species, and the like. The hsa-miR-6777-5p gene can be obtained by a method described in Ladewig E et al., 2012, Genome Res, Vol. 22, p. 1634-1645. Also, "hsa-mir-6777" (miRBase Accession No. MI0022622, SEQ ID NO: 404) having a hairpin-like structure is known as a precursor of "hsa-miR-6777-5p".

The term "hsa-miR-4497 gene" or "hsa-miR-4497" used herein includes the hsa-miR-4497 gene (miRBase Accession No. MIMAT0019032) consisting of the nucleotide sequence represented by SEQ ID NO: 193, a homolog or an ortholog of a different organism species, and the like. The hsa-miR-4497 gene can be obtained by a method described in Jima D D et al., 2010, Blood, Vol. 116, e118-e127. Also, "hsa-mir-4497" (miRBase Accession No. MI0016859, SEQ ID NO: 405) having a hairpin-like structure is known as a precursor of "hsa-miR-4497".

The term "hsa-miR-296-3p gene" or "hsa-miR-296-3p" used herein includes the hsa-miR-296-3p gene (miRBase Accession No. MIMAT0004679) consisting of the nucleotide sequence represented by SEQ ID NO: 194, a homolog or an ortholog of a different organism species, and the like. The hsa-miR-296-3p gene can be obtained by a method described in Houbaviy H B et al., 2003, Dev Cell, Vol. 5, p. 351-358. Also, "hsa-mir-296" (miRBase Accession No. MI0000747, SEQ ID NO: 406) having a hairpin-like structure is known as a precursor of "hsa-miR-296-3p".

The term "hsa-miR-6738-5p gene" or "hsa-miR-6738-5p" used herein includes the hsa-miR-6738-5p gene (miRBase Accession No. MIMAT0027377) consisting of the nucleotide sequence represented by SEQ ID NO: 195, a homolog or an ortholog of a different organism species, and the like. The hsa-miR-6738-5p gene can be obtained by a method described in Ladewig E et al., 2012, Genome Res, Vol. 22, p. 1634-1645. Also, "hsa-mir-6738" (miRBase Accession No. MI0022583, SEQ ID NO: 407) having a hairpin-like structure is known as a precursor of "hsa-miR-6738-5p".

The term "hsa-miR-4731-5p gene" or "hsa-miR-4731-5p" used herein includes the hsa-miR-4731-5p gene (miRBase Accession No. MIMAT0019853) consisting of the nucleotide sequence represented by SEQ ID NO: 196, a homolog or an ortholog of a different organism species, and the like. The hsa-miR-4731-5p gene can be obtained by a method described in Persson H et al., 2011, Cancer Res, Vol. 71, p. 78-86. Also, "hsa-mir-4731" (miRBase Accession No. MI0017368, SEQ ID NO: 408) having a hairpin-like structure is known as a precursor of "hsa-miR-4731-5p".

The term "hsa-miR-6889-5p gene" or "hsa-miR-6889-5p" used herein includes the hsa-miR-6889-5p gene (miRBase Accession No. MIMAT0027678) consisting of the nucleotide sequence represented by SEQ ID NO: 197, a homolog or an ortholog of a different organism species, and the like. The hsa-miR-6889-5p gene can be obtained by a method described in Ladewig E et al., 2012, Genome Res, Vol. 22, p. 1634-1645. Also, "hsa-mir-6889" (miRBase Accession No. MI0022736, SEQ ID NO: 409) having a hairpin-like structure is known as a precursor of "hsa-miR-6889-5p."

The term "hsa-miR-6786-5p gene" or "hsa-miR-6786-5p" used herein includes the hsa-miR-6786-5p gene (miRBase Accession No. MIMAT0027472) consisting of the nucleotide sequence represented by SEQ ID NO: 198, a homolog or an ortholog of a different organism species, and the like. The hsa-miR-6786-5p gene can be obtained by a method described in Ladewig E et al., 2012, Genome Res, Vol. 22, p. 1634-1645. Also, "hsa-mir-6786" (miRBase Accession No. MI0022631, SEQ ID NO: 410) having a hairpin-like structure is known as a precursor of "hsa-miR-6786-5p".

The term "hsa-miR-92a-3p gene" or "hsa-miR-92a-3p" used herein includes the hsa-miR-92a-3p gene (miRBase Accession No. MIMAT0000092) consisting of the nucleotide sequence represented by SEQ ID NO: 199, a homolog or an ortholog of a different organism species, and the like. The hsa-miR-92a-3p gene can be obtained by a method described in Mourelatos Z et al., 2002, Genes Dev, Vol. 16, p. 720-728. Also, "hsa-mir-92a-1 and hsa-mir-92a-2" (miRBase Accession Nos. MI0000093 and MI0000094, SEQ ID NOs: 411 and 358) having a hairpin-like structure are known as precursors of "hsa-miR-92a-3p".

The term "hsa-miR-4294 gene" or "hsa-miR-4294" used herein includes the hsa-miR-4294 gene (miRBase Accession No. MIMAT0016849) consisting of the nucleotide sequence represented by SEQ ID NO: 200, a homolog or an ortholog of a different organism species, and the like. The hsa-miR-4294 gene can be obtained by a method described in Goff L A et al., 2009, PLoS One, Vol. 4, e7192. Also, "hsa-mir-4294" (miRBase Accession No. MI0015827, SEQ ID NO: 412) having a hairpin-like structure is known as a precursor of "hsa-miR-4294".

The term "hsa-miR-4763-3p gene" or "hsa-miR-4763-3p" used herein includes the hsa-miR-4763-3p gene (miRBase Accession No. MIMAT0019913) consisting of the nucleotide sequence represented by SEQ ID NO: 201, a homolog or an ortholog of a different organism species, and the like. The hsa-miR-4763-3p gene can be obtained by a method described in Persson H et al., 2011, Cancer Res, Vol. 71, p. 78-86. Also, "hsa-mir-4763" (miRBase Accession No. MI0017404, SEQ ID NO: 413) having a hairpin-like structure is known as a precursor of "hsa-miR-4763-3p".

The term "hsa-miR-6076 gene" or "hsa-miR-6076" used herein includes the hsa-miR-6076 gene (miRBase Accession No. MIMAT0023701) consisting of the nucleotide sequence represented by SEQ ID NO: 202, a homolog or an ortholog of a different organism species, and the like. The hsa-miR-6076 gene can be obtained by a method described in Voellenkle C et al., 2012, RNA, Vol. 18, p. 472-484. Also, "hsa-mir-6076" (miRBase Accession No. MI0020353, SEQ ID NO: 414) having a hairpin-like structure is known as a precursor of "hsa-miR-6076".

The term "hsa-miR-663a gene" or "hsa-miR-663a" used herein includes the hsa-miR-663a gene (miRBase Accession No. MIMAT0003326) consisting of the nucleotide sequence represented by SEQ ID NO: 203, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 415) having a hairpin-like structure is known as a precursor of "hsa-miR-663a".

The term "hsa-miR-760 gene" or "hsa-miR-760" used herein includes the hsa-miR-760 gene (miRBase Accession No. MIMAT0004957) consisting of the nucleotide sequence represented by SEQ ID NO: 204, a homolog or an ortholog of a different organism species, and the like. The hsa-miR-760 gene can be obtained by a method described in Berezikov E et al., 2006, Genome Res, Vol. 16, p. 1289-1298. Also, "hsa-mir-760" (miRBase Accession No. MI0005567, SEQ ID NO: 416) having a hairpin-like structure is known as a precursor of "hsa-miR-760".

The term "hsa-miR-4667-5p gene" or "hsa-miR-4667-5p" used herein includes the hsa-miR-4667-5p gene (miRBase Accession No. MIMAT0019743) consisting of the nucleotide sequence represented by SEQ ID NO: 205, a homolog or an ortholog of a different organism species, and the like. The hsa-miR-4667-5p gene can be obtained by a method described in Persson H et al., 2011, Cancer Res, Vol. 71, p. 78-86. Also, "hsa-mir-4667" (miRBase Accession No. MI0017297, SEQ ID NO: 417) having a hairpin-like structure is known as a precursor of "hsa-miR-4667-5p".

The term "hsa-miR-6090 gene" or "hsa-miR-6090" used herein includes the hsa-miR-6090 gene (miRBase Accession No. MIMAT0023715) consisting of the nucleotide sequence represented by SEQ ID NO: 206, a homolog or an ortholog of a different organism species, and the like. The hsa-miR-6090 gene can be obtained by a method described in Yoo J K et al., 2012, Stem Cells Dev, Vol. 21, p. 2049-2057. Also, "hsa-mir-6090" (miRBase Accession No. MI0020367, SEQ ID NO: 418) having a hairpin-like structure is known as a precursor of "hsa-miR-6090".

The term "hsa-miR-4730 gene" or "hsa-miR-4730" used herein includes the hsa-miR-4730 gene (miRBase Accession No. MIMAT0019852) consisting of the nucleotide sequence represented by SEQ ID NO: 207, a homolog or an ortholog of a different organism species, and the like. The hsa-miR-4730 gene can be obtained by a method described in Persson H et al., 2011, Cancer Res, Vol. 71, p. 78-86. Also, "hsa-mir-4730" (miRBase Accession No. MI0017367, SEQ ID NO: 419) having a hairpin-like structure is known as a precursor of "hsa-miR-4730".

The term "hsa-miR-7106-5p gene" or "hsa-miR-7106-5p" used herein includes the hsa-miR-7106-5p gene (miRBase Accession No. MIMAT0028109) consisting of the nucleotide sequence represented by SEQ ID NO: 208, a homolog or an ortholog of a different organism species, and the like. The hsa-miR-7106-5p gene can be obtained by a method described in Ladewig E et al., 2012, Genome Res, Vol. 22, p. 1634-1645. Also, "hsa-mir-7106" (miRBase Accession No. MI0022957, SEQ ID NO: 420) having a hairpin-like structure is known as a precursor of "hsa-miR-7106-5p."

The term "hsa-miR-3196 gene" or "hsa-miR-3196" used herein includes the hsa-miR-3196 gene (miRBase Accession No. MIMAT0015080) consisting of the nucleotide sequence represented by SEQ ID NO: 209, a homolog or an ortholog of a different organism species, and the like. The hsa-miR-3196 gene can be obtained by a method described in Stark M S et al., 2010, PLoS One, Vol. 5, e9685. Also, "hsa-mir-3196" (miRBase Accession No. MI0014241, SEQ ID NO: 421) having a hairpin-like structure is known as a precursor of "hsa-miR-3196".

The term "hsa-miR-5698 gene" or "hsa-miR-5698" used herein includes the hsa-miR-5698 gene (miRBase Accession No. MIMAT0022491) consisting of the nucleotide sequence represented by SEQ ID NO: 210, a homolog or an ortholog of a different organism species, and the like. The hsa-miR-5698 gene can be obtained by a method described in Watahiki A et al., 2011, PLoS One, Vol. 6, e24950. Also, "hsa-mir-5698" (miRBase Accession No. MI0019305, SEQ ID NO: 422) having a hairpin-like structure is known as a precursor of "hsa-miR-5698".

The term "hsa-miR-6087 gene" or "hsa-miR-6087" used herein includes the hsa-miR-6087 gene (miRBase Accession No. MIMAT0023712) consisting of the nucleotide sequence represented by SEQ ID NO: 211, a homolog or an ortholog of a different organism species, and the like. The hsa-miR-6087 gene can be obtained by a method described in Yoo J K et al., 2012, Stem Cells Dev, Vol. 21, p. 2049-2057. Also, "hsa-mir-6087" (miRBase Accession No. MI0020364, SEQ ID NO: 423) having a hairpin-like structure is known as a precursor of "hsa-miR-6087".

The term "hsa-miR-4665-5p gene" or "hsa-miR-4665-5p" used herein includes the hsa-miR-4665-5p gene (miRBase Accession No. MIMAT0019739) consisting of the nucleotide sequence represented by SEQ ID NO: 212, a homolog or an ortholog of a different organism species, and the like. The hsa-miR-4665-5p gene can be obtained by a method described in Persson H et al., 2011, Cancer Res, Vol. 71, p. 78-86. Also, "hsa-mir-4665" (miRBase Accession No. MI0017295, SEQ ID NO: 275) having a hairpin-like structure is known as a precursor of "hsa-miR-4665-5p".

The term "hsa-miR-8059 gene" or "hsa-miR-8059" used herein includes the hsa-miR-8059 gene (miRBase Accession No. MIMAT0030986) consisting of the nucleotide sequence represented by SEQ ID NO: 213, a homolog or an ortholog of a different organism species, and the like. The hsa-miR-8059 gene can be obtained by a method described in Wang H J et al., 2013, Shock, Vol. 39, p. 480-487. Also, "hsa-mir-8059" (miRBase Accession No. MI0025895, SEQ ID NO: 424) having a hairpin-like structure is known as a precursor of "hsa-miR-8059".

The term "hsa-miR-6879-5p gene" or "hsa-miR-6879-5p" used herein includes the hsa-miR-6879-5p gene (miRBase Accession No. MIMAT0027658) consisting of the nucleotide sequence represented by SEQ ID NO: 214, a homolog or an ortholog of a different organism species, and the like. The hsa-miR-6879-5p gene can be obtained by a method described in Ladewig E et al., 2012, Genome Res, Vol. 22, p. 1634-1645. Also, "hsa-mir-6879" (miRBase Accession No. MI0022726, SEQ ID NO: 425) having a hairpin-like structure is known as a precursor of "hsa-miR-6879-5p".

The term "hsa-miR-6717-5p gene" or "hsa-miR-6717-5p" used herein includes the hsa-miR-6717-5p gene (miRBase Accession No. MIMAT0025846) consisting of the nucleotide sequence represented by SEQ ID NO: 666, a homolog or an ortholog of a different organism species, and the like. The hsa-miR-6717-5p gene can be obtained by a method described in Li Y et al., 2012, Gene, Vol. 497, p. 330-335. Also, "hsa-mir-6717" (miRBase Accession No. MI0022551, SEQ ID NO: 677) having a hairpin-like structure is known as a precursor of "hsa-miR-6717-5p".

The term "hsa-miR-3648 gene" or "hsa-miR-3648" used herein includes the hsa-miR-3648 gene (miRBase Accession No. MIMAT0018068) consisting of the nucleotide sequence represented by SEQ ID NO: 667, a homolog or an ortholog of a different organism species, and the like. The hsa-miR-3648 gene can be obtained by a method described in Meiri E et al., 2010, Nucleic Acids Res, Vol. 38, p. 6234-6246. Also, "hsa-mir-3648" (miRBase Accession No. MI0016048, SEQ ID NO: 678) having a hairpin-like structure is known as a precursor of "hsa-miR-3648".

The term "hsa-miR-3162-5p gene" or "hsa-miR-3162-5p" used herein includes the hsa-miR-3162-5p gene (miRBase Accession No. MIMAT0015036) consisting of the nucleotide sequence represented by SEQ ID NO: 668, a homolog or an ortholog of a different organism species, and the like. The hsa-miR-3162-5p gene can be obtained by a method described in Stark M S et al., 2010, PLoS One, Vol. 5, e9685. Also, "hsa-mir-3162" (miRBase Accession No. MI0014192, SEQ ID NO: 679) having a hairpin-like structure is known as a precursor of "hsa-miR-3162-5p".

The term "hsa-miR-1909-3p gene" or "hsa-miR-1909-3p" used herein includes the hsa-miR-1909-3p gene (miRBase Accession No. MIMAT0007883) consisting of the nucleotide sequence represented by SEQ ID NO: 669, a homolog or an ortholog of a different organism species, and the like. The hsa-miR-1909-3p gene can be obtained by a method described in Bar M et al., 2008, Stem Cells, Vol. 26, p. 2496-2505. Also, "hsa-mir-1909" (miRBase Accession No. MI0008330, SEQ ID NO: 680) having a hairpin-like structure is known as a precursor of "hsa-miR-1909-3p".

The term "hsa-miR-8073 gene" or "hsa-miR-8073" used herein includes the hsa-miR-8073 gene (miRBase Accession No. MIMAT0031000) consisting of the nucleotide sequence represented by SEQ ID NO: 670, a homolog or an ortholog of a different organism species, and the like. The hsa-miR-8073 gene can be obtained by a method described in Wang H J et al., 2013, Shock, Vol. 39, p. 480-487. Also, "hsa-mir-8073" (miRBase Accession No. MI0025909, SEQ ID NO: 681) having a hairpin-like structure is known as a precursor of "hsa-miR-8073".

The term "hsa-miR-6769b-5p gene" or "hsa-miR-6769b-5p" used herein includes the hsa-miR-6769b-5p gene (miRBase Accession No. MIMAT0027620) consisting of the nucleotide sequence represented by SEQ ID NO: 671, a homolog or an ortholog of a different organism species, and the like. The hsa-miR-6769b-5p gene can be obtained by a method described in Ladewig E et al., 2012, Genome Res, Vol. 22, p. 1634-1645. Also, "hsa-mir-6769b" (miRBase Accession No. MI0022706, SEQ ID NO: 682) having a hairpin-like structure is known as a precursor of "hsa-miR-6769b-5p".

The term "hsa-miR-6836-3p gene" or "hsa-miR-6836-3p" used herein includes the hsa-miR-6836-3p gene (miRBase Accession No. MIMAT0027575) consisting of the nucleotide sequence represented by SEQ ID NO: 672, a homolog or an ortholog of a different organism species, and the like. The hsa-miR-6836-3p gene can be obtained by a method described in Ladewig E et al., 2012, Genome Res, Vol. 22, p. 1634-1645. Also, "hsa-mir-6836" (miRBase Accession No. MI0022682, SEQ ID NO: 683) having a hairpin-like structure is known as a precursor of "hsa-miR-6836-3p".

The term "hsa-miR-4484 gene" or "hsa-miR-4484" used herein includes the hsa-miR-4484 gene (miRBase Accession No. MIMAT0019018) consisting of the nucleotide sequence represented by SEQ ID NO: 673, a homolog or an ortholog of a different organism species, and the like. The hsa-miR-4484 gene can be obtained by a method described in Jima D D et al., 2010, Blood, Vol. 116, e118-e127. Also, "hsa-mir-4484" (miRBase Accession No. MI0016845, SEQ ID NO: 684) having a hairpin-like structure is known as a precursor of "hsa-miR-4484".

The term "hsa-miR-6819-5p gene" or "hsa-miR-6819-5p" used herein includes the hsa-miR-6819-5p gene (miRBase Accession No. MIMAT0027538) consisting of the nucleotide sequence represented by SEQ ID NO: 674, a homolog or an ortholog of a different organism species, and the like. The hsa-miR-6819-5p gene can be obtained by a method described in Ladewig E et al., 2012, Genome Res, Vol. 22, p. 1634-1645. Also, "hsa-mir-6819" (miRBase Accession No. MI0022664, SEQ ID NO: 685) having a hairpin-like structure is known as a precursor of "hsa-miR-6819-5p".

The term "hsa-miR-6794-5p gene" or "hsa-miR-6794-5p" used herein includes the hsa-miR-6794-5p gene (miRBase Accession No. MIMAT0027488) consisting of the nucleotide sequence represented by SEQ ID NO: 675, a homolog or an ortholog of a different organism species, and the like. The hsa-miR-6794-5p gene can be obtained by a method described in Ladewig E et al., 2012, Genome Res, Vol. 22, p. 1634-1645. Also, "hsa-mir-6794" (miRBase Accession No. MI0022639, SEQ ID NO: 686) having a hairpin-like structure is known as a precursor of "hsa-miR-6794-5p".

The term "hsa-miR-24-3p gene" or "hsa-miR-24-3p" used herein includes the hsa-miR-24-3p gene (miRBase Accession No. MIMAT0000080) consisting of the nucleotide sequence represented by SEQ ID NO: 676, a homolog or an ortholog of a different organism species, and the like. The hsa-miR-24-3p gene can be obtained by a method described in Lagos-Quintana M et al., 2001, Science, Vol. 294, p. 853-858. Also, "hsa-mir-24-1 and hsa-mir-24-2" (miRBase Accession Nos. MI0000080 and MI0000081, SEQ ID NOs: 687 and 688) having a hairpin-like structure are known as precursors of "hsa-miR-24-3p".

A mature miRNA may become a variant due to the sequence cleaved shorter or longer by one to several flanking nucleotides or due to substitution of nucleotides when cut out as the mature miRNA from its RNA precursor having a hairpin-like structure. This variant is called isomiR (Morin R D. et al., 2008, Genome Res., Vol. 18, p. 610-621). The miRBase Release 20 shows the nucleotide sequences represented by SEQ ID NOs: 1 to 214 and 666 to 676 as well as a large number of the nucleotide sequence variants and fragments represented by SEQ ID NOs: 426 to 665 and 689 to 700, called isomiRs. These variants can also be obtained as miRNAs that have a nucleotide sequence represented by any of SEQ ID NOs: 1 to 214 and 666 to 676.

Specifically, among the variants of polynucleotides consisting of a nucleotide sequence represented by any of SEQ ID NOs: 1, 2, 6, 9, 13, 18, 20, 21, 23, 28, 29, 30, 31, 34, 36, 40, 41, 46, 47, 50, 52, 54, 55, 56, 58, 64, 66, 67, 68, 72, 73, 74, 76, 77, 79, 80, 83, 84, 85, 87, 89, 90, 91, 92, 93, 94, 95, 97, 99, 100, 101, 102, 104, 108, 110, 112, 113, 114, 117, 118, 120, 121, 122, 124, 125, 126, 127, 128, 129, 130, 132, 134, 135, 136, 137, 142, 143, 145, 146, 147, 148, 149, 150, 151, 152, 153, 155, 156, 158, 160, 162, 164, 166, 167, 173, 174, 178, 182, 183, 184, 185, 186, 187, 188, 189, 190, 191, 193, 194, 196, 199, 201, 203, 204, 205, 207, 209, 210, 211, 212, 666, 667, 668, 669, 673, and 676 or a nucleotide sequence from the nucleotide sequence by the replacement of u with t according to the present invention, examples of the longest variants registered in miRBase Release 20 include polynucleotides represented by SEQ ID NOs: 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 689, 691, 693, 695, 697, and 699, respectively. Also, among the variants of polynucleotides consisting of the nucleotide sequence represented by any of SEQ ID NOs: 1, 2, 6, 9, 13, 18, 20, 21, 23, 28, 29, 30, 31, 34, 36, 40, 41, 46, 47, 50, 52, 54, 55, 56, 58, 64, 66, 67, 68, 72, 73, 74, 76, 77, 79, 80, 83, 84, 85, 87, 89, 90, 91, 92, 93, 94, 95, 97, 99, 100, 101, 102, 104, 108, 110, 112, 113, 114, 117, 118, 120, 121, 122, 124, 125, 126, 127, 128, 129, 130, 132, 134, 135, 136, 137, 142, 143, 145, 146, 147, 148, 149, 150, 151, 152, 153, 155, 156, 158, 160, 162, 164, 166, 167, 173, 174, 178, 182, 183, 184, 185, 186, 187, 188, 189, 190, 191, 193, 194, 196, 199, 201, 203, 204, 205, 207, 209, 210, 211, 212, 666, 667, 668, 669, 673, and 676 or a nucleotide sequence derived from the nucleotide sequence by the replacement of u with t according to the present invention, examples of shortest variants registered in the miRBase Release 20 include polynucleotides having sequences represented by SEQ ID NOs: 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 561, 563, 565, 567, 569, 571, 573, 575, 577, 579, 581, 583, 585, 587, 589, 591, 593, 595, 597, 599, 601, 603, 605, 607, 609, 611, 613, 615, 617, 619, 621, 623, 625, 627, 629, 631, 633, 635, 637, 639, 641, 643, 645, 647, 649, 651, 653, 655, 657, 659, 661, 663, 665, 690, 692, 694, 696, 698, and 700, respectively. In addition to these variants and fragments, examples thereof include a large number of isomiR polynucleotides consisting of a nucleotide sequence represented by SEQ ID NOs: 1 to 214 and 666 to 676 registered in the miRBase. Examples of the polynucleotide comprising a nucleotide sequence represented by any of SEQ ID NOs: 1 to 214 and 666 to 676 include a polynucleotide represented by any of SEQ ID NOs: 215 to 425 and 677 to 688, which are their respective precursors.

The names and miRBase Accession Nos. (registration numbers) of the genes consisting of a nucleotide sequence represented by SEQ ID NOs: 1 to 700 are shown in Table 1.

The term "capable of specifically binding" used herein means that the nucleic acid probe or the primer used in the present invention binds to a particular target nucleic acid and cannot substantially bind to other nucleic acids.

TABLE 1

| SEQ ID NO: | Gene name | miRBase registration No. |
|---|---|---|
| 1 | hsa-miR-204-3p | MIMAT0022693 |
| 2 | hsa-miR-1247-3p | MIMAT0022721 |
| 3 | hsa-miR-6875-5p | MIMAT0027650 |
| 4 | hsa-miR-6857-5p | MIMAT0027614 |
| 5 | hsa-miR-6726-5p | MIMAT0027353 |
| 6 | hsa-miR-3188 | MIMAT0015070 |
| 7 | hsa-miR-8069 | MIMAT0030996 |
| 8 | hsa-miR-4257 | MIMAT0016878 |
| 9 | hsa-miR-1343-3p | MIMAT0019776 |
| 10 | hsa-miR-7108-5p | MIMAT0028113 |
| 11 | hsa-miR-6825-5p | MIMAT0027550 |
| 12 | hsa-miR-7641 | MIMAT0029782 |
| 13 | hsa-miR-3185 | MIMAT0015065 |
| 14 | hsa-miR-4746-3p | MIMAT0019881 |
| 15 | hsa-miR-6791-5p | MIMAT0027482 |
| 16 | hsa-miR-6893-5p | MIMAT0027686 |
| 17 | hsa-miR-4433b-3p | MIMAT0030414 |
| 18 | hsa-miR-3135b | MIMAT0018985 |

TABLE 1-continued

| SEQ ID NO: | Gene name | miRBase registration No. |
|---|---|---|
| 19 | hsa-miR-6781-5p | MIMAT0027462 |
| 20 | hsa-miR-1908-5p | MIMAT0007881 |
| 21 | hsa-miR-4792 | MIMAT0019964 |
| 22 | hsa-miR-7845-5p | MIMAT0030420 |
| 23 | hsa-miR-4417 | MIMAT0018929 |
| 24 | hsa-miR-3184-5p | MIMAT0015064 |
| 25 | hsa-miR-1225-5p | MIMAT0005572 |
| 26 | hsa-miR-1231 | MIMAT0005586 |
| 27 | hsa-miR-1225-3p | MIMAT0005573 |
| 28 | hsa-miR-150-3p | MIMAT0004610 |
| 29 | hsa-miR-4433-3p | MIMAT0018949 |
| 30 | hsa-miR-6125 | MIMAT0024598 |
| 31 | hsa-miR-4513 | MIMAT0019050 |
| 32 | hsa-miR-6787-5p | MIMAT0027474 |
| 33 | hsa-miR-6784-5p | MIMAT0027468 |
| 34 | hsa-miR-615-5p | MIMAT0004804 |
| 35 | hsa-miR-6765-3p | MIMAT0027431 |
| 36 | hsa-miR-5572 | MIMAT0022260 |
| 37 | hsa-miR-6842-5p | MIMAT0027586 |
| 38 | hsa-miR-8063 | MIMAT0030990 |
| 39 | hsa-miR-6780b-5p | MIMAT0027572 |
| 40 | hsa-miR-187-5p | MIMAT0004561 |
| 41 | hsa-miR-128-1-5p | MIMAT0026477 |
| 42 | hsa-miR-6729-5p | MIMAT0027359 |
| 43 | hsa-miR-6741-5p | MIMAT0027383 |
| 44 | hsa-miR-6757-5p | MIMAT0027414 |
| 45 | hsa-miR-7110-5p | MIMAT0028117 |
| 46 | hsa-miR-7975 | MIMAT0031178 |
| 47 | hsa-miR-1233-5p | MIMAT0022943 |
| 48 | hsa-miR-6845-5p | MIMAT0027590 |
| 49 | hsa-miR-3937 | MIMAT0018352 |
| 50 | hsa-miR-4467 | MIMAT0018994 |
| 51 | hsa-miR-7109-5p | MIMAT0028115 |
| 52 | hsa-miR-6088 | MIMAT0023713 |
| 53 | hsa-miR-6782-5p | MIMAT0027464 |
| 54 | hsa-miR-5195-3p | MIMAT0021127 |
| 55 | hsa-miR-4454 | MIMAT0018976 |
| 56 | hsa-miR-6724-5p | MIMAT0025856 |
| 57 | hsa-miR-8072 | MIMAT0030999 |
| 58 | hsa-miR-4516 | MIMAT0019053 |
| 59 | hsa-miR-6756-5p | MIMAT0027412 |
| 60 | hsa-miR-4665-3p | MIMAT0019740 |
| 61 | hsa-miR-6826-5p | MIMAT0027552 |
| 62 | hsa-miR-6820-5p | MIMAT0027540 |
| 63 | hsa-miR-6887-5p | MIMAT0027674 |
| 64 | hsa-miR-3679-5p | MIMAT0018104 |
| 65 | hsa-miR-7847-3p | MIMAT0030422 |
| 66 | hsa-miR-6721-5p | MIMAT0025852 |
| 67 | hsa-miR-3622a-5p | MIMAT0018003 |
| 68 | hsa-miR-939-5p | MIMAT0004982 |
| 69 | hsa-miR-602 | MIMAT0003270 |
| 70 | hsa-miR-7977 | MIMAT0031180 |
| 71 | hsa-miR-6749-5p | MIMAT0027398 |
| 72 | hsa-miR-1914-3p | MIMAT0007890 |
| 73 | hsa-miR-4651 | MIMAT0019715 |
| 74 | hsa-miR-4695-5p | MIMAT0019788 |
| 75 | hsa-miR-6848-5p | MIMAT0027596 |
| 76 | hsa-miR-1228-3p | MIMAT0005583 |
| 77 | hsa-miR-642b-3p | MIMAT0018444 |
| 78 | hsa-miR-6746-5p | MIMAT0027392 |
| 79 | hsa-miR-3620-5p | MIMAT0022967 |
| 80 | hsa-miR-3131 | MIMAT0014996 |
| 81 | hsa-miR-6732-5p | MIMAT0027365 |
| 82 | hsa-miR-7113-3p | MIMAT0028124 |
| 83 | hsa-miR-23a-3p | MIMAT0000078 |
| 84 | hsa-miR-3154 | MIMAT0015028 |
| 85 | hsa-miR-4723-5p | MIMAT0019838 |
| 86 | hsa-miR-3663-3p | MIMAT0018085 |
| 87 | hsa-miR-4734 | MIMAT0019859 |
| 88 | hsa-miR-6816-5p | MIMAT0027532 |
| 89 | hsa-miR-4442 | MIMAT0018960 |
| 90 | hsa-miR-4476 | MIMAT0019003 |
| 91 | hsa-miR-423-5p | MIMAT0004748 |
| 92 | hsa-miR-1249 | MIMAT0005901 |
| 93 | hsa-miR-6515-3p | MIMAT0025487 |
| 94 | hsa-miR-887-3p | MIMAT0004951 |
| 95 | hsa-miR-4741 | MIMAT0019871 |

TABLE 1-continued

| SEQ ID NO: | Gene name | miRBase registration No. |
|---|---|---|
| 96 | hsa-miR-6766-3p | MIMAT0027433 |
| 97 | hsa-miR-4673 | MIMAT0019755 |
| 98 | hsa-miR-6779-5p | MIMAT0027458 |
| 99 | hsa-miR-4706 | MIMAT0019806 |
| 100 | hsa-miR-1268b | MIMAT0018925 |
| 101 | hsa-miR-4632-5p | MIMAT0022977 |
| 102 | hsa-miR-3197 | MIMAT0015082 |
| 103 | hsa-miR-6798-5p | MIMAT0027496 |
| 104 | hsa-miR-711 | MIMAT0012734 |
| 105 | hsa-miR-6840-3p | MIMAT0027583 |
| 106 | hsa-miR-6763-5p | MIMAT0027426 |
| 107 | hsa-miR-6727-5p | MIMAT0027355 |
| 108 | hsa-miR-371a-5p | MIMAT0004687 |
| 109 | hsa-miR-6824-5p | MIMAT0027548 |
| 110 | hsa-miR-4648 | MIMAT0019710 |
| 111 | hsa-miR-1227-5p | MIMAT0022941 |
| 112 | hsa-miR-564 | MIMAT0003228 |
| 113 | hsa-miR-3679-3p | MIMAT0018105 |
| 114 | hsa-miR-2861 | MIMAT0013802 |
| 115 | hsa-miR-6737-5p | MIMAT0027375 |
| 116 | hsa-miR-575 | MIMAT0003240 |
| 117 | hsa-miR-4725-3p | MIMAT0019844 |
| 118 | hsa-miR-6716-5p | MIMAT0025844 |
| 119 | hsa-miR-4675 | MIMAT0019757 |
| 120 | hsa-miR-1915-3p | MIMAT0007892 |
| 121 | hsa-miR-671-5p | MIMAT0003880 |
| 122 | hsa-miR-3656 | MIMAT0018076 |
| 123 | hsa-miR-6722-3p | MIMAT0025854 |
| 124 | hsa-miR-4707-5p | MIMAT0019807 |
| 125 | hsa-miR-4449 | MIMAT0018968 |
| 126 | hsa-miR-1202 | MIMAT0005865 |
| 127 | hsa-miR-4649-5p | MIMAT0019711 |
| 128 | hsa-miR-744-5p | MIMAT0004945 |
| 129 | hsa-miR-642a-3p | MIMAT0020924 |
| 130 | hsa-miR-451a | MIMAT0001631 |
| 131 | hsa-miR-6870-5p | MIMAT0027640 |
| 132 | hsa-miR-4443 | MIMAT0018961 |
| 133 | hsa-miR-6808-5p | MIMAT0027516 |
| 134 | hsa-miR-4728-5p | MIMAT0019849 |
| 135 | hsa-miR-937-5p | MIMAT0022938 |
| 136 | hsa-miR-135a-3p | MIMAT0004595 |
| 137 | hsa-miR-663b | MIMAT0005867 |
| 138 | hsa-miR-1343-5p | MIMAT0027038 |
| 139 | hsa-miR-6822-5p | MIMAT0027544 |
| 140 | hsa-miR-6803-5p | MIMAT0027506 |
| 141 | hsa-miR-6805-3p | MIMAT0027511 |
| 142 | hsa-miR-128-2-5p | MIMAT0031095 |
| 143 | hsa-miR-4640-5p | MIMAT0019699 |
| 144 | hsa-miR-1469 | MIMAT0007347 |
| 145 | hsa-miR-92a-2-5p | MIMAT0004508 |
| 146 | hsa-miR-3940-5p | MIMAT0019229 |
| 147 | hsa-miR-4281 | MIMAT0016907 |
| 148 | hsa-miR-1260b | MIMAT0015041 |
| 149 | hsa-miR-4758-5p | MIMAT0019903 |
| 150 | hsa-miR-1915-5p | MIMAT0007891 |
| 151 | hsa-miR-5001-5p | MIMAT0021021 |
| 152 | hsa-miR-4286 | MIMAT0016916 |
| 153 | hsa-miR-6126 | MIMAT0024599 |
| 154 | hsa-miR-6789-5p | MIMAT0027478 |
| 155 | hsa-miR-4459 | MIMAT0018981 |
| 156 | hsa-miR-1268a | MIMAT0005922 |
| 157 | hsa-miR-6752-5p | MIMAT0027404 |
| 158 | hsa-miR-6131 | MIMAT0024615 |
| 159 | hsa-miR-6800-5p | MIMAT0027500 |
| 160 | hsa-miR-4532 | MIMAT0019071 |
| 161 | hsa-miR-6872-3p | MIMAT0027645 |
| 162 | hsa-miR-718 | MIMAT0012735 |
| 163 | hsa-miR-6769a-5p | MIMAT0027438 |
| 164 | hsa-miR-4707-3p | MIMAT0019808 |
| 165 | hsa-miR-6765-5p | MIMAT0027430 |
| 166 | hsa-miR-4739 | MIMAT0019868 |
| 167 | hsa-miR-4525 | MIMAT0019064 |
| 168 | hsa-miR-4270 | MIMAT0016900 |
| 169 | hsa-miR-4534 | MIMAT0019073 |
| 170 | hsa-miR-6785-5p | MIMAT0027470 |
| 171 | hsa-miR-6850-5p | MIMAT0027600 |
| 172 | hsa-miR-4697-5p | MIMAT0019791 |
| 173 | hsa-miR-1260a | MIMAT0005911 |
| 174 | hsa-miR-4486 | MIMAT0019020 |
| 175 | hsa-miR-6880-5p | MIMAT0027660 |
| 176 | hsa-miR-6802-5p | MIMAT0027504 |
| 177 | hsa-miR-6861-5p | MIMAT0027623 |
| 178 | hsa-miR-92b-5p | MIMAT0004792 |
| 179 | hsa-miR-1238-5p | MIMAT0022947 |
| 180 | hsa-miR-6851-5p | MIMAT0027602 |
| 181 | hsa-miR-7704 | MIMAT0030019 |
| 182 | hsa-miR-149-3p | MIMAT0004609 |
| 183 | hsa-miR-4689 | MIMAT0019778 |
| 184 | hsa-miR-4688 | MIMAT0019777 |
| 185 | hsa-miR-125a-3p | MIMAT0004602 |
| 186 | hsa-miR-23b-3p | MIMAT0000418 |
| 187 | hsa-miR-614 | MIMAT0003282 |
| 188 | hsa-miR-1913 | MIMAT0007888 |
| 189 | hsa-miR-16-5p | MIMAT0000069 |
| 190 | hsa-miR-675-5p | MIMAT0004284 |
| 191 | hsa-miR-486-3p | MIMAT0004762 |
| 192 | hsa-miR-6777-5p | MIMAT0027454 |
| 193 | hsa-miR-4497 | MIMAT0019032 |
| 194 | hsa-miR-296-3p | MIMAT0004679 |
| 195 | hsa-miR-6738-5p | MIMAT0027377 |
| 196 | hsa-miR-4731-5p | MIMAT0019853 |
| 197 | hsa-miR-6889-5p | MIMAT0027678 |
| 198 | hsa-miR-6786-5p | MIMAT0027472 |
| 199 | hsa-miR-92a-3p | MIMAT0000092 |
| 200 | hsa-miR-4294 | MIMAT0016849 |
| 201 | hsa-miR-4763-3p | MIMAT0019913 |
| 202 | hsa-miR-6076 | MIMAT0023701 |
| 203 | hsa-miR-663a | MIMAT0003326 |
| 204 | hsa-miR-760 | MIMAT0004957 |
| 205 | hsa-miR-4667-5p | MIMAT0019743 |
| 206 | hsa-miR-6090 | MIMAT0023715 |
| 207 | hsa-miR-4730 | MIMAT0019852 |
| 208 | hsa-miR-7106-5p | MIMAT0028109 |
| 209 | hsa-miR-3196 | MIMAT0015080 |
| 210 | hsa-miR-5698 | MIMAT0022491 |
| 211 | hsa-miR-6087 | MIMAT0023712 |
| 212 | hsa-miR-4665-5p | MIMAT0019739 |
| 213 | hsa-miR-8059 | MIMAT0030986 |
| 214 | hsa-miR-6879-5p | MIMAT0027658 |
| 215 | hsa-mir-204 | MI0000284 |
| 216 | hsa-mir-1247 | MI0006382 |
| 217 | hsa-mir-6875 | MI0022722 |
| 218 | hsa-mir-6857 | MI0022703 |
| 219 | hsa-mir-6726 | MI0022571 |
| 220 | hsa-mir-3188 | MI0014232 |
| 221 | hsa-mir-8069 | MI0025905 |
| 222 | hsa-mir-4257 | MI0015856 |
| 223 | hsa-mir-1343 | MI0017320 |
| 224 | hsa-mir-7108 | MI0022959 |
| 225 | hsa-mir-6825 | MI0022670 |
| 226 | hsa-mir-7641-1 | MI0024975 |
| 227 | hsa-mir-7641-2 | MI0024976 |
| 228 | hsa-mir-3185 | MI0014227 |
| 229 | hsa-mir-4746 | MI0017385 |
| 230 | hsa-mir-6791 | MI0022636 |
| 231 | hsa-mir-6893 | MI0022740 |
| 232 | hsa-mir-4433b | MI0025511 |
| 233 | hsa-mir-3135b | MI0016809 |
| 234 | hsa-mir-6781 | MI0022626 |
| 235 | hsa-mir-1908 | MI0008329 |
| 236 | hsa-mir-4792 | MI0017439 |
| 237 | hsa-mir-7845 | MI0025515 |
| 238 | hsa-mir-4417 | MI0016753 |
| 239 | hsa-mir-3184 | MI0014226 |
| 240 | hsa-mir-1225 | MI0006311 |
| 241 | hsa-mir-1231 | MI0006321 |
| 242 | hsa-mir-150 | MI0000479 |
| 243 | hsa-mir-4433 | MI0016773 |
| 244 | hsa-mir-6125 | MI0021259 |
| 245 | hsa-mir-4513 | MI0016879 |
| 246 | hsa-mir-6787 | MI0022632 |
| 247 | hsa-mir-6784 | MI0022629 |
| 248 | hsa-mir-615 | MI0003628 |
| 249 | hsa-mir-6765 | MI0022610 |

TABLE 1-continued

| SEQ ID NO: | Gene name | miRBase registration No. |
|---|---|---|
| 250 | hsa-mir-5572 | MI0019117 |
| 251 | hsa-mir-6842 | MI0022688 |
| 252 | hsa-mir-8063 | MI0025899 |
| 253 | hsa-mir-6780b | MI0022681 |
| 254 | hsa-mir-187 | MI0000274 |
| 255 | hsa-mir-128-1 | MI0000447 |
| 256 | hsa-mir-6729 | MI0022574 |
| 257 | hsa-mir-6741 | MI0022586 |
| 258 | hsa-mir-6757 | MI0022602 |
| 259 | hsa-mir-7110 | MI0022961 |
| 260 | hsa-mir-7975 | MI0025751 |
| 261 | hsa-mir-1233-1 | MI0006323 |
| 262 | hsa-mir-1233-2 | MI0015973 |
| 263 | hsa-mir-6845 | MI0022691 |
| 264 | hsa-mir-3937 | MI0016593 |
| 265 | hsa-mir-4467 | MI0016818 |
| 266 | hsa-mir-7109 | MI0022960 |
| 267 | hsa-mir-6088 | MI0020365 |
| 268 | hsa-mir-6782 | MI0022627 |
| 269 | hsa-mir-5195 | MI0018174 |
| 270 | hsa-mir-4454 | MI0016800 |
| 271 | hsa-mir-6724 | MI0022559 |
| 272 | hsa-mir-8072 | MI0025908 |
| 273 | hsa-mir-4516 | MI0016882 |
| 274 | hsa-mir-6756 | MI0022601 |
| 275 | hsa-mir-4665 | MI0017295 |
| 276 | hsa-mir-6826 | MI0022671 |
| 277 | hsa-mir-6820 | MI0022665 |
| 278 | hsa-mir-6887 | MI0022734 |
| 279 | hsa-mir-3679 | MI0016080 |
| 280 | hsa-mir-7847 | MI0025517 |
| 281 | hsa-mir-6721 | MI0022556 |
| 282 | hsa-mir-3622a | MI0016013 |
| 283 | hsa-mir-939 | MI0005761 |
| 284 | hsa-mir-602 | MI0003615 |
| 285 | hsa-mir-7977 | MI0025753 |
| 286 | hsa-mir-6749 | MI0022594 |
| 287 | hsa-mir-1914 | MI0008335 |
| 288 | hsa-mir-4651 | MI0017279 |
| 289 | hsa-mir-4695 | MI0017328 |
| 290 | hsa-mir-6848 | MI0022694 |
| 291 | hsa-mir-1228 | MI0006318 |
| 292 | hsa-mir-642b | MI0016685 |
| 293 | hsa-mir-6746 | MI0022591 |
| 294 | hsa-mir-3620 | MI0016011 |
| 295 | hsa-mir-3131 | MI0014151 |
| 296 | hsa-mir-6732 | MI0022577 |
| 297 | hsa-mir-7113 | MI0022964 |
| 298 | hsa-mir-23a | MI0000079 |
| 299 | hsa-mir-3154 | MI0014182 |
| 300 | hsa-mir-4723 | MI0017359 |
| 301 | hsa-mir-3663 | MI0016064 |
| 302 | hsa-mir-4734 | MI0017371 |
| 303 | hsa-mir-6816 | MI0022661 |
| 304 | hsa-mir-4442 | MI0016785 |
| 305 | hsa-mir-4476 | MI0016828 |
| 306 | hsa-mir-423 | MI0001445 |
| 307 | hsa-mir-1249 | MI0006384 |
| 308 | hsa-mir-6515 | MI0022227 |
| 309 | hsa-mir-887 | MI0005562 |
| 310 | hsa-mir-4741 | MI0017379 |
| 311 | hsa-mir-6766 | MI0022611 |
| 312 | hsa-mir-4673 | MI0017304 |
| 313 | hsa-mir-6779 | MI0022624 |
| 314 | hsa-mir-4706 | MI0017339 |
| 315 | hsa-mir-1268b | MI0016748 |
| 316 | hsa-mir-4632 | MI0017259 |
| 317 | hsa-mir-3197 | MI0014245 |
| 318 | hsa-mir-6798 | MI0022643 |
| 319 | hsa-mir-711 | MI0012488 |
| 320 | hsa-mir-6840 | MI0022686 |
| 321 | hsa-mir-6763 | MI0022608 |
| 322 | hsa-mir-6727 | MI0022572 |
| 323 | hsa-mir-371a | MI0000779 |
| 324 | hsa-mir-6824 | MI0022669 |
| 325 | hsa-mir-4648 | MI0017275 |
| 326 | hsa-mir-1227 | MI0006316 |
| 327 | hsa-mir-564 | MI0003570 |
| 328 | hsa-mir-2861 | MI0013006 |
| 329 | hsa-mir-6737 | MI0022582 |
| 330 | hsa-mir-575 | MI0003582 |
| 331 | hsa-mir-4725 | MI0017362 |
| 332 | hsa-mir-6716 | MI0022550 |
| 333 | hsa-mir-4675 | MI0017306 |
| 334 | hsa-mir-1915 | MI0008336 |
| 335 | hsa-mir-671 | MI0003760 |
| 336 | hsa-mir-3656 | MI0016056 |
| 337 | hsa-mir-6722 | MI0022557 |
| 338 | hsa-mir-4707 | MI0017340 |
| 339 | hsa-mir-4449 | MI0016792 |
| 340 | hsa-mir-1202 | MI0006334 |
| 341 | hsa-mir-4649 | MI0017276 |
| 342 | hsa-mir-744 | MI0005559 |
| 343 | hsa-mir-642a | MI0003657 |
| 344 | hsa-mir-451a | MI0001729 |
| 345 | hsa-mir-6870 | MI0022717 |
| 346 | hsa-mir-4443 | MI0016786 |
| 347 | hsa-mir-6808 | MI0022653 |
| 348 | hsa-mir-4728 | MI0017365 |
| 349 | hsa-mir-937 | MI0005759 |
| 350 | hsa-mir-135a-1 | MI0000452 |
| 351 | hsa-mir-663b | MI0006336 |
| 352 | hsa-mir-6822 | MI0022667 |
| 353 | hsa-mir-6803 | MI0022648 |
| 354 | hsa-mir-6805 | MI0022650 |
| 355 | hsa-mir-128-2 | MI0000727 |
| 356 | hsa-mir-4640 | MI0017267 |
| 357 | hsa-mir-1469 | MI0007074 |
| 358 | hsa-mir-92a-2 | MI0000094 |
| 359 | hsa-mir-3940 | MI0016597 |
| 360 | hsa-mir-4281 | MI0015885 |
| 361 | hsa-mir-1260b | MI0014197 |
| 362 | hsa-mir-4758 | MI0017399 |
| 363 | hsa-mir-5001 | MI0017867 |
| 364 | hsa-mir-4286 | MI0015894 |
| 365 | hsa-mir-6126 | MI0021260 |
| 366 | hsa-mir-6789 | MI0022634 |
| 367 | hsa-mir-4459 | MI0016805 |
| 368 | hsa-mir-1268a | MI0006405 |
| 369 | hsa-mir-6752 | MI0022597 |
| 370 | hsa-mir-6131 | MI0021276 |
| 371 | hsa-mir-6800 | MI0022645 |
| 372 | hsa-mir-4532 | MI0016899 |
| 373 | hsa-mir-6872 | MI0022719 |
| 374 | hsa-mir-718 | MI0012489 |
| 375 | hsa-mir-6769a | MI0022614 |
| 376 | hsa-mir-4739 | MI0017377 |
| 377 | hsa-mir-4525 | MI0016892 |
| 378 | hsa-mir-4270 | MI0015878 |
| 379 | hsa-mir-4534 | MI0016901 |
| 380 | hsa-mir-6785 | MI0022630 |
| 381 | hsa-mir-6850 | MI0022696 |
| 382 | hsa-mir-4697 | MI0017330 |
| 383 | hsa-mir-1260a | MI0006394 |
| 384 | hsa-mir-4486 | MI0016847 |
| 385 | hsa-mir-6880 | MI0022727 |
| 386 | hsa-mir-6802 | MI0022647 |
| 387 | hsa-mir-6861 | MI0022708 |
| 388 | hsa-mir-92b | MI0003560 |
| 389 | hsa-mir-1238 | MI0006328 |
| 390 | hsa-mir-6851 | MI0022697 |
| 391 | hsa-mir-7704 | MI0025240 |
| 392 | hsa-mir-149 | MI0000478 |
| 393 | hsa-mir-4689 | MI0017322 |
| 394 | hsa-mir-4688 | MI0017321 |
| 395 | hsa-mir-125a | MI0000469 |
| 396 | hsa-mir-23b | MI0000439 |
| 397 | hsa-mir-614 | MI0003627 |
| 398 | hsa-mir-1913 | MI0008334 |
| 399 | hsa-mir-16-1 | MI0000070 |
| 400 | hsa-mir-16-2 | MI0000115 |
| 401 | hsa-mir-675 | MI0005416 |
| 402 | hsa-mir-486 | MI0002470 |
| 403 | hsa-mir-486-2 | MI0023622 |

TABLE 1-continued

| SEQ ID NO: | Gene name | miRBase registration No. |
|---|---|---|
| 404 | hsa-mir-6777 | MI0022622 |
| 405 | hsa-mir-4497 | MI0016859 |
| 406 | hsa-mir-296 | MI0000747 |
| 407 | hsa-mir-6738 | MI0022583 |
| 408 | hsa-mir-4731 | MI0017368 |
| 409 | hsa-mir-6889 | MI0022736 |
| 410 | hsa-mir-6786 | MI0022631 |
| 411 | hsa-mir-92a-1 | MI0000093 |
| 412 | hsa-mir-4294 | MI0015827 |
| 413 | hsa-mir-4763 | MI0017404 |
| 414 | hsa-mir-6076 | MI0020353 |
| 415 | hsa-mir-663a | MI0003672 |
| 416 | hsa-mir-760 | MI0005567 |
| 417 | hsa-mir-4667 | MI0017297 |
| 418 | hsa-mir-6090 | MI0020367 |
| 419 | hsa-mir-4730 | MI0017367 |
| 420 | hsa-mir-7106 | MI0022957 |
| 421 | hsa-mir-3196 | MI0014241 |
| 422 | hsa-mir-5698 | MI0019305 |
| 423 | hsa-mir-6087 | MI0020364 |
| 424 | hsa-mir-8059 | MI0025895 |
| 425 | hsa-mir-6879 | MI0022726 |
| 426 | isomiR example 1 of SEQ ID NO: 1 | — |
| 427 | isomiR example 2 of SEQ ID NO: 1 | — |
| 428 | isomiR example 1 of SEQ ID NO: 2 | — |
| 429 | isomiR example 2 of SEQ ID NO: 2 | — |
| 430 | isomiR example 1 of SEQ ID NO: 6 | — |
| 431 | isomiR example 2 of SEQ ID NO: 6 | — |
| 432 | isomiR example 1 of SEQ ID NO: 9 | — |
| 433 | isomiR example 2 of SEQ ID NO: 9 | — |
| 434 | isomiR example 1 of SEQ ID NO: 13 | — |
| 435 | isomiR example 2 of SEQ ID NO: 13 | — |
| 436 | isomiR example 1 of SEQ ID NO: 18 | — |
| 437 | isomiR example 2 of SEQ ID NO: 18 | — |
| 438 | isomiR example 1 of SEQ ID NO: 20 | — |
| 439 | isomiR example 2 of SEQ ID NO: 20 | — |
| 440 | isomiR example 1 of SEQ ID NO: 21 | — |
| 441 | isomiR example 2 of SEQ ID NO: 21 | — |
| 442 | isomiR example 1 of SEQ ID NO: 23 | — |
| 443 | isomiR example 2 of SEQ ID NO: 23 | — |
| 444 | isomiR example 1 of SEQ ID NO: 28 | — |
| 445 | isomiR example 2 of SEQ ID NO: 28 | — |
| 446 | isomiR example 1 of SEQ ID NO: 29 | — |
| 447 | isomiR example 2 of SEQ ID NO: 29 | — |
| 448 | isomiR example 1 of SEQ ID NO: 30 | — |
| 449 | isomiR example 2 of SEQ ID NO: 30 | — |
| 450 | isomiR example 1 of SEQ ID NO: 31 | — |
| 451 | isomiR example 2 of SEQ ID NO: 31 | — |
| 452 | isomiR example 1 of SEQ ID NO: 34 | — |
| 453 | isomiR example 2 of SEQ ID NO: 34 | — |
| 454 | isomiR example 1 of SEQ ID NO: 36 | — |
| 455 | isomiR example 2 of SEQ ID NO: 36 | — |
| 456 | isomiR example 1 of SEQ ID NO: 40 | — |
| 457 | isomiR example 2 of SEQ ID NO: 40 | — |
| 458 | isomiR example 1 of SEQ ID NO: 41 | — |
| 459 | isomiR example 2 of SEQ ID NO: 41 | — |
| 460 | isomiR example 1 of SEQ ID NO: 46 | — |
| 461 | isomiR example 2 of SEQ ID NO: 46 | — |
| 462 | isomiR example 1 of SEQ ID NO: 47 | — |
| 463 | isomiR example 2 of SEQ ID NO: 47 | — |
| 464 | isomiR example 1 of SEQ ID NO: 50 | — |
| 465 | isomiR example 2 of SEQ ID NO: 50 | — |
| 466 | isomiR example 1 of SEQ ID NO: 52 | — |
| 467 | isomiR example 2 of SEQ ID NO: 52 | — |
| 468 | isomiR example 1 of SEQ ID NO: 54 | — |
| 469 | isomiR example 2 of SEQ ID NO: 54 | — |
| 470 | isomiR example 1 of SEQ ID NO: 55 | — |
| 471 | isomiR example 2 of SEQ ID NO: 55 | — |
| 472 | isomiR example 1 of SEQ ID NO: 56 | — |
| 473 | isomiR example 2 of SEQ ID NO: 56 | — |
| 474 | isomiR example 1 of SEQ ID NO: 58 | — |
| 475 | isomiR example 2 of SEQ ID NO: 58 | — |
| 476 | isomiR example 1 of SEQ ID NO: 64 | — |
| 477 | isomiR example 2 of SEQ ID NO: 64 | — |
| 478 | isomiR example 1 of SEQ ID NO: 66 | — |
| 479 | isomiR example 2 of SEQ ID NO: 66 | — |
| 480 | isomiR example 1 of SEQ ID NO: 67 | — |
| 481 | isomiR example 2 of SEQ ID NO: 67 | — |
| 482 | isomiR example 1 of SEQ ID NO: 68 | — |
| 483 | isomiR example 2 of SEQ ID NO: 68 | — |
| 484 | isomiR example 1 of SEQ ID NO: 72 | — |
| 485 | isomiR example 2 of SEQ ID NO: 72 | — |
| 486 | isomiR example 1 of SEQ ID NO: 73 | — |
| 487 | isomiR example 2 of SEQ ID NO: 73 | — |
| 488 | isomiR example 1 of SEQ ID NO: 74 | — |
| 489 | isomiR example 2 of SEQ ID NO: 74 | — |
| 490 | isomiR example 1 of SEQ ID NO: 76 | — |
| 491 | isomiR example 2 of SEQ ID NO: 76 | — |
| 492 | isomiR example 1 of SEQ ID NO: 77 | — |
| 493 | isomiR example 2 of SEQ ID NO: 77 | — |
| 494 | isomiR example 1 of SEQ ID NO: 79 | — |
| 495 | isomiR example 2 of SEQ ID NO: 79 | — |
| 496 | isomiR example 1 of SEQ ID NO: 80 | — |
| 497 | isomiR example 2 of SEQ ID NO: 80 | — |
| 498 | isomiR example 1 of SEQ ID NO: 83 | — |
| 499 | isomiR example 2 of SEQ ID NO: 83 | — |
| 500 | isomiR example 1 of SEQ ID NO: 84 | — |
| 501 | isomiR example 2 of SEQ ID NO: 84 | — |
| 502 | isomiR example 1 of SEQ ID NO: 85 | — |
| 503 | isomiR example 2 of SEQ ID NO: 85 | — |
| 504 | isomiR example 1 of SEQ ID NO: 87 | — |
| 505 | isomiR example 2 of SEQ ID NO: 87 | — |
| 506 | isomiR example 1 of SEQ ID NO: 89 | — |
| 507 | isomiR example 2 of SEQ ID NO: 89 | — |
| 508 | isomiR example 1 of SEQ ID NO: 90 | — |
| 509 | isomiR example 2 of SEQ ID NO: 90 | — |
| 510 | isomiR example 1 of SEQ ID NO: 91 | — |
| 511 | isomiR example 2 of SEQ ID NO: 91 | — |
| 512 | isomiR example 1 of SEQ ID NO: 92 | — |
| 513 | isomiR example 2 of SEQ ID NO: 92 | — |
| 514 | isomiR example 1 of SEQ ID NO: 93 | — |
| 515 | isomiR example 2 of SEQ ID NO: 93 | — |
| 516 | isomiR example 1 of SEQ ID NO: 94 | — |
| 517 | isomiR example 2 of SEQ ID NO: 94 | — |
| 518 | isomiR example 1 of SEQ ID NO: 95 | — |
| 519 | isomiR example 2 of SEQ ID NO: 95 | — |
| 520 | isomiR example 1 of SEQ ID NO: 97 | — |
| 521 | isomiR example 2 of SEQ ID NO: 97 | — |
| 522 | isomiR example 1 of SEQ ID NO: 99 | — |
| 523 | isomiR example 2 of SEQ ID NO: 99 | — |
| 524 | isomiR example 1 of SEQ ID NO: 100 | — |
| 525 | isomiR example 2 of SEQ ID NO: 100 | — |
| 526 | isomiR example 1 of SEQ ID NO: 101 | — |
| 527 | isomiR example 2 of SEQ ID NO: 101 | — |
| 528 | isomiR example 1 of SEQ ID NO: 102 | — |
| 529 | isomiR example 2 of SEQ ID NO: 102 | — |
| 530 | isomiR example 1 of SEQ ID NO: 104 | — |
| 531 | isomiR example 2 of SEQ ID NO: 104 | — |
| 532 | isomiR example 1 of SEQ ID NO: 108 | — |
| 533 | isomiR example 2 of SEQ ID NO: 108 | — |
| 534 | isomiR example 1 of SEQ ID NO: 110 | — |
| 535 | isomiR example 2 of SEQ ID NO: 110 | — |
| 536 | isomiR example 1 of SEQ ID NO: 112 | — |
| 537 | isomiR example 2 of SEQ ID NO: 112 | — |
| 538 | isomiR example 1 of SEQ ID NO: 113 | — |
| 539 | isomiR example 2 of SEQ ID NO: 113 | — |
| 540 | isomiR example 1 of SEQ ID NO: 114 | — |
| 541 | isomiR example 2 of SEQ ID NO: 114 | — |
| 542 | isomiR example 1 of SEQ ID NO: 117 | — |
| 543 | isomiR example 2 of SEQ ID NO: 117 | — |
| 544 | isomiR example 1 of SEQ ID NO: 118 | — |
| 545 | isomiR example 2 of SEQ ID NO: 118 | — |
| 546 | isomiR example 1 of SEQ ID NO: 120 | — |
| 547 | isomiR example 2 of SEQ ID NO: 120 | — |
| 548 | isomiR example 1 of SEQ ID NO: 121 | — |
| 549 | isomiR example 2 of SEQ ID NO: 121 | — |
| 550 | isomiR example 1 of SEQ ID NO: 122 | — |
| 551 | isomiR example 2 of SEQ ID NO: 122 | — |
| 552 | isomiR example 1 of SEQ ID NO: 124 | — |
| 553 | isomiR example 2 of SEQ ID NO: 124 | — |
| 554 | isomiR example 1 of SEQ ID NO: 125 | — |
| 555 | isomiR example 2 of SEQ ID NO: 125 | — |
| 556 | isomiR example 1 of SEQ ID NO: 126 | — |
| 557 | isomiR example 2 of SEQ ID NO: 126 | — |

TABLE 1-continued

| SEQ ID NO: | Gene name | miRBase registration No. |
|---|---|---|
| 558 | isomiR example 1 of SEQ ID NO: 127 | — |
| 559 | isomiR example 2 of SEQ ID NO: 127 | — |
| 560 | isomiR example 1 of SEQ ID NO: 128 | — |
| 561 | isomiR example 2 of SEQ ID NO: 128 | — |
| 562 | isomiR example 1 of SEQ ID NO: 129 | — |
| 563 | isomiR example 2 of SEQ ID NO: 129 | — |
| 564 | isomiR example 1 of SEQ ID NO: 130 | — |
| 565 | isomiR example 2 of SEQ ID NO: 130 | — |
| 566 | isomiR example 1 of SEQ ID NO: 132 | — |
| 567 | isomiR example 2 of SEQ ID NO: 132 | — |
| 568 | isomiR example 1 of SEQ ID NO: 134 | — |
| 569 | isomiR example 2 of SEQ ID NO: 134 | — |
| 570 | isomiR example 1 of SEQ ID NO: 135 | — |
| 571 | isomiR example 2 of SEQ ID NO: 135 | — |
| 572 | isomiR example 1 of SEQ ID NO: 136 | — |
| 573 | isomiR example 2 of SEQ ID NO: 136 | — |
| 574 | isomiR example 1 of SEQ ID NO: 137 | — |
| 575 | isomiR example 2 of SEQ ID NO: 137 | — |
| 576 | isomiR example 1 of SEQ ID NO: 142 | — |
| 577 | isomiR example 2 of SEQ ID NO: 142 | — |
| 578 | isomiR example 1 of SEQ ID NO: 143 | — |
| 579 | isomiR example 2 of SEQ ID NO: 143 | — |
| 580 | isomiR example 1 of SEQ ID NO: 145 | — |
| 581 | isomiR example 2 of SEQ ID NO: 145 | — |
| 582 | isomiR example 1 of SEQ ID NO: 146 | — |
| 583 | isomiR example 2 of SEQ ID NO: 146 | — |
| 584 | isomiR example 1 of SEQ ID NO: 147 | — |
| 585 | isomiR example 2 of SEQ ID NO: 147 | — |
| 586 | isomiR example 1 of SEQ ID NO: 148 | — |
| 587 | isomiR example 2 of SEQ ID NO: 148 | — |
| 588 | isomiR example 1 of SEQ ID NO: 149 | — |
| 589 | isomiR example 2 of SEQ ID NO: 149 | — |
| 590 | isomiR example 1 of SEQ ID NO: 150 | — |
| 591 | isomiR example 2 of SEQ ID NO: 150 | — |
| 592 | isomiR example 1 of SEQ ID NO: 151 | — |
| 593 | isomiR example 2 of SEQ ID NO: 151 | — |
| 594 | isomiR example 1 of SEQ ID NO: 152 | — |
| 595 | isomiR example 2 of SEQ ID NO: 152 | — |
| 596 | isomiR example 1 of SEQ ID NO: 153 | — |
| 597 | isomiR example 2 of SEQ ID NO: 153 | — |
| 598 | isomiR example 1 of SEQ ID NO: 155 | — |
| 599 | isomiR example 2 of SEQ ID NO: 155 | — |
| 600 | isomiR example 1 of SEQ ID NO: 156 | — |
| 601 | isomiR example 2 of SEQ ID NO: 156 | — |
| 602 | isomiR example 1 of SEQ ID NO: 158 | — |
| 603 | isomiR example 2 of SEQ ID NO: 158 | — |
| 604 | isomiR example 1 of SEQ ID NO: 160 | — |
| 605 | isomiR example 2 of SEQ ID NO: 160 | — |
| 606 | isomiR example 1 of SEQ ID NO: 162 | — |
| 607 | isomiR example 2 of SEQ ID NO: 162 | — |
| 608 | isomiR example 1 of SEQ ID NO: 164 | — |
| 609 | isomiR example 2 of SEQ ID NO: 164 | — |
| 610 | isomiR example 1 of SEQ ID NO: 166 | — |
| 611 | isomiR example 2 of SEQ ID NO: 166 | — |
| 612 | isomiR example 1 of SEQ ID NO: 167 | — |
| 613 | isomiR example 2 of SEQ ID NO: 167 | — |
| 614 | isomiR example 1 of SEQ ID NO: 173 | — |
| 615 | isomiR example 2 of SEQ ID NO: 173 | — |
| 616 | isomiR example 1 of SEQ ID NO: 174 | — |
| 617 | isomiR example 2 of SEQ ID NO: 174 | — |
| 618 | isomiR example 1 of SEQ ID NO: 178 | — |
| 619 | isomiR example 2 of SEQ ID NO: 178 | — |
| 620 | isomiR example 1 of SEQ ID NO: 182 | — |
| 621 | isomiR example 2 of SEQ ID NO: 182 | — |
| 622 | isomiR example 1 of SEQ ID NO: 183 | — |
| 623 | isomiR example 2 of SEQ ID NO: 183 | — |
| 624 | isomiR example 1 of SEQ ID NO: 184 | — |
| 625 | isomiR example 2 of SEQ ID NO: 184 | — |
| 626 | isomiR example 1 of SEQ ID NO: 185 | — |
| 627 | isomiR example 2 of SEQ ID NO: 185 | — |
| 628 | isomiR example 1 of SEQ ID NO: 186 | — |
| 629 | isomiR example 2 of SEQ ID NO: 186 | — |
| 630 | isomiR example 1 of SEQ ID NO: 187 | — |
| 631 | isomiR example 2 of SEQ ID NO: 187 | — |
| 632 | isomiR example 1 of SEQ ID NO: 188 | — |
| 633 | isomiR example 2 of SEQ ID NO: 188 | — |
| 634 | isomiR example 1 of SEQ ID NO: 189 | — |
| 635 | isomiR example 2 of SEQ ID NO: 189 | — |
| 636 | isomiR example 1 of SEQ ID NO: 190 | — |
| 637 | isomiR example 2 of SEQ ID NO: 190 | — |
| 638 | isomiR example 1 of SEQ ID NO: 191 | — |
| 639 | isomiR example 2 of SEQ ID NO: 191 | — |
| 640 | isomiR example 1 of SEQ ID NO: 193 | — |
| 641 | isomiR example 2 of SEQ ID NO: 193 | — |
| 642 | isomiR example 1 of SEQ ID NO: 194 | — |
| 643 | isomiR example 2 of SEQ ID NO: 194 | — |
| 644 | isomiR example 1 of SEQ ID NO: 196 | — |
| 645 | isomiR example 2 of SEQ ID NO: 196 | — |
| 646 | isomiR example 1 of SEQ ID NO: 199 | — |
| 647 | isomiR example 2 of SEQ ID NO: 199 | — |
| 648 | isomiR example 1 of SEQ ID NO: 201 | — |
| 649 | isomiR example 2 of SEQ ID NO: 201 | — |
| 650 | isomiR example 1 of SEQ ID NO: 203 | — |
| 651 | isomiR example 2 of SEQ ID NO: 203 | — |
| 652 | isomiR example 1 of SEQ ID NO: 204 | — |
| 653 | isomiR example 2 of SEQ ID NO: 204 | — |
| 654 | isomiR example 1 of SEQ ID NO: 205 | — |
| 655 | isomiR example 2 of SEQ ID NO: 205 | — |
| 656 | isomiR example 1 of SEQ ID NO: 207 | — |
| 657 | isomiR example 2 of SEQ ID NO: 207 | — |
| 658 | isomiR example 1 of SEQ ID NO: 209 | — |
| 659 | isomiR example 2 of SEQ ID NO: 209 | — |
| 660 | isomiR example 1 of SEQ ID NO: 210 | — |
| 661 | isomiR example 2 of SEQ ID NO: 210 | — |
| 662 | isomiR example 1 of SEQ ID NO: 211 | — |
| 663 | isomiR example 2 of SEQ ID NO: 211 | — |
| 664 | isomiR example 1 of SEQ ID NO: 212 | — |
| 665 | isomiR example 2 of SEQ ID NO: 212 | — |
| 666 | hsa-miR-6717-5p | MIMAT0025846 |
| 667 | hsa-miR-3648 | MIMAT0018068 |
| 668 | hsa-miR-3162-5p | MIMAT0015036 |
| 669 | hsa-miR-1909-3p | MIMAT0007883 |
| 670 | hsa-miR-8073 | MIMAT0031000 |
| 671 | hsa-miR-6769b-5p | MIMAT0027620 |
| 672 | hsa-miR-6836-3p | MIMAT0027575 |
| 673 | hsa-miR-4484 | MIMAT0019018 |
| 674 | hsa-miR-6819-5p | MIMAT0027538 |
| 675 | hsa-miR-6794-5p | MIMAT0027488 |
| 676 | hsa-miR-24-3p | MIMAT0000080 |
| 677 | hsa-mir-6717 | MI0022551 |
| 678 | hsa-mir-3648 | MI0016048 |
| 679 | hsa-mir-3162 | MI0014192 |
| 680 | hsa-mir-1909 | MI0008330 |
| 681 | hsa-mir-8073 | MI0025909 |
| 682 | hsa-mir-6769b | MI0022706 |
| 683 | hsa-mir-6836 | MI0022682 |
| 684 | hsa-mir-4484 | MI0016845 |
| 685 | hsa-mir-6819 | MI0022664 |
| 686 | hsa-mir-6794 | MI0022639 |
| 687 | hsa-mir-24-1 | MI0000080 |
| 688 | hsa-mir-24-2 | MI0000081 |
| 689 | isomiR example 1 of SEQ ID NO: 666 | — |
| 690 | isomiR example 2 of SEQ ID NO: 666 | — |
| 691 | isomiR example 1 of SEQ ID NO: 667 | — |
| 692 | isomiR example 2 of SEQ ID NO: 667 | — |
| 693 | isomiR example 1 of SEQ ID NO: 668 | — |
| 694 | isomiR example 2 of SEQ ID NO: 668 | — |
| 695 | isomiR example 1 of SEQ ID NO: 669 | — |
| 696 | isomiR example 2 of SEQ ID NO: 669 | — |
| 697 | isomiR example 1 of SEQ ID NO: 673 | — |
| 698 | isomiR example 2 of SEQ ID NO: 673 | — |
| 699 | isomiR example 1 of SEQ ID NO: 676 | — |
| 700 | isomiR example 2 of SEQ ID NO: 676 | — |

The present specification encompasses the contents described in the specifications and/or drawings of Japanese Patent Application No. 2014-125036 and No. 2015-070379 from which the present application claims priority.

Advantageous Effect of Invention

According to the present invention, esophageal cancer can be detected easily and high accuracy. For example, the presence or absence of esophageal cancer in a patient can be easily detected by using, as indicators, the determined expression levels of several miRNAs in blood, serum, and/or plasma of the patients, which can be collected with limited invasiveness.

BRIEF DESCRIPTION OF DRAWINGS

FIG. 4 (schematic B) discriminant scores obtained from the discriminant prepared for the training cohort as to the expression level measurement values of hsa-miR-204-3p (SEQ ID NO: 1), hsa-miR-6726-5p (SEQ ID NO: 5), hsa-miR-4723-5p (SEQ ID NO: 85), hsa-miR-1343-5p (SEQ ID NO: 138), hsa-miR-4739 (SEQ ID NO: 166), and hsa-miR-6717-5p (SEQ ID NO: 666) in 16 esophageal cancer patients, 47 healthy subjects, 30 pancreatic cancer patients, 33 bile duct cancer patients, 20 colorectal cancer patients, 17 stomach cancer patients, 20 liver cancer patients, and 6 benign pancreaticobiliary disease patients selected as validation cohort were plotted on the ordinate against the sample groups on the abscissa. The dotted line in the diagram depicts the discriminant boundary that offered a discriminant score of 0 and discriminated between both of the groups.

DESCRIPTION OF EMBODIMENTS

Figure 1:
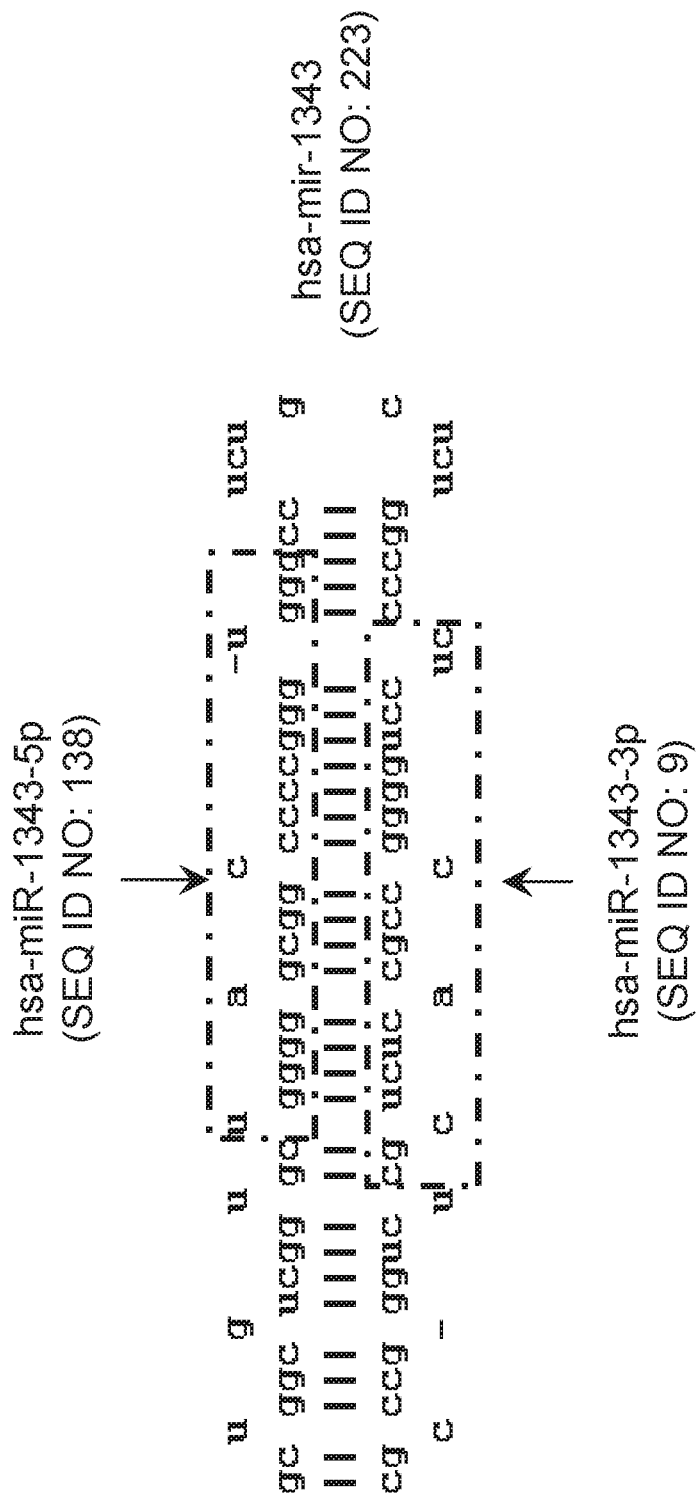
FIG. 1 This figure shows the relationship between hsa-miR-1343-3p consisting of a nucleotide sequence represented by SEQ ID NO: 9 and hsa-miR-1343-5p consisting of a nucleotide sequence represented by SEQ ID NO: 138, which are produced from a precursor hsa-mir-1343 consisting of a nucleotide sequence represented by SEQ ID NO: 223.

Hereinafter, the present invention will be further described in detail specifically.

1. Target Nucleic Acid for Esophageal Cancer

Primary target nucleic acids that can be used as esophageal cancer markers for detecting the presence and/or absence of esophageal cancer or esophageal cancer cells using the nucleic acid probe or the primer for the detection of esophageal cancer defined above according to the present invention is at least one miRNAs selected from the group consisting of the following miRNAs: hsa-miR-204-3p, hsa-miR-1247-3p, hsa-miR-6875-5p, hsa-miR-6857-5p, hsa-miR-6726-5p, hsa-miR-3188, hsa-miR-8069, hsa-miR-4257, hsa-miR-1343-3p, hsa-miR-7108-5p, hsa-miR-6825-5p, hsa-miR-7641, hsa-miR-3185, hsa-miR-4746-3p, hsa-miR-6791-5p, hsa-miR-6893-5p, hsa-miR-4433b-3p, hsa-miR-3135b, hsa-miR-6781-5p, hsa-miR-1908-5p, hsa-miR-4792, hsa-miR-7845-5p, hsa-miR-4417, hsa-miR-3184-5p, hsa-miR-1225-5p, hsa-miR-1231, hsa-miR-1225-3p, hsa-miR-150-3p, hsa-miR-4433-3p, hsa-miR-6125, hsa-miR-4513, hsa-miR-6787-5p, hsa-miR-6784-5p, hsa-miR-615-5p, hsa-miR-6765-3p, hsa-miR-5572, hsa-miR-6842-5p, hsa-miR-8063, hsa-miR-6780b-5p, hsa-miR-187-5p, hsa-miR-128-1-5p, hsa-miR-6729-5p, hsa-miR-6741-5p, hsa-miR-6757-5p, hsa-miR-7110-5p, hsa-miR-7975, hsa-miR-1233-5p, hsa-miR-6845-5p, hsa-miR-3937, hsa-miR-4467, hsa-miR-7109-5p, hsa-miR-6088, hsa-miR-6782-5p, hsa-miR-5195-3p, hsa-miR-4454, hsa-miR-6724-5p, hsa-miR-8072, hsa-miR-4516, hsa-miR-6756-5p, hsa-miR-4665-3p, hsa-miR-6826-5p, hsa-miR-6820-5p, hsa-miR-6887-5p, hsa-miR-3679-5p, hsa-miR-7847-3p, hsa-miR-6721-5p, hsa-miR-3622a-5p, hsa-miR-939-5p, hsa-miR-602, hsa-miR-7977, hsa-miR-6749-5p, hsa-miR-1914-3p, hsa-miR-4651, hsa-miR-4695-5p, hsa-miR-6848-5p, hsa-miR-1228-3p, hsa-miR-642b-3p, hsa-miR-6746-5p, hsa-miR-3620-5p, hsa-miR-3131, hsa-miR-6732-5p, hsa-miR-7113-3p, hsa-miR-23a-3p, hsa-miR-3154, hsa-miR-4723-5p, hsa-miR-3663-3p, hsa-miR-4734, hsa-miR-6816-5p, hsa-miR-4442, hsa-miR-4476, hsa-miR-423-5p, hsa-miR-1249, hsa-miR-6515-3p, hsa-miR-887-3p, hsa-miR-4741, hsa-miR-6766-3p, hsa-miR-4673, hsa-miR-6779-5p, hsa-miR-4706, hsa-miR-1268b, hsa-miR-4632-5p, hsa-miR-3197, hsa-miR-6798-5p, hsa-miR-711, hsa-miR-6840-3p, hsa-miR-6763-5p, hsa-miR-6727-5p, hsa-miR-371a-5p, hsa-miR-6824-5p, hsa-miR-4648, hsa-miR-1227-5p, hsa-miR-564, hsa-miR-3679-3p, hsa-miR-2861, hsa-miR-6737-5p, hsa-miR-4725-3p, hsa-miR-6716-5p, hsa-miR-4675, hsa-miR-1915-3p, hsa-miR-671-5p, hsa-miR-3656, hsa-miR-6722-3p, hsa-miR-4707-5p, hsa-miR-4449, hsa-miR-1202, hsa-miR-4649-5p, hsa-miR-744-5p, hsa-miR-642a-3p, hsa-miR- 451a, hsa-miR-6870-5p, hsa-miR-4443, hsa-miR-6808-5p, hsa-miR-4728-5p, hsa-miR-937-5p, hsa-miR-135a-3p, hsa-miR-663b, hsa-miR-1343-5p, hsa-miR-6822-5p, hsa-miR-6803-5p, hsa-miR-6805-3p, hsa-miR-128-2-5p, hsa-miR-4640-5p, hsa-miR-1469, hsa-miR-92a-2-5p, hsa-miR-3940-5p, hsa-miR-4281, hsa-miR-1260b, hsa-miR-4758-5p, hsa-miR-1915-5p, hsa-miR-5001-5p, hsa-miR-4286, hsa-miR-6126, hsa-miR-6789-5p, hsa-miR-4459, hsa-miR-1268a, hsa-miR-6752-5p, hsa-miR-6131, hsa-miR-6800-5p, hsa-miR-4532, hsa-miR-6872-3p, hsa-miR-718, hsa-miR-6769a-5p, hsa-miR-4707-3p, hsa-miR-6765-5p, hsa-miR-4739, hsa-miR-4525, hsa-miR-4270, hsa-miR-4534, hsa-miR-6785-5p, hsa-miR-6850-5p, hsa-miR-4697-5p, hsa-miR-1260a, hsa-miR-4486, hsa-miR-6880-5p, hsa-miR-6802-5p, hsa-miR-6861-5p, hsa-miR-92b-5p, hsa-miR-1238-5p, hsa-miR-6851-5p, hsa-miR-7704, hsa-miR-149-3p, hsa-miR-4689, hsa-miR-4688, hsa-miR-125a-3p, hsa-miR-23b-3p, hsa-miR-614, hsa-miR-1913, hsa-miR-16-5p, hsa-miR-6717-5p, hsa-miR-3648, hsa-miR-3162-5p, hsa-miR-1909-3p, hsa-miR-8073, hsa-miR-6769b-5p, hsa-miR-6836-3p, hsa-miR-4484, hsa-miR-6819-5p, and hsa-miR-6794-5p. Furthermore, miRNAs selected from other esophageal cancer markers that can be combined with these miRNAs, i.e., hsa-miR-575 and hsa-miR-24-3p, can also be preferably used as a target nucleic acid. Moreover, at least one miRNA selected from the group consisting of the following other esophageal cancer markers that can be combined with these miRNAs, i.e., hsa-miR-675-5p, hsa-miR-486-3p, hsa-miR-6777-5p, hsa-miR-4497, hsa-miR-296-3p, hsa-miR-6738-5p, hsa-miR-4731-5p, hsa-miR-6889-5p, hsa-miR-6786-5p, hsa-miR-92a-3p, hsa-miR-4294, hsa-miR-4763-3p, hsa-miR-6076, hsa-miR-663a, hsa-miR-760, hsa-miR-4667-5p, hsa-miR-6090, hsa-miR-4730, hsa-miR-7106-5p, hsa-miR-3196, hsa-miR-5698, hsa-miR-6087, hsa-miR-4665-5p, hsa-miR-8059 and hsa-miR-6879-5p can also be preferably used as target nucleic acids.

These miRNAs include, for example, a human gene comprising a nucleotide sequence represented by any of SEQ ID NOs: 1 to 214 and 666 to 676 (i.e., hsa-miR-204-3p, hsa-miR-1247-3p, hsa-miR-6875-5p, hsa-miR-6857-5p, hsa-miR-6726-5p, hsa-miR-3188, hsa-miR-8069, hsa-miR-4257, hsa-miR-1343-3p, hsa-miR-7108-5p, hsa-miR-6825-5p, hsa-miR-7641, hsa-miR-3185, hsa-miR-4746-3p, hsa-miR-6791-5p, hsa-miR-6893-5p, hsa-miR-4433b-3p, hsa-miR-3135b, hsa-miR-6781-5p, hsa-miR-1908-5p, hsa-miR-4792, hsa-miR-7845-5p, hsa-miR-4417, hsa-miR-3184-5p, hsa-miR-1225-5p, hsa-miR-1231, hsa-miR-1225-3p, hsa-miR-150-3p, hsa-miR-4433-3p, hsa-miR-6125, hsa-miR-4513, hsa-miR-6787-5p, hsa-miR-6784-5p, hsa-miR-615-5p, hsa-miR-6765-3p, hsa-miR-5572, hsa-miR-6842-5p, hsa-miR-8063, hsa-miR-6780b-5p, hsa-miR-187-5p, hsa-miR-128-1-5p, hsa-miR-6729-5p, hsa-miR-6741-5p, hsa-miR-6757-5p, hsa-miR-7110-5p, hsa-miR-7975, hsa-miR-1233-5p, hsa-miR-6845-5p, hsa-miR-3937, hsa-miR-4467, hsa-miR-7109-5p, hsa-miR-6088, hsa-miR-6782-5p, hsa-miR-5195-3p, hsa-miR-4454, hsa-miR-6724-5p, hsa-miR-8072, hsa-miR-4516, hsa-miR-6756-5p, hsa-miR-4665-3p, hsa-miR-6826-5p, hsa-miR-6820-5p, hsa-miR-6887-5p, hsa-miR-3679-5p, hsa-miR-7847-3p, hsa-miR-6721-5p, hsa-miR-3622a-5p, hsa-miR-939-5p, hsa-miR-602, hsa-miR-7977, hsa-miR-6749-5p, hsa-miR-1914-3p, hsa-miR-4651, hsa-miR-4695-5p, hsa-miR-6848-5p, hsa-miR-1228-3p, hsa-miR-642b-3p, hsa-miR-6746-5p, hsa-miR-3620-5p, hsa-miR-3131, hsa-miR-6732-5p, hsa-miR-7113-3p, hsa-miR-23a-3p, hsa-miR-3154, hsa-miR-4723-5p, hsa-miR-3663-3p, hsa-miR-4734, hsa-miR-6816-5p, hsa-miR-4442, hsa-miR-4476, hsa-miR-423-5p, hsa-miR-1249, hsa-miR-6515-3p, hsa-miR-887-3p, hsa-miR-4741, hsa-miR-6766-3p, hsa-miR-4673, hsa-miR-6779-5p, hsa-miR-4706, hsa-miR-1268b, hsa-miR-4632-5p, hsa-miR-3197, hsa-miR-6798-5p, hsa-miR-711, hsa-miR-6840-3p, hsa-miR-6763-5p, hsa-miR-6727-5p, hsa-miR-371a-5p, hsa-miR-6824-5p, hsa-miR-4648, hsa-miR-1227-5p, hsa-miR-564, hsa-miR-3679-3p, hsa-miR-2861, hsa-miR-6737-5p, hsa-miR-4725-3p, hsa-miR-6716-5p, hsa-miR-4675, hsa-miR-1915-3p, hsa-miR-671-5p, hsa-miR-3656, hsa-miR-6722-3p, hsa-miR-4707-5p, hsa-miR-4449, hsa-miR-1202, hsa-miR-4649-5p, hsa-miR-744-5p, hsa-miR-642a-3p, hsa-miR-451a, hsa-miR-6870-5p, hsa-miR-4443, hsa-miR-6808-5p, hsa-miR-4728-5p, hsa-miR-937-5p, hsa-miR-135a-3p, hsa-miR-663b, hsa-miR-1343-5p, hsa-miR-6822-5p, hsa-miR-6803-5p, hsa-miR-6805-3p, hsa-miR-128-2-5p, hsa-miR-4640-5p, hsa-miR-1469, hsa-miR-92a-2-5p, hsa-miR-3940-5p, hsa-miR-4281, hsa-miR-1260b, hsa-miR-4758-5p, hsa-miR-1915-5p, hsa-miR-5001-5p, hsa-miR-4286, hsa-miR-6126, hsa-miR-6789-5p, hsa-miR-4459, hsa-miR-1268a, hsa-miR-6752-5p, hsa-miR-6131, hsa-miR-6800-5p, hsa-miR-4532, hsa-miR-6872-3p, hsa-miR-718, hsa-miR-6769a-5p, hsa-miR-4707-3p, hsa-miR-6765-5p, hsa-miR-4739, hsa-miR-4525, hsa-miR-4270, hsa-miR-4534, hsa-miR-6785-5p, hsa-miR-6850-5p, hsa-miR-4697-5p, hsa-miR-1260a, hsa-miR-4486, hsa-miR-6880-5p, hsa-miR-6802-5p, hsa-miR-6861-5p, hsa-miR-92b-5p, hsa-miR-1238-5p, hsa-miR-6851-5p, hsa-miR-7704, hsa-miR-149-3p, hsa-miR-4689, hsa-miR-4688, hsa-miR-125a-3p, hsa-miR-23b-3p, hsa-miR-614, hsa-miR-1913, hsa-miR-16-5p, hsa-miR-6717-5p, hsa-miR-3648, hsa-miR-3162-5p, hsa-miR-1909-3p, hsa-miR-8073, hsa-miR-6769b-5p, hsa-miR-6836-3p, hsa-miR-4484, hsa-miR-6819-5p, hsa-miR-6794-5p hsa-miR-575, hsa-miR-24-3p, hsa-miR-675-5p, hsa-miR-486-3p, hsa-miR-6777-5p, hsa-miR-4497, hsa-miR-296-3p, hsa-miR-6738-5p, hsa-miR-4731-5p, hsa-miR-6889-5p, hsa-miR-6786-5p, hsa-miR-92a-3p, hsa-miR-4294, hsa-miR-4763-3p, hsa-miR-6076, hsa-miR-663a, hsa-miR-760, hsa-miR-4667-5p, hsa-miR-6090, hsa-miR-4730, hsa-miR-7106-5p, hsa-miR-3196, hsa-miR-5698, hsa-miR-6087, hsa-miR-4665-5p, hsa-miR-8059 and hsa-miR-6879-5p, respectively), a congener thereof, a transcript thereof, and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 700 or a transcript thereof, more preferably the transcript, i.e., a miRNA or its precursor RNA (pri-miRNA or pre-miRNA).

The first target gene is the hsa-miR-204-3p gene, a congener thereof, a transcript thereof, or a variant or a derivative thereof. None of the previously known reports show that change in the expression of the gene or the transcript thereof can serve as a marker for esophageal cancer.

The second target gene is the hsa-miR-1247-3p gene, a congener thereof, a transcript thereof, or a variant or a derivative thereof. None of the previously known reports show that change in the expression of the gene or the transcript thereof can serve as a marker for esophageal cancer.

The third target gene is the hsa-miR-6875-5p gene, a congener thereof, a transcript thereof, or a variant or a derivative thereof. None of the previously known reports show that change in the expression of the gene or the transcript thereof can serve as a marker for esophageal cancer.

The fourth target gene is the hsa-miR-6857-5p gene, a congener thereof, a transcript thereof, or a variant or a derivative thereof. None of the previously known reports show that change in the expression of the gene or the transcript thereof can serve as a marker for esophageal cancer.

The fifth target gene is the hsa-miR-6726-5p gene, a congener thereof, a transcript thereof, or a variant or a derivative thereof. None of the previously known reports show that change in the expression of the gene or the transcript thereof can serve as a marker for esophageal cancer.

The sixth target gene is the hsa-miR-3188 gene, a congener thereof, a transcript thereof, or a variant or a derivative thereof. None of the previously known reports show that change in the expression of the gene or the transcript thereof can serve as a marker for esophageal cancer.

The seventh target gene is the hsa-miR-8069 gene, a congener thereof, a transcript thereof, or a variant or a derivative thereof. None of the previously known reports show that change in the expression of the gene or the transcript thereof can serve as a marker for esophageal cancer.

The eighth target gene is the hsa-miR-4257 gene, a congener thereof, a transcript thereof, or a variant or a derivative thereof. None of the previously known reports show that change in the expression of the gene or the transcript thereof can serve as a marker for esophageal cancer.

The ninth target gene is the hsa-miR-1343-3p gene, a congener thereof, a transcript thereof, or a variant or a derivative thereof. None of the previously known reports show that change in the expression of the gene or the transcript thereof can serve as a marker for esophageal cancer.

The 10th target gene is the hsa-miR-7108-5p gene, a congener thereof, a transcript thereof, or a variant or a derivative thereof. None of the previously known reports show that change in the expression of the gene or the transcript thereof can serve as a marker for esophageal cancer.

The 11th target gene is the hsa-miR-6825-5p gene, a congener thereof, a transcript thereof, or a variant or a derivative thereof. None of the previously known reports show that change in the expression of the gene or the transcript thereof can serve as a marker for esophageal cancer.

The 12th target gene is the hsa-miR-7641 gene, a congener thereof, a transcript thereof, or a variant or a derivative thereof. None of the previously known reports show that change in the expression of the gene or the transcript thereof can serve as a marker for esophageal cancer.

The 13th target gene is the hsa-miR-3185 gene, a congener thereof, a transcript thereof, or a variant or a derivative thereof. None of the previously known reports show that change in the expression of the gene or the transcript thereof can serve as a marker for esophageal cancer.

The 14th target gene is the hsa-miR-4746-3p gene, a congener thereof, a transcript thereof, or a variant or a derivative thereof. None of the previously known reports show that change in the expression of the gene or the transcript thereof can serve as a marker for esophageal cancer.

The 15th target gene is the hsa-miR-6791-5p gene, a congener thereof, a transcript thereof, or a variant or a derivative thereof. None of the previously known reports show that change in the expression of the gene or the transcript thereof can serve as a marker for esophageal cancer.

The 16th target gene is the hsa-miR-6893-5p gene, a congener thereof, a transcript thereof, or a variant or a derivative thereof. None of the previously known reports show that change in the expression of the gene or the transcript thereof can serve as a marker for esophageal cancer.

The 17th target gene is the hsa-miR-4433b-3p gene, a congener thereof, a transcript thereof, or a variant or a derivative thereof. None of the previously known reports show that change in the expression of the gene or the transcript thereof can serve as a marker for esophageal cancer.

The 18th target gene is the hsa-miR-3135b gene, a congener thereof, a transcript thereof, or a variant or a derivative thereof. None of the previously known reports show that change in the expression of the gene or the transcript thereof can serve as a marker for esophageal cancer.

The 19th target gene is the hsa-miR-6781-5p gene, a congener thereof, a transcript thereof, or a variant or a derivative thereof. None of the previously known reports show that change in the expression of the gene or the transcript thereof can serve as a marker for esophageal cancer.

The 20th target gene is the hsa-miR-1908-5p gene, a congener thereof, a transcript thereof, or a variant or a derivative thereof. None of the previously known reports show that change in the expression of the gene or the transcript thereof can serve as a marker for esophageal cancer.

The 21st target gene is the hsa-miR-4792 gene, a congener thereof, a transcript thereof, or a variant or a derivative thereof. None of the previously known reports show that change in the expression of the gene or the transcript thereof can serve as a marker for esophageal cancer.

The 22nd target gene is the hsa-miR-7845-5p gene, a congener thereof, a transcript thereof, or a variant or a derivative thereof. None of the previously known reports show that change in the expression of the gene or the transcript thereof can serve as a marker for esophageal cancer.

The 23rd target gene is the hsa-miR-4417 gene, a congener thereof, a transcript thereof, or a variant or a derivative thereof. None of the previously known reports show that change in the expression of the gene or the transcript thereof can serve as a marker for esophageal cancer.

The 24th target gene is the hsa-miR-3184-5p gene, a congener thereof, a transcript thereof, or a variant or a derivative thereof. None of the previously known reports show that change in the expression of the gene or the transcript thereof can serve as a marker for esophageal cancer.

The 25th target gene is the hsa-miR-1225-5p gene, a congener thereof, a transcript thereof, or a variant or a derivative thereof. None of the previously known reports show that change in the expression of the gene or the transcript thereof can serve as a marker for esophageal cancer.

The 26th target gene is the hsa-miR-1231 gene, a congener thereof, a transcript thereof, or a variant or a derivative thereof. None of the previously known reports show that change in the expression of the gene or the transcript thereof can serve as a marker for esophageal cancer.

The 27th target gene is the hsa-miR-1225-3p gene, a congener thereof, a transcript thereof, or a variant or a derivative thereof. None of the previously known reports show that change in the expression of the gene or the transcript thereof can serve as a marker for esophageal cancer.

The 28th target gene is the hsa-miR-150-3p gene, a congener thereof, a transcript thereof, or a variant or a derivative thereof. None of the previously known reports show that change in the expression of the gene or the transcript thereof can serve as a marker for esophageal cancer.

The 29th target gene is the hsa-miR-4433-3p gene, a congener thereof, a transcript thereof, or a variant or a derivative thereof. None of the previously known reports show that change in the expression of the gene or the transcript thereof can serve as a marker for esophageal cancer.

The 30th target gene is the hsa-miR-6125 gene, a congener thereof, a transcript thereof, or a variant or a derivative thereof. None of the previously known reports show that change in the expression of the gene or the transcript thereof can serve as a marker for esophageal cancer.

The 31st target gene is the hsa-miR-4513 gene, a congener thereof, a transcript thereof, or a variant or a derivative thereof. None of the previously known reports show that change in the expression of the gene or the transcript thereof can serve as a marker for esophageal cancer.

The 32nd target gene is the hsa-miR-6787-5p gene, a congener thereof, a transcript thereof, or a variant or a derivative thereof. None of the previously known reports show that change in the expression of the gene or the transcript thereof can serve as a marker for esophageal cancer.

The 33rd target gene is the hsa-miR-6784-5p gene, a congener thereof, a transcript thereof, or a variant or a derivative thereof. None of the previously known reports show that change in the expression of the gene or the transcript thereof can serve as a marker for esophageal cancer.

The 34th target gene is the hsa-miR-615-5p gene, a congener thereof, a transcript thereof, or a variant or a derivative thereof. None of the previously known reports show that change in the expression of the gene or the transcript thereof can serve as a marker for esophageal cancer.

The 35th target gene is the hsa-miR-6765-3p gene, a congener thereof, a transcript thereof, or a variant or a derivative thereof. None of the previously known reports show that change in the expression of the gene or the transcript thereof can serve as a marker for esophageal cancer.

The 36th target gene is the hsa-miR-5572 gene, a congener thereof, a transcript thereof, or a variant or a derivative thereof. None of the previously known reports show that change in the expression of the gene or the transcript thereof can serve as a marker for esophageal cancer.

The 37th target gene is the hsa-miR-6842-5p gene, a congener thereof, a transcript thereof, or a variant or a derivative thereof. None of the previously known reports show that change in the expression of the gene or the transcript thereof can serve as a marker for esophageal cancer.

The 38th target gene is the hsa-miR-8063 gene, a congener thereof, a transcript thereof, or a variant or a derivative thereof. None of the previously known reports show that change in the expression of the gene or the transcript thereof can serve as a marker for esophageal cancer.

The 39th target gene is the hsa-miR-6780b-5p gene, a congener thereof, a transcript thereof, or a variant or a derivative thereof. None of the previously known reports show that change in the expression of the gene or the transcript thereof can serve as a marker for esophageal cancer.

The 40th target gene is the hsa-miR-187-5p gene, a congener thereof, a transcript thereof, or a variant or a derivative thereof. None of the previously known reports show that change in the expression of the gene or the transcript thereof can serve as a marker for esophageal cancer.

The 41st target gene is the hsa-miR-128-1-5p gene, a congener thereof, a transcript thereof, or a variant or a derivative thereof. None of the previously known reports show that change in the expression of the gene or the transcript thereof can serve as a marker for esophageal cancer.

The 42nd target gene is the hsa-miR-6729-5p gene, a congener thereof, a transcript thereof, or a variant or a derivative thereof. None of the previously known reports show that change in the expression of the gene or the transcript thereof can serve as a marker for esophageal cancer.

The 43rd target gene is the hsa-miR-6741-5p gene, a congener thereof, a transcript thereof, or a variant or a derivative thereof. None of the previously known reports show that change in the expression of the gene or the transcript thereof can serve as a marker for esophageal cancer.

The 44th target gene is the hsa-miR-6757-5p gene, a congener thereof, a transcript thereof, or a variant or a derivative thereof. None of the previously known reports show that change in the expression of the gene or the transcript thereof can serve as a marker for esophageal cancer.

The 45th target gene is the hsa-miR-7110-5p gene, a congener thereof, a transcript thereof, or a variant or a derivative thereof. None of the previously known reports show that change in the expression of the gene or the transcript thereof can serve as a marker for esophageal cancer.

The 46th target gene is the hsa-miR-7975 gene, a congener thereof, a transcript thereof, or a variant or a derivative thereof. None of the previously known reports show that change in the expression of the gene or the transcript thereof can serve as a marker for esophageal cancer.

The 47th target gene is the hsa-miR-1233-5p gene, a congener thereof, a transcript thereof, or a variant or a derivative thereof. None of the previously known reports show that change in the expression of the gene or the transcript thereof can serve as a marker for esophageal cancer.

The 48th target gene is the hsa-miR-6845-5p gene, a congener thereof, a transcript thereof, or a variant or a derivative thereof. None of the previously known reports show that change in the expression of the gene or the transcript thereof can serve as a marker for esophageal cancer.

The 49th target gene is the hsa-miR-3937 gene, a congener thereof, a transcript thereof, or a variant or a derivative thereof. None of the previously known reports show that change in the expression of the gene or the transcript thereof can serve as a marker for esophageal cancer.

The 50th target gene is the hsa-miR-4467 gene, a congener thereof, a transcript thereof, or a variant or a derivative thereof. None of the previously known reports show that change in the expression of the gene or the transcript thereof can serve as a marker for esophageal cancer.

The 51st target gene is the hsa-miR-7109-5p gene, a congener thereof, a transcript thereof, or a variant or a derivative thereof. None of the previously known reports show that change in the expression of the gene or the transcript thereof can serve as a marker for esophageal cancer.

The 52nd target gene is the hsa-miR-6088 gene, a congener thereof, a transcript thereof, or a variant or a derivative thereof. None of the previously known reports show that change in the expression of the gene or the transcript thereof can serve as a marker for esophageal cancer.

The 53rd target gene is the hsa-miR-6782-5p gene, a congener thereof, a transcript thereof, or a variant or a derivative thereof. None of the previously known reports show that change in the expression of the gene or the transcript thereof can serve as a marker for esophageal cancer.

The 54th target gene is the hsa-miR-5195-3p gene, a congener thereof, a transcript thereof, or a variant or a derivative thereof. None of the previously known reports show that change in the expression of the gene or the transcript thereof can serve as a marker for esophageal cancer.

The 55th target gene is the hsa-miR-4454 gene, a congener thereof, a transcript thereof, or a variant or a derivative thereof. None of the previously known reports show that change in the expression of the gene or the transcript thereof can serve as a marker for esophageal cancer.

The 56th target gene is the hsa-miR-6724-5p gene, a congener thereof, a transcript thereof, or a variant or a derivative thereof. None of the previously known reports show that change in the expression of the gene or the transcript thereof can serve as a marker for esophageal cancer.

The 57th target gene is the hsa-miR-8072 gene, a congener thereof, a transcript thereof, or a variant or a derivative thereof. None of the previously known reports show that change in the expression of the gene or the transcript thereof can serve as a marker for esophageal cancer.

The 58th target gene is the hsa-miR-4516 gene, a congener thereof, a transcript thereof, or a variant or a derivative thereof. None of the previously known reports show that change in the expression of the gene or the transcript thereof can serve as a marker for esophageal cancer.

The 59th target gene is the hsa-miR-6756-5p gene, a congener thereof, a transcript thereof, or a variant or a derivative thereof. None of the previously known reports show that change in the expression of the gene or the transcript thereof can serve as a marker for esophageal cancer.

The 60th target gene is the hsa-miR-4665-3p gene, a congener thereof, a transcript thereof, or a variant or a derivative thereof. None of the previously known reports show that change in the expression of the gene or the transcript thereof can serve as a marker for esophageal cancer.

The 61st target gene is the hsa-miR-6826-5p gene, a congener thereof, a transcript thereof, or a variant or a derivative thereof. None of the previously known reports show that change in the expression of the gene or the transcript thereof can serve as a marker for esophageal cancer.

The 62nd target gene is the hsa-miR-6820-5p gene, a congener thereof, a transcript thereof, or a variant or a derivative thereof. None of the previously known reports show that change in the expression of the gene or the transcript thereof can serve as a marker for esophageal cancer.

The 63rd target gene is the hsa-miR-6887-5p gene, a congener thereof, a transcript thereof, or a variant or a derivative thereof. None of the previously known reports show that change in the expression of the gene or the transcript thereof can serve as a marker for esophageal cancer.

The 64th target gene is the hsa-miR-3679-5p gene, a congener thereof, a transcript thereof, or a variant or a derivative thereof. None of the previously known reports show that change in the expression of the gene or the transcript thereof can serve as a marker for esophageal cancer.

The 65th target gene is the hsa-miR-7847-3p gene, a congener thereof, a transcript thereof, or a variant or a derivative thereof. None of the previously known reports show that change in the expression of the gene or the transcript thereof can serve as a marker for esophageal cancer.

The 66th target gene is the hsa-miR-6721-5p gene, a congener thereof, a transcript thereof, or a variant or a derivative thereof. None of the previously known reports show that change in the expression of the gene or the transcript thereof can serve as a marker for esophageal cancer.

The 67th target gene is the hsa-miR-3622a-5p gene, a congener thereof, a transcript thereof, or a variant or a derivative thereof. None of the previously known reports show that change in the expression of the gene or the transcript thereof can serve as a marker for esophageal cancer.

The 68th target gene is the hsa-miR-939-5p gene, a congener thereof, a transcript thereof, or a variant or a derivative thereof. None of the previously known reports show that change in the expression of the gene or the transcript thereof can serve as a marker for esophageal cancer.

The 69th target gene is the hsa-miR-602 gene, a congener thereof, a transcript thereof, or a variant or a derivative thereof. None of the previously known reports show that change in the expression of the gene or the transcript thereof can serve as a marker for esophageal cancer.

The 70th target gene is the hsa-miR-7977 gene, a congener thereof, a transcript thereof, or a variant or a derivative thereof. None of the previously known reports show that change in the expression of the gene or the transcript thereof can serve as a marker for esophageal cancer.

The 71st target gene is the hsa-miR-6749-5p gene, a congener thereof, a transcript thereof, or a variant or a derivative thereof. None of the previously known reports show that change in the expression of the gene or the transcript thereof can serve as a marker for esophageal cancer.

The 72nd target gene is the hsa-miR-1914-3p gene, a congener thereof, a transcript thereof, or a variant or a derivative thereof. None of the previously known reports show that change in the expression of the gene or the transcript thereof can serve as a marker for esophageal cancer.

The 73rd target gene is the hsa-miR-4651 gene, a congener thereof, a transcript thereof, or a variant or a derivative thereof. None of the previously known reports show that change in the expression of the gene or the transcript thereof can serve as a marker for esophageal cancer.

The 74th target gene is the hsa-miR-4695-5p gene, a congener thereof, a transcript thereof, or a variant or a derivative thereof. None of the previously known reports show that change in the expression of the gene or the transcript thereof can serve as a marker for esophageal cancer.

The 75th target gene is the hsa-miR-6848-5p gene, a congener thereof, a transcript thereof, or a variant or a derivative thereof. None of the previously known reports show that change in the expression of the gene or the transcript thereof can serve as a marker for esophageal cancer.

The 76th target gene is the hsa-miR-1228-3p gene, a congener thereof, a transcript thereof, or a variant or a derivative thereof. None of the previously known reports show that change in the expression of the gene or the transcript thereof can serve as a marker for esophageal cancer.

The 77th target gene is the hsa-miR-642b-3p gene, a congener thereof, a transcript thereof, or a variant or a derivative thereof. None of the previously known reports show that change in the expression of the gene or the transcript thereof can serve as a marker for esophageal cancer.

The 78th target gene is the hsa-miR-6746-5p gene, a congener thereof, a transcript thereof, or a variant or a derivative thereof. None of the previously known reports show that change in the expression of the gene or the transcript thereof can serve as a marker for esophageal cancer.

The 79th target gene is the hsa-miR-3620-5p gene, a congener thereof, a transcript thereof, or a variant or a derivative thereof. None of the previously known reports show that change in the expression of the gene or the transcript thereof can serve as a marker for esophageal cancer.

The 80th target gene is the hsa-miR-3131 gene, a congener thereof, a transcript thereof, or a variant or a derivative thereof. None of the previously known reports show that change in the expression of the gene or the transcript thereof can serve as a marker for esophageal cancer.

The 81st target gene is the hsa-miR-6732-5p gene, a congener thereof, a transcript thereof, or a variant or a derivative thereof. None of the previously known reports show that change in the expression of the gene or the transcript thereof can serve as a marker for esophageal cancer.

The 82nd target gene is the hsa-miR-7113-3p gene, a congener thereof, a transcript thereof, or a variant or a derivative thereof. None of the previously known reports show that change in the expression of the gene or the transcript thereof can serve as a marker for esophageal cancer.

The 83rd target gene is the hsa-miR-23a-3p gene, a congener thereof, a transcript thereof, or a variant or a derivative thereof. None of the previously known reports show that change in the expression of the gene or the transcript thereof can serve as a marker for esophageal cancer.

The 84th target gene is the hsa-miR-3154 gene, a congener thereof, a transcript thereof, or a variant or a derivative thereof. None of the previously known reports show that change in the expression of the gene or the transcript thereof can serve as a marker for esophageal cancer.

The 85th target gene is the hsa-miR-4723-5p gene, a congener thereof, a transcript thereof, or a variant or a derivative thereof. None of the previously known reports show that change in the expression of the gene or the transcript thereof can serve as a marker for esophageal cancer.

The 86th target gene is the hsa-miR-3663-3p gene, a congener thereof, a transcript thereof, or a variant or a derivative thereof. None of the previously known reports show that change in the expression of the gene or the transcript thereof can serve as a marker for esophageal cancer.

The 87th target gene is the hsa-miR-4734 gene, a congener thereof, a transcript thereof, or a variant or a derivative thereof. None of the previously known reports show that change in the expression of the gene or the transcript thereof can serve as a marker for esophageal cancer.

The 88th target gene is the hsa-miR-6816-5p gene, a congener thereof, a transcript thereof, or a variant or a derivative thereof. None of the previously known reports show that change in the expression of the gene or the transcript thereof can serve as a marker for esophageal cancer.

The 89th target gene is the hsa-miR-4442 gene, a congener thereof, a transcript thereof, or a variant or a derivative thereof. None of the previously known reports show that change in the expression of the gene or the transcript thereof can serve as a marker for esophageal cancer.

The 90th target gene is the hsa-miR-4476 gene, a congener thereof, a transcript thereof, or a variant or a derivative thereof. None of the previously known reports show that change in the expression of the gene or the transcript thereof can serve as a marker for esophageal cancer.

The 91st target gene is the hsa-miR-423-5p gene, a congener thereof, a transcript thereof, or a variant or a derivative thereof. None of the previously known reports show that change in the expression of the gene or the transcript thereof can serve as a marker for esophageal cancer.

The 92nd target gene is the hsa-miR-1249 gene, a congener thereof, a transcript thereof, or a variant or a derivative thereof. None of the previously known reports show that change in the expression of the gene or the transcript thereof can serve as a marker for esophageal cancer.

The 93rd target gene is the hsa-miR-6515-3p gene, a congener thereof, a transcript thereof, or a variant or a derivative thereof. None of the previously known reports show that change in the expression of the gene or the transcript thereof can serve as a marker for esophageal cancer.

The 94th target gene is the hsa-miR-887-3p gene, a congener thereof, a transcript thereof, or a variant or a derivative thereof. None of the previously known reports show that change in the expression of the gene or the transcript thereof can serve as a marker for esophageal cancer.

The 95th target gene is the hsa-miR-4741 gene, a congener thereof, a transcript thereof, or a variant or a derivative thereof. None of the previously known reports show that change in the expression of the gene or the transcript thereof can serve as a marker for esophageal cancer.

The 96th target gene is the hsa-miR-6766-3p gene, a congener thereof, a transcript thereof, or a variant or a derivative thereof. None of the previously known reports show that change in the expression of the gene or the transcript thereof can serve as a marker for esophageal cancer.

The 97th target gene is the hsa-miR-4673 gene, a congener thereof, a transcript thereof, or a variant or a derivative thereof. None of the previously known reports show that change in the expression of the gene or the transcript thereof can serve as a marker for esophageal cancer.

The 98th target gene is the hsa-miR-6779-5p gene, a congener thereof, a transcript thereof, or a variant or a derivative thereof. None of the previously known reports show that change in the expression of the gene or the transcript thereof can serve as a marker for esophageal cancer.

The 99th target gene is the hsa-miR-4706 gene, a congener thereof, a transcript thereof, or a variant or a derivative thereof. None of the previously known reports show that change in the expression of the gene or the transcript thereof can serve as a marker for esophageal cancer.

The 100th target gene is the hsa-miR-1268b gene, a congener thereof, a transcript thereof, or a variant or a derivative thereof. None of the previously known reports show that change in the expression of the gene or the transcript thereof can serve as a marker for esophageal cancer.

The 101st target gene is the hsa-miR-4632-5p gene, a congener thereof, a transcript thereof, or a variant or a derivative thereof. None of the previously known reports show that change in the expression of the gene or the transcript thereof can serve as a marker for esophageal cancer.

The 102nd target gene is the hsa-miR-3197 gene, a congener thereof, a transcript thereof, or a variant or a derivative thereof. None of the previously known reports show that change in the expression of the gene or the transcript thereof can serve as a marker for esophageal cancer.

The 103rd target gene is the hsa-miR-6798-5p gene, a congener thereof, a transcript thereof, or a variant or a derivative thereof. None of the previously known reports show that change in the expression of the gene or the transcript thereof can serve as a marker for esophageal cancer.

The 104th target gene is the hsa-miR-711 gene, a congener thereof, a transcript thereof, or a variant or a derivative thereof. None of the previously known reports show that change in the expression of the gene or the transcript thereof can serve as a marker for esophageal cancer.

The 105th target gene is the hsa-miR-6840-3p gene, a congener thereof, a transcript thereof, or a variant or a derivative thereof. None of the previously known reports show that change in the expression of the gene or the transcript thereof can serve as a marker for esophageal cancer.

The 106th target gene is the hsa-miR-6763-5p gene, a congener thereof, a transcript thereof, or a variant or a derivative thereof. None of the previously known reports show that change in the expression of the gene or the transcript thereof can serve as a marker for esophageal cancer.

The 107th target gene is the hsa-miR-6727-5p gene, a congener thereof, a transcript thereof, or a variant or a derivative thereof. None of the previously known reports show that change in the expression of the gene or the transcript thereof can serve as a marker for esophageal cancer.

The 108th target gene is the hsa-miR-371a-5p gene, a congener thereof, a transcript thereof, or a variant or a derivative thereof. None of the previously known reports show that change in the expression of the gene or the transcript thereof can serve as a marker for esophageal cancer.

The 109th target gene is the hsa-miR-6824-5p gene, a congener thereof, a transcript thereof, or a variant or a derivative thereof. None of the previously known reports show that change in the expression of the gene or the transcript thereof can serve as a marker for esophageal cancer.

The 110th target gene is the hsa-miR-4648 gene, a congener thereof, a transcript thereof, or a variant or a derivative thereof. None of the previously known reports show that change in the expression of the gene or the transcript thereof can serve as a marker for esophageal cancer.

The 111th target gene is the hsa-miR-1227-5p gene, a congener thereof, a transcript thereof, or a variant or a derivative thereof. None of the previously known reports show that change in the expression of the gene or the transcript thereof can serve as a marker for esophageal cancer.

The 112th target gene is the hsa-miR-564 gene, a congener thereof, a transcript thereof, or a variant or a derivative thereof. None of the previously known reports show that change in the expression of the gene or the transcript thereof can serve as a marker for esophageal cancer.

The 113th target gene is the hsa-miR-3679-3p gene, a congener thereof, a transcript thereof, or a variant or a derivative thereof. None of the previously known reports show that change in the expression of the gene or the transcript thereof can serve as a marker for esophageal cancer.

The 114th target gene is the hsa-miR-2861 gene, a congener thereof, a transcript thereof, or a variant or a derivative thereof. None of the previously known reports show that change in the expression of the gene or the transcript thereof can serve as a marker for esophageal cancer.

The 115th target gene is the hsa-miR-6737-5p gene, a congener thereof, a transcript thereof, or a variant or a derivative thereof. None of the previously known reports show that change in the expression of the gene or the transcript thereof can serve as a marker for esophageal cancer.

The 116th target gene is the hsa-miR-575 gene, a congener thereof, a transcript thereof, or a variant or a derivative thereof. The previously known report shows that change in the expression of the gene or the transcript thereof can serve as a marker for esophageal cancer (Patent Literature 1).

The 117th target gene is the hsa-miR-4725-3p gene, a congener thereof, a transcript thereof, or a variant or a derivative thereof. None of the previously known reports show that change in the expression of the gene or the transcript thereof can serve as a marker for esophageal cancer.

The 118th target gene is the hsa-miR-6716-5p gene, a congener thereof, a transcript thereof, or a variant or a derivative thereof. None of the previously known reports show that change in the expression of the gene or the transcript thereof can serve as a marker for esophageal cancer.

The 119th target gene is the hsa-miR-4675 gene, a congener thereof, a transcript thereof, or a variant or a derivative thereof. None of the previously known reports show that change in the expression of the gene or the transcript thereof can serve as a marker for esophageal cancer.

The 120th target gene is the hsa-miR-1915-3p gene, a congener thereof, a transcript thereof, or a variant or a derivative thereof. None of the previously known reports show that change in the expression of the gene or the transcript thereof can serve as a marker for esophageal cancer.

The 121st target gene is the hsa-miR-671-5p gene, a congener thereof, a transcript thereof, or a variant or a derivative thereof. None of the previously known reports show that change in the expression of the gene or the transcript thereof can serve as a marker for esophageal cancer.

The 122nd target gene is the hsa-miR-3656 gene, a congener thereof, a transcript thereof, or a variant or a derivative thereof. None of the previously known reports show that change in the expression of the gene or the transcript thereof can serve as a marker for esophageal cancer.

The 123rd target gene is the hsa-miR-6722-3p gene, a congener thereof, a transcript thereof, or a variant or a derivative thereof. None of the previously known reports show that change in the expression of the gene or the transcript thereof can serve as a marker for esophageal cancer.

The 124th target gene is the hsa-miR-4707-5p gene, a congener thereof, a transcript thereof, or a variant or a derivative thereof. None of the previously known reports show that change in the expression of the gene or the transcript thereof can serve as a marker for esophageal cancer.

The 125th target gene is the hsa-miR-4449 gene, a congener thereof, a transcript thereof, or a variant or a derivative thereof. None of the previously known reports show that change in the expression of the gene or the transcript thereof can serve as a marker for esophageal cancer.

The 126th target gene is the hsa-miR-1202 gene, a congener thereof, a transcript thereof, or a variant or a derivative thereof. None of the previously known reports show that change in the expression of the gene or the transcript thereof can serve as a marker for esophageal cancer.

The 127th target gene is the hsa-miR-4649-5p gene, a congener thereof, a transcript thereof, or a variant or a derivative thereof. None of the previously known reports show that change in the expression of the gene or the transcript thereof can serve as a marker for esophageal cancer.

The 128th target gene is the hsa-miR-744-5p gene, a congener thereof, a transcript thereof, or a variant or a derivative thereof. None of the previously known reports show that change in the expression of the gene or the transcript thereof can serve as a marker for esophageal cancer.

The 129th target gene is the hsa-miR-642a-3p gene, a congener thereof, a transcript thereof, or a variant or a derivative thereof. None of the previously known reports show that change in the expression of the gene or the transcript thereof can serve as a marker for esophageal cancer.

The 130th target gene is the hsa-miR-451a gene, a congener thereof, a transcript thereof, or a variant or a derivative thereof. None of the previously known reports show that change in the expression of the gene or the transcript thereof can serve as a marker for esophageal cancer.

The 131st target gene is the hsa-miR-6870-5p gene, a congener thereof, a transcript thereof, or a variant or a derivative thereof. None of the previously known reports show that change in the expression of the gene or the transcript thereof can serve as a marker for esophageal cancer.

The 132nd target gene is the hsa-miR-4443 gene, a congener thereof, a transcript thereof, or a variant or a derivative thereof. None of the previously known reports show that change in the expression of the gene or the transcript thereof can serve as a marker for esophageal cancer.

The 133rd target gene is the hsa-miR-6808-5p gene, a congener thereof, a transcript thereof, or a variant or a derivative thereof. None of the previously known reports show that change in the expression of the gene or the transcript thereof can serve as a marker for esophageal cancer.

The 134th target gene is the hsa-miR-4728-5p gene, a congener thereof, a transcript thereof, or a variant or a derivative thereof. None of the previously known reports show that change in the expression of the gene or the transcript thereof can serve as a marker for esophageal cancer.

The 135th target gene is the hsa-miR-937-5p gene, a congener thereof, a transcript thereof, or a variant or a derivative thereof. None of the previously known reports show that change in the expression of the gene or the transcript thereof can serve as a marker for esophageal cancer.

The 136th target gene is the hsa-miR-135a-3p gene, a congener thereof, a transcript thereof, or a variant or a derivative thereof. None of the previously known reports show that change in the expression of the gene or the transcript thereof can serve as a marker for esophageal cancer.

The 137th target gene is the hsa-miR-663b gene, a congener thereof, a transcript thereof, or a variant or a derivative thereof. None of the previously known reports show that change in the expression of the gene or the transcript thereof can serve as a marker for esophageal cancer.

The 138th target gene is the hsa-miR-1343-5p gene, a congener thereof, a transcript thereof, or a variant or a derivative thereof. None of the previously known reports show that change in the expression of the gene or the transcript thereof can serve as a marker for esophageal cancer.

The 139th target gene is the hsa-miR-6822-5p gene, a congener thereof, a transcript thereof, or a variant or a derivative thereof. None of the previously known reports show that change in the expression of the gene or the transcript thereof can serve as a marker for esophageal cancer.

The 140th target gene is the hsa-miR-6803-5p gene, a congener thereof, a transcript thereof, or a variant or a derivative thereof. None of the previously known reports show that change in the expression of the gene or the transcript thereof can serve as a marker for esophageal cancer.

The 141st target gene is the hsa-miR-6805-3p gene, a congener thereof, a transcript thereof, or a variant or a derivative thereof. None of the previously known reports show that change in the expression of the gene or the transcript thereof can serve as a marker for esophageal cancer.

The 142nd target gene is the hsa-miR-128-2-5p gene, a congener thereof, a transcript thereof, or a variant or a derivative thereof. None of the previously known reports show that change in the expression of the gene or the transcript thereof can serve as a marker for esophageal cancer.

The 143rd target gene is the hsa-miR-4640-5p gene, a congener thereof, a transcript thereof, or a variant or a derivative thereof. None of the previously known reports show that change in the expression of the gene or the transcript thereof can serve as a marker for esophageal cancer.

The 144th target gene is the hsa-miR-1469 gene, a congener thereof, a transcript thereof, or a variant or a derivative thereof. None of the previously known reports show that change in the expression of the gene or the transcript thereof can serve as a marker for esophageal cancer.

The 145th target gene is the hsa-miR-92a-2-5p gene, a congener thereof, a transcript thereof, or a variant or a derivative thereof. None of the previously known reports show that change in the expression of the gene or the transcript thereof can serve as a marker for esophageal cancer.

The 146th target gene is the hsa-miR-3940-5p gene, a congener thereof, a transcript thereof, or a variant or a derivative thereof. None of the previously known reports show that change in the expression of the gene or the transcript thereof can serve as a marker for esophageal cancer.

The 147th target gene is the hsa-miR-4281 gene, a congener thereof, a transcript thereof, or a variant or a derivative thereof. None of the previously known reports show that change in the expression of the gene or the transcript thereof can serve as a marker for esophageal cancer.

The 148th target gene is the hsa-miR-1260b gene, a congener thereof, a transcript thereof, or a variant or a derivative thereof. None of the previously known reports show that change in the expression of the gene or the transcript thereof can serve as a marker for esophageal cancer.

The 149th target gene is the hsa-miR-4758-5p gene, a congener thereof, a transcript thereof, or a variant or a derivative thereof. None of the previously known reports show that change in the expression of the gene or the transcript thereof can serve as a marker for esophageal cancer.

The 150th target gene is the hsa-miR-1915-5p gene, a congener thereof, a transcript thereof, or a variant or a derivative thereof. None of the previously known reports show that change in the expression of the gene or the transcript thereof can serve as a marker for esophageal cancer.

The 151st target gene is the hsa-miR-5001-5p gene, a congener thereof, a transcript thereof, or a variant or a derivative thereof. None of the previously known reports show that change in the expression of the gene or the transcript thereof can serve as a marker for esophageal cancer.

The 152nd target gene is the hsa-miR-4286 gene, a congener thereof, a transcript thereof, or a variant or a derivative thereof. None of the previously known reports show that change in the expression of the gene or the transcript thereof can serve as a marker for esophageal cancer.

The 153rd target gene is the hsa-miR-6126 gene, a congener thereof, a transcript thereof, or a variant or a derivative thereof. None of the previously known reports show that change in the expression of the gene or the transcript thereof can serve as a marker for esophageal cancer.

The 154th target gene is the hsa-miR-6789-5p gene, a congener thereof, a transcript thereof, or a variant or a derivative thereof. None of the previously known reports show that change in the expression of the gene or the transcript thereof can serve as a marker for esophageal cancer.

The 155th target gene is the hsa-miR-4459 gene, a congener thereof, a transcript thereof, or a variant or a derivative thereof. None of the previously known reports show that change in the expression of the gene or the transcript thereof can serve as a marker for esophageal cancer.

The 156th target gene is the hsa-miR-1268a gene, a congener thereof, a transcript thereof, or a variant or a derivative thereof. None of the previously known reports show that change in the expression of the gene or the transcript thereof can serve as a marker for esophageal cancer.

The 157th target gene is the hsa-miR-6752-5p gene, a congener thereof, a transcript thereof, or a variant or a derivative thereof. None of the previously known reports show that change in the expression of the gene or the transcript thereof can serve as a marker for esophageal cancer.

The 158th target gene is the hsa-miR-6131 gene, a congener thereof, a transcript thereof, or a variant or a derivative thereof. None of the previously known reports show that change in the expression of the gene or the transcript thereof can serve as a marker for esophageal cancer.

The 159th target gene is the hsa-miR-6800-5p gene, a congener thereof, a transcript thereof, or a variant or a derivative thereof. None of the previously known reports show that change in the expression of the gene or the transcript thereof can serve as a marker for esophageal cancer.

The 160th target gene is the hsa-miR-4532 gene, a congener thereof, a transcript thereof, or a variant or a derivative thereof. None of the previously known reports show that change in the expression of the gene or the transcript thereof can serve as a marker for esophageal cancer.

The 161st target gene is the hsa-miR-6872-3p gene, a congener thereof, a transcript thereof, or a variant or a derivative thereof. None of the previously known reports show that change in the expression of the gene or the transcript thereof can serve as a marker for esophageal cancer.

The 162nd target gene is the hsa-miR-718 gene, a congener thereof, a transcript thereof, or a variant or a derivative thereof. None of the previously known reports show that change in the expression of the gene or the transcript thereof can serve as a marker for esophageal cancer.

The 163rd target gene is the hsa-miR-6769a-5p gene, a congener thereof, a transcript thereof, or a variant or a derivative thereof. None of the previously known reports show that change in the expression of the gene or the transcript thereof can serve as a marker for esophageal cancer.

The 164th target gene is the hsa-miR-4707-3p gene, a congener thereof, a transcript thereof, or a variant or a derivative thereof. None of the previously known reports show that change in the expression of the gene or the transcript thereof can serve as a marker for esophageal cancer.

The 165th target gene is the hsa-miR-6765-5p gene, a congener thereof, a transcript thereof, or a variant or a derivative thereof. None of the previously known reports show that change in the expression of the gene or the transcript thereof can serve as a marker for esophageal cancer.

The 166th target gene is the hsa-miR-4739 gene, a congener thereof, a transcript thereof, or a variant or a derivative thereof. None of the previously known reports show that change in the expression of the gene or the transcript thereof can serve as a marker for esophageal cancer.

The 167th target gene is the hsa-miR-4525 gene, a congener thereof, a transcript thereof, or a variant or a derivative thereof. None of the previously known reports show that change in the expression of the gene or the transcript thereof can serve as a marker for esophageal cancer.

The 168th target gene is the hsa-miR-4270 gene, a congener thereof, a transcript thereof, or a variant or a derivative thereof. None of the previously known reports show that change in the expression of the gene or the transcript thereof can serve as a marker for esophageal cancer.

The 169th target gene is the hsa-miR-4534 gene, a congener thereof, a transcript thereof, or a variant or a derivative thereof. None of the previously known reports show that change in the expression of the gene or the transcript thereof can serve as a marker for esophageal cancer.

The 170th target gene is the hsa-miR-6785-5p gene, a congener thereof, a transcript thereof, or a variant or a derivative thereof. None of the previously known reports show that change in the expression of the gene or the transcript thereof can serve as a marker for esophageal cancer.

The 171st target gene is the hsa-miR-6850-5p gene, a congener thereof, a transcript thereof, or a variant or a derivative thereof. None of the previously known reports show that change in the expression of the gene or the transcript thereof can serve as a marker for esophageal cancer.

The 172nd target gene is the hsa-miR-4697-5p gene, a congener thereof, a transcript thereof, or a variant or a derivative thereof. None of the previously known reports show that change in the expression of the gene or the transcript thereof can serve as a marker for esophageal cancer.

The 173rd target gene is the hsa-miR-1260a gene, a congener thereof, a transcript thereof, or a variant or a derivative thereof. None of the previously known reports show that change in the expression of the gene or the transcript thereof can serve as a marker for esophageal cancer.

The 174th target gene is the hsa-miR-4486 gene, a congener thereof, a transcript thereof, or a variant or a derivative thereof. None of the previously known reports show that change in the expression of the gene or the transcript thereof can serve as a marker for esophageal cancer.

The 175th target gene is the hsa-miR-6880-5p gene, a congener thereof, a transcript thereof, or a variant or a derivative thereof. None of the previously known reports show that change in the expression of the gene or the transcript thereof can serve as a marker for esophageal cancer.

The 176th target gene is the hsa-miR-6802-5p gene, a congener thereof, a transcript thereof, or a variant or a derivative thereof. None of the previously known reports show that change in the expression of the gene or the transcript thereof can serve as a marker for esophageal cancer.

The 177th target gene is the hsa-miR-6861-5p gene, a congener thereof, a transcript thereof, or a variant or a derivative thereof. None of the previously known reports show that change in the expression of the gene or the transcript thereof can serve as a marker for esophageal cancer.

The 178th target gene is the hsa-miR-92b-5p gene, a congener thereof, a transcript thereof, or a variant or a derivative thereof. None of the previously known reports show that change in the expression of the gene or the transcript thereof can serve as a marker for esophageal cancer.

The 179th target gene is the hsa-miR-1238-5p gene, a congener thereof, a transcript thereof, or a variant or a derivative thereof. None of the previously known reports show that change in the expression of the gene or the transcript thereof can serve as a marker for esophageal cancer.

The 180th target gene is the hsa-miR-6851-5p gene, a congener thereof, a transcript thereof, or a variant or a derivative thereof. None of the previously known reports show that change in the expression of the gene or the transcript thereof can serve as a marker for esophageal cancer.

The 181st target gene is the hsa-miR-7704 gene, a congener thereof, a transcript thereof, or a variant or a derivative thereof. None of the previously known reports show that change in the expression of the gene or the transcript thereof can serve as a marker for esophageal cancer.

The 182nd target gene is the hsa-miR-149-3p gene, a congener thereof, a transcript thereof, or a variant or a derivative thereof. None of the previously known reports show that change in the expression of the gene or the transcript thereof can serve as a marker for esophageal cancer.

The 183rd target gene is the hsa-miR-4689 gene, a congener thereof, a transcript thereof, or a variant or a derivative thereof. None of the previously known reports show that change in the expression of the gene or the transcript thereof can serve as a marker for esophageal cancer.

The 184th target gene is the hsa-miR-4688 gene, a congener thereof, a transcript thereof, or a variant or a derivative thereof. None of the previously known reports show that change in the expression of the gene or the transcript thereof can serve as a marker for esophageal cancer.

The 185th target gene is the hsa-miR-125a-3p gene, a congener thereof, a transcript thereof, or a variant or a derivative thereof. None of the previously known reports show that change in the expression of the gene or the transcript thereof can serve as a marker for esophageal cancer.

The 186th target gene is the hsa-miR-23b-3p gene, a congener thereof, a transcript thereof, or a variant or a derivative thereof. None of the previously known reports show that change in the expression of the gene or the transcript thereof can serve as a marker for esophageal cancer.

The 187th target gene is the hsa-miR-614 gene, a congener thereof, a transcript thereof, or a variant or a derivative thereof. None of the previously known reports show that change in the expression of the gene or the transcript thereof can serve as a marker for esophageal cancer.

The 188th target gene is the hsa-miR-1913 gene, a congener thereof, a transcript thereof, or a variant or a derivative thereof. None of the previously known reports show that change in the expression of the gene or the transcript thereof can serve as a marker for esophageal cancer.

The 189th target gene is the hsa-miR-16-5p gene, a congener thereof, a transcript thereof, or a variant or a derivative thereof. None of the previously known reports show that change in the expression of the gene or the transcript thereof can serve as a marker for esophageal cancer.

The 190th target gene is the hsa-miR-675-5p gene, a congener thereof, a transcript thereof, or a variant or a derivative thereof. None of the previously known reports show that change in the expression of the gene or the transcript thereof can serve as a marker for esophageal cancer.

The 191st target gene is the hsa-miR-486-3p gene, a congener thereof, a transcript thereof, or a variant or a derivative thereof. None of the previously known reports show that change in the expression of the gene or the transcript thereof can serve as a marker for esophageal cancer.

The 192nd target gene is the hsa-miR-6777-5p gene, a congener thereof, a transcript thereof, or a variant or a derivative thereof. None of the previously known reports show that change in the expression of the gene or the transcript thereof can serve as a marker for esophageal cancer.

The 193rd target gene is the hsa-miR-4497 gene, a congener thereof, a transcript thereof, or a variant or a derivative thereof. None of the previously known reports show that change in the expression of the gene or the transcript thereof can serve as a marker for esophageal cancer.

The 194th target gene is the hsa-miR-296-3p gene, a congener thereof, a transcript thereof, or a variant or a derivative thereof. None of the previously known reports show that change in the expression of the gene or the transcript thereof can serve as a marker for esophageal cancer.

The 195th target gene is the hsa-miR-6738-5p gene, a congener thereof, a transcript thereof, or a variant or a derivative thereof. None of the previously known reports show that change in the expression of the gene or the transcript thereof can serve as a marker for esophageal cancer.

The 196th target gene is the hsa-miR-4731-5p gene, a congener thereof, a transcript thereof, or a variant or a derivative thereof. None of the previously known reports show that change in the expression of the gene or the transcript thereof can serve as a marker for esophageal cancer.

The 197th target gene is the hsa-miR-6889-5p gene, a congener thereof, a transcript thereof, or a variant or a derivative thereof. None of the previously known reports show that change in the expression of the gene or the transcript thereof can serve as a marker for esophageal cancer.

The 198th target gene is the hsa-miR-6786-5p gene, a congener thereof, a transcript thereof, or a variant or a derivative thereof. None of the previously known reports show that change in the expression of the gene or the transcript thereof can serve as a marker for esophageal cancer.

The 199th target gene is the hsa-miR-92a-3p gene, a congener thereof, a transcript thereof, or a variant or a derivative thereof. The previously known report shows that change in the expression of the gene or the transcript thereof can serve as a marker for esophageal cancer (Patent Literature 1).

The 200th target gene is the hsa-miR-4294 gene, a congener thereof, a transcript thereof, or a variant or a derivative thereof. None of the previously known reports show that change in the expression of the gene or the transcript thereof can serve as a marker for esophageal cancer.

The 201st target gene is the hsa-miR-4763-3p gene, a congener thereof, a transcript thereof, or a variant or a derivative thereof. None of the previously known reports show that change in the expression of the gene or the transcript thereof can serve as a marker for esophageal cancer.

The 202nd target gene is the hsa-miR-6076 gene, a congener thereof, a transcript thereof, or a variant or a derivative thereof. None of the previously known reports show that change in the expression of the gene or the transcript thereof can serve as a marker for esophageal cancer.

The 203rd target gene is the hsa-miR-663a gene, a congener thereof, a transcript thereof, or a variant or a derivative thereof. The previously known report shows that change in the expression of the gene or the transcript thereof can serve as a marker for esophageal cancer (Patent Literature 1).

The 204th target gene is the hsa-miR-760 gene, a congener thereof, a transcript thereof, or a variant or a derivative thereof. None of the previously known reports show that change in the expression of the gene or the transcript thereof can serve as a marker for esophageal cancer.

The 205th target gene is the hsa-miR-4667-5p gene, a congener thereof, a transcript thereof, or a variant or a derivative thereof. None of the previously known reports show that change in the expression of the gene or the transcript thereof can serve as a marker for esophageal cancer.

The 206th target gene is the hsa-miR-6090 gene, a congener thereof, a transcript thereof, or a variant or a derivative thereof. None of the previously known reports show that change in the expression of the gene or the transcript thereof can serve as a marker for esophageal cancer.

The 207th target gene is the hsa-miR-4730 gene, a congener thereof, a transcript thereof, or a variant or a derivative thereof. None of the previously known reports show that change in the expression of the gene or the transcript thereof can serve as a marker for esophageal cancer.

The 208th target gene is the hsa-miR-7106-5p gene, a congener thereof, a transcript thereof, or a variant or a derivative thereof. None of the previously known reports show that change in the expression of the gene or the transcript thereof can serve as a marker for esophageal cancer.

The 209th target gene is the hsa-miR-3196 gene, a congener thereof, a transcript thereof, or a variant or a derivative thereof. None of the previously known reports show that change in the expression of the gene or the transcript thereof can serve as a marker for esophageal cancer.

The 210th target gene is the hsa-miR-5698 gene, a congener thereof, a transcript thereof, or a variant or a derivative thereof. None of the previously known reports show that change in the expression of the gene or the transcript thereof can serve as a marker for esophageal cancer.

The 211th target gene is the hsa-miR-6087 gene, a congener thereof, a transcript thereof, or a variant or a derivative thereof. None of the previously known reports show that change in the expression of the gene or the transcript thereof can serve as a marker for esophageal cancer.

The 212th target gene is the hsa-miR-4665-5p gene, a congener thereof, a transcript thereof, or a variant or a derivative thereof. None of the previously known reports show that change in the expression of the gene or the transcript thereof can serve as a marker for esophageal cancer.

The 213th target gene is the hsa-miR-8059 gene, a congener thereof, a transcript thereof, or a variant or a derivative thereof. None of the previously known reports show that change in the expression of the gene or the transcript thereof can serve as a marker for esophageal cancer.

The 214th target gene is the hsa-miR-6879-5p gene, a congener thereof, a transcript thereof, or a variant or a derivative thereof. None of the previously known reports show that change in the expression of the gene or the transcript thereof can serve as a marker for esophageal cancer.

The 215th target gene is the hsa-miR-6717-5p gene, a congener thereof, a transcript thereof, or a variant or a derivative thereof. None of the previously known reports show that change in the expression of the gene or the transcript thereof can serve as a marker for esophageal cancer.

The 216th target gene is the hsa-miR-3648 gene, a congener thereof, a transcript thereof, or a variant or a derivative thereof. None of the previously known reports show that change in the expression of the gene or the transcript thereof can serve as a marker for esophageal cancer.

The 217th target gene is the hsa-miR-3162-5p gene, a congener thereof, a transcript thereof, or a variant or a derivative thereof. None of the previously known reports show that change in the expression of the gene or the transcript thereof can serve as a marker for colorectal esophageal cancer.

The 218th target gene is the hsa-miR-1909-3p gene, a congener thereof, a transcript thereof, or a variant or a derivative thereof. None of the previously known reports show that change in the expression of the gene or the transcript thereof can serve as a marker for esophageal cancer.

The 219th target gene is the hsa-miR-8073 gene, a congener thereof, a transcript thereof, or a variant or a derivative thereof. None of the previously known reports show that change in the expression of the gene or the transcript thereof can serve as a marker for esophageal cancer.

The 220th target gene is the hsa-miR-6769b-5p gene, a congener thereof, a transcript thereof, or a variant or a derivative thereof. None of the previously known reports show that change in the expression of the gene or the transcript thereof can serve as a marker for esophageal cancer.

The 221st target gene is the hsa-miR-6836-3p gene, a congener thereof, a transcript thereof, or a variant or a derivative thereof. None of the previously known reports show that change in the expression of the gene or the transcript thereof can serve as a marker for esophageal cancer.

The 222nd target gene is the hsa-miR-4484 gene, a congener thereof, a transcript thereof, or a variant or a derivative thereof. None of the previously known reports show that change in the expression of the gene or the transcript thereof can serve as a marker for esophageal cancer.

The 223rd target gene is the hsa-miR-6819-5p gene, a congener thereof, a transcript thereof, or a variant or a derivative thereof. None of the previously known reports show that change in the expression of the gene or the transcript thereof can serve as a marker for esophageal cancer.

The 224th target gene is the hsa-miR-6794-5p gene, a congener thereof, a transcript thereof, or a variant or a derivative thereof. None of the previously known reports show that change in the expression of the gene or the transcript thereof can serve as a marker for esophageal cancer.

The 225th target gene is the hsa-miR-24-3p gene, a congener thereof, a transcript thereof, or a variant or a derivative thereof. The previously known report shows that change in the expression of the gene or the transcript thereof can serve as a marker for esophageal cancer (Patent Literature 1).

2. Nucleic Acid Probe or Primer for Detection of Esophageal Cancer

In the present invention, a nucleic acid capable of specifically binding to any of the target nucleic acids as the esophageal cancer markers described above can be used as a nucleic acid, for example, a nucleic acid probe or a primer, for the detection or diagnosis of esophageal cancer.

In the present invention, the nucleic acid probes or the primers that can be used for detecting esophageal cancer or for diagnosing esophageal cancer enable qualitative and/or quantitative measurement of the presence, expression level, or existing amount (abundance) of any of the target nucleic acids as the esophageal cancer markers described above, for example, human-derived hsa-miR-204-3p, hsa-miR-1247-3p, hsa-miR-6875-5p, hsa-miR-6857-5p, hsa-miR-6726-5p, hsa-miR-3188, hsa-miR-8069, hsa-miR-4257, hsa-miR-1343-3p, hsa-miR-7108-5p, hsa-miR-6825-5p, hsa-miR-7641, hsa-miR-3185, hsa-miR-4746-3p, hsa-miR-6791-5p, hsa-miR-6893-5p, hsa-miR-4433b-3p, hsa-miR-3135b, hsa-miR-6781-5p, hsa-miR-1908-5p, hsa-miR-4792, hsa-miR-7845-5p, hsa-miR-4417, hsa-miR-3184-5p, hsa-miR-1225-5p, hsa-miR-1231, hsa-miR-1225-3p, hsa-miR-150-3p, hsa-miR-4433-3p, hsa-miR-6125, hsa-miR-4513, hsa-miR-6787-5p, hsa-miR-6784-5p, hsa-miR-615-5p, hsa-miR-6765-3p, hsa-miR-5572, hsa-miR-6842-5p, hsa-miR-8063, hsa-miR-6780b-5p, hsa-miR-187-5p, hsa-miR-128-1-5p, hsa-miR-6729-5p, hsa-miR-6741-5p, hsa-miR-6757-5p, hsa-miR-7110-5p, hsa-miR-7975, hsa-miR-1233-5p, hsa-miR-6845-5p, hsa-miR-3937, hsa-miR-4467, hsa-miR-7109-5p, hsa-miR-6088, hsa-miR-6782-5p, hsa-miR-5195-3p, hsa-miR-4454, hsa-miR-6724-5p, hsa-miR-8072, hsa-miR-4516, hsa-miR-6756-5p, hsa-miR-4665-3p, hsa-miR-6826-5p, hsa-miR-6820-5p, hsa-miR-6887-5p, hsa-miR-3679-5p, hsa-miR-7847-3p, hsa-miR-6721-5p, hsa-miR-3622a-5p, hsa-miR-939-5p, hsa-miR-602, hsa-miR-7977, hsa-miR-6749-5p, hsa-miR-1914-3p, hsa-miR-4651, hsa-miR-4695-5p, hsa-miR-6848-5p, hsa-miR-1228-3p, hsa-miR-642b-3p, hsa-miR-6746-5p, hsa-miR-3620-5p, hsa-miR-3131, hsa-miR-6732-5p, hsa-miR-7113-3p, hsa-miR-23a-3p, hsa-miR-3154, hsa-miR-4723-5p, hsa-miR-3663-3p, hsa-miR-4734, hsa-miR-6816-5p, hsa-miR-4442, hsa-miR-4476, hsa-miR-423-5p, hsa-miR-1249, hsa-miR-6515-3p, hsa-miR-887-3p, hsa-miR-4741, hsa-miR-6766-3p, hsa-miR-4673, hsa-miR-6779-5p, hsa-miR-4706, hsa-miR-1268b, hsa-miR-4632-5p, hsa-miR-3197, hsa-miR-6798-5p, hsa-miR-711, hsa-miR-6840-3p, hsa-miR-6763-5p, hsa-miR-6727-5p, hsa-miR-371a-5p, hsa-miR-6824-5p, hsa-miR-4648, hsa-miR-1227-5p, hsa-miR-564, hsa-miR-3679-3p, hsa-miR-2861, hsa-miR-6737-5p, hsa-miR-4725-3p, hsa-miR-6716-5p, hsa-miR-4675, hsa-miR-1915-3p, hsa-miR-671-5p, hsa-miR-3656, hsa-miR-6722-3p, hsa-miR-4707-5p, hsa-miR-4449, hsa-miR-1202, hsa-miR-4649-5p, hsa-miR-744-5p, hsa-miR-642a-3p, hsa-miR-451a, hsa-miR-6870-5p, hsa-miR-4443, hsa-miR-6808-5p, hsa-miR-4728-5p, hsa-miR-937-5p, hsa-miR-135a-3p, hsa-miR-663b, hsa-miR-1343-5p, hsa-miR-6822-5p, hsa-miR-6803-5p, hsa-miR-6805-3p, hsa-miR-128-2-5p, hsa-miR-4640-5p, hsa-miR-1469, hsa-miR-92a-2-5p, hsa-miR-3940-5p, hsa-miR-4281, hsa-miR-1260b, hsa-miR-4758-5p, hsa-miR-1915-5p, hsa-miR-5001-5p, hsa-miR-4286, hsa-miR-6126, hsa-miR-6789-5p, hsa-miR-4459, hsa-miR-1268a, hsa-miR-6752-5p, hsa-miR-6131, hsa-miR-6800-5p, hsa-miR-4532, hsa-miR-6872-3p, hsa-miR-718, hsa-miR-6769a-5p, hsa-miR-4707-3p, hsa-miR-6765-5p, hsa-miR- 4739, hsa-miR-4525, hsa-miR-4270, hsa-miR-4534, hsa-miR-6785-5p, hsa-miR-6850-5p, hsa-miR-4697-5p, hsa-miR-1260a, hsa-miR-4486, hsa-miR-6880-5p, hsa-miR-6802-5p, hsa-miR-6861-5p, hsa-miR-92b-5p, hsa-miR-1238-5p, hsa-miR-6851-5p, hsa-miR-7704, hsa-miR-149-3p, hsa-miR-4689, hsa-miR-4688, hsa-miR-125a-3p, hsa-miR-23b-3p, hsa-miR-614, hsa-miR-1913, hsa-miR-16-5p, hsa-miR-6717-5p, hsa-miR-3648, hsa-miR-3162-5p, hsa-miR-1909-3p, hsa-miR-8073, hsa-miR-6769b-5p, hsa-miR-6836-3p, hsa-miR-4484, hsa-miR-6819-5p, and hsa-miR-6794-5p or a combination thereof: congeners thereof: transcripts thereof: or variants or derivatives thereof; and, optionally in combination therewith, hsa-miR-575, and hsa-miR-24-3p or a combination thereof: congeners thereof: transcripts thereof: or variants or derivatives thereof; and, optionally in combination therewith, hsa-miR-675-5p, hsa-miR-486-3p, hsa-miR-6777-5p, hsa-miR-4497, hsa-miR-296-3p, hsa-miR-6738-5p, hsa-miR-4731-5p, hsa-miR-6889-5p, hsa-miR-6786-5p, hsa-miR-92a-3p, hsa-miR-4294, hsa-miR-4763-3p, hsa-miR-6076, hsa-miR-663a, hsa-miR-760, hsa-miR-4667-5p, hsa-miR-6090, hsa-miR-4730, hsa-miR-7106-5p, hsa-miR-3196, hsa-miR-5698, hsa-miR-6087, hsa-miR-4665-5p, hsa-miR-8059, and hsa-miR-6879-5p or a combination thereof, congeners thereof, transcripts thereof, or variants or derivatives thereof.

The expression levels of the target nucleic acids described above are increased or decreased (hereinafter, referred to as "increased/decreased") depending on the types of the target nucleic acids in a subject having esophageal cancer as compared with healthy subjects. Hence, the nucleic acid of the present invention can be effectively used for measuring expression levels of the target nucleic acids described above in body fluids from a subject (e.g., humans) suspected of having esophageal cancer and body fluids from healthy subjects and thereby detecting esophageal cancer through the comparison thereof.

The nucleic acid probes or the primers that can be used in the present invention is a nucleic acid probe capable of specifically binding to a polynucleotide consisting of a nucleotide sequence represented by at least one of SEQ ID NOs: 1 to 115, 117 to 189, and 666 to 675, or a primer for amplifying a polynucleotide consisting of a nucleotide sequence represented by at least one of SEQ ID NOs: 1 to 115, 117 to 189, and 666 to 675.

The nucleic acid probes or the primers that can be further used in the present invention can comprise a nucleic acid probe capable of specifically binding to a polynucleotide consisting of a nucleotide sequence represented by any of SEQ ID NOs: 116 and 676, or a primer for amplifying a polynucleotide consisting of a nucleotide sequence represented by SEQ ID NOs: 116 and 676.

The nucleic acid probes or the primers that can be used in the present invention may further comprise a nucleic acid probe capable of specifically binding to a polynucleotide consisting of a nucleotide sequence represented by at least one of SEQ ID NOs: 190 to 214, or a primer for amplifying a polynucleotide consisting of a nucleotide sequence represented by at least one of SEQ ID NOs: 190 to 214.

Specifically, these nucleic acid probes or primers comprise a combination of one or more polynucleotides selected from a group of polynucleotides comprising nucleotide sequences represented by any of SEQ ID NOs: 1 to 700 or nucleotide sequences from the nucleotide sequences by the replacement of u with t, and a complementary polynucleotide group thereof, a group of polynucleotides respectively hybridizing under stringent conditions (mentioned later) to DNAs consisting of nucleotide sequences complementary to these nucleotide sequences, and a complementary polynucleotide group thereof, and a group of polynucleotides comprising 15 or more, preferably 17 or more consecutive nucleotides that are from the nucleotide sequences of these polynucleotide groups. These polynucleotides can be used as nucleic acid probes and primers for detecting the esophageal cancer markers as target nucleic acids.

More specifically, examples of the nucleic acid probes or the primers that can be used in the present invention include one or more polynucleotide(s) selected from the group consisting of the following polynucleotides (a) to (e):

(a) a polynucleotide consisting of a nucleotide sequence represented by any of SEQ ID NOs: 1 to 115, 117 to 189, and 666 to 675, or a nucleotide sequence from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 115, 117 to 189, and 666 to 675, (c) a polynucleotide consisting of a nucleotide sequence complementary to a nucleotide sequence represented by any of SEQ ID NOs: 1 to 115, 117 to 189, and 666 to 675, or a nucleotide sequence from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 115, 117 to 189, and 666 to 675, or a nucleotide sequence from the nucleotide sequence by the replacement of u with t, and (e) a polynucleotide hybridizing under stringent conditions to any of the polynucleotides (a) to (d).

In addition to at least one polynucleotides selected from any of the group consisting of the polynucleotides (a) to (e), the nucleic acid probe or the primer that can be used in the present invention may further comprise a polynucleotide selected from the group consisting of the following polynucleotides (f) to (j);

(f) a polynucleotide consisting of a nucleotide sequence represented by SEQ ID NOs: 116 to 676 or a nucleotide sequence from the nucleotide sequence by the replacement of u with t, a variant thereof, a derivative thereof, or a fragment thereof comprising 15 or more consecutive nucleotides, (g) a polynucleotide comprising a nucleotide sequence represented by SEQ ID NOs: 116 to 676, (h) a polynucleotide consisting of a nucleotide sequence complementary to a nucleotide sequence represented by SEQ ID NOs: 116 to 676 or a nucleotide sequence from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by SEQ ID NOs: 116 to 676 or a nucleotide sequence from the nucleotide sequence by the replacement of u with t, and (j) a polynucleotide hybridizing under stringent conditions to any of the polynucleotides (f) to (i).

In addition to at least one polynucleotides selected from any of the group consisting of the polynucleotides (a) to (j), the nucleic acid probes or the primers that can be used in the present invention may further comprise a polynucleotide selected from the group consisting of the following polynucleotides (k) to (o):

(k) a polynucleotide consisting of a nucleotide sequence represented by any of SEQ ID NOs: 190 to 214 or a nucleotide sequence from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 190 to 214, (m) a polynucleotide consisting of a nucleotide sequence complementary to a nucleotide sequence represented by any of SEQ ID NOs: 190 to 214 or a nucleotide sequence from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 190 to 214 or a nucleotide sequence from the nucleotide sequence by the replacement of u with t, and (o) a polynucleotide hybridizing under stringent conditions to any of the polynucleotides (k) to (n).

For the above-mentioned polynucleotides, the "fragment thereof comprising 15 or more consecutive nucleotides" can comprise, but is not limited to, the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, or the like, and is from the nucleotide sequence of each polynucleotide.

These polynucleotides or fragments thereof used in the present invention may each be DNA or may each be RNA.

The polynucleotides that can be used in the present invention can be prepared by use of a general technique such as a DNA recombination technique, a PCR method, or a method using an automatic DNA/RNA synthesizer.

The DNA recombination technique and the PCR method may employ techniques described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-204-3p, hsa-miR-1247-3p, hsa-miR-6875-5p, hsa-miR-6857-5p, hsa-miR-6726-5p, hsa-miR-3188, hsa-miR-8069, hsa-miR-4257, hsa-miR-1343-3p, hsa-miR-7108-5p, hsa-miR-6825-5p, hsa-miR-7641, hsa-miR-3185, hsa-miR-4746-3p, hsa-miR-6791-5p, hsa-miR-6893-5p, hsa-miR-4433b-3p, hsa-miR-3135b, hsa-miR-6781-5p, hsa-miR-1908-5p, hsa-miR-4792, hsa-miR-7845-5p, hsa-miR-4417, hsa-miR-3184-5p, hsa-miR-1225-5p, hsa-miR-1231, hsa-miR-1225-3p, hsa-miR-150-3p, hsa-miR-4433-3p, hsa-miR-6125, hsa-miR-4513, hsa-miR-6787-5p, hsa-miR-6784-5p, hsa-miR-615-5p, hsa-miR-6765-3p, hsa-miR-5572, hsa-miR-6842-5p, hsa-miR-8063, hsa-miR-6780b-5p, hsa-miR-187-5p, hsa-miR-128-1-5p, hsa-miR-6729-5p, hsa-miR-6741-5p, hsa-miR-6757-5p, hsa-miR-7110-5p, hsa-miR-7975, hsa-miR-1233-5p, hsa-miR-6845-5p, hsa-miR-3937, hsa-miR-4467, hsa-miR-7109-5p, hsa-miR-6088, hsa-miR-6782-5p, hsa-miR-5195-3p, hsa-miR-4454, hsa-miR-6724-5p, hsa-miR-8072, hsa-miR-4516, hsa-miR-6756-5p, hsa-miR-4665-3p, hsa-miR-6826-5p, hsa-miR-6820-5p, hsa-miR-6887-5p, hsa-miR-3679-5p, hsa-miR-7847-3p, hsa-miR-6721-5p, hsa-miR-3622a-5p, hsa-miR-939-5p, hsa-miR-602, hsa-miR-7977, hsa-miR-6749-5p, hsa-miR-1914-3p, hsa-miR-4651, hsa-miR-4695-5p, hsa-miR-6848-5p, hsa-miR-1228-3p, hsa-miR-642b-3p, hsa-miR-6746-5p, hsa-miR-3620-5p, hsa-miR-3131, hsa-miR-6732-5p, hsa-miR-7113-3p, hsa-miR-23a-3p, hsa-miR-3154, hsa-miR-4723-5p, hsa-miR-3663-3p, hsa-miR-4734, hsa-miR-6816-5p, hsa-miR-4442, hsa-miR-4476, hsa-miR-423-5p, hsa-miR-1249, hsa-miR-6515-3p, hsa-miR-887-3p, hsa-miR-4741, hsa-miR-6766-3p, hsa-miR-4673, hsa-miR-6779-5p, hsa-miR-4706, hsa-miR-1268b, hsa-miR-4632-5p, hsa-miR-3197, hsa-miR-6798-5p, hsa-miR-711, hsa-miR-6840-3p, hsa-miR-6763-5p, hsa-miR-6727-5p, hsa-miR-371a-5p, hsa-miR-6824-5p, hsa-miR-4648, hsa-miR-1227-5p, hsa-miR-564, hsa-miR-3679-3p, hsa-miR-2861, hsa-miR-6737-5p, hsa-miR-575, hsa-miR-4725-3p, hsa-miR-6716-5p, hsa-miR-4675, hsa-miR-1915-3p, hsa-miR-671-5p, hsa-miR-3656, hsa-miR-6722-3p, hsa-miR-4707-5p, hsa-miR-4449, hsa-miR-1202, hsa-miR-4649-5p, hsa-miR-744-5p, hsa-miR-642a-3p, hsa-miR-451a, hsa-miR-6870-5p, hsa-miR-4443, hsa-miR-6808-5p, hsa-miR-4728-5p, hsa-miR-937-5p, hsa-miR-135a-3p, hsa-miR-663b, hsa-miR-1343-5p, hsa-miR-6822-5p, hsa-miR-6803-5p, hsa-miR-6805-3p, hsa-miR-128-2-5p, hsa-miR-4640-5p, hsa-miR-1469, hsa-miR-92a-2-5p, hsa-miR-3940-5p, hsa-miR-4281, hsa-miR-1260b, hsa-miR-4758-5p, hsa-miR-1915-5p, hsa-miR-5001-5p, hsa-miR-4286, hsa-miR-6126, hsa-miR-6789-5p, hsa-miR-4459, hsa-miR-1268a, hsa-miR-6752-5p, hsa-miR-6131, hsa-miR-6800-5p, hsa-miR-4532, hsa-miR-6872-3p, hsa-miR-718, hsa-miR-6769a-5p, hsa-miR-4707-3p, hsa-miR-6765-5p, hsa-miR-4739, hsa-miR-4525, hsa-miR-4270, hsa-miR-4534, hsa-miR-6785-5p, hsa-miR-6850-5p, hsa-miR-4697-5p, hsa-miR-1260a, hsa-miR-4486, hsa-miR-6880-5p, hsa-miR-6802-5p, hsa-miR-6861-5p, hsa-miR-92b-5p, hsa-miR-1238-5p, hsa-miR-6851-5p, hsa-miR-7704, hsa-miR-149-3p, hsa-miR-4689, hsa-miR-4688, hsa-miR-125a-3p, hsa-miR-23b-3p, hsa-miR-614, hsa-miR-1913, hsa-miR-16-5p, hsa-miR-6717-5p, hsa-miR-3648, hsa-miR-3162-5p, hsa-miR-1909-3p, hsa-miR-8073, hsa-miR-6769b-5p, hsa-miR-6836-3p, hsa-miR-4484, hsa-miR-6819-5p, hsa-miR-6794-5p hsa-miR-675-5p, hsa-miR-24-3p, hsa-miR-486-3p, hsa-miR-6777-5p, hsa-miR-4497, hsa-miR-296-3p, hsa-miR-6738-5p, hsa-miR-4731-5p, hsa-miR-6889-5p, hsa-miR-6786-5p, hsa-miR-92a-3p, hsa-miR-4294, hsa-miR-4763-3p, hsa-miR-6076, hsa-miR-663a, hsa-miR-760, hsa-miR-4667-5p, hsa-miR-6090, hsa-miR-4730, hsa-miR-7106-5p, hsa-miR-3196, hsa-miR-5698, hsa-miR-6087, hsa-miR-4665-5p, hsa-miR-8059 and hsa-miR-6879-5p represented by SEQ ID NOs: 1 to 214 and 666 to 676 are known in the art, and their acquisition methods are also known as mentioned above. Therefore, each polynucleotide that can be used as a nucleic acid probe or a primer in the present invention can be prepared by cloning the gene.

Such nucleic acid probes or primers can be chemically synthesized using an automatic DNA synthesizer. In general, the phosphoramidite method is used in this synthesis, and single-stranded DNA up to approximately 100 nucleotides can be automatically synthesized by this method. The automatic DNA synthesizer is commercially available from, for example, Polygen GmbH, ABI, or Applied Biosystems, Inc.

Alternatively, the polynucleotides of the present invention can also be prepared by cDNA cloning methods. The cDNA cloning technique may employ, for example, microRNA Cloning Kit Wako.

In this context, the sequences of the nucleic acid probes and the primers for detecting the polynucleotide consisting of a nucleotide sequence represented by any of SEQ ID NOs: 1 to 214 and 666 to 676 do not exist as miRNAs or precursors thereof in the living body or in vivo. For example, the nucleotide sequences represented by SEQ ID NO: 9 and SEQ ID NO: 138 are produced from the precursor represented by SEQ ID NO: 223. This precursor has a hairpin-like structure as shown in FIG. 1, and the nucleotide sequences represented by SEQ ID NO: 9 and SEQ ID NO: 138 have mismatch sequences with each other. Likewise, a nucleotide sequence completely complementary to the nucleotide sequence represented by SEQ ID NO: 9 or SEQ ID NO: 138 is not naturally produced in vivo. As such, the nucleic acid probe and the primer for detecting the nucleotide sequence represented by any of SEQ ID NOs: 1 to 214 and 666 to 676 have artificial nucleotide sequences that do not exist in the living body or in vivo.

3. Kit or Device for Detection of Esophageal Cancer

The present invention also provides a kit or a device for the detection of esophageal cancer, comprising one or more polynucleotides (which may include a variant, a fragment, or a derivative thereof; hereinafter, also referred to as a polynucleotide for detection) that can be used as nucleic acid probes or primers in the present invention for measuring target nucleic acids as esophageal cancer markers.

The target nucleic acids as esophageal cancer markers according to the present invention are selected from the following group A:

(Group A) hsa-miR-204-3p, hsa-miR-1247-3p, hsa-miR-6875-5p, hsa-miR-6857-5p, hsa-miR-6726-5p, hsa-miR-3188, hsa-miR-8069, hsa-miR-4257, hsa-miR-1343-3p, hsa-miR-7108-5p, hsa-miR-6825-5p, hsa-miR-7641, hsa-miR-3185, hsa-miR-4746-3p, hsa-miR-6791-5p, hsa-miR-6893-5p, hsa-miR-4433b-3p, hsa-miR-3135b, hsa-miR-6781-5p, hsa-miR-1908-5p, hsa-miR-4792, hsa-miR-7845-5p, hsa-miR-4417, hsa-miR-3184-5p, hsa-miR-1225-5p, hsa-miR-1231, hsa-miR-1225-3p, hsa-miR-150-3p, hsa-miR-4433-3p, hsa-miR-6125, hsa-miR-4513, hsa-miR-6787-5p, hsa-miR-6784-5p, hsa-miR-615-5p, hsa-miR-6765-3p, hsa-miR-5572, hsa-miR-6842-5p, hsa-miR-8063, hsa-miR-6780b-5p, hsa-miR-187-5p, hsa-miR-128-1-5p, hsa-miR-6729-5p, hsa-miR-6741-5p, hsa-miR-6757-5p, hsa-miR-7110-5p, hsa-miR-7975, hsa-miR-1233-5p, hsa-miR-6845-5p, hsa-miR-3937, hsa-miR-4467, hsa-miR-7109-5p, hsa-miR-6088, hsa-miR-6782-5p, hsa-miR-5195-3p, hsa-miR-4454, hsa-miR-6724-5p, hsa-miR-8072, hsa-miR-4516, hsa-miR-6756-5p, hsa-miR-4665-3p, hsa-miR-6826-5p, hsa-miR-6820-5p, hsa-miR-6887-5p, hsa-miR-3679-5p, hsa-miR-7847-3p, hsa-miR-6721-5p, hsa-miR-3622a-5p, hsa-miR-939-5p, hsa-miR-602, hsa-miR-7977, hsa-miR-6749-5p, hsa-miR-1914-3p, hsa-miR-4651, hsa-miR-4695-5p, hsa-miR-6848-5p, hsa-miR-1228-3p, hsa-miR-642b-3p, hsa-miR-6746-5p, hsa-miR-3620-5p, hsa-miR-3131, hsa-miR-6732-5p, hsa-miR-7113-3p, hsa-miR-23a-3p, hsa-miR-3154, hsa-miR-4723-5p, hsa-miR-3663-3p, hsa-miR-4734, hsa-miR-6816-5p, hsa-miR-4442, hsa-miR-4476, hsa-miR-423-5p, hsa-miR-1249, hsa-miR-6515-3p, hsa-miR-887-3p, hsa-miR-4741, hsa-miR-6766-3p, hsa-miR-4673, hsa-miR-6779-5p, hsa-miR-4706, hsa-miR-1268b, hsa-miR-4632-5p, hsa-miR-3197, hsa-miR-6798-5p, hsa-miR-711, hsa-miR-6840-3p, hsa-miR-6763-5p, hsa-miR-6727-5p, hsa-miR-371a-5p, hsa-miR-6824-5p, hsa-miR-4648, hsa-miR-1227-5p, hsa-miR-564, hsa-miR-3679-3p, hsa-miR-2861, hsa-miR-6737-5p, hsa-miR-4725-3p, hsa-miR-6716-5p, hsa-miR-4675, hsa-miR-1915-3p, hsa-miR-671-5p, hsa-miR-3656, hsa-miR-6722-3p, hsa-miR-4707-5p, hsa-miR-4449, hsa-miR-1202, hsa-miR-4649-5p, hsa-miR-744-5p, hsa-miR-642a-3p, hsa-miR-451a, hsa-miR-6870-5p, hsa-miR-4443, hsa-miR-6808-5p, hsa-miR-4728-5p, hsa-miR-937-5p, hsa-miR-135a-3p, hsa-miR-663b, hsa-miR-1343-5p, hsa-miR-6822-5p, hsa-miR-6803-5p, hsa-miR-6805-3p, hsa-miR-128-2-5p, hsa-miR-4640-5p, hsa-miR-1469, hsa-miR-92a-2-5p, hsa-miR-3940-5p, hsa-miR-4281, hsa-miR-1260b, hsa-miR-4758-5p, hsa-miR-1915-5p, hsa-miR-5001-5p, hsa-miR-4286, hsa-miR-6126, hsa-miR-6789-5p, hsa-miR-4459, hsa-miR-1268a, hsa-miR-6752-5p, hsa-miR-6131, hsa-miR-6800-5p, hsa-miR-4532, hsa-miR-6872-3p, hsa-miR-718, hsa-miR-6769a-5p, hsa-miR-4707-3p, hsa-miR-6765-5p, hsa-miR-4739, hsa-miR-4525, hsa-miR-4270, hsa-miR-4534, hsa-miR-6785-5p, hsa-miR-6850-5p, hsa-miR-4697-5p, hsa-miR-1260a, hsa-miR-4486, hsa-miR-6880-5p, hsa-miR-6802-5p, hsa-miR-6861-5p, hsa-miR-92b-5p, hsa-miR-1238-5p, hsa-miR-6851-5p, hsa-miR-7704, hsa-miR-149-3p, hsa-miR-4689, hsa-miR-4688, hsa-miR-125a-3p, hsa-miR-23b-3p, hsa-miR-614, hsa-miR-1913, hsa-miR-16-5p, hsa-miR-6717-5p, hsa-miR-3648, hsa-miR-3162-5p, hsa-miR-1909-3p, hsa-miR-8073, hsa-miR-6769b-5p, hsa-miR-6836-3p, hsa-miR-4484, hsa-miR-6819-5p and hsa-miR-6794-5p.

Additional target nucleic acids that may be optionally used in the measurement are selected from the following group B:

(Group B) hsa-miR-575 and hsa-miR-24-3p.

Additional target nucleic acids that may be further optionally used in the measurement are selected from the following group C:

(Group C) hsa-miR-675-5p, hsa-miR-486-3p, hsa-miR-6777-5p, hsa-miR-4497, hsa-miR-296-3p, hsa-miR-6738-5p, hsa-miR-4731-5p, hsa-miR-6889-5p, hsa-miR-6786-5p, hsa-miR-92a-3p, hsa-miR-4294, hsa-miR-4763-3p, hsa-miR-6076, hsa-miR-663a, hsa-miR-760, hsa-miR-4667-5p, hsa-miR-6090, hsa-miR-4730, hsa-miR-7106-5p, hsa-miR-3196, hsa-miR-5698, hsa-miR-6087, hsa-miR-4665-5p, hsa-miR-8059 and hsa-miR-6879-5p.

The kit or the device of the present invention comprises one or more nucleic acid(s) capable of specifically binding to any of the target nucleic acids as the esophageal cancer markers described above, preferably one or more polynucleotide(s) selected from the polynucleotides described in the preceding Section 2, or variant(s) thereof, etc.

Specifically, the kit or the device of the present invention can comprise at least one polynucleotide comprising (or consisting of) a nucleotide sequence represented by any of SEQ ID NOs: 1 to 115, 117 to 189, and 666 to 675 or a nucleotide sequence from the nucleotide sequence by the replacement of u with t, polynucleotide(s) comprising (or consisting of) a complementary sequence thereof, polynucleotide(s) hybridizing under stringent conditions to any of these polynucleotides, or variant(s) or fragment(s) comprising 15 or more consecutive nucleotides of any of these polynucleotide sequences.

The kit or the device of the present invention can further comprise one or more polynucleotides comprising (or consisting of) a nucleotide sequence represented by SEQ ID NOs: 116 and 676 or a nucleotide sequence from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The kit or the device of the present invention can further comprise one or more polynucleotides comprising (or consisting of) a nucleotide sequence represented by any of SEQ ID NOs: 190 to 214 or a nucleotide sequence from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The fragment(s) that can be comprised in the kit or the device of the present invention is/are, for example, one or more polynucleotides, preferably two or more polynucleotides selected from the group consisting of the following polynucleotides (1) to (3):

(1) a polynucleotide comprising 15 or more consecutive nucleotides that are from a nucleotide sequence derived from a nucleotide sequence represented by any of SEQ ID NOs: 1 to 115, 117 to 189, and 666 to 675 by the replacement of u with t, or a complementary sequence thereof;

(2) a polynucleotide comprising 15 or more consecutive nucleotides that are from a nucleotide sequence derived from a nucleotide sequence represented by SEQ ID NOs: 116 and 676 by the replacement of u with t, or a complementary sequence thereof, and (3) a polynucleotide comprising 15 or more consecutive nucleotides that are from a nucleotide sequence derived from a nucleotide sequence represented by any of SEQ ID NOs: 190 to 214 by the replacement of u with t, or a complementary sequence thereof.

In a preferred embodiment, the polynucleotide is a polynucleotide consisting of a nucleotide sequence represented by any of SEQ ID NOs: 1 to 115, 117 to 189, and 666 to 675 or a nucleotide sequence from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 116 and 676 or a nucleotide sequence from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 190 to 214 or a nucleotide sequence from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of nucleotides in the range of from, for example, 15 consecutive nucleotides to less than the total number of nucleotides of the sequence, from 17 consecutive nucleotides to less than the total number of nucleotides of the sequence, or 19 consecutive nucleotides to less than the total number of nucleotides of the sequence, in the nucleotide sequence of each polynucleotide.

Specific examples of the combination of aforementioned polynucleotides constituting the kit or the device of the present invention can include a combination of 2, 3, 4, 5, 6, 7, 8, 9, 10 or more of the polynucleotides as relevant to the combinations of SEQ ID NOs: 1 to 214 and 666 to 676 shown in Table 1. However, these are given merely for illustrative purposes, and all of various other possible combinations are included in the present invention.

The aforementioned combination constituting the kit or the device for discriminating an esophageal cancer patient from a healthy subject according to the present invention is desirably, for example, a combination of two or more aforementioned polynucleotides consisting of the nucleotide sequences represented by SEQ ID NOs: 1 to 214 and 666 to 676 shown in Table 1. Usually, a combination of two of these polynucleotides can produce adequate performance.

The combination of two polynucleotides for specifically discriminating an esophageal cancer patient from a healthy subject is preferably a combination comprising at least one of newly found polynucleotides consisting of the nucleotide sequences represented by SEQ ID NOs: 1 to 115, 117 to 189 and 666 to 675, among the combinations constituted by two of the polynucleotides consisting of the nucleotide sequences represented by SEQ ID NOs: 1 to 214 and 666 to 676.

The combination of polynucleotides with cancer type specificity capable of discriminating an esophageal cancer patient not only from a healthy subject but also from other cancer patients is preferably, for example, a combination of two polynucleotides comprising at least one polynucleotide selected from the group consisting of polynucleotides consisting of the nucleotide sequences represented by SEQ ID NOs: 1, 2, 5, 8, 22, 32, 33, 35, 43, 44, 56, 85, 98, 106, 109, 115, 121, 126, 133, 138, 155, 157, 166, 177, 179, 185, 202, 212, 666, 667, 668, 669, 670, 671, 672, 673, 674, 675 and 676 (hereinafter, this group is referred to as "cancer type-specific polynucleotide group 1"); and any of the polynucleotides of the other SEQ ID NOs.

The combination of polynucleotides with cancer type specificity is more preferably a combination of multiple polynucleotides selected from cancer type-specific polynucleotide group 1.

The combination of polynucleotides with cancer type specificity is further preferably a combination comprising at least one polynucleotide selected from the group consisting of or more for polynucleotides consisting of the nucleotide sequences represented by SEQ ID NOs: 1, 22, 85, 109, 121, 126, 133, 138, 166, and 666 (hereinafter, this group is referred to as "cancer type-specific polynucleotide group 2") included in cancer type-specific polynucleotide group 1, among the combinations of multiple polynucleotides selected from the cancer type-specific polynucleotide group 1.

The number of the polynucleotides with cancer type specificity may be 1, 2, 3, 4, 5, 6, 7, 8, 9, 10 or more in the combination and is more preferably 6 or more in the combination. Usually, the combination of 6 polynucleotides of these polynucleotides can produce adequate performance.

Non-limiting examples of the combination of the polynucleotide consisting of the nucleotide sequence represented by SEQ ID NO: 1 or a complementary sequence thereof with polynucleotides consisting of nucleotide sequences represented by SEQ ID NOs of five polynucleotides selected from the cancer type-specific polynucleotide group 1 or complementary sequences thereof are listed below.

(1) a combination of polynucleotides consisting of the nucleotide sequences represented by SEQ ID NOs: 1, 85, 138, 166, 666, and 668 (markers: hsa-miR-4739, hsa-miR-1343-5p, hsa-miR-204-3p, hsa-miR-4723-5p, hsa-miR-3162-5p, and hsa-miR-6717-5p);

(2) a combination of polynucleotides consisting of the nucleotide sequences represented by SEQ ID NOs: 1, 85, 98, 138, 166, and 666 (markers: hsa-miR-4739, hsa-miR-1343-5p, hsa-miR-6779-5p, hsa-miR-204-3p, hsa-miR-4723-5p, and hsa-miR-6717-5p);

(3) a combination of polynucleotides consisting of the nucleotide sequences represented by SEQ ID NOs: 1, 85, 138, 155, 166, and 666 (markers: hsa-miR-4739, hsa-miR-1343-5p, hsa-miR-204-3p, hsa-miR-4723-5p, hsa-miR-4459, and hsa-miR-6717-5p);

(4) a combination of polynucleotides consisting of the nucleotide sequences represented by SEQ ID NOs: 1, 5, 85, 138, 166, and 666 (markers: hsa-miR-4739, hsa-miR-1343-5p, hsa-miR-204-3p, hsa-miR-4723-5p, hsa-miR-6726-5p, and hsa-miR-6717-5p); and (5) a combination of polynucleotides consisting of the nucleotide sequences represented by SEQ ID NOs: 1, 35, 85, 138, 166, and 666 (markers: hsa-miR-4739, hsa-miR-1343-5p, hsa-miR-204-3p, hsa-miR-4723-5p, hsa-miR-6765-3p, and hsa-miR-6717-5p).

Non-limiting examples of the combination of the polynucleotide consisting of the nucleotide sequence represented by SEQ ID NO: 22 or a complementary sequence thereof with polynucleotides consisting of nucleotide sequences represented by SEQ ID NOs of five polynucleotides selected from the cancer type-specific polynucleotide group 1 or complementary sequences thereof are further listed.

(1) a combination of SEQ ID NOs: 1, 22, 85, 138, 166 and 666 (markers: hsa-miR-4739, hsa-miR-1343-5p, hsa-miR-7845-5p, hsa-miR-204-3p, hsa-miR-4273-5p, and hsa-miR-6717-5p);

(2) a combination of polynucleotides consisting of the nucleotide sequences represented by SEQ ID NOs: 22, 32, 121, 133, 166, and 666 (markers: hsa-miR-4739, hsa-miR-7845-5p, hsa-miR-671-5p, hsa-miR-6787-5p, hsa-miR-6808-5p, and hsa-miR-6717-5p);

(3) a combination of polynucleotides consisting of the nucleotide sequences represented by SEQ ID NOs: 1, 22, 126, 138, 166, and 666 (markers: hsa-miR-4739, hsa-miR-1202, hsa-miR-1343-5p, hsa-miR-7845-5p, hsa-miR-204-3p, and hsa-miR-6717-5p);

(4) a combination of polynucleotides consisting of the nucleotide sequences represented by SEQ ID NOs: 1, 22, 121, 155, 166, and 666 (markers: hsa-miR-4739, hsa-miR-7845-5p, hsa-miR-671-5p, hsa-miR-204-3p, hsa-miR-4459, and hsa-miR-6717-5p); and (5) a combination of polynucleotides consisting of the nucleotide sequences represented by SEQ ID NOs: 22, 32, 109, 121, 666, and 667 (markers: hsa-miR-7845-5p, hsa-miR-671-5p, hsa-miR-3648, hsa-miR-6787-5p, hsa-miR-6824-5p, and hsa-miR-6717-5p).

Non-limiting examples of the combination of the polynucleotide consisting of the nucleotide sequence represented by SEQ ID NO: 85 or a complementary sequence thereof with polynucleotides consisting of nucleotide sequences represented by SEQ ID NOs of five polynucleotides selected from the cancer type-specific polynucleotide group 1 or complementary sequences thereof are further listed below.

(1) a combination of polynucleotides consisting of the nucleotide sequences represented by SEQ ID NOs: 85, 138, 166, 185, 666, and 669 (markers: miR-4739, miR-1343-5p, miR-125a-3p, miR-4723-5p, miR-1909-3p, and miR-6717-5p);

(2) a combination of polynucleotides consisting of the nucleotide sequences represented by SEQ ID NOs: 85, 138, 166, 185, 666, and 676 (markers: miR-4739, miR-1343-5p, miR-125a-3p, miR-4723-5p, miR-6717-5p, and miR-24-3p);

(3) a combination of polynucleotides consisting of the nucleotide sequences represented by SEQ ID NOs: 85, 138, 166, 177, 185, and 666 (markers: miR-4739, miR-1343-5p, miR-125a-3p, miR-4723-5p, miR-6861-5p, and miR-6717-5p);

(4) a combination of polynucleotides consisting of the nucleotide sequences represented by SEQ ID NOs: 85, 138, 166, 185, 666, and 667 (markers: miR-4739, miR-1343-5p, miR-3648, miR-125a-3p, miR-4723-5p, and miR-6717-5p); and (5) a combination of polynucleotides consisting of the nucleotide sequences represented by SEQ ID NOs: 33, 85, 138, 166, 185, and 666 (markers: miR-6784-5p, miR-4739, miR-1343-5p, miR-125a-3p, miR-4723-5p, and miR-6717-5p).

Non-limiting examples of the combination of the polynucleotide consisting of the nucleotide sequence represented by SEQ ID NO: 109 or a complementary sequence thereof with polynucleotides consisting of nucleotide sequences represented by SEQ ID NOs of five polynucleotides selected from the cancer type-specific polynucleotide group 1 or complementary sequences thereof are further listed below.

(1) a combination of polynucleotides consisting of the nucleotide sequences represented by SEQ ID NOs: 109, 121, 126, 138, 166, and 666 (markers: miR-4739, miR-1202, miR-1343-5p, miR-671-5p, miR-6824-5p, and miR-6717-5p);

(2) a combination of polynucleotides consisting of the nucleotide sequences represented by SEQ ID NOs: 1, 85, 109, 138, 166, and 666 (markers: miR-4739, miR-1343-5p, miR-204-3p, miR-4723-5p, miR-6824-5p, miR-6717-5p);

(3) a combination of polynucleotides consisting of the nucleotide sequences represented by SEQ ID NOs: 1, 109, 121, 138, 166, and 666 (markers: miR-4739, miR-1343-5p, miR-671-5p, miR-204-3p, miR-6824-5p, and miR-6717-5p);

(4) a combination of polynucleotides consisting of the nucleotide sequences represented by SEQ ID NOs: 109, 126, 138, 166, 666, and 676 (markers: miR-4739, miR-1202, miR-1343-5p, miR-6824-5p, miR-6717-5p, and miR-24-3p); and (5) a combination of polynucleotides consisting of the nucleotide sequences represented by SEQ ID NOs: 109, 126, 138, 166, 202, and 666 (markers: miR-4739, miR-1202, miR-1343-5p, miR-6824-5p, miR-6076, and miR-6717-5p).

Non-limiting examples of the combination of the polynucleotide consisting of the nucleotide sequence represented by SEQ ID NO: 121 or a complementary sequence thereof with polynucleotides consisting of nucleotide sequences represented by SEQ ID NOs of five polynucleotides selected from the cancer type-specific polynucleotide group 1 or complementary sequences thereof are further listed below.

(1) a combination of polynucleotides consisting of the nucleotide sequences represented by SEQ ID NOs: 1, 121, 138, 166, 666, and 668 (markers: miR-4739, miR-1343-5p, miR-671-5p, miR-204-3p, miR-3162-5p, and miR-6717-5p);

(2) a combination of polynucleotides consisting of the nucleotide sequences represented by SEQ ID NOs: 1, 33, 121, 138, 166, and 666 (markers: miR-6784-5p, miR-4739, miR-1343-5p, miR-671-5p, miR-204-3p, and miR-6717-5p);

(3) a combination of polynucleotides consisting of the nucleotide sequences represented by SEQ ID NOs: 1, 85, 121, 138, 166, and 666 (markers: miR-4739, miR-1343-5p, miR-671-5p, miR-204-3p, miR-4723-5p, and miR-6717-5p);

(4) a combination of polynucleotides consisting of the nucleotide sequences represented by SEQ ID NOs: 1, 121, 138, 166, 179, and 666 (markers: miR-4739, miR-1343-5p, miR-671-5p, miR-204-3p, miR-1238-5p, and miR-6717-5p); and (5) a combination of polynucleotides consisting of the nucleotide sequences represented by SEQ ID NOs: 1, 121, 138, 166, 177, and 666 (markers: miR-4739, miR-1343-5p, miR-671-5p, miR-204-3p, miR-6861-5p, and miR-6717-5p).

Non-limiting examples of the combination of the polynucleotide consisting of the nucleotide sequence represented by SEQ ID NO: 126 or a complementary sequence thereof with polynucleotides consisting of nucleotide sequences represented by SEQ ID NOs of five polynucleotides selected from the cancer type-specific polynucleotide group 1 or complementary sequences thereof are further listed below.

(1) a combination of polynucleotides consisting of the nucleotide sequences represented by SEQ ID NOs: 32, 109, 126, 138, 166, and 666 (markers: miR-4739, miR-1202, miR-1343-5p, miR-6787-5p, miR-6824-5p, and miR-6717-5p);

(2) a combination of polynucleotides consisting of the nucleotide sequences represented by SEQ ID NOs: 1, 85, 126, 138, 166, and 666 (markers: miR-4739, miR-1202, miR-1343-5p, miR-204-3p, miR-4723-5p, and miR-6717-5p);

(3) a combination of polynucleotides consisting of the nucleotide sequences represented by SEQ ID NOs: 1, 109, 126, 138, 166, and 666 (markers: miR-4739, miR-1202, miR-1343-5p, miR-204-3p, miR-6824-5p, and miR-6717-5p);

(4) a combination of polynucleotides consisting of the nucleotide sequences represented by SEQ ID NOs: 22, 109, 126, 138, 166, and 666 (markers: miR-4739, miR-1202, miR-1343-5p, miR-7845-5p, miR-6824-5p, and miR-6717-5p); and (5) a combination of SEQ ID NOs: 109, 126, 138, 157, 166, and 666 (markers: miR-4739, miR-1202, miR-6752-5p, miR-1343-5p, miR-6824-5p, and miR-6717-5p).

Non-limiting examples of the combination of the polynucleotide consisting of the nucleotide sequence represented by SEQ ID NO: 133 or a complementary sequence thereof with polynucleotides consisting of nucleotide sequences represented by SEQ ID NOs of five polynucleotides selected from the cancer type-specific polynucleotide group 1 or complementary sequences thereof are further listed below.

(1) a combination of polynucleotides consisting of the nucleotide sequences represented by SEQ ID NOs: 126, 133, 138, 166, 666, and 672 (markers: miR-4739, miR-1202, miR-1343-5p, miR-6808-5p, miR-6836-3p, and miR-6717-5p);

(2) a combination of polynucleotides consisting of the nucleotide sequences represented by SEQ ID NOs: 126, 133, 138, 166, 666 (markers: miR-4739, miR-1202, miR-1343-5p, miR-6808-5p, and miR-6717-5p);

(3) a combination of polynucleotides consisting of the nucleotide sequences represented by SEQ ID NOs: 109, 126, 133, 138, 166, and 666 (markers: miR-4739, miR-1202, miR-1343-5p, miR-6824-5p, miR-6808-5p, and miR-6717-5p);

(4) a combination of SEQ ID NOs: 126, 133, 138, 166, 666, and 673 (markers: miR-4739, miR-1202, miR-1343-5p, miR-4484, miR-6808-5p, and miR-6717-5p); and (5) a combination of polynucleotides consisting of the nucleotide sequences represented by SEQ ID NOs: 126, 133, 138, 166, 666, and 675 (markers: miR-4739, miR-1202, miR-1343-5p, miR-6794-5p, miR-6808-5p, and miR-6717-5p).

Non-limiting examples of the combination of the polynucleotide consisting of the nucleotide sequence represented by SEQ ID NO: 138 or a complementary sequence thereof with polynucleotides consisting of nucleotide sequences represented by SEQ ID NOs of five polynucleotides selected from the cancer type-specific polynucleotide group 1 or complementary sequences thereof are further listed below.

(1) a combination of polynucleotides consisting of the nucleotide sequences represented by SEQ ID NOs: 1, 85, 138, 166, 666, and 669 (markers: miR-4739, miR-1343-5p, miR-204-3p, miR-4723-5p, miR-1909-3p, and miR-6717-5p);

(2) a combination of polynucleotides consisting of the nucleotide sequences represented by SEQ ID NOs: 8, 85, 138, 166, 185, and 666 (markers: miR-4739, miR-1343-5p, miR-125a-3p, miR-4723-5p, miR-4257, and miR-6717-5p);

(3) a combination of polynucleotides consisting of the nucleotide sequences represented by SEQ ID NOs: 1, 35, 121, 138, 166, and 666 (markers: miR-4739, miR-1343-5p, miR-671-5p, miR-204-3p, miR-6765-3p, and miR-6717-5p);

(4) a combination of polynucleotides consisting of the nucleotide sequences represented by SEQ ID NOs: 1, 121, 126, 138, 166, and 666 (markers: miR-4739, miR-1202, miR-1343-5p, miR-671-5p, miR-204-3p, and miR-6717-5p); and (5) a combination of polynucleotides consisting of the nucleotide sequences represented by SEQ ID NOs: 1, 121, 138, 166, 666, and 672 (markers: miR-4739, miR-1343-5p, miR-671-5p, miR-204-3p, miR-6836-3p, and miR-6717-5p).

Non-limiting examples of the combination of the polynucleotide consisting of the nucleotide sequence represented by SEQ ID NO: 166 or a complementary sequence thereof with polynucleotides consisting of nucleotide sequences represented by SEQ ID NOs of five polynucleotides selected from the cancer type-specific polynucleotide group 1 or complementary sequences thereof are further listed below.

(1) a combination of polynucleotides consisting of the nucleotide sequences represented by SEQ ID NOs: 1, 85, 138, 166, 666, and 672 (markers: miR-4739, miR-1343-5p, miR-204-3p, miR-4723-5p, miR-6836-3p, and miR-6717-5p);

(2) a combination of polynucleotides consisting of the nucleotide sequences represented by SEQ ID NOs: 56, 85, 138, 166, 185, and 666 (markers: miR-4739, miR-1343-5p, miR-125a-3p, miR-6724-5p, miR-4723-5p, and miR-6717-5p);

(3) a combination of polynucleotides consisting of the nucleotide sequences represented by SEQ ID NOs: 1, 32, 121, 138, 166, and 666 (markers: miR-4739, miR-1343-5p, miR-671-5p, miR-204-3p, miR-6787-5p, and miR-6717-5p);

(4) a combination of polynucleotides consisting of the nucleotide sequences represented by SEQ ID NOs: 1, 22, 121, 138, 166, and 666 (markers: miR-4739, miR-1343-5p, miR-7845-5p, miR-671-5p, miR-204-3p, and miR-6717-5p); and (5) a combination of polynucleotides consisting of the nucleotide sequences represented by SEQ ID NOs: 5, 85, 138, 166, 185, and 666 (markers: miR-4739, miR-1343-5p, miR-125a-3p, miR-4723-5p, miR-6726-5p, and miR-6717-5p).

Non-limiting examples of the combination of the polynucleotide consisting of the nucleotide sequence represented by SEQ ID NO: 666 or a complementary sequence thereof with polynucleotides consisting of nucleotide sequences represented by SEQ ID NOs of five polynucleotides selected from the cancer type-specific polynucleotide group 1 or complementary sequences thereof are further listed below.

(1) a combination of polynucleotides consisting of the nucleotide sequences represented by SEQ ID NOs: 1, 121, 138, 157, 166, and 666 (markers: miR-4739, miR-6752-5p, miR-1343-5p, miR-671-5p, miR-204-3p, and miR-6717-5p);

(2) a combination of polynucleotides consisting of the nucleotide sequences represented by SEQ ID NOs: 1, 85, 133, 138, 166, and 666 (markers: miR-4739, miR-1343-5p, miR-204-3p, miR-4723-5p, miR-6808-5p, and miR-6717-5p);

(3) a combination of polynucleotides consisting of the nucleotide sequences represented by SEQ ID NOs: 1, 121, 138, 166, 185, and 666 (markers: miR-4739, miR-1343-5p, miR-671-5p, miR-204-3p, miR-125a-3p, and miR-6717-5p);

(4) a combination of polynucleotides consisting of the nucleotide sequences represented by SEQ ID NOs: 1, 121, 138, 166, 666, and 667 (markers: miR-4739, miR-1343-5p, miR-671-5p, miR-3648, miR-204-3p, and miR-6717-5p); and (5) a combination of SEQ ID NOs: 85, 138, 166, 185, and 666 (markers: miR-4739, miR-1343-5p, miR-125a-3p, miR-4723-5p, and miR-6717-5p).

The kit or the device of the present invention can also comprise a polynucleotide that is already known or that will be found in the future, to enable detection of esophageal cancer in addition to the polynucleotide(s) (which can include a variant, a fragment, and a derivative) according to the present invention.

The kit of the present invention can also comprise an antibody for measuring marker(s) for esophageal cancer examination known in the art, such as CEA or SCC, in addition to the polynucleotide(s), etc., according to the present invention described above.

These polynucleotides comprised in the kit of the present invention may be packaged in different containers either individually or in any combination.

The kit of the present invention may comprise a kit for extracting nucleic acids (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above are bonded or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring target nucleic acids through the use of hybridization using this array.

The kit or the device of the present invention comprises nucleic acids capable of specifically binding to the polynucleotides of at least one, preferably at least two, more preferably at least three, most preferably at least five to any of the esophageal cancer marker miRNAs, respectively, of the group 1 described above. The kit or the device of the present invention can optionally further comprise nucleic acids capable of specifically binding to the polynucleotides of at least one, preferably at least two, more preferably at least three, most preferably at least five to any of the esophageal cancer marker miRNAs, respectively, of the group 2 described above.

The kit or the device of the present invention can be used for detecting esophageal cancer as described in the Section 4 below.

4. Method for Detecting Esophageal Cancer

The present invention further provides a method for detecting esophageal cancer, comprising using the kit or the device of the present invention (comprising the above-mentioned nucleic acid(s) that can be used in the present invention) described in the preceding Section "3. Kit or device for detection of esophageal cancer" to measure expression levels of one or more esophageal cancer-derived genes represented by an expression level(s) of esophageal cancer-derived gene(s) selected from the following group 1 of miRNAs, i.e., hsa-miR-204-3p, hsa-miR-1247-3p, hsa-miR-6875-5p, hsa-miR-6857-5p, hsa-miR-6726-5p, hsa-miR-3188, hsa-miR-8069, hsa-miR-4257, hsa-miR-1343-3p, hsa-miR-7108-5p, hsa-miR-6825-5p, hsa-miR-7641, hsa-miR-3185, hsa-miR-4746-3p, hsa-miR-6791-5p, hsa-miR-6893-5p, hsa-miR-4433b-3p, hsa-miR-3135b, hsa-miR-6781-5p, hsa-miR-1908-5p, hsa-miR-4792, hsa-miR-7845-5p, hsa-miR-4417, hsa-miR-3184-5p, hsa-miR-1225-5p, hsa-miR-1231, hsa-miR-1225-3p, hsa-miR-150-3p, hsa-miR-4433-3p, hsa-miR-6125, hsa-miR-4513, hsa-miR-6787-5p, hsa-miR-6784-5p, hsa-miR-615-5p, hsa-miR-6765-3p, hsa-miR-5572, hsa-miR-6842-5p, hsa-miR-8063, hsa-miR-6780b-5p, hsa-miR-187-5p, hsa-miR-128-1-5p, hsa-miR-6729-5p, hsa-miR-6741-5p, hsa-miR-6757-5p, hsa-miR-7110-5p, hsa-miR-7975, hsa-miR-1233-5p, hsa-miR-6845-5p, hsa-miR-3937, hsa-miR-4467, hsa-miR-7109-5p, hsa-miR-6088, hsa-miR-6782-5p, hsa-miR-5195-3p, hsa-miR-4454, hsa-miR-6724-5p, hsa-miR-8072, hsa-miR-4516, hsa-miR-6756-5p, hsa-miR-4665-3p, hsa-miR-6826-5p, hsa-miR-6820-5p, hsa-miR-6887-5p, hsa-miR-3679-5p, hsa-miR-7847-3p, hsa-miR-6721-5p, hsa-miR-3622a-5p, hsa-miR-939-5p, hsa-miR-602, hsa-miR-7977, hsa-miR-6749-5p, hsa-miR-1914-3p, hsa-miR-4651, hsa-miR-4695-5p, hsa-miR-6848-5p, hsa-miR-1228-3p, hsa-miR-642b-3p, hsa-miR-6746-5p, hsa-miR-3620-5p, hsa-miR-3131, hsa-miR-6732-5p, hsa-miR-7113-3p, hsa-miR-23a-3p, hsa-miR-3154, hsa-miR-4723-5p, hsa-miR-3663-3p, hsa-miR-4734, hsa-miR-6816-5p, hsa-miR-4442, hsa-miR-4476, hsa-miR-423-5p, hsa-miR-1249, hsa-miR-6515-3p, hsa-miR-887-3p, hsa-miR-4741, hsa-miR-6766-3p, hsa-miR-4673, hsa-miR-6779-5p, hsa-miR-4706, hsa-miR-1268b, hsa-miR-4632-5p, hsa-miR-3197, hsa-miR-6798-5p, hsa-miR-711, hsa-miR-6840-3p, hsa-miR-6763-5p, hsamiR-6727-5p, hsa-miR-371a-5p, hsa-miR-6824-5p, hsa-miR-4648, hsa-miR-1227-5p, hsa-miR-564, hsa-miR-3679-3p, hsa-miR-2861, hsa-miR-6737-5p, hsa-miR-4725-3p, hsa-miR-6716-5p, hsa-miR-4675, hsa-miR-1915-3p, hsa-miR-671-5p, hsa-miR-3656, hsa-miR-6722-3p, hsa-miR-4707-5p, hsa-miR-4449, hsa-miR-1202, hsa-miR-4649-5p, hsa-miR-744-5p, hsa-miR-642a-3p, hsa-miR-451a, hsa-miR-6870-5p, hsa-miR-4443, hsa-miR-6808-5p, hsa-miR-4728-5p, hsa-miR-937-5p, hsa-miR-135a-3p, hsa-miR-663b, hsa-miR-1343-5p, hsa-miR-6822-5p, hsa-miR-6803-5p, hsa-miR-6805-3p, hsa-miR-128-2-5p, hsa-miR-4640-5p, hsa-miR-1469, hsa-miR-92a-2-5p, hsa-miR-3940-5p, hsa-miR-4281, hsa-miR-1260b, hsa-miR-4758-5p, hsa-miR-1915-5p, hsa-miR-5001-5p, hsa-miR-4286, hsa-miR-6126, hsa-miR-6789-5p, hsa-miR-4459, hsa-miR-1268a, hsa-miR-6752-5p, hsa-miR-6131, hsa-miR-6800-5p, hsa-miR-4532, hsa-miR-6872-3p, hsa-miR-718, hsa-miR-6769a-5p, hsa-miR-4707-3p, hsa-miR-6765-5p, hsa-miR-4739, hsa-miR-4525, hsa-miR-4270, hsa-miR-4534, hsa-miR-6785-5p, hsa-miR-6850-5p, hsa-miR-4697-5p, hsa-miR-1260a, hsa-miR-4486, hsa-miR-6880-5p, hsa-miR-6802-5p, hsa-miR-6861-5p, hsa-miR-92b-5p, hsa-miR-1238-5p, hsa-miR-6851-5p, hsa-miR-7704, hsa-miR-149-3p, hsa-miR-4689, hsa-miR-4688, hsa-miR-125a-3p, hsa-miR-23b-3p, hsa-miR-614, hsa-miR-1913, hsa-miR-16-5p, hsa-miR-6717-5p, hsa-miR-3648, hsa-miR-3162-5p, hsa-miR-1909-3p, hsa-miR-8073, hsa-miR-6769b-5p, hsa-miR-6836-3p, hsa-miR-4484, hsa-miR-6819-5p, and hsa-miR-6794-5p; and optionally expression levels of esophageal cancer-derived gene(s) selected from the following group 2: i.e., hsa-miR-575 and hsa-miR-24-3p; and optionally expression levels of esophageal cancer-derived gene(s) selected from the following group 3: i.e., hsa-miR-675-5p, hsa-miR-486-3p, hsa-miR-6777-5p, hsa-miR-4497, hsa-miR-296-3p, hsa-miR-6738-5p, hsa-miR-4731-5p, hsa-miR-6889-5p, hsa-miR-6786-5p, hsa-miR-92a-3p, hsa-miR-4294, hsa-miR-4763-3p, hsa-miR-6076, hsa-miR-663a, hsa-miR-760, hsa-miR-4667-5p, hsa-miR-6090, hsa-miR-4730, hsa-miR-7106-5p, hsa-miR-3196, hsa-miR-5698, hsa-miR-6087, hsa-miR-4665-5p, hsa-miR-8059, and hsa-miR-6879-5p in a sample in vitro, further comparing, for example, the expression level of the gene described above in the sample (e.g., blood, serum, or plasma) collected from a subject suspected of having esophageal cancer with a control expression level in the sample collected from a healthy subject (including a non-esophageal cancer patient), and evaluating the subject as having esophageal cancer when the expression level of the target nucleic acid is different between the samples.

This method of the present invention enables a limitedly invasive, early diagnosis of the cancer with high sensitivity and high specificity and thereby brings about early treatment and improved prognosis. In addition, exacerbation of the disease or the effectiveness of surgical, radiotherapeutic, and chemotherapeutic treatments can be monitored.

The method for extracting the esophageal cancer-derived gene(s) from the sample such as blood, serum, or plasma according to the present invention is/are particularly preferably prepared by the addition of a reagent for RNA extraction in 3D-Gene™ RNA extraction reagent from liquid sample kit (Toray Industries, Inc.). A general acidic phenol method (acid guanidinium-phenol-chloroform (AGPC)) may be used, or Trizol™ (Life Technologies Corp.) may be used. The esophageal cancer-derived gene(s) may be prepared by the addition of a reagent for RNA extraction containing acidic phenol, such as Trizol™ (Life Technologies Corp.) or Isogen (Nippon Gene Co., Ltd.). Alternatively, a kit such as miRNeasy™ Mini Kit (Qiagen N.V.) may be used, though the method is not limited thereto.

The present invention also provides use of the kit or the device of the present invention for detecting in vitro an expression product(s) of an esophageal cancer-derived miRNA gene(s) in a sample from a subject.

In the method of the present invention, the kit or the device described above comprising a single polynucleotide or any possible combination of polynucleotides that can be used in the present invention as described above.

In the detection or (gentice) diagnosis of esophageal cancer according to the present invention, each polynucleotide contained in the kit or the device of the present invention can be used as a probe or a primer. In the case of using the polynucleotide as a primer, TaqMan™ MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine from a subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of esophageal cancer or the detection of the presence or absence of esophageal cancer. Specifically, the detection of esophageal cancer using the kit or the device can be performed by detecting in vitro expression level(s) of gene(s) using the nucleic acid probe(s) or the primer(s) contained in the kit or the device in a sample such as blood, serum, plasma, or urine from a subject suspected of having esophageal cancer. The subject suspected of having esophageal cancer can be evaluated as having esophageal cancer when the expression level(s) of target miRNA marker(s) measured using polynucleotide(s) (including variant(s), fragment(s), and derivative(s) thereof) consisting of a nucleotide sequence(s) represented by at least one of SEQ ID NOs: 1 to 115, 117 to 189, and 666 to 675 or a complementary sequence(s) thereof, and optionally nucleotide sequence(s) represented by one or more of SEQ ID NOs: 116 and 676 or a complementary sequence thereof, and optionally a nucleotide sequence(s) represented by one or more of SEQ ID NOs: 190 to 214 or a complementary sequence(s) thereof, in the sample such as blood, serum, plasma, or urine of the subject has a statistically significantly higher or lower than the expression level(s) thereof in the sample such as blood, serum, or plasma, or urine of a healthy subject.

The method of the present invention can be combined with a diagnostic imaging method such as esophagography, endoscopy, CT scan, MRI scan, endosonography, or ultrasonography. The method of the present invention is capable of specifically detecting esophageal cancer and can substantially discriminate esophageal cancer from the other cancers.

The method for detecting the absence of an expression product of esophageal cancer-derived gene(s) or the presence of the expression product(s) of esophageal cancer-derived gene(s) in a sample using the kit or the device of the present invention comprises collecting a body fluid such as blood, serum, plasma, or urine of a subject, and measuring the expression level(s) of the target gene(s) contained therein using one or more polynucleotides (including variant(s), fragment(s), and derivative(s)) selected from the polynucleotide group of the present invention, to evaluate the presence or absence of esophageal cancer or to detect esophageal cancer. Using the method for detecting esophageal cancer according to the present invention, for example, the presence or absence of amelioration of the disease or the degree of amelioration thereof in an esophageal cancer patient given a therapeutic drug for the amelioration of the disease can be also evaluated or diagnosed.

The method of the present invention can comprise, for example, the following steps (a), (b), and (c):

(a) a step of contacting in vitro a sample from a subject with polynucleotide(s) contained in the kit or the device of the present invention;

(b) a step of measuring expression level(s) of the target nucleic acid in the sample using the polynucleotide(s) as nucleic acid probe(s) or primer(s); and (c) a step of evaluating the presence or absence of esophageal cancer (cells) in the subject on the basis of the measurement results in the step (b).

Specifically, the present invention provides a method for detecting esophageal cancer, comprising measuring expression level(s) of target nucleic acid(s) in a sample of a subject using a nucleic acid(s) capable of specifically binding to at least one (preferably at least two) polynucleotides selected from the group consisting of miR-204-3p, miR-1247-3p, miR-6875-5p, miR-6857-5p, miR-6726-5p, miR-3188, miR-8069, miR-4257, miR-1343-3p, miR-7108-5p, miR-6825-5p, miR-7641, miR-3185, miR-4746-3p, miR-6791-5p, miR-6893-5p, miR-4433b-3p, miR-3135b, miR-6781-5p, miR-1908-5p, miR-4792, miR-7845-5p, miR-4417, miR-3184-5p, miR-1225-5p, miR-1231, miR-1225-3p, miR-150-3p, miR-4433-3p, miR-6125, miR-4513, miR-6787-5p, miR-6784-5p, miR-615-5p, miR-6765-3p, miR-5572, miR-6842-5p, miR-8063, miR-6780b-5p, miR-187-5p, miR-128-1-5p, miR-6729-5p, miR-6741-5p, miR-6757-5p, miR-7110-5p, miR-7975, miR-1233-5p, miR-6845-5p, miR-3937, miR-4467, miR-7109-5p, miR-6088, miR-6782-5p, miR-5195-3p, miR-4454, miR-6724-5p, miR-8072, miR-4516, miR-6756-5p, miR-4665-3p, miR-6826-5p, miR-6820-5p, miR-6887-5p, miR-3679-5p, miR-7847-3p, miR-6721-5p, miR-3622a-5p, miR-939-5p, miR-602, miR-7977, miR-6749-5p, miR-1914-3p, miR-4651, miR-4695-5p, miR-6848-5p, miR-1228-3p, miR-642b-3p, miR-6746-5p, miR-3620-5p, miR-3131, miR-6732-5p, miR-7113-3p, miR-23a-3p, miR-3154, miR-4723-5p, miR-3663-3p, miR-4734, miR-6816-5p, miR-4442, miR-4476, miR-423-5p, miR-1249, miR-6515-3p, miR-887-3p, miR-4741, miR-6766-3p, miR-4673, miR-6779-5p, miR-4706, miR-1268b, miR-4632-5p, miR-3197, miR-6798-5p, miR-711, miR-6840-3p, miR-6763-5p, miR-6727-5p, miR-371a-5p, miR-6824-5p, miR-4648, miR-1227-5p, miR-564, miR-3679-3p, miR-2861, miR-6737-5p, miR-4725-3p, miR-6716-5p, miR-4675, miR-1915-3p, miR-671-5p, miR-3656, miR-6722-3p, miR-4707-5p, miR-4449, miR-1202, miR-4649-5p, miR-744-5p, miR-642a-3p, miR-451a, miR-6870-5p, miR-4443, miR-6808-5p, miR-4728-5p, miR-937-5p, miR-135a-3p, miR-663b, miR-1343-5p, miR-6822-5p, miR-6803-5p, miR-6805-3p, miR-128-2-5p, miR-4640-5p, miR-1469, miR-92a-2-5p, miR-3940-5p, miR-4281, miR-1260b, miR-4758-5p, miR-1915-5p, miR-5001-5p, miR-4286, miR-6126, miR-6789-5p, miR-4459, miR-1268a, miR-6752-5p, miR-6131, miR-6800-5p, miR-4532, miR-6872-3p, miR-718, miR-6769a-5p, miR-4707-3p, miR-6765-5p, miR-4739, miR-4525, miR-4270, miR-4534, miR-6785-5p, miR-6850-5p, miR-4697-5p, miR-1260a, miR-4486, miR-6880-5p, miR-6802-5p, miR-6861-5p, miR-92b-5p, miR-1238-5p, miR-6851-5p, miR-7704, miR-149-3p, miR-4689, miR-4688, miR-125a-3p, miR-23b-3p, miR-614, miR-1913, miR-16-5p, miR-6717-5p, miR-3648, miR-3162-5p, miR-1909-3p, miR-8073, miR-6769b-5p, miR-6836-3p, miR-4484, miR-6819-5p and miR-6794-5p; and evaluating in vitro whether or not the subject has esophageal cancer in the subject using the above-measured expression levels and a control expression level of healthy subject(s) measured in the same way as above.

The term "evaluation" used herein is evaluation support based on results of in vitro examination, not physician's judgment.

As described above, in a preferred embodiment of the method of the present invention, specifically, miR-204-3p is hsa-miR-204-3p, miR-1247-3p is hsa-miR-1247-3p, miR-6875-5p is hsa-miR-6875-5p, miR-6857-5p is hsa-miR-6857-5p, miR-6726-5p is hsa-miR-6726-5p, miR-3188 is hsa-miR-3188, miR-8069 is hsa-miR-8069, miR-4257 is hsa-miR-4257, miR-1343-3p is hsa-miR-1343-3p, miR-7108-5p is hsa-miR-7108-5p, miR-6825-5p is hsa-miR-6825-5p, miR-7641 is hsa-miR-7641, miR-3185 is hsa-miR-3185, miR-4746-3p is hsa-miR-4746-3p, miR-6791-5p is hsa-miR-6791-5p, miR-6893-5p is hsa-miR-6893-5p, miR-4433b-3p is hsa-miR-4433b-3p, miR-3135b is hsa-miR-3135b, miR-6781-5p is hsa-miR-6781-5p, miR-1908-5p is hsa-miR-1908-5p, miR-4792 is hsa-miR-4792, miR-7845-5p is hsa-miR-7845-5p, miR-4417 is hsa-miR-4417, miR-3184-5p is hsa-miR-3184-5p, miR-1225-5p is hsa-miR-1225-5p, miR-1231 is hsa-miR-1231, miR-1225-3p is hsa-miR-1225-3p, miR-150-3p is hsa-miR-150-3p, miR-4433-3p is hsa-miR-4433-3p, miR-6125 is hsa-miR-6125, miR-4513 is hsa-miR-4513, miR-6787-5p is hsa-miR-6787-5p, miR-6784-5p is hsa-miR-6784-5p, miR-615-5p is hsa-miR-615-5p, miR-6765-3p is hsa-miR-6765-3p, miR-5572 is hsa-miR-5572, miR-6842-5p is hsa-miR-6842-5p, miR-8063 is hsa-miR-8063, miR-6780b-5p is hsa-miR-6780b-5p, miR-187-5p is hsa-miR-187-5p, miR-128-1-5p is hsa-miR-128-1-5p, miR-6729-5p is hsa-miR-6729-5p, miR-6741-5p is hsa-miR-6741-5p, miR-6757-5p is hsa-miR-6757-5p, miR-7110-5p is hsa-miR-7110-5p, miR-7975 is hsa-miR-7975, miR-1233-5p is hsa-miR-1233-5p, miR-6845-5p is hsa-miR-6845-5p, miR-3937 is hsa-miR-3937, miR-4467 is hsa-miR-4467, miR-7109-5p is hsa-miR-7109-5p, miR-6088 is hsa-miR-6088, miR-6782-5p is hsa-miR-6782-5p, miR-5195-3p is hsa-miR-5195-3p, miR-4454 is hsa-miR-4454, miR-6724-5p is hsa-miR-6724-5p, miR-8072 is hsa-miR-8072, miR-4516 is hsa-miR-4516, miR-6756-5p is hsa-miR-6756-5p, miR-4665-3p is hsa-miR-4665-3p, miR-6826-5p is hsa-miR-6826-5p, miR-6820-5p is hsa-miR-6820-5p, miR-6887-5p is hsa-miR-6887-5p, miR-3679-5p is hsa-miR-3679-5p, miR-7847-3p is hsa-miR-7847-3p, miR-6721-5p is hsa-miR-6721-5p, miR-3622a-5p is hsa-miR-3622a-5p, miR-939-5p is hsa-miR-939-5p, miR-602 is hsa-miR-602, miR-7977 is hsa-miR-7977, miR-6749-5p is hsa-miR-6749-5p, miR-1914-3p is hsa-miR-1914-3p, miR-4651 is hsa-miR-4651, miR-4695-5p is hsa-miR-4695-5p, miR-6848-5p is hsa-miR-6848-5p, miR-1228-3p is hsa-miR-1228-3p, miR-642b-3p is hsa-miR-642b-3p, miR-6746-5p is hsa-miR-6746-5p, miR-3620-5p is hsa-miR-3620-5p, miR-3131 is hsa-miR-3131, miR-6732-5p is hsa-miR-6732-5p, miR-7113-3p is hsa-miR-7113-3p, miR-23a-3p is hsa-miR-23a-3p, miR-3154 is hsa-miR-3154, miR-4723-5p is hsa-miR-4723-5p, miR-3663-3p is hsa-miR-3663-3p, miR-4734 is hsa-miR-4734, miR-6816-5p is hsa-miR-6816-5p, miR-4442 is hsa-miR-4442, miR-4476 is hsa-miR-4476, miR-423-5p is hsa-miR-423-5p, miR-1249 is hsa-miR-1249, miR-6515-3p is hsa-miR-6515-3p, miR-887-3p is hsa-miR-887-3p, miR-4741 is hsa-miR-4741, miR-6766-3p is hsa-miR-6766-3p, miR-4673 is hsa-miR-4673, miR-6779-5p is hsa-miR-6779-5p, miR-4706 is hsa-miR-4706, miR-1268b is hsa-miR-1268b, miR-4632-5p is hsa-miR-4632-5p, miR-3197 is hsa-miR-3197, miR-6798-5p is hsa-miR-6798-5p, miR-711 is hsa-miR-711, miR-6840-3p is hsa-miR-6840-3p, miR-6763-5p is hsa-miR-6763-5p, miR-6727-5p is hsa-miR-6727-5p, miR-371a-5p is hsa-miR-371a-5p, miR-6824-5p is hsa-miR-6824-5p, miR-4648 is hsa-miR-4648, miR-1227-5p is hsa-miR-1227-5p, miR-564 is hsa-miR-564, miR-3679-3p is hsa-miR-3679-3p, miR-2861 is hsa-miR-2861, miR-6737-5p is hsa-miR-6737-5p, miR-4725-3p is hsa-miR-4725-3p, miR-6716-5p is hsa-miR-6716-5p, miR-4675 is hsa-miR-4675, miR-1915-3p is hsa-miR-1915-3p, miR-671-5p is hsa-miR-671-5p, miR-3656 is hsa-miR-3656, miR-6722-3p is hsa-miR-6722-3p, miR-4707-5p is hsa-miR-4707-5p, miR-4449 is hsa-miR-4449, miR-1202 is hsa-miR-1202, miR-4649-5p is hsa-miR-4649-5p, miR-744-5p is hsa-miR-744-5p, miR-642a-3p is hsa-miR-642a-3p, miR-451a is hsa-miR-451a, miR-6870-5p is hsa-miR-6870-5p, miR-4443 is hsa-miR-4443, miR-6808-5p is hsa-miR-6808-5p, miR-4728-5p is hsa-miR-4728-5p, miR-937-5p is hsa-miR-937-5p, miR-135a-3p is hsa-miR-135a-3p, miR-663b is hsa-miR-663b, miR-1343-5p is hsa-miR-1343-5p, miR-6822-5p is hsa-miR-6822-5p, miR-6803-5p is hsa-miR-6803-5p, miR-6805-3p is hsa-miR-6805-3p, miR-128-2-5p is hsa-miR-128-2-5p, miR-4640-5p is hsa-miR-4640-5p, miR-1469 is hsa-miR-1469, miR-92a-2-5p is hsa-miR-92a-2-5p, miR-3940-5p is hsa-miR-3940-5p, miR-4281 is hsa-miR-4281, miR-1260b is hsa-miR-1260b, miR-4758-5p is hsa-miR-4758-5p, miR-1915-5p is hsa-miR-1915-5p, miR-5001-5p is hsa-miR-5001-5p, miR-4286 is hsa-miR-4286, miR-6126 is hsa-miR-6126, miR-6789-5p is hsa-miR-6789-5p, miR-4459 is hsa-miR-4459, miR-1268a is hsa-miR-1268a, miR-6752-5p is hsa-miR-6752-5p, miR-6131 is hsa-miR-6131, miR-6800-5p is hsa-miR-6800-5p, miR-4532 is hsa-miR-4532, miR-6872-3p is hsa-miR-6872-3p, miR-718 is hsa-miR-718, miR-6769a-5p is hsa-miR-6769a-5p, miR-4707-3p is hsa-miR-4707-3p, miR-6765-5p is hsa-miR-6765-5p, miR-4739 is hsa-miR-4739, miR-4525 is hsa-miR-4525, miR-4270 is hsa-miR-4270, miR-4534 is hsa-miR-4534, miR-6785-5p is hsa-miR-6785-5p, miR-6850-5p is hsa-miR-6850-5p, miR-4697-5p is hsa-miR-4697-5p, miR-1260a is hsa-miR-1260a, miR-4486 is hsa-miR-4486, miR-6880-5p is hsa-miR-6880-5p, miR-6802-5p is hsa-miR-6802-5p, miR-6861-5p is hsa-miR-6861-5p, miR-92b-5p is hsa-miR-92b-5p, miR-1238-5p is hsa-miR-1238-5p, miR-6851-5p is hsa-miR-6851-5p, miR-7704 is hsa-miR-7704, miR-149-3p is hsa-miR-149-3p, miR-4689 is hsa-miR-4689, miR-4688 is hsa-miR-4688, miR-125a-3p is hsa-miR-125a-3p, miR-23b-3p is hsa-miR-23b-3p, miR-614 is hsa-miR-614, miR-1913 is hsa-miR-1913, miR-16-5p is hsa-miR-16-5p, miR-6717-5p is hsa-miR-6717-5p, miR-3648 is hsa-miR-3648, miR-3162-5p is hsa-miR-3162-5p, miR-1909-3p is hsa-miR-1909-3p, miR-8073 is hsa-miR-8073, miR-6769b-5p is hsa-miR-6769b-5p, miR-6836-3p is hsa-miR-6836-3p, miR-4484 is hsa-miR-4484, miR-6819-5p is hsa-miR-6819-5p, and miR-6794-5p is hsa-miR-6794-5p.

In a preferred embodiment of the method of the present invention, specifically, the nucleic acid(s) (specifically, probe(s) or primer(s)) is selected from the group consisting of the following polynucleotides (a) to (e):

(a) a polynucleotide consisting of a nucleotide sequence represented by any of SEQ ID NOs: 1 to 115, 117 to 189, and 666 to 675 or a nucleotide sequence from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 115, 117 to 189, and 666 to 675, (c) a polynucleotide consisting of a nucleotide sequence complementary to a nucleotide sequence represented by any of SEQ ID NOs: 1 to 115, 117 to 189, and 666 to 675 or a nucleotide sequence from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 115, 117 to 189, and 666 to 675 or a nucleotide sequence from the nucleotide sequence by the replacement of u with t, and (e) a polynucleotide hybridizing under stringent conditions to any of the polynucleotides (a) to (d).

In the method of the present invention, a nucleic acid capable of specifically binding to a polynucleotide selected from miR-575 and miR-24-3p can be further used.

Specifically, miR-575 is hsa-miR-575, and miR-24-3p is hsa-miR-24-3p.

Specifically, the nucleic acid(s) is/are further selected from the group consisting of the following polynucleotides (f) to (j):

(f) a polynucleotide consisting of a nucleotide sequence represented by any of SEQ ID NOs: 116 and 676 or a nucleotide sequence from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 116 and 676, (h) a polynucleotide consisting of a nucleotide sequence complementary to a nucleotide sequence represented by any of SEQ ID NOs: 116 and 676 or a nucleotide sequence from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 116 and 676 or a nucleotide sequence from the nucleotide sequence by the replacement of u with t, and (j) a polynucleotide hybridizing under stringent conditions to any of the polynucleotides (f) to (i).

The nucleic acid(s) in the method of the present invention can further comprise a nucleic acid capable of specifically binding to at least one polynucleotides selected from the following miRNAs: miR-675-5p, miR-486-3p, miR-6777-5p, miR-4497, miR-296-3p, miR-6738-5p, miR-4731-5p, miR-6889-5p, miR-6786-5p, miR-92a-3p, miR-4294, miR-4763-3p, miR-6076, miR-663a, miR-760, miR-4667-5p, miR-6090, miR-4730, miR-7106-5p, miR-3196, miR-5698, miR-6087, miR-4665-5p, miR-8059 and miR-6879-5p.

In a preferred embodiment, as for such nucleic acids, specifically, miR-675-5p is hsa-miR-675-5p, miR-486-3p is hsa-miR-486-3p, miR-6777-5p is hsa-miR-6777-5p, miR-4497 is hsa-miR-4497, miR-296-3p is hsa-miR-296-3p, miR-6738-5p is hsa-miR-6738-5p, miR-4731-5p is hsa-miR-4731-5p, miR-6889-5p is hsa-miR-6889-5p, miR-6786-5p is hsa-miR-6786-5p, miR-92a-3p is hsa-miR-92a-

3p, miR-4294 is hsa-miR-4294, miR-4763-3p is hsa-miR-4763-3p, miR-6076 is hsa-miR-6076, miR-663a is hsa-miR-663a, miR-760 is hsa-miR-760, miR-4667-5p is hsa-miR-4667-5p, miR-6090 is hsa-miR-6090, miR-4730 is hsa-miR-4730, miR-7106-5p is hsa-miR-7106-5p, miR-3196 is hsa-miR-3196, miR-5698 is hsa-miR-5698, miR-6087 is hsa-miR-6087, miR-4665-5p is hsa-miR-4665-5p, miR-8059 is hsa-miR-8059, and miR-6879-5p is hsa-miR-6879-5p.

In a preferred embodiment, such nucleic acid(s) is specifically polynucleotide(s) selected from the group consisting of the following polynucleotides (k) to (o):

(k) a polynucleotide consisting of a nucleotide sequence represented by any of SEQ ID NOs: 190 to 214 or a nucleotide sequence from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 190 to 214, (m) a polynucleotide consisting of a nucleotide sequence complementary to a nucleotide sequence represented by any of SEQ ID NOs: 190 to 214 or a nucleotide sequence from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 190 to 214 or a nucleotide sequence from the nucleotide sequence by the replacement of u with t, and (o) a polynucleotide hybridizing under stringent conditions to any of the polynucleotides (k) to (n).

Examples of the sample used in the method of the present invention can include samples prepared from living tissues (preferably esophageal tissues) or body fluids such as blood, serum, plasma, and urine from subject. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

The subject used herein refers to a mammal, for example, a human, a monkey, a mouse or a rat without any limitation, and is preferably a human.

The steps of the method of the present invention can be changed according to the type of the sample to be assayed.

In the case of using RNA as an analyte, the detection of esophageal cancer (cells) can comprise, for example, the following steps (a), (b), and (c):

(a) a step of binding RNA prepared from a sample from a subject or complementary polynucleotides (cDNAs) transcribed from the RNA to a polynucleotides in the kit or the device of the present invention;

(b) a step of measuring the sample-derived RNA or the cDNA(s) synthesized from the RNA, which is/are bound to the polynucleotide(s) by hybridization using the polynucleotide(s) as nucleic acid probe(s) or by quantitative RT-PCR using the polynucleotide(s) as primer(s); and (c) a step of evaluating the presence or absence of esophageal cancer (or esophageal cancer-derived gene expression) on the basis of the measurement results of the step (b).

For example, various hybridization methods can be used for detecting, examining, evaluating, or diagnosing esophageal cancer (or esophageal cancer-derived gene expression) in vitro according to the present invention. For example, Northern blot, Southern blot, RT-PCR, DNA chip analysis, in situ hybridization, Northern hybridization, or Southern hybridization can be used as such a hybridization method.

In the case of using the Northern blot, the presence or absence of expression of each gene or the expression level thereof in the RNA can be detected or measured by use of the nucleic acid probe(s) that can be used in the present invention. Specific examples thereof can include a method which comprises labeling the nucleic acid probe (or a complementary strand) with a radioisotope ($^{32}$P, $^{33}$P, $^{35}$S, etc.), a fluorescent material, or the like, hybridizing the labeled product with the tissue-derived RNA from a subject, which is transferred to a nylon membrane or the like according to a routine method, and then detecting and measuring a signal from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which comprises preparing cDNA from the tissue-derived RNA of a subject according to a routine method, hybridizing a pair of primers (consisting of a plus strand and a reverse strand binding to the cDNA) of the present invention with the cDNA such that the region of each target gene can be amplified with the cDNA as a template, and performing PCR according to a routine method to detect the obtained double-stranded DNA. The method for detecting the double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the nucleic acid probes (single-stranded or double-stranded) of the present invention is attached to a substrate (solid phase) is used. Regions having the attached nucleic acid probes are referred to as probe spots, and regions having no attached nucleic acid probe are referred to as blank spots. A group of genes immobilized on a solid-phase substrate is generally called a nucleic acid chip, a nucleic acid array, a microarray, or the like. The DNA or RNA array includes a DNA or RNA macroarray and a DNA or RNA microarray. The term "chip" used herein includes any of these arrays. 3D-Gene™ Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal from the label on the nucleic acid probes using an image detector (examples thereof can include Typhoon 9410 (GE Healthcare) and 3D-Gene™ scanner (Toray Industries, Inc.)).

The "stringent conditions" used herein are, as mentioned above, conditions under which a nucleic acid probe hybridizes to its target sequence to a larger extent (e.g., a measurement value equal to or larger than "(a mean of background measurement values)+(a standard deviation of the background measurement values)×2") than that for other sequences.

The stringent conditions are defined by hybridization and subsequent washing conditions. Examples of the hybridization conditions include, but not limited to, 30° C. to 60° C. for 1 to 24 hours in a solution containing SSC, a surfactant, formamide, dextran sulfate, blocking agent(s), etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably comprise 3-10×SSC and 0.1-1% SDS. Examples of the conditions for the washing, following the hybridization, which is another condition to define the stringent conditions, can include conditions comprising continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus (+) strand even by washing under such conditions. Specifically, examples of such a complementary strand can include a strand consisting of a nucleotide sequence in a completely complementary relationship with the nucleotide sequence of the target plus strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using polynucleotide fragments in the kit of the present invention as primers include treatment for approximately 15 seconds to 1 minute at 5 to 10° C. plus a Tm value calculated from the sequences of the primers, using a PCR buffer having composition such as 10 mM Tris-HCL (pH 8.3), 50 mM KCL, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan™ MicroRNA Assays (Life Technologies Corp.); LNA™-based MicroRNA PCR (Exiqon); or Ncode™ miRNA qRT-PCT kit (Invitrogen Corp.) may be used.

For the calculation of gene expression levels, statistical treatment described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of $2^6$, preferably $2^8$, more preferably $2^{10}$ or larger in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method comprising measuring target genes or gene expression levels in a sample from a subject using the polynucleotide, the kit, or the device (e.g., chip) for detection of the present invention, or a combination thereof, preparing a discriminant (discriminant function) with gene expression levels in a sample from an esophageal cancer patient and a sample from a healthy subject as supervising samples, and determining or evaluating the presence and/or absence of the esophageal cancer-derived genes in the sample.

Specifically, the present invention further provides the method comprising: a first step of measuring in vitro expression levels of target genes (target nucleic acid) in multiple samples that were known to be able to determine or evaluate the presence and/or absence of the esophageal cancer-derived gene in the samples, using the polynucleotides, the kit, or the device (e.g., chip) for detection of the present invention, or a combination thereof; a second step of constructing a discriminant with the measurement values of the expression levels of the target genes that was obtained in the first step as supervising samples; a third step of measuring in vitro expression levels of the target gene in a sample from a subject in the same way as in the first step; and a fourth step of assigning the measurement values of the expression levels of the target gene obtained in the third step into the discriminant obtained in the second step, and determining or evaluating the presence or absence of the esophageal cancer-derived gene in the sample on the basis of the results obtained from the discriminant, wherein the target gene can be detected using the polynucleotide or using a polynucleotide for the detection, that was contained in the polynucleotide, the kit or the device (e.g., chip). In this context, the discriminant can be prepared by use of Fisher's discriminant analysis, nonlinear discriminant analysis based on Mahalanobis' distance, neural network, Support Vector Machine (SVM), or the like, though the method is not limited thereto.

When a clustering boundary is a straight line or a hyperplane, the linear discriminant analysis is a method for determining the association of a cluster using Formula 1 as a discriminant. In this formula, x represents an explanatory variable, w represents a coefficient of the explanatory variable, and w0 represents a constant term.

$$f(x) = w_0 + \sum_{i=1}^{n} w_i x_i \qquad \text{Formula 1}$$

Values obtained from the discriminant are referred to as discriminant scores. The measurement values of a newly offered data set can be assigned as explanatory variables to the discriminant to determine clusters by the signs of the discriminant scores.

The Fisher's discriminant analysis, one type of linear discriminant analysis, is a dimensionality reduction method for selecting a dimension suitable for discriminating classes, and constructs a highly discriminating synthetic variable by focusing on the variance of the synthetic variables and minimizing the variance of data having the same label (Venables, W. N. et al., Modern Applied Statistics with S. Fourth edition. Springer, 2002). In the Fisher's discriminant analysis, direction w of projection is determined so as to maximize Formula 2. In this formula, $\mu$ represents an average input, $n_g$ represents the number of data associate with class g, and $\mu_g$ represents an average input of the data associate with class g. The numerator and the denominator are the interclass variance and the intraclass variance, respectively, when each data is projected in the direction of the vector w. Discriminant coefficient $w_i$ is determined by maximizing this ratio (Takafumi Kanamori et al., "Pattern Recognition", Kyoritsu Shuppan Co., Ltd. (2009); and Richard O. et al., Pattern Classification Second Edition, Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i:y_i=g} (w^T x_i - w^T \mu_g)(w^T x_i - w^T \mu_g)}$$ Formula 2

$$\text{subject to } \mu = \sum_{i=1}^{n} \frac{x_i}{n}, \mu_g = \sum_{i:u_i=g}^{n} \frac{x_i}{n_g}$$

The Mahalanobis' distance is calculated according to Formula 3 in consideration of data correlation and can be used as nonlinear discriminant analysis for determining, a cluster in which a data point belongs to, based on a short Mahalanobis' distance from the data point to that cluster. In this formula, $\mu$ represents a central vector of each cluster, and $S^{-1}$ represents an inverse matrix of the variance-covariance matrix of the cluster. The central vector is calculated from explanatory variable x, and an average vector, a median value vector, or the like can be used.

$$D(x, \mu) = \{(x - \mu)^t S^{-1} (x - \mu)\}^{\frac{1}{2}}$$ Formula 3

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be assigned as explanatory variables to the discriminant to determine classes. In this respect, the result of the discriminant analysis may be classes, may be a probability of data to be classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, a RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (2004); Nello Cristianini et al., Introduction to SVM, Kyoritsu Shuppan Co., Ltd. (2008)).

C-support vector classification (C-SVC), one type of SVM, comprises preparing a hyperplane by supervising a data set with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., an esophageal cancer patient group and a healthy subject group. For example, esophageal tissue examination can be used for each subject to be confirmed either as an esophageal cancer patient or as a healthy subject.

Next, a data set consisting of comprehensive gene expression levels of serum-derived samples of the two divided groups (hereinafter, this data set is referred to as a training cohort) is prepared, and a C-SVC discriminant is determined by using genes that were found to differ clearly in their gene expression levels between the two groups as explanatory variables and using this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_a \frac{1}{2} a^T Q a - e^T a \text{ subject to}$$ Formula 4

$$y^T a = 0, 0 \le a_i \le C, i = 1, \ldots, l,$$

Formula 5 is a finally obtained discriminant, and a group in which the data point belongs to can be determined on the basis of the sign of a value obtained according to the discriminant. In this formula, x represents a support vector, y represents a label indicating the association of a group, a represents the corresponding coefficient, b represents a constant term, and K represents a kernel function.

$$f(x) = \text{sgn}\left(\sum_{i=1}^{l} y_i a_i K(x_i, x) + b\right)$$ Formula 5

For example, a RBF kernel defined by Formula 6 can be used as the kernel function. In this context, x represents a support vector, and y represents a kernel parameter for adjusting the complexity of the hyperplane.

$$K(x_i, x_j) = \exp(-r\|x_i - x_j\|^2), r<0$$ Formula 6

In addition, an approach such as neural network, k-nearest neighbor algorithms, decision trees, or logistic regression analysis can be selected as a method for determining or evaluating the presence and/or absence of expression of an esophageal cancer-derived target gene in a sample from a subject, or for evaluating the expression level thereof by comparison with a control from a healthy subject.

The method of the present invention can comprise, for example, the following steps (a), (b), and (c):

(a) a step of measuring expression level(s) of target gene(s) in tissues containing esophageal cancer-derived genes from esophageal cancer patients and/or samples already known to be tissues containing no esophageal cancer-derived gene(s) from healthy subjects, using the polynucleotide, the kit, or the device (e.g., DNA chip) for detection according to the present invention;

(b) a step of preparing the discriminants of Formulas 1 to 3, 5, and 6 described above from the measurement values of the expression level measured in the step (a); and (c) a step of measuring an expression level of the target gene in a sample from a subject using the polynucleotide, the kit, or the device (e.g., DNA chip) for diagnosis (detection) according to the present invention, assigning the obtained measurement value(s) into the discriminants prepared in the step (b), and determining or evaluating the presence and/or absence of expression of the esophageal cancer-derived target gene in the sample, or evaluating the expression level thereof by comparison with a healthy subject-derived control, on the basis of the obtained results. In this context, in the discriminants of Formulas 1 to 3, 5, and 6, x represents an explanatory variable and includes a value obtained by measuring a polynucleotide selected from the polynucleotides described above in the Section 2 above, or a fragment thereof. Specifically, the explanatory variable for discriminating an esophageal cancer patient from a healthy subject according to the present invention is gene expression level(s) selected from, for example, the following expression levels (1) to (3):

(1) gene expression level(s) in the serum of an esophageal cancer patient or a healthy subject measured by any DNA comprising 15 or more consecutive nucleotides in a nucleotide sequence represented by any of SEQ ID NOs: 1 to 115, 117 to 189, and 666 to 675 or a complementary sequence thereof, (2) gene expression level(s) in the serum of an esophageal cancer patient or a healthy subject measured by any DNA comprising 15 or more consecutive nucleotides in a nucleotide sequence represented by SEQ ID NOs: 116 and 676 or a complementary sequence thereof, and (3) gene expression level(s) in the serum of an esophageal cancer patient or a healthy subject measured by any DNA comprising 15 or more consecutive nucleotides in a nucleotide sequence represented by any of SEQ ID NOs: 190 to 214 or a complementary sequence thereof.

As described above, for the method for determining or evaluating the presence and/or absence of esophageal cancer-derived gene(s) in a sample from a subject, the preparation of a discriminant requires a discriminant prepared in a training cohort. For enhancing the discrimination accuracy of the discriminant, it is necessary for the discriminant to use genes that show clear difference between two groups in the training cohort.

Each gene that is used for an explanatory variable in a discriminant is preferably determined as follows. First, comprehensive gene expression levels of an esophageal cancer patient group and comprehensive gene expression levels of a healthy subject group, both of which are in a training cohort, are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) as the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the statistical test, the absolute value (fold change) of an expression ratio of a median value of each gene expression level between gene expression levels of an esophageal cancer patient group and gene expression levels of a healthy subject group may be calculated to select a gene that is used for an explanatory variable in a discriminant. Alternatively, ROC curves may be prepared using gene expression levels of an esophageal cancer patient group and a healthy subject group, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discriminant accuracy include a method of constructing a discriminant in every combination of genes that satisfy the significance level being P value, and a method of repetitively evaluating a discriminant while increasing the number of genes for use one by one in a descending order of difference in gene expression level (Furey T S. et al., 2000, Bioinformatics, Vol. 16, p. 906-14). A gene expression level of another independent esophageal cancer patient or healthy subject is assigned as an explanatory variable to this discriminant to calculate discriminant Specifically, the found gene set for diagnosis and the discriminant constructed using the gene set for diagnosis can be evaluated in an independent sample cohort to find a more universal gene set for diagnosis capable of detecting esophageal cancer and a more universal method for discriminating esophageal cancer.

Split-sample method is preferably used for evaluating the discriminant performance (generality). Specifically, a data set is divided into a training cohort and genes in serum from a patient confirmed to be negative using CEA but finally found to have esophageal cancer by detailed examination such as computed tomography using a contrast medium, with genes expressed in serum from a patient having no esophageal cancer.

For example, the gene set for diagnosis is set to any combination selected from one or two or more of the polynucleotides based on a nucleotide sequence represented by any of SEQ ID NOs: 1 to 115, 177 to 189, and 666 to 675 or a complementary sequence thereof as described above; and optionally one or two or more of the polynucleotides based on a nucleotide sequence represented by SEQ ID NOs: 116 and 676 or a complementary sequence thereof, and optionally one or two or more of the polynucleotides based on a nucleotide sequence represented by any of SEQ ID NOs: 190 to 214 or a complementary sequence thereof. Further, a discriminant is constructed using expression levels of the gene set for diagnosis in samples from class I esophageal cancer patients as a result of tissue diagnosis and samples from class II healthy subjects as a result of tissue diagnosis. As a result, the presence or absence of esophageal cancer-derived genes in an unknown sample can be determined with 100% accuracy at the maximum by measuring expression levels of the gene set for diagnosis in an unknown sample.

EXAMPLES

Hereinafter, the present invention will be described further specifically with reference to Examples below. However, the scope of the present invention is not intended to be limited by these Examples.

Reference Example 1

<Collection of Samples from Esophageal Cancer Patient and Healthy Subject>

Sera were collected using VENOJECT II vacuum blood collecting tube VP-AS109K60 (Terumo Corp.) from 100 healthy subjects and 34 esophageal cancer patients (3 cases with stage IB, 1 case with stage IIA, 5 cases with stage IIB, 4 cases with stage IIIA, 7 cases with stage IIIB, 2 cases with stage IIIC, and 1 case with yp stage IA, 3 cases with yp stage IIA, 2 cases with yp stage IIB, 5 cases with yp stage IIIA, and 1 case with yp stage IIIC as samples (yp) stage-classified by pathological examination after treatment) with no primary cancer found other than esophageal cancer after acquisition of informed consent, and used as a training cohort. Likewise, sera were collected using VENOJECT II vacuum blood collecting tube VP-AS109K60 (Terumo Corp.) from 50 healthy subjects and 16 esophageal cancer patients (3 cases with stage IIA, 2 cases with stage IIIA, 2 cases with stage IIIC, and 1 case with yp stage 0, 1 case with yp stage IA, 2 cases with yp stage IIA, 2 cases with yp stage IIIA, 1 case with yp stage IIIB, 1 case with yp stage IIIC, and 1 case with yp stage IV as samples (yp) stage-classified by pathological examination after treatment) with no primary cancer found other than esophageal cancer after acquisition of informed consent, and used as a validation cohort.

<Extraction of Total RNA>

Total RNA was obtained from 300 μL of the serum sample obtained from each of 200 persons in total of 150 healthy subjects and 50 esophageal cancer patients included in the training cohort and the validation cohort, using a reagent for RNA extraction in 3D-Gene™ RNA extraction reagent from liquid sample kit (Toray Industries, Inc.) according to the protocol provided by the manufacturer.

<Measurement of Gene Expression Level> miRNAs in the total RNA obtained from the serum samples of each of 200 persons in total of 150 healthy subjects and 50 esophageal cancer patients included in the training cohort and the validation cohort were fluorescently labeled using 3D-Gene™ miRNA Labeling kit (Toray Industries, Inc.) according to the protocol (ver 2.20) provided by the manufacturer. The oligo DNA chip used was 3D-Gene™ Human miRNA Oligo chip (Toray Industries, Inc.) with attached probes having sequences complementary to 2,555 miRNAs among the miRNAs registered in miR-Base Release 20. Hybridization between the miRNAs in the total RNA and the probes on the DNA chip under stringent conditions and washing following the hybridization were performed according to the protocol provided by the manufacturer. The DNA chip was scanned using 3D-Gene™ scanner (Toray Industries, Inc.) to obtain images. Fluorescence intensity was digitized using 3D-Gene™ Extraction (Toray Industries, Inc.). The digitized fluorescence intensity was converted to a logarithmic value having a nucleotide of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the sera were obtained for the 50 esophageal cancer patients and the 150 healthy subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/.) and MASS package 7.3-30 (Venables, W. N. & Ripley, B. D. (2002) Modern Applied Statistics with S. Fourth Edition. Springer, New York. ISBN 0-387-95457-0).

Reference Example 2

<Collection of Samples of Cancers Other than Esophageal Cancer>

Serum was collected using VENOJECT II vacuum blood collecting tube VP-AS109K60 (Terumo Corp.) from each of 69 pancreatic cancer patients, 66 bile duct cancer patients, 30 colorectal cancer patients, 33 stomach cancer patients, 32 liver cancer patients, and 15 benign pancreaticobiliary disease patients confirmed to have no cancer in other organs after acquisition of informed consent, and used as a training cohort together with the samples of 34 esophageal cancer patients and 103 healthy subjects of Reference Example 1.

Likewise, Sera were collected using VENOJECT II vacuum blood collecting tube VP-AS109K60 (Terumo Corp.) from each of 30 pancreatic cancer patients, 33 bile duct cancer patients, 20 colorectal cancer patients, 17 stomach cancer patients, 20 liver cancer patients, and 6 benign pancreaticobiliary disease patients confirmed to have no cancer in other organs after acquisition of informed consent, and used as a validation cohort together with the samples of 16 esophageal cancer patients confirmed to have no cancer in organs other than the esophagus and 47 healthy subjects of Reference Example 1. Subsequent operations were conducted in the same way as in Reference Example 1.

Example 1

<Selection of Gene Markers Using Samples of Training Cohort, and Method for Evaluating Esophageal Cancer Discriminant Performance of the Single Gene Marker Using the Validation Cohort>

In this Example, a gene marker for discriminating an esophageal cancer patient from a healthy subject was selected from the training cohort and studied in samples of the validation cohort independent of the training cohort, for a method for evaluating the esophageal cancer discriminant performance of each selected gene marker alone.

Specifically, first, the miRNA expression levels of the training cohort and the validation cohort obtained in the preceding Reference Examples were combined and normalized by quantile normalization.

Next, genes for diagnosis were selected using the training cohort. Here, in order to acquire diagnostic markers with higher reliability, only genes having the expression level of $2^6$ or higher in 50% or more of the samples in either of the esophageal cancer patient group of the training cohort or the healthy subject group of the training cohort were selected. In order to further acquire statistically significant genes for discriminating an esophageal cancer patient group from a healthy subject group, the P value obtained by two-tailed t-test assuming equal variance as to each gene expression level was corrected by the Bonferroni method, and genes that satisfied p<0.01 were acquired as gene markers for use in explanatory variables of a discriminant. The result is described in Table 2 mentioned later.

In this way, hsa-miR-204-3p, hsa-miR-1247-3p, hsa-miR-6875-5p, hsa-miR-6857-5p, hsa-miR-6726-5p, hsa-miR-3188, hsa-miR-8069, hsa-miR-4257, hsa-miR-1343-3p, hsa-miR-7108-5p, hsa-miR-6825-5p, hsa-miR-7641, hsa-miR-3185, hsa-miR-4746-3p, hsa-miR-6791-5p, hsa-miR-6893-5p, hsa-miR-4433b-3p, hsa-miR-3135b, hsa-miR-6781-5p, hsa-miR-1908-5p, hsa-miR-4792, hsa-miR-7845-5p, hsa-miR-4417, hsa-miR-3184-5p, hsa-miR-1225-5p, hsa-miR-1231, hsa-miR-1225-3p, hsa-miR-150-3p, hsa-miR-4433-3p, hsa-miR-6125, hsa-miR-4513, hsa-miR-6787-5p, hsa-miR-6784-5p, hsa-miR-615-5p, hsa-miR-6765-3p, hsa-miR-5572, hsa-miR-6842-5p, hsa-miR-8063, hsa-miR-6780b-5p, hsa-miR-187-5p, hsa-miR-128-1-5p, hsa-miR-6729-5p, hsa-miR-6741-5p, hsa-miR-6757-5p, hsa-miR-7110-5p, hsa-miR-7975, hsa-miR-1233-5p, hsa-miR-6845-5p, hsa-miR-3937, hsa-miR-4467, hsa-miR-7109-5p, hsa-miR-6088, hsa-miR-6782-5p, hsa-miR-5195-3p, hsa-miR-4454, hsa-miR-6724-5p, hsa-miR-8072, hsa-miR-4516, hsa-miR-6756-5p, hsa-miR-4665-3p, hsa-miR-6826-5p, hsa-miR-6820-5p, hsa-miR-6887-5p, hsa-miR-3679-5p, hsa-miR-7847-3p, hsa-miR-6721-5p, hsa-miR-3622a-5p, hsa-miR-939-5p, hsa-miR-602, hsa-miR-7977, hsa-miR-6749-5p, hsa-miR-1914-3p, hsa-miR-4651, hsa-miR-4695-5p, hsa-miR-6848-5p, hsa-miR-1228-3p, hsa-miR-642b-3p, hsa-miR-6746-5p, hsa-miR-3620-5p, hsa-miR-3131, hsa-miR-6732-5p, hsa-miR-7113-3p, hsa-miR-23a-3p, hsa-miR-3154, hsa-miR-4723-5p, hsa-miR-3663-3p, hsa-miR-4734, hsa-miR-6816-5p, hsa-miR-4442, hsa-miR-4476, hsa-miR-423-5p, hsa-miR-1249, hsa-miR-6515-3p, hsa-miR-887-3p, hsa-miR-4741, hsa-miR-6766-3p, hsa-miR-4673, hsa-miR-6779-5p, hsa-miR-4706, hsa-miR-1268b, hsa-miR-4632-5p, hsa-miR-3197, hsa-miR-6798-5p, hsa-miR-711, hsa-miR-6840-3p, hsa-miR-6763-5p, hsa-miR-6727-5p, hsa-miR-371a-5p, hsa-miR-6824-5p, hsa-miR-4648, hsa-miR-1227-5p, hsa-miR-564, hsa-miR-3679-3p, hsa-miR-2861, hsa-miR-6737-5p, hsa-miR-575, hsa-miR-4725-3p, hsa-miR-6716-5p, hsa-miR-4675, hsa-miR-1915-3p, hsa-miR-671-5p, hsa-miR-3656, hsa-miR-6722-3p, hsa-miR-4707-5p, hsa-miR-4449, hsa-miR-1202, hsa-miR-4649-5p, hsa-miR-744-5p, hsa-miR-642a-3p, hsa-miR-451a, hsa-miR-6870-5p, hsa-miR-4443, hsa-miR-6808-5p, hsa-miR-4728-5p, hsa-miR-937-5p, hsa-miR-135a-3p, hsa-miR-663b, hsa-miR-1343-5p, hsa-miR-6822-5p, hsa-miR-6803-5p, hsa-miR-6805-3p, hsa-miR-128-2-5p, hsa-miR-4640-5p, hsa-miR-1469, hsa-miR-92a-2-5p, hsa-miR-3940-5p, hsa-miR-4281, hsa-miR-1260b, hsa-miR-4758-5p, hsa-miR-1915-5p, hsa-miR-5001-5p, hsa-miR-4286, hsa-miR-6126, hsa-miR-6789-5p, hsa-miR-4459, hsa-miR-1268a, hsa-miR-6752-5p, hsa-miR-6131, hsa-miR-6800-5p, hsa-miR-4532, hsa-miR-6872-3p, hsa-miR-718, hsa-miR-6769a-5p, hsa-miR-4707-3p, hsa-miR-6765-5p, hsa-miR-4739, hsa-miR-4525, hsa-miR-4270, hsa-miR-4534, hsa-miR-6785-5p, hsa-miR-6850-5p, hsa-miR-4697-5p, hsa-miR-1260a, hsa-miR-4486, hsa-miR-6880-5p, hsa-miR-6802-5p, hsa-miR-6861-5p, hsa-miR-92b-5p, hsa-miR-1238-5p, hsa-miR-6851-5p, hsa-miR-7704, hsa-miR-149-3p, hsa-miR-4689, hsa-miR-4688, hsa-miR-125a-3p, hsa-miR-23b-3p, hsa-miR-614, hsa-miR-1913 and hsa-miR-16-5p genes, and polynucleotides consisting of the nucleotide sequences represented by SEQ ID NOs: 1 to 189 related thereto were found.

Among them, genes newly found as markers for examining the presence or absence of esophageal cancer are polynucleotides consisting of the nucleotide sequences represented by SEQ ID NOs: 1 to 115 and 117 to 189.

A discriminant for determining the presence or absence of esophageal cancer was further prepared by Fisher's discriminant analysis with the expression levels of these genes as indicators. Specifically, any polynucleotide consisting of a nucleotide sequence represented by any of SEQ ID NOs: 1 to 189 found in the training cohort was apply for Formula 2 above to construct a discriminant. Calculated accuracy, sensitivity, and specificity are shown in Table 3 mentioned later. In this respect, a discriminant coefficient and a constant term are shown in Table 4.

In this context, for example, 42 polynucleotides consisting of the nucleotide sequences represented by SEQ ID NOs: 1, 3, 4, 5, 6, 9, 10, 13, 15, 17, 18, 19, 26, 28, 29, 30, 32, 33, 35, 40, 41, 43, 55, 58, 61, 63, 67, 68, 70, 76, 77, 80, 90, 92, 93, 95, 109, 116, 119, 122, 127 and 150 were selected as markers capable of determining esophageal cancer even in any of 3 stage I samples included in the training cohort.

Figure 2:
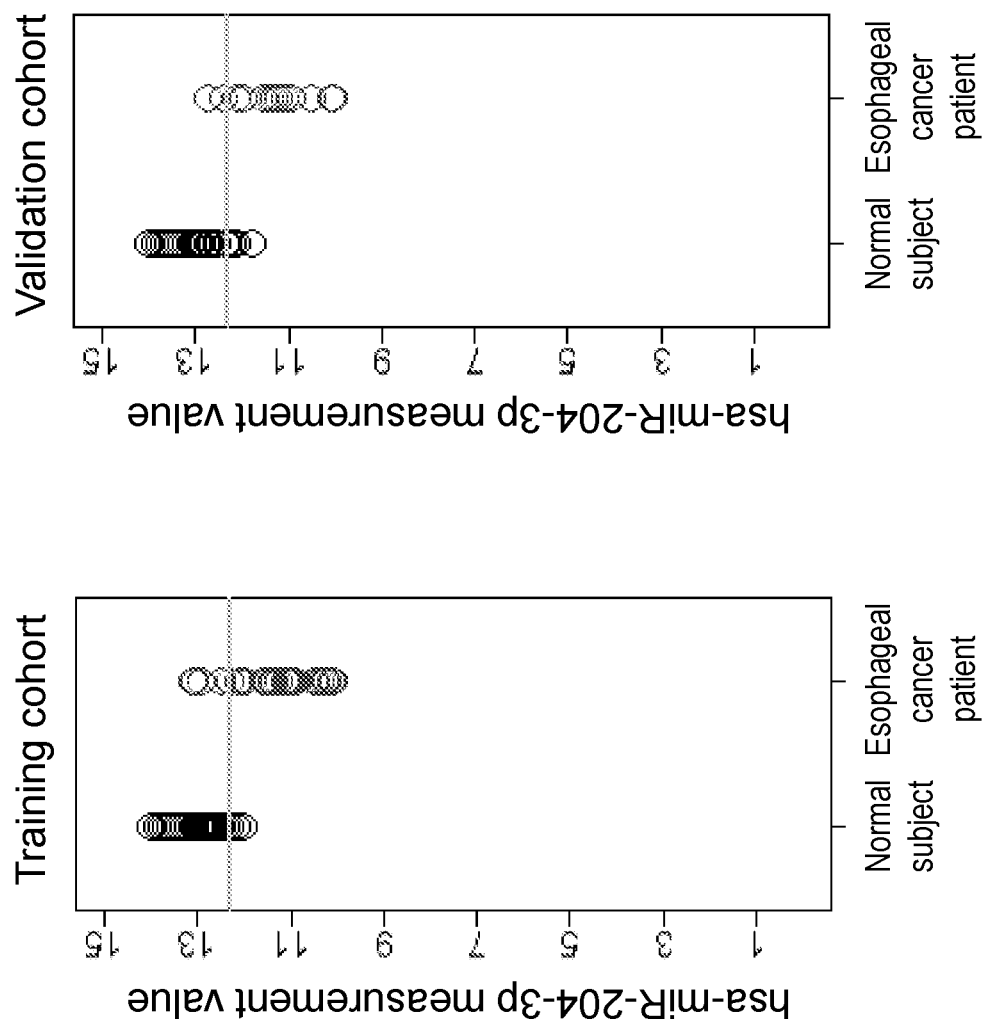
FIG. 2 Left diagram: the expression level measurement values of hsa-miR-204-3p (SEQ ID NO: 1) in healthy subjects (100 persons) and esophageal cancer patients (34 persons) selected as a training cohort were each plotted on the ordinate. The horizontal line in the diagram depicts a threshold (12.3) that was optimized by Fisher's discriminant analysis and discriminated between the two groups. Right diagram: the expression level measurement values of hsa-miR-204-3p (SEQ ID NO: 1) in healthy subjects (50 persons) and esophageal cancer patients (16 persons) selected as a validation cohort were each plotted on the ordinate. The horizontal line in the diagram depicts the threshold (12.3) that was set in the training cohort and discriminated between both of the groups.

Accuracy, sensitivity, and specificity for the validation cohort were calculated using the discriminant thus prepared, and the discriminant performance of the selected polynucleotides was validated using independent samples (Table 3). For example, the gene expression level measurement value of the nucleotide sequence represented by SEQ ID NO: 1 was compared between the healthy subjects (100 persons) and the esophageal cancer patients (34 persons) in the training cohort. As a result, the expression level measurement values were found to be significantly lower in the esophageal cancer patient group than in the healthy subject group (see the left diagram of FIG. 2). These results were also reproducible for the healthy subjects (50 persons) and the esophageal cancer patients (16 persons) in the validation cohort (see the right diagram of FIG. 2). Likewise, the results obtained about the other polynucleotides shown in SEQ ID NOs: 2 to 189 showed that the expression level measurement values were significantly lower (−) or higher (+) in the esophageal cancer patient group than in the healthy subject group (Table 2). These results were able to be validated in the validation cohort. For example, as for this nucleotide sequence represented by SEQ ID NO: 1, the number of correctly or incorrectly identified samples in the detection of esophageal cancer in the validation cohort was calculated using the threshold (12.3) that was set in the training cohort and discriminated between the two groups. As a result, 13 true positives, 48 true negatives, 2 false positives, and 3 false negatives were obtained. From these values, 92.4% accuracy, 81.2% sensitivity, and 96% specificity were obtained as detection performance. In this way, the detection performance was calculated as to any of the polynucleotides shown in SEQ ID NOs: 1 to 189, and described in Table 3. Likewise, 129 polynucleotides consisting of the nucleotide sequences represented by SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 102, 103, 104, 106, 107, 109, 110, 112, 113, 114, 115, 116, 117, 119, 120, 130, 131, 134, 139, 143, 151, 159, 173, 182, 185, 186, 187, 188 and 189 shown in Table 2 exhibited sensitivity of 81.2%, 87.5%, 93.8%, 100%, 87.5%, 87.5%, 81.2%, 75%, 87.5%, 100%, 100%, 87.5%, 81.2%, 75%, 87.5%, 87.5%, 81.2%, 93.8%, 93.8%, 81.2%, 100%, 87.5%, 68.8%, 87.5%, 81.2%, 75%, 87.5%, 81.2%, 81.2%, 87.5%, 75%, 68.8%, 81.2%, 75%, 68.8%, 100%, 68.8%, 87.5%, 87.5%, 81.2%, 68.8%, 75%, 75%, 87.5%, 68.8%, 62.5%, 93.8%, 75%, 81.2%, 62.5%, 56.2%, 56.2%, 56.2%, 75%, 68.8%, 62.5%, 62.5%, 62.5%, 68.8%, 68.8%, 68.8%, 56.2%, 56.2%, 56.2%, 81.2%, 56.2%, 50%, 68.8%, 75%, 56.2%, 56.2%, 56.2%, 62.5%, 43.8%, 50%, 56.2%, 56.2%, 68.8%, 62.5%, 62.5%, 68.8%, 56.2%, 43.8%, 62.5%, 56.2%, 43.8%, 43.8%, 75%, 56.2%, 56.2%, 62.5%, 56.2%, 87.5%, 43.8%, 50%, 43.8%, 50%, 56.2%, 43.8%, 50%, 43.8%, 68.8%, 62.5%, 56.2%, 43.8%, 43.8%, 56.2%, 56.2%, 62.5%, 56.2%, 62.5%, 50%, 68.8%, 56.2%, 43.8%, 62.5%, 43.8%, 43.8%, 43.8%, 43.8%, 50%, 56.2%, 43.8%, 43.8%, 75%, 62.5%, 43.8%, 50% and 62.5%, respectively, in the validation cohort (Table 3). As seen from Comparative Example mentioned later, the existing marker SCC for esophageal cancer had sensitivity of 37.5% in the validation cohort (Table 5-2), demonstrating that the 129 polynucleotides consisting of the nucleotide sequences represented by SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 102, 103, 104, 106, 107, 109, 110, 112, 113, 114, 115, 116, 117, 119, 120, 130, 131, 134, 139, 143, 151, 159, 173, 182, 185, 186, 187, 188 and 189 can discriminate, each alone, esophageal cancer in the validation cohort with sensitivity beyond SCC.

Thus, these polynucleotides can detect even early esophageal cancer and contribute to the early diagnosis of esophageal cancer.

Example 2

<Method for Evaluating Esophageal Cancer Discriminant Performance by Combination of Multiple Gene Markers Using Samples in the Validation Cohort>

In this Example, a method for evaluating esophageal cancer discriminant performance by a combination of the gene markers selected in Example 1 was studied. Specifically, Fisher's discriminant analysis was conducted as to 17,766 combinations of any two of the expression level measurement values of the newly found polynucleotides consisting of the nucleotide sequences represented by SEQ ID NOs: 1 to 115 and 117 to 189 among the polynucleotides consisting of the nucleotide sequences represented by SEQ ID NOs: 1 to 189 selected in Example 1, to construct a discriminant for determining the presence or absence of esophageal cancer. Next, accuracy, sensitivity, and specificity in the validation cohort were calculated using the discriminant thus prepared, and the discriminant performance of the selected polynucleotides was validated using the independent samples.

Figure 3:
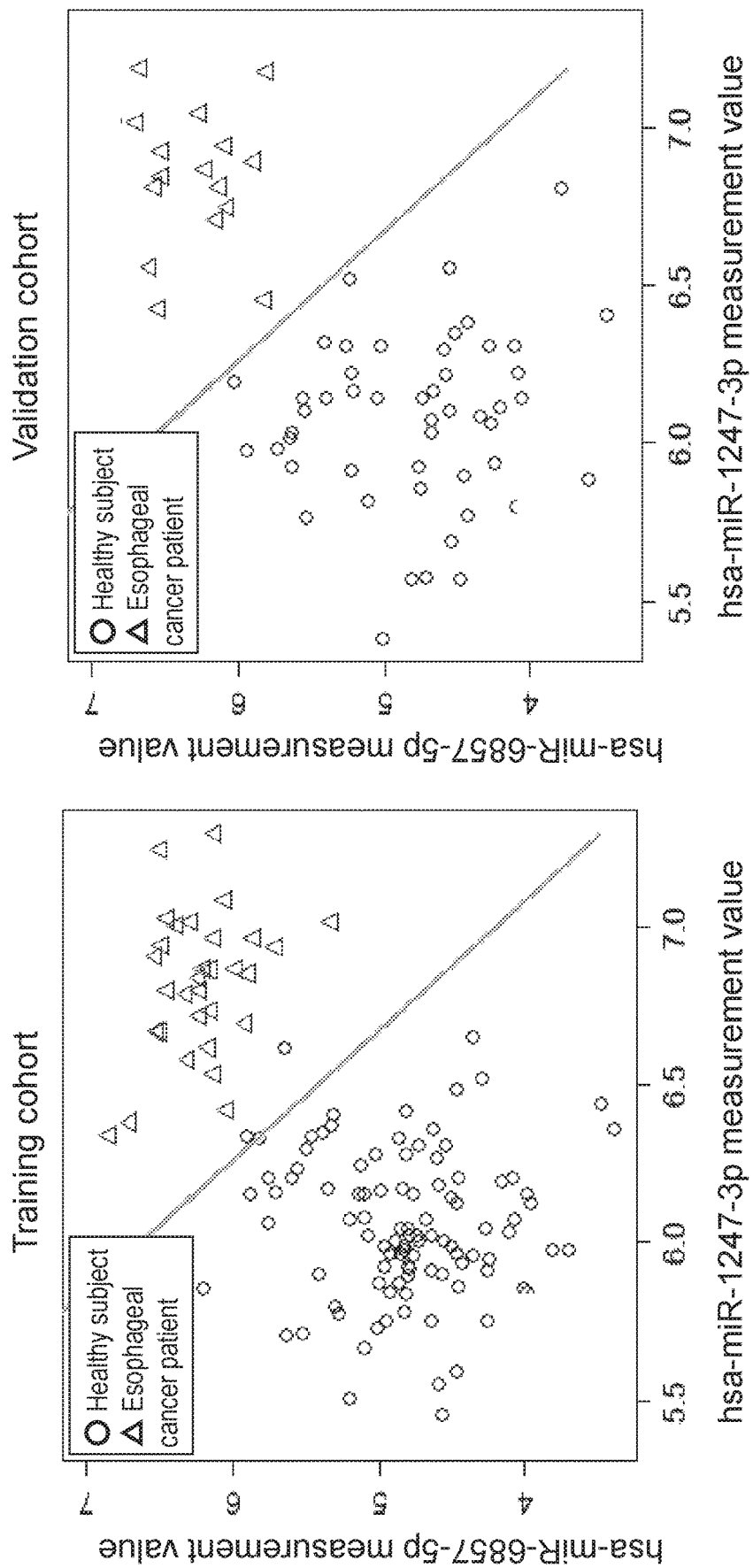
FIG. 3 Left diagram: the expression level measurement values of hsa-miR-1247-3p (SEQ ID NO: 2) in healthy subjects (100 persons, circles) and esophageal cancer patients (34 persons, triangles) selected as training cohort were each plotted on the abscissa against their expression level measurement values of hsa-miR-6857-5p (SEQ ID NO: 4) on the ordinate. The line in the diagram depicts a discriminant function (0=2.42x+y−21.17) that was optimized by Fisher's discriminant analysis and discriminated between both of the groups. Right diagram: the expression level measurement values of hsa-miR-1247-3p (SEQ ID NO: 2) in healthy subjects (50 persons, circles) and esophageal cancer patients (34 persons, triangles) selected as validation cohort were each plotted on the abscissa against their expression level measurement values of hsa-miR-6857-5p (SEQ ID NO: 4) on the ordinate. The line in the diagram depicts the threshold (0=2.42x+y−21.17) that was set in the training cohort and discriminated between both of the groups.

For example, the gene expression level measurement values of the nucleotide sequences represented by SEQ ID NO: 2 and SEQ ID NO: 4 were compared between the healthy subjects (100 persons) and the esophageal cancer patients (34 persons) in the training cohort. As a result, a variance diagram that significantly separated the measurement values of the esophageal cancer patient group from those of the healthy subject group was obtained (see the left diagram of FIG. 3). These results were also reproducible for the healthy subjects (50 persons) and the esophageal cancer patients (16 persons) in the validation cohort (see the right diagram of FIG. 3). Likewise, a variance diagram that significantly separated the measurement values of the esophageal cancer patient group from those of the healthy subject group was also obtained as to the other combinations of any two of the gene expression level measurement values of the newly found polynucleotides consisting of the nucleotide sequences represented by SEQ ID NOs: 1 to 115 and 117 to 189. These results were able to be validated in the validation cohort. As shown in FIG. 3, for example, as for these nucleotide sequences represented by SEQ ID NO: 2 and SEQ ID NO: 4, the number of samples that were correctly or incorrectly identified esophageal cancer was calculated using the function $(0=2.42x+y-21.17)$ that was set in the training cohort and discriminated between the two groups. As a result, 15 true positives, 49 true negatives, 1 false positive, and 1 false negative were obtained. From these values, 97% accuracy, 93.8% sensitivity, and 98% specificity were obtained as the detection performance. In this way, the detection performance was calculated for the combinations of two of the polynucleotides consisting of the nucleotide sequences represented by SEQ ID NOs: 1 to 189. Among them, 188 combinations comprising the expression level measurement value of the polynucleotide consisting of the nucleotide sequence represented by SEQ ID NO: 1 and the detection performance thereof were described in Table 6 as an example. For example, any of combinations of the expression level measurement values of the polynucleotides consisting of the nucleotide sequences represented by SEQ ID NOs: 1 and 6, SEQ ID NOs: 1 and 9, SEQ ID NOs: 1 and 13, and SEQ ID NOs: 1 and 14 exhibited sensitivity of 100% in the validation cohort. Likewise, any of the remaining combinations of two polynucleotides consisting of the nucleotide sequences represented by SEQ ID NO: 1 and any of SEQ ID NOs: 2 to 189 also exhibited sensitivity of 81% or higher, which was beyond the sensitivity (37.5%) of the existing marker SCC for esophageal cancer (Table 5-2). The 17,096 combinations that showed sensitivity beyond SCC were obtained for the validation cohort. All of the nucleotide sequences 1 to 189 described in Table 2 obtained in Example 1 were employed at least once in these combinations. Thus, a combination of the expression level measurement values of two of the polynucleotides consisting of the nucleotide sequences represented by SEQ ID NOs: 1 to 189 also produced excellent esophageal cancer detection sensitivity.

Markers for the detection of esophageal cancer with better sensitivity are obtained by further combining 3, 4, 5, 6, 7, 8, 9, 10 or more of the expression level measurement values of the polynucleotides consisting of the nucleotide sequences represented by SEQ ID NOs: 1 to 189. For example, the newly found polynucleotides consisting of the nucleotide sequences represented by SEQ ID NOs: 1 to 115 and 117 to 189 among the polynucleotides consisting of the nucleotide sequences represented by SEQ ID NOs: 1 to 189 selected in Example 1 were measured to obtain their expression levels between the healthy subject group and the esophageal cancer group in the validation cohort. All of the polynucleotides were ranked in the descending order of their P values based on the Student's t-test which indicates statistical significance of difference between groups (i.e., one having the lowest P value was ranked in the first place), and esophageal cancer detection sensitivity was evaluated using combinations of one or more polynucleotides to which the polynucleotides were added one by one from the top to the bottom according to the rank. In short, the order in which the polynucleotides were combined in this evaluation is in reverse in terms of SEQ ID Nos from SEQ ID NO: 189 to SEQ ID NOs: 188, 187, ... shown in Table 2. As a result, the sensitivity in the validation cohort was 31.2% for 1 polynucleotide (SEQ ID NO: 189), 56.2% for 2 polynucleotides (SEQ ID NOs: 188 and 189), 75.0% for 3 polynucleotides (SEQ ID NOs: 187 to 189), 93.8% for 5 polynucleotides (SEQ ID NOs: 185 to 189), 100% for 11 polynucleotides (SEQ ID NOs: 179 to 189), 100% for 30 polynucleotides (SEQ ID NOs: 160 to 189), 100% for 50 polynucleotides (SEQ ID NOs: 140 to 189), 100% for 100 polynucleotides (SEQ ID NOs: 89 to 115 and 117 to 189), 100% for 150 polynucleotides (SEQ ID NOs: 39 to 115 and 117 to 189), and 100% for 189 polynucleotides (SEQ ID NOs: 1 to 115 and 117 to 189).

These results demonstrated that a combination of multiple polynucleotides can produce higher esophageal cancer discriminant performance than that of each polynucleotide alone or a combination of a fewer number of polynucleotides. In this context, the combinations of multiple polynucleotides are not limited to the combinations of the polynucleotides added in the order of statistically significant difference as described above, and any combination of multiple polynucleotides can be used in the detection of esophageal cancer.

From these results, it can be concluded that all of the polynucleotides consisting of the nucleotide sequences represented by SEQ ID NOs: 1 to 189 serve as excellent markers for the detection of esophageal cancer.

TABLE 2

| SEQ ID NO: | Gene name | P value after Bonferroni correction | Expression level in esophageal cancer patient relative to healthy subject |
|---|---|---|---|
| 1 | hsa-miR-204-3p | 3.17E−32 | − |
| 2 | hsa-miR-1247-3p | 5.11E−32 | + |
| 3 | hsa-miR-6875-5p | 5.55E−29 | + |
| 4 | hsa-miR-6857-5p | 3.05E−27 | + |
| 5 | hsa-miR-6726-5p | 2.44E−26 | − |
| 6 | hsa-miR-3188 | 1.00E−24 | + |
| 7 | hsa-miR-8069 | 1.45E−24 | + |
| 8 | hsa-miR-4257 | 2.73E−23 | − |
| 9 | hsa-miR-1343-3p | 4.31E−23 | − |
| 10 | hsa-miR-7108-5p | 4.94E−23 | + |
| 11 | hsa-miR-6825-5p | 5.79E−23 | + |
| 12 | hsa-miR-7641 | 7.55E−23 | − |
| 13 | hsa-miR-3185 | 7.72E−22 | + |
| 14 | hsa-miR-4746-3p | 1.19E−21 | + |
| 15 | hsa-miR-6791-5p | 7.82E−21 | + |
| 16 | hsa-miR-6893-5p | 7.89E−21 | − |
| 17 | hsa-miR-4433b-3p | 8.03E−21 | + |
| 18 | hsa-miR-3135b | 1.34E−20 | − |
| 19 | hsa-miR-6781-5p | 2.01E−20 | + |
| 20 | hsa-miR-1908-5p | 2.19E−20 | + |
| 21 | hsa-miR-4792 | 2.39E−20 | + |
| 22 | hsa-miR-7845-5p | 3.30E−20 | + |
| 23 | hsa-miR-4417 | 7.21E−20 | + |
| 24 | hsa-miR-3184-5p | 1.29E−19 | + |
| 25 | hsa-miR-1225-5p | 1.55E−19 | + |
| 26 | hsa-miR-1231 | 3.51E−19 | + |
| 27 | hsa-miR-1225-3p | 3.85E−19 | + |
| 28 | hsa-miR-150-3p | 6.30E−19 | − |
| 29 | hsa-miR-4433-3p | 7.27E−19 | + |
| 30 | hsa-miR-6125 | 2.07E−18 | + |
| 31 | hsa-miR-4513 | 2.51E−18 | − |
| 32 | hsa-miR-6787-5p | 2.87E−18 | − |
| 33 | hsa-miR-6784-5p | 3.57E−18 | + |
| 34 | hsa-miR-615-5p | 8.70E−18 | − |
| 35 | hsa-miR-6765-3p | 1.34E−17 | − |
| 36 | hsa-miR-5572 | 1.62E−17 | + |
| 37 | hsa-miR-6842-5p | 2.45E−17 | + |
| 38 | hsa-miR-8063 | 2.69E−17 | − |
| 39 | hsa-miR-6780b-5p | 3.33E−17 | + |
| 40 | hsa-miR-187-5p | 9.41E−17 | − |

TABLE 2-continued

| SEQ ID NO: | Gene name | P value after Bonferroni correction | Expression level in esophageal cancer patient relative to healthy subject |
|---|---|---|---|
| 41 | hsa-miR-128-1-5p | 9.79E−17 | + |
| 42 | hsa-miR-6729-5p | 1.08E−16 | + |
| 43 | hsa-miR-6741-5p | 9.63E−16 | − |
| 44 | hsa-miR-6757-5p | 1.95E−15 | − |
| 45 | hsa-miR-7110-5p | 2.20E−15 | + |
| 46 | hsa-miR-7975 | 2.43E−15 | − |
| 47 | hsa-miR-1233-5p | 2.66E−15 | − |
| 48 | hsa-miR-6845-5p | 3.62E−15 | + |
| 49 | hsa-miR-3937 | 1.05E−14 | + |
| 50 | hsa-miR-4467 | 1.31E−14 | + |
| 51 | hsa-miR-7109-5p | 1.80E−14 | − |
| 52 | hsa-miR-6088 | 1.95E−14 | − |
| 53 | hsa-miR-6782-5p | 2.52E−14 | + |
| 54 | hsa-miR-5195-3p | 2.64E−14 | − |
| 55 | hsa-miR-4454 | 3.79E−14 | − |
| 56 | hsa-miR-6724-5p | 5.19E−14 | + |
| 57 | hsa-miR-8072 | 6.32E−14 | + |
| 58 | hsa-miR-4516 | 1.64E−13 | − |
| 59 | hsa-miR-6756-5p | 2.32E−13 | − |
| 60 | hsa-miR-4665-3p | 2.91E−13 | + |
| 61 | hsa-miR-6826-5p | 4.31E−13 | − |
| 62 | hsa-miR-6820-5p | 6.77E−13 | − |
| 63 | hsa-miR-6887-5p | 9.53E−13 | − |
| 64 | hsa-miR-3679-5p | 1.05E−12 | + |
| 65 | hsa-miR-7847-3p | 1.11E−12 | − |
| 66 | hsa-miR-6721-5p | 1.24E−12 | + |
| 67 | hsa-miR-3622a-5p | 2.38E−12 | − |
| 68 | hsa-miR-939-5p | 2.39E−12 | + |
| 69 | hsa-miR-602 | 3.03E−12 | + |
| 70 | hsa-miR-7977 | 5.99E−12 | − |
| 71 | hsa-miR-6749-5p | 8.45E−12 | − |
| 72 | hsa-miR-1914-3p | 8.68E−12 | − |
| 73 | hsa-miR-4651 | 9.05E−12 | − |
| 74 | hsa-miR-4695-5p | 9.79E−12 | + |
| 75 | hsa-miR-6848-5p | 1.17E−11 | + |
| 76 | hsa-miR-1228-3p | 1.56E−11 | + |
| 77 | hsa-miR-642b-3p | 1.71E−11 | − |
| 78 | hsa-miR-6746-5p | 2.34E−11 | − |
| 79 | hsa-miR-3620-5p | 2.79E−11 | + |
| 80 | hsa-miR-3131 | 2.99E−11 | − |
| 81 | hsa-miR-6732-5p | 3.68E−11 | + |
| 82 | hsa-miR-7113-3p | 5.38E−11 | + |
| 83 | hsa-miR-23a-3p | 5.53E−11 | − |
| 84 | hsa-miR-3154 | 6.89E−11 | + |
| 85 | hsa-miR-4723-5p | 9.65E−11 | − |
| 86 | hsa-miR-3663-3p | 3.45E−10 | − |
| 87 | hsa-miR-4734 | 3.66E−10 | + |
| 88 | hsa-miR-6816-5p | 4.49E−10 | + |
| 89 | hsa-miR-4442 | 5.02E−10 | − |
| 90 | hsa-miR-4476 | 5.16E−10 | − |
| 91 | hsa-miR-423-5p | 6.10E−10 | − |
| 92 | hsa-miR-1249 | 6.19E−10 | + |
| 93 | hsa-miR-6515-3p | 6.91E−10 | + |
| 94 | hsa-miR-887-3p | 7.28E−10 | − |
| 95 | hsa-miR-4741 | 9.08E−10 | + |
| 96 | hsa-miR-6766-3p | 1.13E−09 | + |
| 97 | hsa-miR-4673 | 2.76E−09 | + |
| 98 | hsa-miR-6779-5p | 2.82E−09 | − |
| 99 | hsa-miR-4706 | 3.75E−09 | − |
| 100 | hsa-miR-1268b | 5.40E−09 | + |
| 101 | hsa-miR-4632-5p | 5.60E−09 | + |
| 102 | hsa-miR-3197 | 6.35E−09 | + |
| 103 | hsa-miR-6798-5p | 9.47E−09 | + |
| 104 | hsa-miR-711 | 9.91E−09 | + |
| 105 | hsa-miR-6840-3p | 1.16E−08 | − |
| 106 | hsa-miR-6763-5p | 1.21E−08 | + |
| 107 | hsa-miR-6727-5p | 1.25E−08 | − |
| 108 | hsa-miR-371a-5p | 1.88E−08 | − |
| 109 | hsa-miR-6824-5p | 2.00E−08 | + |
| 110 | hsa-miR-4648 | 2.81E−08 | + |
| 111 | hsa-miR-1227-5p | 2.85E−08 | + |
| 112 | hsa-miR-564 | 5.06E−08 | − |
| 113 | hsa-miR-3679-3p | 5.14E−08 | + |
| 114 | hsa-miR-2861 | 6.22E−08 | − |
| 115 | hsa-miR-6737-5p | 6.48E−08 | + |

TABLE 2-continued

| SEQ ID NO: | Gene name | P value after Bonferroni correction | Expression level in esophageal cancer patient relative to healthy subject |
|---|---|---|---|
| 116 | hsa-miR-575 | 1.06E−07 | − |
| 117 | hsa-miR-4725-3p | 1.31E−07 | + |
| 118 | hsa-miR-6716-5p | 1.39E−07 | + |
| 119 | hsa-miR-4675 | 1.85E−07 | − |
| 120 | hsa-miR-1915-3p | 1.89E−07 | + |
| 121 | hsa-miR-671-5p | 1.89E−07 | − |
| 122 | hsa-miR-3656 | 2.14E−07 | + |
| 123 | hsa-miR-6722-3p | 2.15E−07 | + |
| 124 | hsa-miR-4707-5p | 2.32E−07 | + |
| 125 | hsa-miR-4449 | 2.73E−07 | + |
| 126 | hsa-miR-1202 | 4.73E−07 | − |
| 127 | hsa-miR-4649-5p | 1.23E−06 | − |
| 128 | hsa-miR-744-5p | 1.53E−06 | + |
| 129 | hsa-miR-642a-3p | 1.70E−06 | − |
| 130 | hsa-miR-451a | 2.39E−06 | − |
| 131 | hsa-miR-6870-5p | 2.74E−06 | + |
| 132 | hsa-miR-4443 | 3.08E−06 | + |
| 133 | hsa-miR-6808-5p | 3.57E−06 | + |
| 134 | hsa-miR-4728-5p | 4.15E−06 | − |
| 135 | hsa-miR-937-5p | 4.83E−06 | − |
| 136 | hsa-miR-135a-3p | 7.39E−06 | + |
| 137 | hsa-miR-663b | 8.35E−06 | − |
| 138 | hsa-miR-1343-5p | 9.72E−06 | + |
| 139 | hsa-miR-6822-5p | 1.03E−05 | + |
| 140 | hsa-miR-6803-5p | 1.05E−05 | + |
| 141 | hsa-miR-6805-3p | 1.86E−05 | + |
| 142 | hsa-miR-128-2-5p | 2.08E−05 | − |
| 143 | hsa-miR-4640-5p | 2.71E−05 | + |
| 144 | hsa-miR-1469 | 2.75E−05 | + |
| 145 | hsa-miR-92a-2-5p | 3.53E−05 | + |
| 146 | hsa-miR-3940-5p | 4.11E−05 | + |
| 147 | hsa-miR-4281 | 4.74E−05 | − |
| 148 | hsa-miR-1260b | 7.11E−05 | − |
| 149 | hsa-miR-4758-5p | 7.66E−05 | − |
| 150 | hsa-miR-1915-5p | 7.76E−05 | − |
| 151 | hsa-miR-5001-5p | 9.17E−05 | − |
| 152 | hsa-miR-4286 | 1.58E−04 | − |
| 153 | hsa-miR-6126 | 1.61E−04 | + |
| 154 | hsa-miR-6789-5p | 1.64E−04 | + |
| 155 | hsa-miR-4459 | 2.00E−04 | + |
| 156 | hsa-miR-1268a | 2.18E−04 | + |
| 157 | hsa-miR-6752-5p | 2.64E−04 | + |
| 158 | hsa-miR-6131 | 2.95E−04 | − |
| 159 | hsa-miR-6800-5p | 3.49E−04 | + |
| 160 | hsa-miR-4532 | 4.53E−04 | − |
| 161 | hsa-miR-6872-3p | 5.66E−04 | − |
| 162 | hsa-miR-718 | 6.77E−04 | + |
| 163 | hsa-miR-6769a-5p | 7.66E−04 | − |
| 164 | hsa-miR-4707-3p | 7.90E−04 | + |
| 165 | hsa-miR-6765-5p | 8.10E−04 | + |
| 166 | hsa-miR-4739 | 1.05E−03 | + |
| 167 | hsa-miR-4525 | 1.09E−03 | − |
| 168 | hsa-miR-4270 | 1.26E−03 | − |
| 169 | hsa-miR-4534 | 1.51E−03 | − |
| 170 | hsa-miR-6785-5p | 1.53E−03 | − |
| 171 | hsa-miR-6850-5p | 1.54E−03 | + |
| 172 | hsa-miR-4697-5p | 1.57E−03 | − |
| 173 | hsa-miR-1260a | 1.69E−03 | − |
| 174 | hsa-miR-4486 | 1.83E−03 | + |
| 175 | hsa-miR-6880-5p | 2.43E−03 | + |
| 176 | hsa-miR-6802-5p | 2.70E−03 | − |
| 177 | hsa-miR-6861-5p | 3.25E−03 | + |
| 178 | hsa-miR-92b-5p | 4.09E−03 | + |
| 179 | hsa-miR-1238-5p | 4.13E−03 | + |
| 180 | hsa-miR-6851-5p | 4.42E−03 | + |
| 181 | hsa-miR-7704 | 5.64E−03 | − |
| 182 | hsa-miR-149-3p | 5.75E−03 | − |
| 183 | hsa-miR-4689 | 6.06E−03 | − |
| 184 | hsa-miR-4688 | 9.69E−03 | − |
| 185 | hsa-miR-125a-3p | 2.00E−28 | − |
| 186 | hsa-miR-23b-3p | 7.47E−11 | − |
| 187 | hsa-miR-614 | 1.25E−08 | − |
| 188 | hsa-miR-1913 | 4.37E−08 | + |
| 189 | hsa-miR-16-5p | 3.26E−04 | − |

TABLE 3

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 1 | 94 | 79.4 | 99 | 92.4 | 81.2 | 96 |
| 2 | 96.3 | 91.2 | 98 | 93.9 | 87.5 | 96 |
| 3 | 95.5 | 91.2 | 97 | 90.9 | 93.8 | 90 |
| 4 | 94 | 94.1 | 94 | 97 | 100 | 96 |
| 5 | 91 | 73.5 | 97 | 92.4 | 87.5 | 94 |
| 6 | 94 | 88.2 | 96 | 95.5 | 87.5 | 98 |
| 7 | 91.8 | 82.4 | 95 | 92.4 | 81.2 | 96 |
| 8 | 91.8 | 76.5 | 97 | 89.4 | 75 | 94 |
| 9 | 93.3 | 88.2 | 95 | 93.9 | 87.5 | 96 |
| 10 | 91 | 79.4 | 95 | 92.4 | 100 | 90 |
| 11 | 88.8 | 82.4 | 91 | 93.9 | 100 | 92 |
| 12 | 89.6 | 79.4 | 93 | 93.9 | 87.5 | 96 |
| 13 | 92.5 | 88.2 | 94 | 92.4 | 81.2 | 96 |
| 14 | 92.5 | 88.2 | 94 | 90.9 | 75 | 96 |
| 15 | 90.3 | 88.2 | 91 | 95.5 | 87.5 | 98 |
| 16 | 91.8 | 73.5 | 98 | 93.9 | 87.5 | 96 |
| 17 | 90.3 | 79.4 | 94 | 83.3 | 81.2 | 84 |
| 18 | 97 | 97.1 | 97 | 97 | 93.8 | 98 |
| 19 | 91.8 | 73.5 | 98 | 92.4 | 93.8 | 92 |
| 20 | 91 | 85.3 | 93 | 90.9 | 81.2 | 94 |
| 21 | 91.8 | 85.3 | 94 | 98.5 | 100 | 98 |
| 22 | 94 | 85.3 | 97 | 90.9 | 87.5 | 92 |
| 23 | 92.5 | 79.4 | 97 | 87.9 | 68.8 | 94 |
| 24 | 91.8 | 88.2 | 93 | 92.4 | 87.5 | 94 |
| 25 | 93.3 | 85.3 | 96 | 90.9 | 81.2 | 94 |
| 26 | 89.6 | 76.5 | 94 | 87.9 | 75 | 92 |
| 27 | 93.3 | 85.3 | 96 | 97 | 87.5 | 100 |

TABLE 3-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 28 | 88.8 | 76.5 | 93 | 86.4 | 81.2 | 88 |
| 29 | 88.1 | 82.4 | 90 | 89.4 | 81.2 | 92 |
| 30 | 93.3 | 91.2 | 94 | 93.9 | 87.5 | 96 |
| 31 | 88.8 | 67.6 | 96 | 90.9 | 75 | 96 |
| 32 | 91 | 76.5 | 96 | 87.9 | 68.8 | 94 |
| 33 | 86.6 | 79.4 | 89 | 86.4 | 81.2 | 88 |
| 34 | 90.3 | 76.5 | 95 | 92.4 | 75 | 98 |
| 35 | 89.6 | 70.6 | 96 | 89.4 | 68.8 | 96 |
| 36 | 87.3 | 82.4 | 89 | 92.4 | 100 | 90 |
| 37 | 89.6 | 73.5 | 95 | 89.4 | 68.8 | 96 |
| 38 | 86.6 | 76.5 | 90 | 92.4 | 87.5 | 94 |
| 39 | 88.1 | 67.6 | 95 | 97 | 87.5 | 100 |
| 40 | 89.6 | 82.4 | 92 | 92.4 | 81.2 | 96 |
| 41 | 88.1 | 76.5 | 92 | 81.8 | 68.8 | 86 |
| 42 | 89.6 | 64.7 | 98 | 92.4 | 75 | 98 |
| 43 | 91 | 73.5 | 97 | 87.9 | 75 | 92 |
| 44 | 85.8 | 70.6 | 91 | 97 | 87.5 | 100 |
| 45 | 84.3 | 64.7 | 91 | 84.8 | 68.8 | 90 |
| 46 | 88.1 | 64.7 | 96 | 84.8 | 62.5 | 92 |
| 47 | 88.1 | 67.6 | 95 | 93.9 | 93.8 | 94 |
| 48 | 88.1 | 64.7 | 96 | 86.4 | 75 | 90 |
| 49 | 87.3 | 67.6 | 94 | 92.4 | 81.2 | 96 |
| 50 | 83.6 | 73.5 | 87 | 87.9 | 62.5 | 96 |
| 51 | 83.6 | 64.7 | 90 | 81.8 | 56.2 | 90 |
| 52 | 83.6 | 61.8 | 91 | 83.3 | 56.2 | 92 |
| 53 | 88.8 | 73.5 | 94 | 84.8 | 56.2 | 94 |
| 54 | 89.6 | 76.5 | 94 | 90.9 | 75 | 96 |
| 55 | 86.6 | 67.6 | 93 | 87.9 | 68.8 | 94 |
| 56 | 87.3 | 73.5 | 92 | 81.8 | 62.5 | 88 |
| 57 | 88.1 | 64.7 | 96 | 80.3 | 62.5 | 86 |
| 58 | 88.1 | 64.7 | 96 | 87.9 | 62.5 | 96 |
| 59 | 89.6 | 70.6 | 96 | 81.8 | 68.8 | 86 |
| 60 | 87.3 | 70.6 | 93 | 83.3 | 68.8 | 88 |
| 61 | 85.1 | 58.8 | 94 | 92.4 | 68.8 | 100 |
| 62 | 91 | 69.7 | 98 | 81.8 | 56.2 | 90 |
| 63 | 85.1 | 58.8 | 94 | 84.8 | 56.2 | 94 |
| 64 | 84.3 | 58.8 | 93 | 86.4 | 56.2 | 96 |
| 65 | 81.3 | 55.9 | 90 | 87.9 | 81.2 | 90 |
| 66 | 84.3 | 67.6 | 90 | 77.3 | 56.2 | 84 |
| 67 | 86.6 | 55.9 | 97 | 84.8 | 50 | 96 |
| 68 | 79.1 | 61.8 | 85 | 83.3 | 68.8 | 88 |
| 69 | 84.3 | 58.8 | 93 | 89.4 | 75 | 94 |
| 70 | 85.8 | 52.9 | 97 | 84.8 | 56.2 | 94 |
| 71 | 83.6 | 61.8 | 91 | 86.4 | 56.2 | 96 |
| 72 | 85.1 | 61.8 | 93 | 80.3 | 56.2 | 88 |
| 73 | 84.3 | 50 | 96 | 89.4 | 62.5 | 98 |
| 74 | 79.9 | 52.9 | 89 | 81.8 | 43.8 | 94 |
| 75 | 84.3 | 58.8 | 93 | 78.8 | 50 | 88 |
| 76 | 86.6 | 64.7 | 94 | 81.8 | 56.2 | 90 |
| 77 | 85.1 | 58.8 | 94 | 87.9 | 56.2 | 98 |
| 78 | 81.3 | 55.9 | 90 | 86.4 | 68.8 | 92 |
| 79 | 84.3 | 58.8 | 93 | 84.8 | 62.5 | 92 |
| 80 | 82.8 | 55.9 | 92 | 89.4 | 62.5 | 98 |
| 81 | 82.8 | 64.7 | 89 | 80.3 | 68.8 | 84 |
| 82 | 81.3 | 58.8 | 89 | 83.3 | 56.2 | 92 |
| 83 | 85.8 | 55.9 | 96 | 78.8 | 43.8 | 90 |
| 84 | 85.8 | 58.8 | 95 | 83.3 | 62.5 | 90 |
| 85 | 83.6 | 50 | 95 | 81.8 | 56.2 | 90 |
| 86 | 79.1 | 32.4 | 95 | 83.3 | 43.8 | 96 |
| 87 | 76.9 | 26.5 | 94 | 81.8 | 43.8 | 94 |
| 88 | 85.1 | 70.6 | 90 | 87.9 | 75 | 92 |
| 89 | 81.3 | 52.9 | 91 | 83.3 | 56.2 | 92 |
| 90 | 85.8 | 52.9 | 97 | 84.8 | 56.2 | 94 |
| 91 | 83.6 | 58.8 | 92 | 71.2 | 31.2 | 84 |
| 92 | 80.5 | 41.2 | 93.9 | 83.3 | 62.5 | 90 |
| 93 | 79.1 | 38.2 | 93 | 75.8 | 56.2 | 82 |
| 94 | 79.1 | 50 | 89 | 87.9 | 87.5 | 88 |
| 95 | 85.1 | 55.9 | 95 | 81.8 | 43.8 | 94 |
| 96 | 85.8 | 58.8 | 95 | 80.3 | 50 | 90 |
| 97 | 85.8 | 55.9 | 96 | 83.3 | 43.8 | 96 |
| 98 | 76.9 | 38.2 | 90 | 86.4 | 50 | 98 |
| 99 | 82.8 | 50 | 94 | 84.8 | 56.2 | 94 |
| 100 | 77.6 | 44.1 | 89 | 74.2 | 43.8 | 84 |
| 101 | 85.8 | 52.9 | 97 | 86.4 | 50 | 98 |
| 102 | 85.8 | 64.7 | 93 | 81.8 | 43.8 | 94 |

TABLE 3-continued

| SEQ ID NO: | Training cohort ||| Validation cohort |||
|---|---|---|---|---|---|---|
| | Accuracy (%) | Sensitivity (%) | Specificity (%) | Accuracy (%) | Sensitivity (%) | Specificity (%) |
| 103 | 80.6 | 52.9 | 90 | 80.3 | 68.8 | 84 |
| 104 | 85.8 | 61.8 | 94 | 89.4 | 62.5 | 98 |
| 105 | 79.1 | 38.2 | 93 | 78.8 | 31.2 | 94 |
| 106 | 79.9 | 50 | 90 | 83.3 | 56.2 | 92 |
| 107 | 83.6 | 55.9 | 93 | 84.8 | 43.8 | 98 |
| 108 | 79.9 | 44.1 | 92 | 72.7 | 31.2 | 86 |
| 109 | 84.3 | 47.1 | 97 | 83.3 | 43.8 | 96 |
| 110 | 79.1 | 41.2 | 92 | 89.4 | 56.2 | 100 |
| 111 | 79.9 | 38.2 | 94 | 75.8 | 31.2 | 90 |
| 112 | 85.1 | 50 | 97 | 87.9 | 56.2 | 98 |
| 113 | 82.1 | 47.1 | 94 | 83.3 | 62.5 | 90 |
| 114 | 80.6 | 44.1 | 93 | 86.4 | 56.2 | 96 |
| 115 | 79.9 | 50 | 90 | 83.3 | 62.5 | 90 |
| 116 | 88.1 | 55.9 | 99 | 84.8 | 50 | 96 |
| 117 | 82.8 | 61.8 | 90 | 86.4 | 68.8 | 92 |
| 118 | 82.1 | 47.1 | 94 | 77.3 | 31.2 | 92 |
| 119 | 79.1 | 38.2 | 93 | 89.4 | 56.2 | 100 |
| 120 | 78.4 | 29.4 | 95 | 81.8 | 43.8 | 94 |
| 121 | 80.6 | 41.2 | 94 | 77.3 | 31.2 | 92 |
| 122 | 79.9 | 38.2 | 94 | 78.8 | 18.8 | 98 |
| 123 | 80.6 | 44.1 | 93 | 78.8 | 37.5 | 92 |
| 124 | 79.9 | 50 | 90 | 77.3 | 37.5 | 90 |
| 125 | 79.1 | 32.4 | 95 | 81.8 | 37.5 | 96 |
| 126 | 81.3 | 35.3 | 97 | 80.3 | 37.5 | 94 |
| 127 | 78.4 | 44.1 | 90 | 81.8 | 37.5 | 96 |
| 128 | 80.6 | 38.2 | 95 | 83.3 | 37.5 | 98 |
| 129 | 74.6 | 26.5 | 91 | 72.7 | 18.8 | 90 |
| 130 | 84.3 | 47.1 | 97 | 86.4 | 62.5 | 94 |
| 131 | 79.9 | 32.4 | 96 | 86.4 | 43.8 | 100 |
| 132 | 82.8 | 47.1 | 95 | 80.3 | 31.2 | 96 |
| 133 | 80.6 | 35.3 | 96 | 72.7 | 12.5 | 92 |
| 134 | 76.9 | 32.4 | 92 | 80.3 | 43.8 | 92 |
| 135 | 79.9 | 35.3 | 95 | 80.3 | 31.2 | 96 |
| 136 | 79.9 | 44.1 | 92 | 71.2 | 31.2 | 84 |
| 137 | 74.6 | 23.5 | 92 | 80.3 | 18.8 | 100 |
| 138 | 81.3 | 44.1 | 94 | 81.8 | 37.5 | 96 |
| 139 | 76.9 | 26.5 | 94 | 84.8 | 43.8 | 98 |
| 140 | 76.9 | 35.3 | 91 | 69.7 | 25 | 84 |
| 141 | 76.9 | 35.3 | 91 | 80.3 | 31.2 | 96 |
| 142 | 79.1 | 29.4 | 96 | 83.3 | 31.2 | 100 |
| 143 | 79.1 | 29.4 | 96 | 86.4 | 43.8 | 100 |
| 144 | 77.6 | 26.5 | 95 | 74.2 | 25 | 90 |
| 145 | 78.4 | 32.4 | 94 | 78.8 | 37.5 | 92 |
| 146 | 76.9 | 29.4 | 93 | 77.3 | 31.2 | 92 |
| 147 | 75.4 | 23.5 | 93 | 78.8 | 25 | 96 |
| 148 | 81.3 | 38.2 | 96 | 80.3 | 37.5 | 94 |
| 149 | 82.8 | 38.2 | 98 | 78.8 | 18.8 | 98 |
| 150 | 79.1 | 29.4 | 96 | 78.8 | 31.2 | 94 |
| 151 | 80.6 | 38.2 | 95 | 81.8 | 50 | 92 |
| 152 | 76.1 | 23.5 | 94 | 77.3 | 31.2 | 92 |
| 153 | 73.9 | 23.5 | 91 | 75.8 | 12.5 | 96 |
| 154 | 73.1 | 11.8 | 94 | 75.8 | 31.2 | 90 |
| 155 | 81.3 | 38.2 | 96 | 80.3 | 25 | 98 |
| 156 | 73.1 | 26.5 | 89 | 71.2 | 31.2 | 84 |
| 157 | 73.9 | 17.6 | 93 | 66.7 | 6.2 | 86 |
| 158 | 79.9 | 35.3 | 95 | 80.3 | 31.2 | 96 |
| 159 | 76.9 | 23.5 | 95 | 83.3 | 56.2 | 92 |
| 160 | 77.6 | 23.5 | 96 | 80.3 | 25 | 98 |
| 161 | 79.1 | 29.4 | 96 | 81.8 | 37.5 | 96 |
| 162 | 73.1 | 14.7 | 93 | 69.7 | 0 | 92 |
| 163 | 76.1 | 23.5 | 94 | 75.8 | 12.5 | 96 |
| 164 | 76.1 | 17.6 | 96 | 77.3 | 31.2 | 92 |
| 165 | 78.4 | 23.5 | 97 | 78.8 | 25 | 96 |
| 166 | 79.9 | 29.4 | 97 | 80.3 | 31.2 | 96 |
| 167 | 76.9 | 26.5 | 94 | 77.3 | 6.2 | 100 |
| 168 | 80.6 | 35.3 | 96 | 77.3 | 25 | 94 |
| 169 | 77.6 | 23.5 | 96 | 69.7 | 6.2 | 90 |
| 170 | 79.1 | 29.4 | 96 | 83.1 | 26.7 | 100 |
| 171 | 81.3 | 38.2 | 96 | 75.8 | 31.2 | 90 |
| 172 | 76.1 | 23.5 | 94 | 78.8 | 31.2 | 94 |
| 173 | 77.6 | 26.5 | 95 | 81.8 | 43.8 | 94 |
| 174 | 76.1 | 20.6 | 95 | 81.8 | 31.2 | 98 |
| 175 | 80.6 | 29.4 | 98 | 78.8 | 18.8 | 98 |
| 176 | 79.9 | 26.5 | 98 | 80.3 | 25 | 98 |
| 177 | 79.9 | 29.4 | 97 | 81.8 | 31.2 | 98 |

TABLE 3-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 178 | 73.1 | 11.8 | 94 | 78.8 | 18.8 | 98 |
| 179 | 76.1 | 17.6 | 96 | 77.3 | 12.5 | 98 |
| 180 | 73.1 | 8.8 | 95 | 78.8 | 12.5 | 100 |
| 181 | 76.1 | 29.4 | 92 | 69.7 | 25 | 84 |
| 182 | 76.1 | 20.6 | 95 | 77.3 | 43.8 | 88 |
| 183 | 76.9 | 17.6 | 97 | 78.8 | 12.5 | 100 |
| 184 | 77.6 | 20.6 | 97 | 81.8 | 31.2 | 98 |
| 185 | 95.5 | 85.3 | 99 | 93.9 | 75 | 100 |
| 186 | 83.6 | 50 | 95 | 86.4 | 62.5 | 94 |
| 187 | 79.1 | 47.1 | 90 | 80.3 | 43.8 | 92 |
| 188 | 79.1 | 41.2 | 92 | 83.1 | 50 | 93.9 |
| 189 | 82.1 | 41.2 | 96 | 87.9 | 62.5 | 96 |

TABLE 4

| SEQ ID NO: | Discriminant coefficient | Constant term |
|---|---|---|
| 1 | 1.728 | 21.253 |
| 2 | 4.247 | 27.391 |
| 3 | 4.025 | 37.004 |
| 4 | 1.997 | 11.064 |
| 5 | 3.142 | 30.220 |
| 6 | 3.455 | 21.479 |
| 7 | 7.377 | 95.667 |
| 8 | 2.889 | 18.733 |
| 9 | 2.480 | 18.013 |
| 10 | 4.837 | 44.847 |
| 11 | 2.182 | 14.705 |
| 12 | 1.260 | 8.443 |
| 13 | 2.577 | 18.611 |
| 14 | 2.990 | 19.980 |
| 15 | 5.216 | 48.423 |
| 16 | 2.157 | 17.534 |
| 17 | 3.898 | 31.927 |
| 18 | 2.959 | 22.467 |
| 19 | 5.747 | 60.613 |
| 20 | 4.475 | 52.095 |
| 21 | 2.037 | 14.005 |
| 22 | 3.204 | 21.819 |
| 23 | 5.663 | 46.868 |
| 24 | 2.397 | 19.749 |
| 25 | 3.533 | 26.374 |
| 26 | 3.637 | 24.242 |
| 27 | 3.134 | 17.788 |
| 28 | 2.259 | 14.444 |
| 29 | 3.890 | 28.987 |
| 30 | 5.510 | 66.435 |
| 31 | 3.218 | 18.273 |
| 32 | 4.013 | 33.740 |
| 33 | 3.829 | 48.615 |
| 34 | 2.368 | 14.866 |
| 35 | 1.648 | 13.802 |
| 36 | 2.478 | 16.783 |
| 37 | 3.608 | 21.816 |
| 38 | 2.700 | 21.869 |
| 39 | 3.045 | 27.546 |
| 40 | 2.276 | 22.213 |
| 41 | 2.830 | 21.434 |
| 42 | 8.628 | 108.988 |
| 43 | 4.284 | 28.951 |
| 44 | 2.953 | 20.892 |
| 45 | 1.831 | 14.542 |
| 46 | 2.058 | 19.942 |
| 47 | 2.788 | 30.680 |
| 48 | 3.787 | 36.710 |
| 49 | 4.284 | 37.394 |
| 50 | 2.351 | 23.417 |
| 51 | 5.582 | 40.862 |
| 52 | 3.374 | 33.771 |
| 53 | 3.304 | 20.643 |
| 54 | 3.097 | 20.730 |

TABLE 4-continued

| SEQ ID NO: | Discriminant coefficient | Constant term |
|---|---|---|
| 55 | 2.087 | 23.779 |
| 56 | 4.807 | 48.256 |
| 57 | 5.366 | 66.548 |
| 58 | 4.590 | 60.012 |
| 59 | 5.385 | 44.281 |
| 60 | 4.425 | 25.890 |
| 61 | 2.238 | 13.151 |
| 62 | 3.068 | 21.797 |
| 63 | 3.019 | 18.844 |
| 64 | 2.848 | 19.631 |
| 65 | 3.913 | 24.472 |
| 66 | 4.110 | 31.289 |
| 67 | 2.450 | 13.850 |
| 68 | 2.535 | 19.310 |
| 69 | 3.143 | 20.245 |
| 70 | 2.050 | 19.680 |
| 71 | 5.003 | 49.921 |
| 72 | 4.868 | 36.163 |
| 73 | 5.151 | 55.976 |
| 74 | 4.628 | 34.855 |
| 75 | 4.911 | 36.605 |
| 76 | 4.102 | 25.952 |
| 77 | 2.468 | 22.972 |
| 78 | 3.620 | 23.145 |
| 79 | 4.177 | 33.363 |
| 80 | 2.569 | 17.652 |
| 81 | 3.560 | 30.479 |
| 82 | 3.219 | 18.791 |
| 83 | 1.409 | 7.771 |
| 84 | 4.626 | 27.715 |
| 85 | 2.981 | 26.017 |
| 86 | 4.075 | 49.126 |
| 87 | 5.860 | 70.045 |
| 88 | 4.518 | 45.735 |
| 89 | 3.376 | 31.771 |
| 90 | 1.504 | 10.293 |
| 91 | 2.408 | 17.120 |
| 92 | 3.741 | 22.446 |
| 93 | 4.216 | 28.494 |
| 94 | 2.433 | 17.718 |
| 95 | 3.691 | 36.766 |
| 96 | 4.011 | 23.884 |
| 97 | 2.738 | 15.840 |
| 98 | 6.279 | 44.218 |
| 99 | 3.821 | 29.214 |
| 100 | 3.138 | 31.313 |
| 101 | 4.137 | 33.060 |
| 102 | 3.184 | 30.108 |
| 103 | 3.013 | 31.561 |
| 104 | 3.467 | 28.752 |
| 105 | 3.228 | 28.241 |
| 106 | 3.979 | 27.890 |
| 107 | 6.059 | 77.100 |
| 108 | 3.680 | 26.849 |

TABLE 4-continued

| SEQ ID NO: | Discriminant coefficient | Constant term |
|---|---|---|
| 109 | 4.631 | 30.402 |
| 110 | 1.394 | 8.449 |
| 111 | 6.759 | 64.607 |
| 112 | 1.409 | 7.968 |
| 113 | 3.162 | 19.071 |
| 114 | 5.990 | 73.977 |
| 115 | 5.334 | 38.106 |
| 116 | 1.456 | 8.354 |
| 117 | 4.005 | 39.314 |
| 118 | 3.960 | 26.029 |
| 119 | 2.965 | 22.212 |
| 120 | 4.191 | 46.456 |
| 121 | 3.073 | 19.231 |
| 122 | 4.802 | 55.520 |
| 123 | 6.630 | 56.690 |
| 124 | 4.376 | 32.100 |
| 125 | 3.860 | 25.003 |
| 126 | 2.820 | 18.115 |
| 127 | 2.803 | 28.773 |
| 128 | 2.467 | 17.131 |
| 129 | 2.799 | 21.018 |
| 130 | 1.014 | 8.569 |
| 131 | 3.279 | 24.306 |
| 132 | 2.463 | 15.756 |
| 133 | 5.281 | 36.256 |
| 134 | 4.856 | 33.829 |
| 135 | 4.127 | 34.385 |
| 136 | 2.446 | 18.351 |
| 137 | 3.464 | 30.213 |
| 138 | 3.758 | 39.142 |
| 139 | 3.002 | 17.723 |
| 140 | 6.638 | 74.011 |
| 141 | 2.417 | 18.061 |
| 142 | 2.771 | 29.864 |
| 143 | 4.044 | 31.341 |
| 144 | 5.475 | 55.815 |
| 145 | 1.996 | 18.798 |
| 146 | 4.966 | 60.960 |
| 147 | 3.897 | 45.041 |
| 148 | 2.189 | 18.504 |
| 149 | 5.725 | 48.947 |
| 150 | 1.479 | 9.192 |
| 151 | 4.007 | 30.769 |
| 152 | 2.375 | 17.501 |
| 153 | 3.148 | 34.147 |
| 154 | 4.614 | 45.732 |
| 155 | 3.496 | 28.749 |
| 156 | 3.223 | 36.168 |
| 157 | 3.880 | 43.759 |
| 158 | 2.161 | 22.836 |
| 159 | 4.249 | 36.373 |
| 160 | 3.372 | 40.014 |
| 161 | 2.156 | 12.836 |
| 162 | 3.830 | 25.976 |
| 163 | 4.148 | 26.395 |
| 164 | 3.013 | 19.353 |
| 165 | 4.848 | 51.132 |
| 166 | 3.658 | 41.969 |
| 167 | 2.809 | 19.310 |
| 168 | 5.360 | 42.861 |
| 169 | 3.044 | 20.270 |
| 170 | 2.349 | 21.153 |
| 171 | 5.182 | 58.972 |
| 172 | 4.905 | 38.453 |
| 173 | 2.327 | 16.003 |
| 174 | 2.883 | 20.522 |
| 175 | 2.041 | 15.621 |
| 176 | 4.697 | 39.475 |
| 177 | 3.841 | 27.790 |
| 178 | 3.535 | 28.077 |
| 179 | 3.283 | 21.183 |
| 180 | 4.096 | 26.607 |
| 181 | 7.491 | 103.673 |
| 182 | 5.921 | 55.473 |
| 183 | 3.240 | 30.496 |
| 184 | 3.873 | 27.506 |
| 185 | 1.385 | 7.776 |
| 186 | 1.393 | 7.911 |
| 187 | 1.816 | 11.959 |
| 188 | 3.362 | 20.857 |
| 189 | 1.031 | 6.129 |

TABLE 5-1

Training cohort

| Sample name | Cancer stage | CEA(ng/mL) | SCC(ng/mL) |
|---|---|---|---|
| EC03 | IIIB | 4 | 42.2 |
| EC04 | IIIB | 3.1 | 1 |
| EC05 | IB | 6.2 | 1.9 |
| EC06 | (yp) IIA | 3.3 | 1 |
| EC07 | IIB | 0.7 | 1 |
| EC09 | IIB | 2 | 14.7 |
| EC10 | (yp) IIB | 1.6 | 0.9 |
| EC12 | IIB | 3.3 | 1.2 |
| EC13 | IIIB | 1 | 6 |
| EC15 | IIIA | 2.7 | 2.4 |
| EC17 | IIIC | 4 | 2.1 |
| EC18 | IIIA | 4.6 | 3.2 |
| EC19 | IIIC | 1.3 | 3.8 |
| EC20 | IIIB | 2.5 | 1.5 |
| EC23 | (yp) IIIC | 4 | 0.7 |
| EC24 | IIIB | 5 | 1 |
| EC25 | IIA | なし | なし |
| EC26 | (yp) IIB | 1.4 | 0.9 |
| EC27 | (yp) IIIA | 4.8 | 2.1 |
| EC29 | (yp) IIIA | 3.1 | 0.8 |
| EC30 | IIIB | 3.6 | 0.6 |
| EC31 | IB | 4.7 | 0.9 |
| EC32 | (yp) IIIA | 0.5 | 1.3 |
| EC34 | IIIA | 3.6 | 0.7 |
| EC36 | IIIA | 4.1 | 1.2 |
| EC38 | (yp) IIA | 2.3 | 3.4 |
| EC40 | IIB | 6.6 | 1.6 |
| EC41 | (yp) IIIA | 14.2 | 1.3 |
| EC42 | IIB | 5.2 | 1.2 |
| EC45 | (yp) IA | 3.1 | 0.6 |
| EC47 | IIIB | 2.9 | 1 |
| EC48 | IB | 4 | 1.5 |
| EC49 | (yp) IIA | 1.8 | 8 |
| EC50 | (yp) IIIA | 1.7 | 1.2 |
| Sensitivity | | 12.1% | 36.4% |

TABLE 5-2

Validation cohort

| Sample name | Cancer stage | CEA(ng/mL) | SCC(ng/mL) |
|---|---|---|---|
| EC01 | (yp) IIA | 1.6 | 1.3 |
| EC02 | IIA | 1.3 | 2.4 |
| EC08 | IIIA | 2.1 | 1.1 |
| EC11 | (yp) IV | 1.8 | 1 |
| EC14 | IIA | 7.2 | 1.2 |
| EC16 | (yp) IIIA | 6.3 | 0.9 |
| EC21 | IIA | 3.2 | 2.4 |
| EC22 | (yp) IIA | 4.3 | 2.9 |
| EC28 | IIIA | 1.6 | 0.1 |
| EC33 | (yp) IIIC | 2.1 | 1.9 |
| EC35 | IIIC | 1.6 | 0.6 |
| EC37 | (yp) IIIA | 2.1 | 1 |
| EC39 | (yp) IA | 1.8 | 9.1 |
| EC43 | IIIC | 6.6 | 1.3 |
| EC44 | (yp) IIIB | 2.2 | 11.2 |
| EC46 | (Yp) 0 | 0.7 | 0.6 |
| Sensitivity | | 18.8% | 37.5% |

Each sample that exhibited a value equal to or higher than the reference value of each tumor marker (for CEA: 5 ng/mL, SCC: 1.5 ng/mL) was confirmed to be positive (+), and each sample that exhibited a value equal to or lower than the reference value was confirmed to be negative (−). The cancer stages were classified using samples collected before treatment, as a rule, except that samples stage-classified by pathological examination after treatment were represented by "yp".

TABLE 6

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_2 | 98.5 | 94.1 | 100 | 98.5 | 93.8 | 100 |
| 1_3 | 96.3 | 88.2 | 99 | 92.4 | 87.5 | 94 |
| 1_4 | 95.5 | 85.3 | 99 | 93.9 | 93.8 | 94 |
| 1_5 | 95.5 | 88.2 | 98 | 93.9 | 87.5 | 96 |
| 1_6 | 95.5 | 82.4 | 100 | 98.5 | 100 | 98 |
| 1_7 | 96.3 | 85.3 | 100 | 93.9 | 93.8 | 94 |
| 1_8 | 99.3 | 97.1 | 100 | 93.9 | 93.8 | 94 |
| 1_9 | 98.5 | 100 | 98 | 95.5 | 100 | 94 |
| 1_10 | 96.3 | 88.2 | 99 | 97 | 93.8 | 98 |
| 1_11 | 97 | 88.2 | 100 | 97 | 93.8 | 98 |
| 1_12 | 94.8 | 82.4 | 99 | 93.9 | 87.5 | 96 |
| 1_13 | 94 | 82.4 | 98 | 95.5 | 100 | 94 |
| 1_14 | 96.3 | 88.2 | 99 | 97 | 100 | 96 |
| 1_15 | 94 | 82.4 | 98 | 95.5 | 93.8 | 96 |
| 1_16 | 94 | 79.4 | 99 | 93.9 | 87.5 | 96 |
| 1_17 | 96.3 | 85.3 | 100 | 92.4 | 87.5 | 94 |
| 1_18 | 97 | 88.2 | 100 | 95.5 | 87.5 | 98 |
| 1_19 | 96.3 | 85.3 | 100 | 95.5 | 93.8 | 96 |
| 1_20 | 96.3 | 88.2 | 99 | 97 | 93.8 | 98 |
| 1_21 | 97 | 88.2 | 100 | 98.5 | 93.8 | 100 |
| 1_22 | 98.5 | 94.1 | 100 | 92.4 | 93.8 | 92 |
| 1_23 | 96.3 | 85.3 | 100 | 92.4 | 87.5 | 94 |
| 1_24 | 96.3 | 85.3 | 100 | 93.9 | 87.5 | 96 |
| 1_25 | 95.5 | 82.4 | 100 | 92.4 | 87.5 | 94 |
| 1_26 | 94.8 | 82.4 | 99 | 92.4 | 87.5 | 94 |
| 1_27 | 95.5 | 85.3 | 99 | 95.5 | 93.8 | 96 |
| 1_28 | 93.3 | 76.5 | 99 | 93.9 | 87.5 | 96 |
| 1_29 | 94.8 | 79.4 | 100 | 92.4 | 87.5 | 94 |
| 1_30 | 97.8 | 91.2 | 100 | 95.5 | 93.8 | 96 |
| 1_31 | 95.5 | 85.3 | 99 | 92.4 | 87.5 | 94 |
| 1_32 | 95.5 | 85.3 | 99 | 93.9 | 87.5 | 96 |
| 1_33 | 95.5 | 82.4 | 100 | 89.4 | 87.5 | 90 |
| 1_34 | 97.8 | 91.2 | 100 | 97 | 87.5 | 100 |
| 1_35 | 96.3 | 85.3 | 100 | 93.9 | 87.5 | 96 |
| 1_36 | 94.8 | 82.4 | 99 | 93.9 | 87.5 | 96 |
| 1_37 | 95.5 | 85.3 | 99 | 93.9 | 87.5 | 96 |
| 1_38 | 95.5 | 85.3 | 99 | 93.9 | 93.8 | 94 |
| 1_39 | 97.8 | 94.1 | 99 | 95.5 | 87.5 | 98 |
| 1_40 | 99.3 | 97.1 | 100 | 98.5 | 93.8 | 100 |
| 1_41 | 94.8 | 82.4 | 99 | 93.9 | 87.5 | 96 |
| 1_42 | 94.8 | 85.3 | 98 | 95.5 | 87.5 | 98 |
| 1_43 | 94.8 | 85.3 | 98 | 93.9 | 93.8 | 94 |
| 1_44 | 97.8 | 91.2 | 100 | 97 | 93.8 | 98 |
| 1_45 | 95.5 | 85.3 | 99 | 92.4 | 87.5 | 94 |
| 1_46 | 95.5 | 82.4 | 100 | 95.5 | 87.5 | 98 |
| 1_47 | 97 | 88.2 | 100 | 93.9 | 87.5 | 96 |
| 1_48 | 95.5 | 82.4 | 100 | 93.9 | 87.5 | 96 |
| 1_49 | 94 | 79.4 | 99 | 95.5 | 87.5 | 98 |
| 1_50 | 95.5 | 85.3 | 99 | 92.4 | 93.8 | 92 |
| 1_51 | 95.5 | 82.4 | 100 | 92.4 | 87.5 | 94 |
| 1_52 | 95.5 | 82.4 | 100 | 95.5 | 93.8 | 96 |
| 1_53 | 97 | 88.2 | 100 | 90.9 | 87.5 | 92 |
| 1_54 | 96.3 | 88.2 | 99 | 95.5 | 87.5 | 98 |
| 1_55 | 95.5 | 82.4 | 100 | 95.5 | 87.5 | 98 |
| 1_56 | 96.3 | 88.2 | 99 | 93.9 | 93.8 | 94 |
| 1_57 | 95.5 | 85.3 | 99 | 89.4 | 93.8 | 88 |
| 1_58 | 97.8 | 94.1 | 99 | 97 | 100 | 96 |
| 1_59 | 96.3 | 85.3 | 100 | 95.5 | 100 | 94 |
| 1_60 | 94.8 | 82.4 | 99 | 87.9 | 81.2 | 90 |
| 1_61 | 97.8 | 91.2 | 100 | 98.5 | 93.8 | 100 |
| 1_62 | 95.5 | 84.8 | 99 | 93.9 | 87.5 | 96 |
| 1_63 | 96.3 | 88.2 | 99 | 93.9 | 87.5 | 96 |
| 1_64 | 97 | 88.2 | 100 | 93.9 | 87.5 | 96 |
| 1_65 | 97 | 91.2 | 99 | 92.4 | 93.8 | 92 |
| 1_66 | 94 | 79.4 | 99 | 90.9 | 87.5 | 92 |
| 1_67 | 94 | 79.4 | 99 | 92.4 | 81.2 | 96 |
| 1_68 | 94.8 | 82.4 | 99 | 92.4 | 87.5 | 94 |
| 1_69 | 96.3 | 85.3 | 100 | 92.4 | 87.5 | 94 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_70 | 94.8 | 79.4 | 100 | 95.5 | 87.5 | 98 |
| 1_71 | 96.3 | 88.2 | 99 | 95.5 | 93.8 | 96 |
| 1_72 | 94.8 | 85.3 | 98 | 90.9 | 93.8 | 90 |
| 1_73 | 94.8 | 85.3 | 98 | 92.4 | 87.5 | 94 |
| 1_74 | 94.8 | 82.4 | 99 | 93.9 | 93.8 | 94 |
| 1_75 | 94 | 82.4 | 98 | 92.4 | 87.5 | 94 |
| 1_76 | 94 | 79.4 | 99 | 95.5 | 93.8 | 96 |
| 1_77 | 96.3 | 85.3 | 100 | 90.9 | 87.5 | 92 |
| 1_78 | 95.5 | 85.3 | 99 | 93.9 | 93.8 | 94 |
| 1_79 | 94.8 | 79.4 | 100 | 89.4 | 87.5 | 90 |
| 1_80 | 96.3 | 85.3 | 100 | 93.9 | 87.5 | 96 |
| 1_81 | 94 | 79.4 | 99 | 89.4 | 87.5 | 90 |
| 1_82 | 94.8 | 85.3 | 98 | 92.4 | 93.8 | 92 |
| 1_83 | 94 | 79.4 | 99 | 95.5 | 87.5 | 98 |
| 1_84 | 94.8 | 82.4 | 99 | 93.9 | 87.5 | 96 |
| 1_85 | 96.3 | 85.3 | 100 | 92.4 | 87.5 | 94 |
| 1_86 | 96.3 | 88.2 | 99 | 95.5 | 93.8 | 96 |
| 1_87 | 95.5 | 82.4 | 100 | 90.9 | 81.2 | 94 |
| 1_88 | 95.5 | 82.4 | 100 | 93.9 | 87.5 | 96 |
| 1_89 | 95.5 | 85.3 | 99 | 90.9 | 87.5 | 92 |
| 1_90 | 94 | 79.4 | 99 | 93.9 | 87.5 | 96 |
| 1_91 | 94.8 | 79.4 | 100 | 93.9 | 87.5 | 96 |
| 1_92 | 93.2 | 76.5 | 99 | 92.4 | 87.5 | 94 |
| 1_93 | 94.8 | 82.4 | 99 | 92.4 | 87.5 | 94 |
| 1_94 | 94.8 | 79.4 | 100 | 89.4 | 87.5 | 90 |
| 1_95 | 96.3 | 85.3 | 100 | 90.9 | 87.5 | 92 |
| 1_96 | 94 | 79.4 | 99 | 92.4 | 81.2 | 96 |
| 1_97 | 96.3 | 85.3 | 100 | 93.9 | 87.5 | 96 |
| 1_98 | 95.5 | 82.4 | 100 | 95.5 | 93.8 | 96 |
| 1_99 | 95.5 | 85.3 | 99 | 93.9 | 93.8 | 94 |
| 1_100 | 94.8 | 79.4 | 100 | 92.4 | 87.5 | 94 |
| 1_101 | 95.5 | 85.3 | 99 | 95.5 | 93.8 | 96 |
| 1_102 | 95.5 | 82.4 | 100 | 92.4 | 93.8 | 92 |
| 1_103 | 96.3 | 85.3 | 100 | 89.4 | 93.8 | 88 |
| 1_104 | 96.3 | 85.3 | 100 | 97 | 93.8 | 98 |
| 1_105 | 95.5 | 88.2 | 98 | 92.4 | 87.5 | 94 |
| 1_106 | 94.8 | 82.4 | 99 | 92.4 | 87.5 | 94 |
| 1_107 | 95.5 | 85.3 | 99 | 90.9 | 81.2 | 94 |
| 1_108 | 95.5 | 85.3 | 99 | 89.4 | 93.8 | 88 |
| 1_109 | 96.3 | 85.3 | 100 | 93.9 | 87.5 | 96 |
| 1_110 | 94 | 79.4 | 99 | 95.5 | 93.8 | 96 |
| 1_111 | 94 | 79.4 | 99 | 90.9 | 81.2 | 94 |
| 1_112 | 94 | 79.4 | 99 | 93.9 | 87.5 | 96 |
| 1_113 | 93.3 | 79.4 | 98 | 93.9 | 87.5 | 96 |
| 1_114 | 97 | 88.2 | 100 | 93.9 | 87.5 | 96 |
| 1_115 | 95.5 | 82.4 | 100 | 90.9 | 87.5 | 92 |
| 1_116 | 94 | 79.4 | 99 | 92.4 | 81.2 | 96 |
| 1_117 | 94.8 | 82.4 | 99 | 93.9 | 87.5 | 96 |
| 1_118 | 94.8 | 82.4 | 99 | 93.9 | 87.5 | 96 |
| 1_119 | 95.5 | 85.3 | 99 | 95.5 | 93.8 | 96 |
| 1_120 | 94.8 | 82.4 | 99 | 95.5 | 93.8 | 96 |
| 1_121 | 94 | 79.4 | 99 | 90.9 | 87.5 | 92 |
| 1_122 | 94 | 79.4 | 99 | 92.4 | 87.5 | 94 |
| 1_123 | 94.8 | 79.4 | 100 | 93.9 | 87.5 | 96 |
| 1_124 | 94 | 79.4 | 99 | 93.9 | 87.5 | 96 |
| 1_125 | 94.8 | 82.4 | 99 | 92.4 | 87.5 | 94 |
| 1_126 | 96.3 | 85.3 | 100 | 93.9 | 87.5 | 96 |
| 1_127 | 96.3 | 85.3 | 100 | 92.4 | 93.8 | 92 |
| 1_128 | 96.3 | 88.2 | 99 | 92.4 | 87.5 | 94 |
| 1_129 | 95.5 | 82.4 | 100 | 89.4 | 81.2 | 92 |
| 1_130 | 94 | 79.4 | 99 | 92.4 | 87.5 | 94 |
| 1_131 | 94 | 79.4 | 99 | 95.5 | 87.5 | 98 |
| 1_132 | 95.5 | 82.4 | 100 | 93.9 | 93.8 | 94 |
| 1_133 | 94 | 79.4 | 99 | 95.5 | 87.5 | 98 |
| 1_134 | 97 | 91.2 | 99 | 93.9 | 87.5 | 96 |
| 1_135 | 94.8 | 82.4 | 99 | 93.9 | 87.5 | 96 |
| 1_136 | 95.5 | 82.4 | 100 | 95.5 | 87.5 | 98 |
| 1_137 | 97.8 | 91.2 | 100 | 92.4 | 87.5 | 94 |
| 1_138 | 96.3 | 85.3 | 100 | 97 | 93.8 | 98 |
| 1_139 | 95.5 | 82.4 | 100 | 90.9 | 81.2 | 94 |
| 1_140 | 94 | 79.4 | 99 | 92.4 | 81.2 | 96 |
| 1_141 | 94.8 | 82.4 | 99 | 92.4 | 87.5 | 94 |
| 1_142 | 95.5 | 85.3 | 99 | 90.9 | 87.5 | 92 |
| 1_143 | 95.5 | 82.4 | 100 | 92.4 | 87.5 | 94 |
| 1_144 | 94 | 79.4 | 99 | 92.4 | 81.2 | 96 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_145 | 94.8 | 82.4 | 99 | 95.5 | 87.5 | 98 |
| 1_146 | 94 | 79.4 | 99 | 92.4 | 87.5 | 94 |
| 1_147 | 95.5 | 85.3 | 99 | 93.9 | 93.8 | 94 |
| 1_148 | 94.8 | 79.4 | 100 | 93.9 | 87.5 | 96 |
| 1_149 | 94 | 79.4 | 99 | 95.5 | 87.5 | 98 |
| 1_150 | 96.3 | 85.3 | 100 | 90.9 | 81.2 | 94 |
| 1_151 | 95.5 | 82.4 | 100 | 93.9 | 87.5 | 96 |
| 1_152 | 93.3 | 79.4 | 98 | 93.9 | 87.5 | 96 |
| 1_153 | 96.3 | 88.2 | 99 | 95.5 | 87.5 | 98 |
| 1_154 | 94.8 | 82.4 | 99 | 89.4 | 81.2 | 92 |
| 1_155 | 97 | 88.2 | 100 | 98.5 | 93.8 | 100 |
| 1_156 | 94 | 79.4 | 99 | 90.9 | 81.2 | 94 |
| 1_157 | 93.3 | 79.4 | 98 | 90.9 | 87.5 | 92 |
| 1_158 | 94 | 82.4 | 98 | 95.5 | 87.5 | 98 |
| 1_159 | 94.8 | 79.4 | 100 | 92.4 | 87.5 | 94 |
| 1_160 | 95.5 | 82.4 | 100 | 92.4 | 93.8 | 92 |
| 1_161 | 94 | 79.4 | 99 | 93.9 | 87.5 | 96 |
| 1_162 | 94 | 79.4 | 99 | 93.9 | 87.5 | 96 |
| 1_163 | 94.8 | 82.4 | 99 | 93.9 | 87.5 | 96 |
| 1_164 | 94.8 | 82.4 | 99 | 92.4 | 87.5 | 94 |
| 1_165 | 95.5 | 82.4 | 100 | 93.9 | 87.5 | 96 |
| 1_166 | 94.8 | 79.4 | 100 | 95.5 | 87.5 | 98 |
| 1_167 | 96.3 | 85.3 | 100 | 93.9 | 81.2 | 98 |
| 1_168 | 94.8 | 79.4 | 100 | 92.4 | 87.5 | 94 |
| 1_169 | 96.3 | 85.3 | 100 | 92.4 | 81.2 | 96 |
| 1_170 | 96.3 | 88.2 | 99 | 92.3 | 86.7 | 94 |
| 1_171 | 94.8 | 82.4 | 99 | 92.4 | 81.2 | 96 |
| 1_172 | 95.5 | 85.3 | 99 | 95.5 | 87.5 | 98 |
| 1_173 | 94.8 | 79.4 | 100 | 92.4 | 81.2 | 96 |
| 1_174 | 95.5 | 85.3 | 99 | 95.5 | 93.8 | 96 |
| 1_175 | 95.5 | 82.4 | 100 | 90.9 | 81.2 | 94 |
| 1_176 | 94.8 | 82.4 | 99 | 93.9 | 93.8 | 94 |
| 1_177 | 95.5 | 82.4 | 100 | 93.9 | 93.8 | 94 |
| 1_178 | 94 | 79.4 | 99 | 92.4 | 81.2 | 96 |
| 1_179 | 94 | 79.4 | 99 | 92.4 | 87.5 | 94 |
| 1_180 | 94.8 | 82.4 | 99 | 92.4 | 81.2 | 96 |
| 1_181 | 94 | 79.4 | 99 | 93.9 | 87.5 | 96 |
| 1_182 | 94.8 | 85.3 | 98 | 92.4 | 87.5 | 94 |
| 1_183 | 94 | 79.4 | 99 | 95.5 | 93.8 | 96 |
| 1_184 | 94.8 | 79.4 | 100 | 93.9 | 87.5 | 96 |
| 1_185 | 95.5 | 85.3 | 99 | 97 | 87.5 | 100 |
| 1_186 | 94.8 | 79.4 | 100 | 95.5 | 87.5 | 98 |
| 1_187 | 94 | 79.4 | 99 | 93.9 | 87.5 | 96 |
| 1_188 | 94 | 79.4 | 99 | 93.8 | 93.8 | 93.9 |
| 1_189 | 94.8 | 79.4 | 100 | 93.9 | 87.5 | 96 |

Example 3

<Selection of Gene Markers Using all Samples and Method for Evaluating Esophageal Cancer Discriminant Performance of Acquired Gene Markers>

In this Example, the samples of the training cohort and the validation cohort used in Examples 1 and 2 were integrated, and selection of a gene marker and evaluation of its esophageal cancer discriminant performance were conducted using any of the samples.

Specifically, the miRNA expression levels in the sera of the 50 esophageal cancer patients and the 150 healthy subjects obtained in the preceding Reference Examples were normalized by quantile normalization. In order to acquire diagnosis markers with higher reliability, only genes having a gene expression level of $2^6$ or higher in 50% or more of the samples in either of the esophageal cancer patient group or the healthy subject group were selected in the gene marker selection. In order to further acquire statistical significance for discriminating an esophageal cancer patient group from a healthy subject group, the P value obtained by two-tailed t-test assuming equal variance as to each gene expression level was corrected by the Bonferroni method, and genes that satisfied p<0.01 were selected as gene markers for use in explanatory variables of a discriminant and described in Table 7. In this way, hsa-miR-675-5p, hsa-miR-486-3p, hsa-miR-6777-5p, hsa-miR-4497, hsa-miR-296-3p, hsa-miR-6738-5p, hsa-miR-4731-5p, hsa-miR-6889-5p, hsa-miR-6786-5p, hsa-miR-92a-3p, hsa-miR-4294, hsa-miR-4763-3p, hsa-miR-6076, hsa-miR-663a, hsa-miR-760, hsa-miR-4667-5p, hsa-miR-6090, hsa-miR-4730, hsa-miR-7106-5p, hsa-miR-3196, hsa-miR-5698, hsa-miR-6087, hsa-miR-4665-5p, hsa-miR-8059 and hsa-miR-6879-5p genes, and the nucleotide sequences represented by SEQ ID NOs: 190 to 214 related thereto were found in addition to the genes described in Table 2. As with the nucleotide sequences of SEQ ID NOs: 1 to 189, the results obtained about the polynucleotides shown in the nucleotide sequences of SEQ ID NOs: 190 to 214 also showed that the gene measurement values were significantly lower (−) or higher (+) in the esophageal cancer patient group than in the healthy subject group (Table 7). These results were able to be validated in the validation cohort. Thus, the presence or absence of esophageal cancer in the newly obtained samples can be determined by the methods described in Examples 1 and 2 by using the gene expression level measurement values described in Table 7 either alone or in combination with the gene expression level measurement values described in Table 2.

TABLE 7

| SEQ ID NO: | Gene name | P value after Bonferroni correction | Expression level in esophageal cancer patient relative to healthy subject |
|---|---|---|---|
| 1 | hsa-miR-204-3p | 8.14E−45 | − |
| 2 | hsa-miR-1247-3p | 1.36E−45 | + |
| 3 | hsa-miR-6875-5p | 6.12E−37 | + |
| 4 | hsa-miR-6857-5p | 1.04E−39 | + |
| 5 | hsa-miR-6726-5p | 7.48E−40 | + |
| 6 | hsa-miR-3188 | 6.76E−39 | − |
| 7 | hsa-miR-8069 | 1.65E−29 | + |
| 8 | hsa-miR-4257 | 1.79E−35 | − |
| 9 | hsa-miR-1343-3p | 1.95E−36 | + |
| 10 | hsa-miR-7108-5p | 1.78E−35 | + |
| 11 | hsa-miR-6825-5p | 4.35E−36 | − |
| 12 | hsa-miR-7641 | 1.73E−34 | − |
| 13 | hsa-miR-3185 | 1.35E−33 | + |
| 14 | hsa-miR-4746-3p | 4.69E−34 | + |
| 15 | hsa-miR-6791-5p | 5.41E−32 | + |
| 16 | hsa-miR-6893-5p | 6.65E−32 | + |
| 17 | hsa-miR-4433b-3p | 7.92E−29 | + |
| 18 | hsa-miR-3135b | 9.14E−25 | − |
| 19 | hsa-miR-6781-5p | 1.02E−32 | + |
| 20 | hsa-miR-1908-5p | 1.06E−32 | + |
| 21 | hsa-miR-4792 | 7.47E−32 | + |
| 22 | hsa-miR-7845-5p | 6.13E−29 | + |
| 23 | hsa-miR-4417 | 1.23E−29 | + |
| 24 | hsa-miR-3184-5p | 1.98E−30 | + |
| 25 | hsa-miR-1225-5p | 1.13E−30 | + |
| 26 | hsa-miR-1231 | 1.73E−26 | + |
| 27 | hsa-miR-1225-3p | 4.81E−30 | + |
| 28 | hsa-miR-150-3p | 9.61E−24 | + |
| 29 | hsa-miR-4433-3p | 1.64E−27 | + |
| 30 | hsa-miR-6125 | 7.40E−28 | + |
| 31 | hsa-miR-4513 | 1.69E−23 | + |
| 32 | hsa-miR-6787-5p | 3.22E−27 | − |
| 33 | hsa-miR-6784-5p | 4.73E−27 | + |
| 34 | hsa-miR-615-5p | 9.34E−26 | − |
| 35 | hsa-miR-6765-3p | 7.95E−27 | + |
| 36 | hsa-miR-5572 | 1.59E−27 | − |
| 37 | hsa-miR-6842-5p | 2.94E−27 | − |
| 38 | hsa-miR-8063 | 1.48E−26 | + |
| 39 | hsa-miR-6780b-5p | 3.59E−29 | − |
| 40 | hsa-miR-187-5p | 8.52E−25 | − |
| 41 | hsa-miR-128-1-5p | 5.67E−21 | − |
| 42 | hsa-miR-6729-5p | 1.04E−26 | − |
| 43 | hsa-miR-6741-5p | 7.62E−23 | + |
| 44 | hsa-miR-6757-5p | 1.84E−26 | + |
| 45 | hsa-miR-7110-5p | 1.82E−24 | + |
| 46 | hsa-miR-7975 | 8.82E−24 | − |
| 47 | hsa-miR-1233-5p | 1.28E−26 | − |
| 48 | hsa-miR-6845-5p | 3.06E−24 | − |
| 49 | hsa-miR-3937 | 7.00E−24 | − |
| 50 | hsa-miR-4467 | 5.02E−23 | + |
| 51 | hsa-miR-7109-5p | 2.70E−17 | − |
| 52 | hsa-miR-6088 | 3.91E−22 | − |
| 53 | hsa-miR-6782-5p | 1.72E−19 | − |
| 54 | hsa-miR-5195-3p | 8.97E−24 | − |
| 55 | hsa-miR-4454 | 9.04E−23 | + |
| 56 | hsa-miR-6724-5p | 5.74E−19 | − |
| 57 | hsa-miR-8072 | 6.96E−19 | + |
| 58 | hsa-miR-4516 | 6.08E−22 | − |
| 59 | hsa-miR-6756-5p | 5.52E−19 | − |
| 60 | hsa-miR-4665-3p | 3.30E−20 | − |
| 61 | hsa-miR-6826-5p | 2.65E−21 | + |
| 62 | hsa-miR-6820-5p | 1.83E−18 | + |
| 63 | hsa-miR-6887-5p | 7.93E−19 | − |
| 64 | hsa-miR-3679-5p | 1.14E−21 | − |
| 65 | hsa-miR-7847-3p | 2.20E−20 | − |
| 66 | hsa-miR-6721-5p | 3.96E−16 | + |
| 67 | hsa-miR-3622a-5p | 1.78E−18 | + |
| 68 | hsa-miR-939-5p | 1.12E−17 | − |

TABLE 7-continued

| SEQ ID NO: | Gene name | P value after Bonferroni correction | Expression level in esophageal cancer patient relative to healthy subject |
|---|---|---|---|
| 69 | hsa-miR-602 | 9.30E−19 | + |
| 70 | hsa-miR-7977 | 4.08E−19 | − |
| 71 | hsa-miR-6749-5p | 2.11E−19 | − |
| 72 | hsa-miR-1914-3p | 3.49E−15 | − |
| 73 | hsa-miR-4651 | 9.97E−21 | − |
| 74 | hsa-miR-4695-5p | 1.01E−17 | + |
| 75 | hsa-miR-6848-5p | 1.96E−16 | + |
| 76 | hsa-miR-1228-3p | 1.45E−17 | + |
| 77 | hsa-miR-642b-3p | 3.30E−17 | + |
| 78 | hsa-miR-6746-5p | 2.40E−18 | − |
| 79 | hsa-miR-3620-5p | 3.16E−15 | + |
| 80 | hsa-miR-3131 | 1.67E−20 | − |
| 81 | hsa-miR-6732-5p | 3.23E−17 | + |
| 82 | hsa-miR-7113-3p | 6.47E−18 | + |
| 83 | hsa-miR-23a-3p | 1.75E−15 | + |
| 84 | hsa-miR-3154 | 3.86E−14 | + |
| 85 | hsa-miR-4723-5p | 4.11E−15 | − |
| 86 | hsa-miR-3663-3p | 6.62E−16 | − |
| 87 | hsa-miR-4734 | 9.47E−16 | + |
| 88 | hsa-miR-6816-5p | 1.28E−16 | − |
| 89 | hsa-miR-4442 | 9.49E−16 | + |
| 90 | hsa-miR-4476 | 9.75E−16 | − |
| 91 | hsa-miR-423-5p | 6.53E−13 | + |
| 92 | hsa-miR-1249 | 3.05E−15 | − |
| 93 | hsa-miR-6515-3p | 9.05E−12 | − |
| 94 | hsa-miR-887-3p | 1.74E−15 | + |
| 95 | hsa-miR-4741 | 9.67E−16 | + |
| 96 | hsa-miR-6766-3p | 2.28E−14 | − |
| 97 | hsa-miR-4673 | 2.15E−14 | − |
| 98 | hsa-miR-6779-5p | 3.15E−13 | + |
| 99 | hsa-miR-4706 | 8.59E−16 | + |
| 100 | hsa-miR-1268b | 1.75E−14 | + |
| 101 | hsa-miR-4632-5p | 4.72E−14 | − |
| 102 | hsa-miR-3197 | 6.20E−15 | + |
| 103 | hsa-miR-6798-5p | 1.13E−12 | + |
| 104 | hsa-miR-711 | 1.63E−16 | − |
| 105 | hsa-miR-6840-3p | 1.79E−12 | + |
| 106 | hsa-miR-6763-5p | 1.13E−12 | + |
| 107 | hsa-miR-6727-5p | 1.88E−15 | + |
| 108 | hsa-miR-371a-5p | 5.18E−12 | + |
| 109 | hsa-miR-6824-5p | 1.52E−13 | + |
| 110 | hsa-miR-4648 | 8.82E−15 | − |
| 111 | hsa-miR-1227-5p | 3.56E−11 | − |
| 112 | hsa-miR-564 | 4.80E−13 | − |
| 113 | hsa-miR-3679-3p | 1.57E−12 | − |
| 114 | hsa-miR-2861 | 7.34E−13 | + |
| 115 | hsa-miR-6737-5p | 5.72E−09 | + |
| 116 | hsa-miR-575 | 2.07E−11 | − |
| 117 | hsa-miR-4725-3p | 1.06E−13 | + |
| 118 | hsa-miR-6716-5p | 2.52E−11 | + |
| 119 | hsa-miR-4675 | 2.03E−14 | − |
| 120 | hsa-miR-1915-3p | 1.35E−13 | + |
| 121 | hsa-miR-671-5p | 1.87E−11 | + |
| 122 | hsa-miR-3656 | 7.58E−11 | − |
| 123 | hsa-miR-6722-3p | 9.17E−11 | + |
| 124 | hsa-miR-4707-5p | 1.41E−12 | − |
| 125 | hsa-miR-4449 | 4.22E−12 | + |
| 126 | hsa-miR-1202 | 1.28E−12 | − |
| 127 | hsa-miR-4649-5p | 8.69E−11 | − |
| 128 | hsa-miR-744-5p | 9.90E−11 | − |
| 129 | hsa-miR-642a-3p | 1.42E−09 | + |
| 130 | hsa-miR-451a | 3.46E−12 | + |
| 131 | hsa-miR-6870-5p | 2.08E−12 | + |
| 132 | hsa-miR-4443 | 5.77E−08 | − |
| 133 | hsa-miR-6808-5p | 9.18E−07 | + |
| 134 | hsa-miR-4728-5p | 2.27E−11 | + |
| 135 | hsa-miR-937-5p | 1.97E−08 | + |
| 136 | hsa-miR-135a-3p | 1.01E−07 | + |
| 137 | hsa-miR-663b | 1.89E−09 | + |
| 138 | hsa-miR-1343-5p | 1.68E−10 | + |
| 139 | hsa-miR-6822-5p | 2.82E−09 | − |
| 140 | hsa-miR-6803-5p | 8.05E−07 | − |
| 141 | hsa-miR-6805-3p | 6.65E−10 | − |
| 142 | hsa-miR-128-2-5p | 8.46E−10 | + |
| 143 | hsa-miR-4640-5p | 1.16E−10 | + |

TABLE 7-continued

| SEQ ID NO: | Gene name | P value after Bonferroni correction | Expression level in esophageal cancer patient relative to healthy subject |
|---|---|---|---|
| 144 | hsa-miR-1469 | 2.15E−07 | + |
| 145 | hsa-miR-92a-2-5p | 4.30E−10 | − |
| 146 | hsa-miR-3940-5p | 2.18E−07 | − |
| 147 | hsa-miR-4281 | 2.04E−08 | − |
| 148 | hsa-miR-1260b | 1.61E−08 | − |
| 149 | hsa-miR-4758-5p | 3.25E−08 | − |
| 150 | hsa-miR-1915-5p | 1.01E−07 | + |
| 151 | hsa-miR-5001-5p | 1.96E−08 | − |
| 152 | hsa-miR-4286 | 4.72E−07 | + |
| 153 | hsa-miR-6126 | 3.16E−09 | + |
| 154 | hsa-miR-6789-5p | 8.38E−08 | − |
| 155 | hsa-miR-4459 | 3.24E−08 | − |
| 156 | hsa-miR-1268a | 5.97E−07 | + |
| 157 | hsa-miR-6752-5p | 5.95E−06 | − |
| 158 | hsa-miR-6131 | 1.52E−07 | + |
| 159 | hsa-miR-6800-5p | 1.75E−07 | + |
| 160 | hsa-miR-4532 | 2.82E−05 | + |
| 161 | hsa-miR-6872-3p | 5.54E−07 | − |
| 162 | hsa-miR-718 | 3.56E−05 | − |
| 163 | hsa-miR-6769a-5p | 2.25E−06 | − |
| 164 | hsa-miR-4707-3p | 5.95E−07 | − |
| 165 | hsa-miR-6765-5p | 6.88E−07 | − |
| 166 | hsa-miR-4739 | 5.13E−06 | + |
| 167 | hsa-miR-4525 | 1.01E−06 | + |
| 168 | hsa-miR-4270 | 2.71E−05 | + |
| 169 | hsa-miR-4534 | 0.000121 | − |
| 170 | hsa-miR-6785-5p | 1.06E−06 | + |
| 171 | hsa-miR-6850-5p | 6.01E−05 | + |
| 172 | hsa-miR-4697-5p | 9.68E−08 | + |
| 173 | hsa-miR-1260a | 7.59E−07 | − |
| 174 | hsa-miR-4486 | 6.56E−06 | − |
| 175 | hsa-miR-6880-5p | 8.38E−07 | − |
| 176 | hsa-miR-6802-5p | 4.43E−06 | − |
| 177 | hsa-miR-6861-5p | 4.72E−06 | − |
| 178 | hsa-miR-92b-5p | 5.54E−05 | + |
| 179 | hsa-miR-1238-5p | 1.21E−05 | + |
| 180 | hsa-miR-6851-5p | 6.80E−06 | + |
| 182 | hsa-miR-149-3p | 4.63E−07 | − |
| 183 | hsa-miR-4689 | 6.67E−06 | + |
| 184 | hsa-miR-4688 | 4.38E−07 | − |
| 185 | hsa-miR-125a-3p | 7.44E−39 | − |
| 186 | hsa-miR-23b-3p | 4.37E−18 | − |
| 187 | hsa-miR-614 | 3.43E−14 | + |
| 188 | hsa-miR-1913 | 2.99E−12 | + |
| 189 | hsa-miR-16-5p | 1.45E−08 | + |
| 190 | hsa-miR-675-5p | 5.72E−07 | − |
| 191 | hsa-miR-486-3p | 2.23E−04 | − |
| 192 | hsa-miR-6777-5p | 3.28E−04 | − |
| 193 | hsa-miR-4497 | 3.90E−04 | − |
| 194 | hsa-miR-296-3p | 4.06E−04 | − |
| 195 | hsa-miR-6738-5p | 4.53E−04 | − |
| 196 | hsa-miR-4731-5p | 5.31E−04 | − |
| 197 | hsa-miR-6889-5p | 6.59E−04 | + |
| 198 | hsa-miR-6786-5p | 6.60E−04 | + |
| 199 | hsa-miR-92a-3p | 1.13E−03 | − |
| 200 | hsa-miR-4294 | 1.17E−03 | − |
| 201 | hsa-miR-4763-3p | 1.35E−03 | + |
| 202 | hsa-miR-6076 | 1.38E−03 | + |
| 203 | hsa-miR-663a | 1.52E−03 | − |
| 204 | hsa-miR-760 | 2.13E−03 | + |
| 205 | hsa-miR-4667-5p | 2.18E−03 | + |
| 206 | hsa-miR-6090 | 2.38E−03 | + |
| 207 | hsa-miR-4730 | 2.79E−03 | + |
| 208 | hsa-miR-7106-5p | 2.80E−03 | − |
| 209 | hsa-miR-3196 | 3.86E−03 | + |
| 210 | hsa-miR-5698 | 4.60E−03 | − |
| 211 | hsa-miR-6087 | 5.73E−03 | − |
| 212 | hsa-miR-4665-5p | 5.91E−03 | − |
| 213 | hsa-miR-8059 | 8.38E−03 | − |
| 214 | hsa-miR-6879-5p | 8.44E−03 | + |

Example 4

<Method for Evaluating Esophageal Cancer-Specific Discriminant Performance by Combination of Multiple Gene Markers Using Samples of Validation Cohort>

In this Example, gene markers for diagnosis were selected by comparing gene expression levels of miRNAs in serum of esophageal cancer patients with that of a control group consisting of healthy subjects, pancreatic cancer patients, bile duct cancer patients, colorectal cancer patients, stomach cancer patients, liver cancer patients, and benign pancreaticobiliary disease patients in the same way as the method described in Example 1 using the gene markers selected in Example 1 and targeting the training cohort described in Reference Example 2. The polynucleotides consisting of the nucleotide sequences represented by SEQ ID NOs: 666 to 676 thus newly selected were further combined with the polynucleotides consisting of the nucleotide sequences represented by SEQ ID NOs: 1 to 214 to study a method for evaluating esophageal cancer-specific discriminant performance.

Specifically, first, the miRNA expression levels in the training cohort and the validation cohort obtained in Reference Example 2 mentioned above were combined and normalized by quantile normalization. Next, Fisher's discriminant analysis was conducted as to combinations of 1 to 6 expression level measurement values comprising at least one of the expression level measurement values of the polynucleotides consisting of the nucleotide sequences represented by SEQ ID NOs: 1 to 214 and 666 to 676, to construct a discriminant for determining the presence or absence of esophageal cancer. Next, accuracy, sensitivity, and specificity in the validation cohort were calculated using the discriminant thus prepared, with the esophageal cancer patient group as a positive sample group and, on the other hand, the healthy subject group, the pancreatic cancer patient group, the bile duct cancer patient group, the colorectal cancer patient group, the stomach cancer patient group, the liver cancer patient group, and the benign pancreaticobiliary disease patient group as a negative sample groups. The discriminant performance of the selected polynucleotides was validated using the independent samples.

Most of polynucleotides consisting of the nucleotide sequences represented by these SEQ ID NOs: 1 to 214 and 666 to 676 or complementary sequences thereof were able to provide relatively high accuracy, sensitivity, and specificity in the determination of the presence or absence of esophageal cancer, and furthermore, were able to specifically discriminate esophageal cancer from the other cancers. For example, at least one polynucleotide selected from the group consisting of polynucleotides consisting of the nucleotide sequences represented by SEQ ID NOs: 1, 2, 5, 8, 22, 32, 33, 35, 43, 44, 56, 85, 98, 106, 109, 115, 121, 126, 133, 138, 155, 157, 166, 177, 179, 185, 202, 212, 666, 667, 668, 669, 670, 671, 672, 673, 674, 675 and 676 or complementary sequences thereof (the cancer type-specific polynucleotide group 1) was able to specifically bind to the target marker.

Among the combinations of multiple polynucleotides selected from cancer type-specific polynucleotide group 1, particularly, combinations comprising at least one polynucleotide selected from the group consisting of polynucleotides consisting of the nucleotide sequences represented by SEQ ID NOs: 1, 22, 85, 109, 121, 126, 133, 138, 166, and 666 or complementary sequences thereof (the cancer type-specific polynucleotide group 2) were able to specifically discriminate esophageal cancer from the other cancers with high accuracy.

The number of the polynucleotides with cancer type specificity in the combination described above can be 1, 2, 3, 4, 5, 6, 7, 8, 9, 10 or more for the combination. The combinations of 6 or more of these polynucleotides were able to exhibit discriminant accuracy of 85% or higher. Specific results about the discrimination accuracy of the measurement using each polynucleotide in the cancer type-specific polynucleotide group 2 will be described below.

The discriminant accuracy of the measurement using the polynucleotide consisting of the nucleotide sequence represented by SEQ ID NO: 1 or a complementary sequence thereof is shown in Table 8-1. The measurement using one polynucleotide consisting of the nucleotide sequence represented by SEQ ID NO: 1 or a complementary sequence thereof exhibited accuracy of 65.4% in the training cohort and accuracy of 65.4% in the validation cohort. Also, for example, the measurement using the combinations of two polynucleotides comprising at least one polynucleotide consisting of the nucleotide sequence represented by SEQ ID NO: 1 or a complementary sequence thereof exhibited the highest accuracy of 78.3% in the training cohort and accuracy of 77.7% in the validation cohort. Furthermore, for example, the measurement using the combinations of three polynucleotides comprising at least one polynucleotide consisting of the nucleotide sequence represented by SEQ ID NO: 1 or a complementary sequence thereof exhibited the highest accuracy of 85.9% in the training cohort and accuracy of 79.8% in the validation cohort. Furthermore, for example, the measurement using the combinations of four polynucleotides comprising at least one polynucleotide consisting of the nucleotide sequence represented by SEQ ID NO: 1 or a complementary sequence thereof exhibited the highest accuracy of 89.2% in the training cohort and accuracy of 88.8% in the validation cohort. Furthermore, for example, the measurement using the combinations of five polynucleotides comprising at least one polynucleotide consisting of the nucleotide sequence represented by SEQ ID NO: 1 or a complementary sequence thereof exhibited the highest accuracy of 91.1% in the training cohort and accuracy of 90.4% in the validation cohort. Furthermore, for example, the measurement using the combinations of six polynucleotides comprising at least one polynucleotide consisting of the nucleotide sequence represented by SEQ ID NO: 1 or a complementary sequence thereof exhibited the highest accuracy of 92.7% in the training cohort and accuracy of 93.1% in the validation cohort.

The discriminant accuracy of the measurement using the polynucleotide consisting of the nucleotide sequence represented by SEQ ID NO: 22 or a complementary sequence thereof is shown in Table 8-2. The measurement using one polynucleotide consisting of the nucleotide sequence represented by SEQ ID NO: 22 or a complementary sequence thereof exhibited accuracy of 70.9% in the training cohort and accuracy of 69.1% in the validation cohort. Also, for example, the measurement using the combinations of two polynucleotides comprising at least one polynucleotide consisting of the nucleotide sequence represented by SEQ ID NO: 22 or a complementary sequence thereof exhibited the highest accuracy of 83.0% in the training cohort and accuracy of 77.7% in the validation cohort. Furthermore, for example, the measurement using the combinations of three polynucleotides comprising at least one polynucleotide consisting of the nucleotide sequence represented by SEQ ID NO: 22 or a complementary sequence thereof exhibited the highest accuracy of 86.9% in the training cohort and accuracy of 81.9% in the validation cohort. Furthermore, for example, the measurement using the combinations of four polynucleotides comprising at least one polynucleotide consisting of the nucleotide sequence represented by SEQ ID NO: 22 or a complementary sequence thereof exhibited the highest accuracy of 89.3% in the training cohort and accuracy of 87.2% in the validation cohort. Furthermore, for example, the measurement using the combinations of five polynucleotides comprising at least one polynucleotide consisting of the nucleotide sequence represented by SEQ ID NO: 22 or a complementary sequence thereof exhibited the highest accuracy of 91.4% in the training cohort and accuracy of 86.7% in the validation cohort. Furthermore, for example, the measurement using the combinations of six polynucleotides comprising at least one polynucleotide consisting of the nucleotide sequence represented by SEQ ID NO: 22 or a complementary sequence thereof exhibited the highest accuracy of 91.9% in the training cohort and accuracy of 90.4% in the validation cohort.

The discriminant accuracy of the measurement using the polynucleotide consisting of the nucleotide sequence represented by SEQ ID NO: 85 or a complementary sequence thereof is shown in Table 8-3. The measurement using one polynucleotide consisting of the nucleotide sequence represented by SEQ ID NO: 85 or a complementary sequence thereof exhibited accuracy of 65.2% in the training cohort and accuracy of 61.2% in the validation cohort. Also, for example, the measurement using the combinations of two polynucleotides comprising at least one polynucleotide consisting of the nucleotide sequence represented by SEQ ID NO: 85 or a complementary sequence thereof exhibited the highest accuracy of 79.1% in the training cohort and accuracy of 77.1% in the validation cohort. Furthermore, for example, the measurement using the combinations of three polynucleotides comprising at least one polynucleotide consisting of the nucleotide sequence represented by SEQ ID NO: 85 or a complementary sequence thereof exhibited the highest accuracy of 84.3% in the training cohort and accuracy of 78.1% in the validation cohort. Furthermore, for example, the measurement using the combinations of four polynucleotides comprising at least one polynucleotide consisting of the nucleotide sequence represented by SEQ ID NO: 85 or a complementary sequence thereof exhibited the highest accuracy of 88.5% in the training cohort and accuracy of 88.8% in the validation cohort. Furthermore, for example, the measurement using the combinations of five polynucleotides comprising at least one polynucleotide consisting of the nucleotide sequence represented by SEQ ID NO: 85 or a complementary sequence thereof exhibited the highest accuracy of 90.8% in the training cohort and accuracy of 91.0% in the validation cohort. Furthermore, for example, the measurement using the combinations of six polynucleotides comprising at least one polynucleotide consisting of the nucleotide sequence represented by SEQ ID NO: 85 or a complementary sequence thereof exhibited the highest accuracy of 91.6% in the training cohort and accuracy of 91.0% in the validation cohort.

The discriminant accuracy of the measurement using the polynucleotide consisting of the nucleotide sequence represented by SEQ ID NO: 109 or a complementary sequence thereof is shown in Table 8-4. The measurement using one polynucleotide consisting of the nucleotide sequence represented by SEQ ID NO: 109 or a complementary sequence thereof exhibited accuracy of 57.6% in the training cohort and accuracy of 54.8% in the validation cohort. Also, for example, the measurement using the combinations of two polynucleotides comprising at least one polynucleotide consisting of the nucleotide sequence represented by SEQ ID NO: 109 or a complementary sequence thereof exhibited the highest accuracy of 83.0% in the training cohort and accuracy of 76.1% in the validation cohort. Furthermore, for example, the measurement using the combinations of three polynucleotides comprising at least one polynucleotide consisting of the nucleotide sequence represented by SEQ ID NO: 109 or a complementary sequence thereof exhibited the highest accuracy of 85.9% in the training cohort and accuracy of 81.9% in the validation cohort. Furthermore, for example, the measurement using the combinations of four polynucleotides comprising at least one polynucleotide consisting of the nucleotide sequence represented by SEQ ID NO: 109 or a complementary sequence thereof exhibited the highest accuracy of 88.7% in the training cohort and accuracy of 84.5% in the validation cohort. Furthermore, for example, the measurement using the combinations of five polynucleotides comprising at least one polynucleotide consisting of the nucleotide sequence represented by SEQ ID NO: 109 or a complementary sequence thereof exhibited the highest accuracy of 91.1% in the training cohort and accuracy of 90.4% in the validation cohort. Furthermore, for example, the measurement using the combinations of six polynucleotides comprising at least one polynucleotide consisting of the nucleotide sequence represented by SEQ ID NO: 109 or a complementary sequence thereof exhibited the highest accuracy of 91.9% in the training cohort and accuracy of 90.4% in the validation cohort.

The discriminant accuracy of the measurement using the polynucleotide consisting of the nucleotide sequence represented by SEQ ID NO: 121 or a complementary sequence thereof is shown in Table 8-5. The measurement using one polynucleotide consisting of the nucleotide sequence represented by SEQ ID NO: 121 or a complementary sequence thereof exhibited accuracy of 72.3% in the training cohort and accuracy of 67.6% in the validation cohort. Also, for example, the measurement using the combinations of two polynucleotides comprising at least one polynucleotide consisting of the nucleotide sequence represented by SEQ ID NO: 121 or a complementary sequence thereof exhibited the highest accuracy of 81.9% in the training cohort and accuracy of 73.9% in the validation cohort. Furthermore, for example, the measurement using the combinations of three polynucleotides comprising at least one polynucleotide consisting of the nucleotide sequence represented by SEQ ID NO: 121 or a complementary sequence thereof exhibited the highest accuracy of 86.1% in the training cohort and accuracy of 79.7% in the validation cohort. Furthermore, for example, the measurement using the combinations of four polynucleotides comprising at least one polynucleotide consisting of the nucleotide sequence represented by SEQ ID NO: 121 or a complementary sequence thereof exhibited the highest accuracy of 89.0% in the training cohort and accuracy of 83.0% in the validation cohort. Furthermore, for example, the measurement using the combinations of five polynucleotides comprising at least one polynucleotide consisting of the nucleotide sequence represented by SEQ ID NO: 121 or a complementary sequence thereof exhibited the highest accuracy of 91.4% in the training cohort and accuracy of 86.2% in the validation cohort. Furthermore, for example, the measurement using the combinations of six polynucleotides comprising at least one polynucleotide consisting of the nucleotide sequence represented by SEQ ID NO: 121 or a complementary sequence thereof exhibited the highest accuracy of 91.6% in the training cohort and accuracy of 89.9% in the validation cohort.

The discriminant accuracy of the measurement using the polynucleotide consisting of the nucleotide sequence represented by SEQ ID NO: 126 or a complementary sequence thereof is shown in Table 8-6. The measurement using one polynucleotide consisting of the nucleotide sequence represented by SEQ ID NO: 126 or a complementary sequence thereof exhibited accuracy of 73.6% in the training cohort and accuracy of 66.0% in the validation cohort. Also, for example, the measurement using the combinations of two polynucleotides comprising at least one polynucleotide consisting of the nucleotide sequence represented by SEQ ID NO: 126 or a complementary sequence thereof exhibited the highest accuracy of 83.5% in the training cohort and accuracy of 76.1% in the validation cohort. Furthermore, for example, the measurement using the combinations of three polynucleotides comprising at least one polynucleotide consisting of the nucleotide sequence represented by SEQ ID NO: 126 or a complementary sequence thereof exhibited the highest accuracy of 88.5% in the training cohort and accuracy of 79.8% in the validation cohort. Furthermore, for example, the measurement using the combinations of four polynucleotides comprising at least one polynucleotide consisting of the nucleotide sequence represented by SEQ ID NO: 126 or a complementary sequence thereof exhibited the highest accuracy of 89.8% in the training cohort and accuracy of 84.0% in the validation cohort. Furthermore, for example, the measurement using the combinations of five polynucleotides comprising at least one polynucleotide consisting of the nucleotide sequence represented by SEQ ID NO: 126 or a complementary sequence thereof exhibited the highest accuracy of 91.1% in the training cohort and accuracy of 91.5% in the validation cohort. Furthermore, for example, the measurement using the combinations of six polynucleotides comprising at least one polynucleotide consisting of the nucleotide sequence represented by SEQ ID NO: 126 or a complementary sequence thereof exhibited the highest accuracy of 92.7% in the training cohort and accuracy of 90.4% in the validation cohort.

The discriminant accuracy of the measurement using the polynucleotide consisting of the nucleotide sequence represented by SEQ ID NO: 133 or a complementary sequence thereof is shown in Table 8-7. The measurement using one polynucleotide consisting of the nucleotide sequence represented by SEQ ID NO: 133 or a complementary sequence thereof exhibited accuracy of 52.9% in the training cohort and accuracy of 54.8% in the validation cohort. Also, for example, the measurement using the combinations of two polynucleotides comprising at least one polynucleotide consisting of the nucleotide sequence represented by SEQ ID NO: 133 or a complementary sequence thereof exhibited the highest accuracy of 81.7% in the training cohort and accuracy of 79.3% in the validation cohort. Furthermore, for example, the measurement using the combinations of three polynucleotides comprising at least one polynucleotide consisting of the nucleotide sequence represented by SEQ ID NO: 133 or a complementary sequence thereof exhibited the highest accuracy of 86.1% in the training cohort and accuracy of 83.5% in the validation cohort. Furthermore, for example, the measurement using the combinations of four polynucleotides comprising at least one polynucleotide consisting of the nucleotide sequence represented by SEQ ID NO: 133 or a complementary sequence thereof exhibited the highest accuracy of 89.0% in the training cohort and accuracy of 86.1% in the validation cohort. Furthermore, for example, the measurement using the combinations of five polynucleotides comprising at least one polynucleotide consisting of the nucleotide sequence represented by SEQ ID NO: 133 or a complementary sequence thereof exhibited the highest accuracy of 90.8% in the training cohort and accuracy of 89.4% in the validation cohort. Furthermore, for example, the measurement using the combinations of six polynucleotides comprising at least one polynucleotide consisting of the nucleotide sequence represented by SEQ ID NO: 133 or a complementary sequence thereof exhibited the highest accuracy of 91.3% in the training cohort and accuracy of 89.4% in the validation cohort.

The discriminant accuracy of the measurement using the polynucleotide consisting of the nucleotide sequence represented by SEQ ID NO: 138 or a complementary sequence thereof is shown in Table 8-8. The measurement using one polynucleotide consisting of the nucleotide sequence represented by SEQ ID NO: 138 or a complementary sequence thereof exhibited accuracy of 70.1% in the training cohort and accuracy of 68.1% in the validation cohort. Also, for example, the measurement using the combinations of two polynucleotides comprising at least one polynucleotide consisting of the nucleotide sequence represented by SEQ ID NO: 138 or a complementary sequence thereof exhibited the highest accuracy of 80.1% in the training cohort and accuracy of 77.7% in the validation cohort. Furthermore, for example, the measurement using the combinations of three polynucleotides comprising at least one polynucleotide consisting of the nucleotide sequence represented by SEQ ID NO: 138 or a complementary sequence thereof exhibited the highest accuracy of 85.8% in the training cohort and accuracy of 92.0% in the validation cohort. Furthermore, for example, the measurement using the combinations of four polynucleotides comprising at least one polynucleotide consisting of the nucleotide sequence represented by SEQ ID NO: 138 or a complementary sequence thereof exhibited the highest accuracy of 89.5% in the training cohort and accuracy of 88.8% in the validation cohort. Furthermore, for example, the measurement using the combinations of five polynucleotides comprising at least one polynucleotide consisting of the nucleotide sequence represented by SEQ ID NO: 138 or a complementary sequence thereof exhibited the highest accuracy of 91.6% in the training cohort and accuracy of 90.4% in the validation cohort. Furthermore, for example, the measurement using the combinations of six polynucleotides comprising at least one polynucleotide consisting of the nucleotide sequence represented by SEQ ID NO: 138 or a complementary sequence thereof exhibited the highest accuracy of 91.9% in the training cohort and accuracy of 90.4% in the validation cohort.

The discriminant accuracy of the measurement using the polynucleotide consisting of the nucleotide sequence represented by SEQ ID NO: 166 or a complementary sequence thereof is shown in Table 8-9. The measurement using one polynucleotide consisting of the nucleotide sequence represented by SEQ ID NO: 166 or a complementary sequence thereof exhibited accuracy of 71.7% in the training cohort and accuracy of 72.3% in the validation cohort. Also, for example, the measurement using the combinations of two polynucleotides comprising at least one polynucleotide consisting of the nucleotide sequence represented by SEQ ID NO: 166 or a complementary sequence thereof exhibited the highest accuracy of 80.9% in the training cohort and accuracy of 77.7% in the validation cohort. Furthermore, for example, the measurement using the combinations of three polynucleotides comprising at least one polynucleotide consisting of the nucleotide sequence represented by SEQ ID NO: 166 or a complementary sequence thereof exhibited the highest accuracy of 86.9% in the training cohort and accuracy of 81.9% in the validation cohort. Furthermore, for example, the measurement using the combinations of four polynucleotides comprising at least one polynucleotide consisting of the nucleotide sequence represented by SEQ ID NO: 166 or a complementary sequence thereof exhibited the highest accuracy of 90.1% in the training cohort and accuracy of 87.2% in the validation cohort. Furthermore, for example, the measurement using the combinations of five polynucleotides comprising at least one polynucleotide consisting of the nucleotide sequence represented by SEQ ID NO: 166 or a complementary sequence thereof exhibited the highest accuracy of 92.1% in the training cohort and accuracy of 90.4% in the validation cohort. Furthermore, for example, the measurement using the combinations of six polynucleotides comprising at least one polynucleotide consisting of the nucleotide sequence represented by SEQ ID NO: 166 or a complementary sequence thereof exhibited the highest accuracy of 91.6% in the training cohort and accuracy of 91.5% in the validation cohort.

The discriminant accuracy of the measurement using the polynucleotide consisting of the nucleotide sequence represented by SEQ ID NO: 666 or a complementary sequence thereof is shown in Table 8-10. The measurement using one polynucleotide consisting of the nucleotide sequence represented by SEQ ID NO: 666 or a complementary sequence thereof exhibited accuracy of 56.0% in the training cohort and accuracy of 53.2% in the validation cohort. Also, for example, the measurement using the combinations of two polynucleotides comprising at least one polynucleotide consisting of the nucleotide sequence represented by SEQ ID NO: 666 or a complementary sequence thereof exhibited the highest accuracy of 81.2% in the training cohort and accuracy of 78.2% in the validation cohort. Furthermore, for example, the measurement using the combinations of three polynucleotides comprising at least one polynucleotide consisting of the nucleotide sequence represented by SEQ ID NO: 666 or a complementary sequence thereof exhibited the highest accuracy of 85.9% in the training cohort and accuracy of 81.4% in the validation cohort. Furthermore, for example, the measurement using the combinations of four polynucleotides comprising at least one polynucleotide consisting of the nucleotide sequence represented by SEQ ID NO: 666 or a complementary sequence thereof exhibited the highest accuracy of 89.2% in the training cohort and accuracy of 89.9% in the validation cohort. Furthermore, for example, the measurement using the combinations of five polynucleotides comprising at least one polynucleotide consisting of the nucleotide sequence represented by SEQ ID NO: 666 or a complementary sequence thereof exhibited the highest accuracy of 91.3% in the training cohort and accuracy of 91.0% in the validation cohort. Furthermore, for example, the measurement using the combinations of six polynucleotides comprising at least one polynucleotide consisting of the nucleotide sequence represented by SEQ ID NO: 666 or a complementary sequence thereof exhibited the highest accuracy of 92.1% in the training cohort and accuracy of 91.5% in the validation cohort.

Figure 4A:
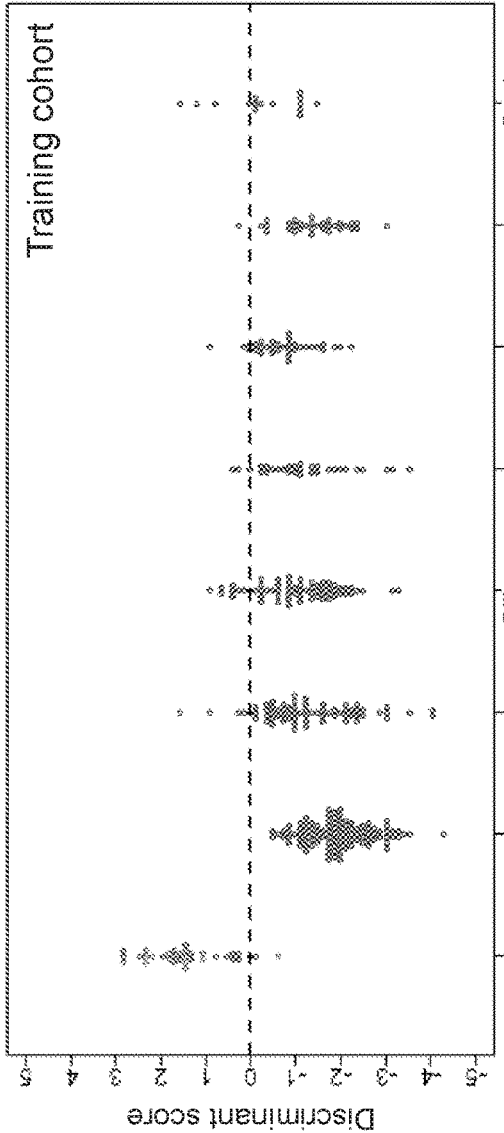
FIG. 4 (schematic A) a discriminant (−2.65×hsa-miR-4739−3.01×hsa-miR-1343-5p+0.69×hsa-miR-204-3p+0.95×hsa-miR-4723-5p−0.56×hsa-miR-6726-5p−0.99×hsa-miR-6717-5p+57.33) was prepared by use of Fisher's discriminant analysis from the expression level measurement values of hsa-miR-204-3p (SEQ ID NO: 1), hsa-miR-6726-5p (SEQ ID NO: 5), hsa-miR-4723-5p (SEQ ID NO: 85), hsa-miR-1343-5p (SEQ ID NO: 138), hsa-miR-4739 (SEQ ID NO: 166), and hsa-miR-6717-5p (SEQ ID NO: 666) in 34 esophageal cancer patients, 103 healthy subjects, 69 pancreatic cancer patients, 66 bile duct cancer patients, 30 colorectal cancer patients, 33 stomach cancer patients, 32 liver cancer patients, and 15 benign pancreaticobiliary disease patients selected as training cohorts, and discriminant scores obtained from the discriminant were plotted on the ordinate against the sample groups on the abscissa. The dotted line in the diagram depicts a discrimination boundary that offered a discriminant score of 0 and discriminated between the groups.
Figure 4B:
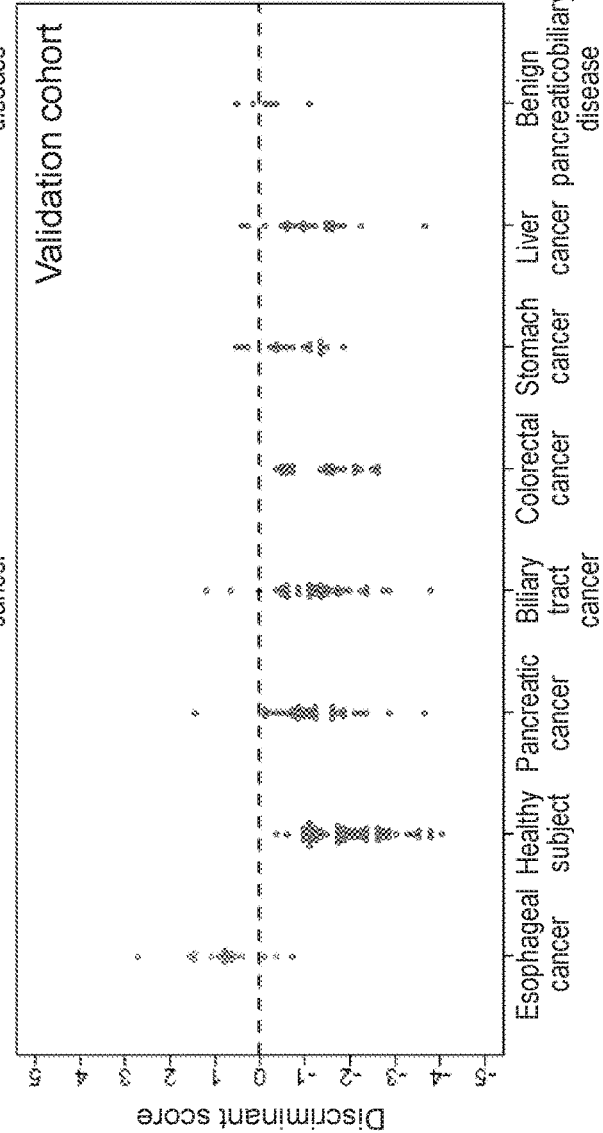

The expression level measurement values of the polynucleotides consisting of the nucleotide sequences represented by SEQ ID NOs: 1, 5, 85, 138, 166, and 666 were compared among 34 esophageal cancer patients, 103 healthy subjects, 69 pancreatic cancer patients, 66 bile duct cancer patients, 30 colorectal cancer patients, 33 stomach cancer patients, 32 liver cancer patients, and 15 benign pancreaticobiliary disease patients in the training cohort. As a result, a variance diagram that significantly separated the discriminant score of the esophageal cancer patient group from the discriminant scores of the other groups was obtained in the training cohort (see FIG. 4 (schematic A)). These results were also reproducible for the validation cohort (see FIG. 4 (schematic B)).

TABLE 8-1

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1 | 65.4 | 76.5 | 64.4 | 65.4 | 62.5 | 65.7 |
| 1_22 | 78.3 | 85.3 | 77.6 | 77.7 | 87.5 | 76.7 |
| 1_22_126 | 85.9 | 100 | 84.5 | 79.8 | 87.5 | 79.1 |
| 1_138_166_666 | 89.2 | 94.1 | 88.8 | 88.8 | 81.2 | 89.5 |
| 1_121_138_166_666 | 91.1 | 94.1 | 90.8 | 90.4 | 87.5 | 90.7 |
| 1_85_138_166_666_668 | 90.6 | 94.1 | 90.2 | 91.5 | 81.2 | 92.4 |
| 1_85_98_138_166_666 | 90.8 | 97.1 | 90.2 | 92 | 87.5 | 92.4 |
| 1_85_138_155_166_666 | 91.9 | 97.1 | 91.4 | 91.5 | 81.2 | 92.4 |
| 1_5_85_138_166_666 | 92.7 | 91.2 | 92.8 | 93.1 | 81.2 | 94.2 |
| 1_35_85_138_166_666 | 90.8 | 97.1 | 90.2 | 91 | 81.2 | 91.9 |

TABLE 8-2

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 22 | 70.9 | 76.5 | 70.4 | 69.1 | 75 | 68.6 |
| 22_126 | 83 | 88.2 | 82.5 | 77.7 | 75 | 77.9 |
| 22_126_166 | 86.9 | 100 | 85.6 | 81.9 | 81.2 | 82 |
| 22_98_166_666 | 89.3 | 94.1 | 88.8 | 87.2 | 100 | 86 |
| 22_98_166_666_668 | 91.4 | 94.1 | 91.1 | 86.7 | 81.2 | 87.2 |
| 1_22_85_138_166_666 | 91.3 | 94.1 | 91.1 | 91.5 | 81.2 | 92.4 |
| 22_32_121_133_166_666 | 91.6 | 100 | 90.8 | 88.3 | 81.2 | 89 |
| 1_22_126_138_166_666 | 91.3 | 100 | 90.5 | 92 | 87.5 | 92.4 |
| 1_22_121_155_166_666 | 90.1 | 91.2 | 89.9 | 89.9 | 93.8 | 89.5 |
| 22_32_109_121_666_667 | 91.9 | 97.1 | 91.4 | 90.4 | 81.2 | 91.2 |

TABLE 8-3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 85 | 65.2 | 73.5 | 64.4 | 61.2 | 12.5 | 65.7 |
| 2_85 | 79.1 | 91.2 | 77.9 | 77.1 | 68.8 | 77.9 |
| 85_138_667 | 84.3 | 94.1 | 83.3 | 78.1 | 56.2 | 80.1 |
| 22_85_166_666 | 88.5 | 94.1 | 87.9 | 88.8 | 81.2 | 89.5 |
| 1_85_138_166_666 | 90.8 | 97.1 | 90.2 | 91 | 81.2 | 91.9 |
| 85_138_166_185_666_669 | 91.1 | 97.1 | 90.5 | 90.4 | 75 | 91.9 |
| 85_138_166_185_666_676 | 91.3 | 97.1 | 90.8 | 91 | 87.5 | 91.3 |
| 85_138_166_177_185_666 | 91.3 | 97.1 | 90.8 | 89.9 | 75 | 91.3 |
| 85_138_166_185_666_667 | 91.6 | 97.1 | 91.1 | 89.8 | 75 | 91.2 |
| 33_85_138_166_185_666 | 91.6 | 97.1 | 91.1 | 91 | 81.2 | 91.9 |

TABLE 8-4

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 109 | 57.6 | 64.7 | 56.9 | 54.8 | 56.2 | 54.7 |
| 33_109 | 83 | 100 | 81.3 | 76.1 | 81.2 | 75.6 |
| 22_109_126 | 85.9 | 94.1 | 85.1 | 81.9 | 75 | 82.6 |
| 33_109_121_667 | 88.7 | 94.1 | 88.2 | 84.5 | 81.2 | 84.8 |
| 109_126_138_166_666 | 91.1 | 97.1 | 90.5 | 90.4 | 81.2 | 91.3 |
| 109_121_126_138_166_666 | 91.6 | 97.1 | 91.1 | 90.4 | 87.5 | 90.7 |
| 1_85_109_138_166_666 | 91.1 | 97.1 | 90.5 | 91 | 81.2 | 91.9 |
| 1_109_121_138_166_666 | 90.8 | 91.2 | 90.8 | 89.9 | 87.5 | 90.1 |

TABLE 8-4-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 109_126_138_166_666_676 | 91.9 | 100 | 91.1 | 90.4 | 81.2 | 91.3 |
| 109_126_138_166_202_666 | 91.1 | 97.1 | 90.5 | 90.4 | 81.2 | 91.3 |

TABLE 8-5

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 121 | 72.3 | 73.5 | 72.1 | 67.6 | 43.8 | 69.8 |
| 2_121 | 81.9 | 91.2 | 81 | 73.9 | 75 | 73.8 |
| 22_121_667 | 86.1 | 94.1 | 85.3 | 79.7 | 87.5 | 78.9 |
| 22_109_121_126 | 89 | 91.2 | 88.8 | 83 | 81.2 | 83.1 |
| 22_32_109_121_666 | 91.4 | 100 | 90.5 | 86.2 | 68.8 | 87.8 |
| 1_121_138_166_666_668 | 90.3 | 91.2 | 90.2 | 89.9 | 75 | 91.3 |
| 1_33_121_138_166_666 | 91.6 | 100 | 90.8 | 89.9 | 87.5 | 90.1 |
| 1_85_121_138_166_666 | 90.6 | 94.1 | 90.2 | 92 | 87.5 | 92.4 |
| 1_121_38_166_179_666 | 90.6 | 94.1 | 90.2 | 91 | 87.5 | 91.3 |
| 1_121_138_166_177_666 | 91.1 | 94.1 | 90.8 | 91 | 87.5 | 91.3 |

TABLE 8-6

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 126 | 73.6 | 76.5 | 73.3 | 66 | 25 | 69.8 |
| 126_138 | 83.5 | 88.2 | 83 | 76.1 | 43.8 | 79.1 |
| 109_126_138 | 88.5 | 94.1 | 87.9 | 79.8 | 68.8 | 80.8 |
| 22_126_166_202 | 89.8 | 100 | 88.8 | 84 | 81.2 | 84.3 |
| 1_126_138_166_666 | 91.1 | 97.1 | 90.5 | 91.5 | 87.5 | 91.9 |
| 32_109_126_138_166_666 | 91.9 | 100 | 91.1 | 92 | 87.5 | 92.4 |
| 1_85_126_138_166_666 | 90.8 | 97.1 | 90.2 | 91 | 81.2 | 91.9 |
| 1_109_126_138_166_666 | 92.7 | 100 | 91.9 | 90.4 | 81.2 | 91.3 |
| 22_109_126_138_166_666 | 91.3 | 100 | 90.5 | 89.9 | 81.2 | 90.7 |
| 109_126_138_157_166_666 | 91.1 | 97.1 | 90.5 | 90.4 | 81.2 | 91.3 |

TABLE 8-7

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 133 | 52.9 | 50 | 53.2 | 54.8 | 56.2 | 54.7 |
| 33_133 | 81.7 | 94.1 | 80.5 | 79.3 | 81.2 | 79.1 |
| 22_126_133 | 86.1 | 94.1 | 85.3 | 83.5 | 93.8 | 82.6 |
| 22_126_133_667 | 89 | 100 | 87.9 | 86.1 | 93.8 | 85.4 |
| 126_133_138_166_666 | 90.8 | 97.1 | 90.2 | 89.4 | 87.5 | 89.5 |
| 126_133_138_166_666_672 | 90.8 | 97.1 | 90.2 | 89.4 | 87.5 | 89.5 |
| 126_133_138_166_666_ | 90.8 | 97.1 | 90.2 | 89.4 | 87.5 | 89.5 |
| 109_126_133_138_166_666 | 91.3 | 97.1 | 90.8 | 89.4 | 81.2 | 90.1 |
| 126_133_138_166_666_673 | 91.1 | 97.1 | 90.5 | 89.4 | 87.5 | 89.5 |
| 126_133_138_166_666_675 | 91.1 | 97.1 | 90.5 | 89.4 | 87.5 | 89.5 |

TABLE 8-8

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 138 | 70.1 | 70.6 | 70 | 68.1 | 68.8 | 68 |
| 33_138 | 80.1 | 94.1 | 78.7 | 77.7 | 75 | 77.9 |
| 138_166_666 | 85.8 | 94.1 | 85 | 92 | 93.8 | 91.9 |
| 138_166_185_666 | 89.5 | 97.1 | 88.8 | 88.8 | 93.8 | 88.4 |
| 85_138_166_185_666 | 91.6 | 97.1 | 91.1 | 90.4 | 75 | 91.9 |
| 1_85_138_166_666_669 | 90.8 | 97.1 | 90.2 | 91 | 81.2 | 91.9 |
| 8_85_138_166_185_666 | 91.6 | 97.1 | 91.1 | 91 | 81.2 | 91.9 |
| 1_35_121_138_166_666 | 91.9 | 97.1 | 91.4 | 90.4 | 87.5 | 90.7 |
| 1_121_126_138_166_666 | 90.8 | 97.1 | 90.2 | 90.4 | 87.5 | 90.7 |
| 1_121_138_166_666_672 | 91.3 | 94.1 | 91.1 | 89.9 | 87.5 | 90.1 |

TABLE 8-9

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 166 | 71.7 | 91.2 | 69.8 | 72.3 | 75 | 72.1 |
| 33_166 | 80.9 | 94.1 | 79.6 | 77.7 | 68.8 | 78.5 |
| 22_126_166 | 86.9 | 100 | 85.6 | 81.9 | 81.2 | 82 |
| 22_121_166_666 | 90.1 | 97.1 | 89.4 | 87.2 | 93.8 | 86.6 |
| 121_138_166_185_666 | 92.1 | 97.1 | 91.6 | 90.4 | 93.8 | 90.1 |
| 1_85_138_166_666_672 | 91.6 | 97.1 | 91.1 | 91.5 | 81.2 | 92.4 |
| 56_85_138_166_185_666 | 91.6 | 97.1 | 91.1 | 89.4 | 75 | 90.7 |
| 1_32_121_138_166_666 | 91.3 | 100 | 90.5 | 91 | 81.2 | 91.9 |
| 1_22_121_138_166_666 | 91.3 | 100 | 90.5 | 89.9 | 87.5 | 90.1 |
| 5_85_138_166_185_666 | 90.8 | 97.1 | 90.2 | 89.4 | 87.5 | 89.5 |

TABLE 8-10

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 666 | 56 | 41.2 | 57.5 | 53.2 | 75 | 51.2 |
| 33_666 | 81.2 | 85.3 | 80.7 | 78.2 | 62.5 | 79.7 |
| 2_32_666 | 85.9 | 97.1 | 84.8 | 81.4 | 68.8 | 82.6 |
| 98_138_166_666 | 89.2 | 91.2 | 89 | 89.9 | 87.5 | 90.1 |
| 98_138_166_666_668 | 91.3 | 91.2 | 91.4 | 91 | 87.5 | 91.3 |
| 1_121_138_157_166_666 | 90.8 | 94.1 | 90.5 | 90.4 | 87.5 | 90.7 |
| 1_85_133_138_166_666 | 92.1 | 97.1 | 91.6 | 91.5 | 81.2 | 92.4 |
| 1_121_138_166_185_666 | 91.3 | 100 | 90.5 | 91 | 87.5 | 91.3 |
| 1_121_138_166_666_667 | 91.1 | 97.1 | 90.5 | 90.4 | 87.5 | 90.6 |
| 85_138_166_185_666 | 91.6 | 97.1 | 91.1 | 90.4 | 75 | 91.9 |

Comparative Example 1

<Esophageal Cancer Discriminant Performance of Existing Tumor Marker in Blood>

The concentrations of the existing esophageal cancer tumor markers CEA and SCC in blood were measured in the training cohort and the validation cohort obtained in the preceding Reference Examples. When the concentrations of these tumor markers in blood are higher than the reference values described in Non-Patent Literature 3 above (CEA: 5 ng/mL, SCC: 1.5 ng/mL), subjects are suspected of having cancer, as a rule. Thus, whether or not the concentrations of CEA and SCC in blood exceeded their reference values was confirmed for each sample, and the results were assessed for the ability of these tumor markers to detect cancer in esophageal cancer patients. The sensitivity of each existing marker in the training cohort and the validation cohort was calculated. The results are shown in Table 5. The sensitivity of CEA was as low as 12.1% in the training cohort, and was as low as 18.8% in the validation cohort, whereas the sensitivity of SCC remained at 36.4% in the training cohort and 37.5% in the validation cohort, demonstrating that neither of the markers are useful in the detection of esophageal cancer (Tables 5-1 and 5-2).

On the other hand, as shown above in Tables 3 and 6 of Examples 1 and 2, it can be concluded that in all of the polynucleotides consisting of the nucleotide sequences represented by SEQ ID NOs: 1 to 189, combinations of 1 or 2 polynucleotides exhibiting sensitivity beyond the existing esophageal cancer markers are presented and thus such polynucleotides serve as excellent diagnosis markers.

As shown in these Examples and Comparative Example, the kit, etc., and the method of the present invention can detect esophageal cancer with higher sensitivity than the existing tumor markers and therefore permit early detection and treatment of esophageal cancer. As a result, survival rates can be improved, and a therapeutic option of endoscopic therapy or photo dynamic therapy, which places less burden on patients, can also be applied.

INDUSTRIAL APPLICABILITY

According to the present invention, esophageal cancer can be effectively detected by a simple and inexpensive method. This enables early detection, diagnosis and treatment of esophageal cancer. The method of the present invention can detect esophageal cancer with limited invasiveness using the blood of a patient and therefore allows esophageal cancer to be detected conveniently and rapidly.

All publications, patents, and patent applications cited herein are incorporated herein by reference in their entirety.

The invention claimed is:

1. A method for detecting esophageal cancer in a human subject, comprising measuring expression level of hsa-miR-6857-5p in a blood, serum or plasma sample of the subject, comparing the measured expression level of hsa-miR-6857-5p to a control expression level for a healthy subject;
detecting an increased level of hsa-miR-6857-5p in the sample from the subject as compared to the control expression level;
wherein the increased level of hsa-miR-6857-5p indicates that the subject has esophageal cancer; and
wherein the method further comprises treating the subject for the esophageal cancer or performing a diagnostic procedure on the subject with the esophageal cancer;
wherein the treating comprises surgery, radiotherapy, chemotherapy, or a combination thereof; and
wherein the diagnostic procedure comprises esophagography, endoscopy, CT scan, MRI scan, endosonography, or ultrasonography.

2. The method according to claim 1, comprising performing the diagnostic procedure on the subject.

3. The method according to claim 1, wherein the expression level of hsa-miR-6857-5p in the is measured by using a device comprising a nucleic acid(s) that specifically binds to hsa-miR-6857-5p.

4. The method according to claim 3, wherein the device further comprises at least one nucleic acid capable of specifically binding to at least one polynucleotide selected from the group consisting of other esophageal cancer markers: miR-1247-3p, miR-6875-5p, miR-6726-5p, miR-3188, miR-8069, miR-4257, miR-1343-3p, miR-7108-5p, miR-6825-5p, miR-7641, miR-3185, miR-4746-3p, miR-6791-5p, miR-6893-5p, miR-4433b-3p, miR-3135b, miR-6781-5p, miR-1908-5p, miR-4792, miR-7845-5p, miR-4417, miR-3184-5p, miR-1225-5p, miR-1231, miR-1225-3p, miR-150-3p, miR-4433-3p, miR-6125, miR-4513, miR-6787-5p, miR-6784-5p, miR-615-5p, miR-6765-3p, miR-5572, miR-6842-5p, miR-8063, miR-6780b-5p, miR-187-5p, miR-128-1-5p, miR-6729-5p, miR-6741-5p, miR-6757-5p, miR-7110-5p, miR-7975, miR-1233-5p, miR-6845-5p, miR-3937, miR-4467, miR-7109-5p, miR-6088, miR-6782-5p, miR-5195-3p, miR-4454, miR-6724-5p, miR-8072, miR-4516, miR-6756-5p, miR-4665-3p, miR-6826-5p, miR-6820-5p, miR-6887-5p, miR-3679-5p, miR-7847-3p, miR-6721-5p, miR-3622a-5p, miR-939-5p, miR-602, miR-7977, miR-6749-5p, miR-1914-3p, miR-4651, miR-4695-5p, miR-6848-5p, miR-1228-5p, miR-642b-3p, miR-6746-5p, miR-3620-5p, miR-3131, miR-6732-5p, miR-7113-3p, miR-23a-3p, miR-3154, miR-4723-5p, miR-3663-3p, miR-4734, miR-6816-5p, miR-4442, miR-4476, miR-423-5p, miR-1249, miR-6515-3p, miR-887-3p, miR-4741, miR-6766-3p, miR-4673, miR-6779-5p, miR-4706, miR-1268b, miR-4632-5p, miR-3197, miR-6798-5p, miR-711, miR-6840-3p, miR-6763-5p, miR-6727-5p, miR-371a-5p, miR-6824-5p, miR-4648, miR-1227-5p, miR-564, miR-3679-3p, miR-2861, miR-6737-5p, miR-4725-3p, miR-6716-5p, miR-4675, miR-1915-3p, miR-671-5p, miR-3656, miR-6722-3p, miR-4707-5p, miR-4449, miR-1202, miR-4649-5p, miR-744-5p, miR-642a-3p, miR-451a, miR-6870-5p, miR-4443, miR-6808-5p, miR-4728-5p, miR-937-5p, miR-135a-3p, miR-663b, miR-1343-5p, miR-6822-5p, miR-6803-5p, miR-6805-3p, miR-128-2-5p, miR-4640-5p, miR-1469, miR-92a-2-5p, miR-3940-5p, miR-4281, miR-1260b, miR-4758-5p, miR-1915-5p, miR-5001-5p, miR-4286, miR-6126, miR-6789-5p, miR-4459, miR-1268a, miR-6752-5p, miR-6131, miR-6800-5p, miR-4532, miR-6872-3p, miR-718, miR-6769a-5p, miR-4707-3p, miR-6765-5p, miR-4739, miR-4525, miR-4270, miR-4534, miR-6785-5p, miR-6850-5p, miR-4697-5p, miR-1260a, miR-4486, miR-6880-5p, miR-6802-5p, miR-6861-5p, miR-92b-5p, miR-1238-5p, miR-6851-5p, miR-7704, miR-149-3p, miR-4689, miR-4688, miR-125a-3p, miR-23b-3p, miR-614, miR-1913, miR-16-5p, miR-6717-5p, miR-3648, miR-3162-5p, miR-1909-3p, miR-8073, miR-6769b-5p, miR-6836-3p, miR-4484, miR-6819-5p, and miR-6794-5p, and/or miR-575, miR-24-3p, miR-675-5p, miR-486-3p, miR-6777-5p, miR-4497, miR-296-3p, miR-6738-5p, miR-4731-5p, miR-6889-5p, miR-6786-5p, miR-92a-3p, miR-4294, miR-4763-3p, miR-6076, miR-663a, miR-760, miR-4667-5p, miR-6090, miR-4730, miR-7106-5p, miR-3196, miR-5698, miR-6087, miR-4665-5p, miR-8059, and miR-6879-5p.

5. The method according to claim 1, wherein the expression level of hsa-miR-6857-5p in the sample is measured by using a kit comprising a nucleic acid(s) that specifically binds to hsa-miR-6857-5p.

6. The method according to claim 5, wherein the kit further comprises at least one nucleic acid capable of specifically binding to at least one polynucleotide selected from the group consisting of other esophageal cancer markers: miR-1247-3p, miR-6875-5p, miR-6726-5p, miR-3188, miR-8069, miR-4257, miR-1343-3p, miR-7108-5p, miR-6825-5p, miR-7641, miR-3185, miR-4746-3p, miR-6791-5p, miR-6893-5p, miR-4433b-3p, miR-3135b, miR-6781-5p, miR-1908-5p, miR-4792, miR-7845-5p, miR-4417, miR-3184-5p, miR-1225-5p, miR-1231, miR-1225-3p, miR-150-3p, miR-4433-3p, miR-6125, miR-4513, miR-6787-5p, miR-6784-5p, miR-615-5p, miR-6765-3p, miR-5572, miR-6842-5p, miR-8063, miR-6780b-5p, miR-187-5p, miR-128-1-5p, miR-6729-5p, miR-6741-5p, miR-6757-5p, miR-7110-5p, miR-7975, miR-1233-5p, miR-6845-5p, miR-3937, miR-4467, miR-7109-5p, miR-6088, miR-6782-

5p, miR-5195-3p, miR-4454, miR-6724-5p, miR-8072, miR-4516, miR-6756-5p, miR-4665-3p, miR-6826-5p, miR-6820-5p, miR-6887-5p, miR-3679-5p, miR-7847-3p, miR-6721-5p, miR-3622a-5p, miR-939-5p, miR-602, miR-7977, miR-6749-5p, miR-1914-3p, miR-4651, miR-4695-5p, miR-6848-5p, miR-1228-3p, miR-642b-3p, miR-6746-5p, miR-3620-5p, miR-3131, miR-6732-5p, miR-7113-3p, miR-23a-3p, miR-3154, miR-4723-5p, miR-3663-3p, miR-4734, miR-6816-5p, miR-4442, miR-4476, miR-423-5p, miR-1249, miR-6515-3p, miR-887-3p, miR-4741, miR-6766-3p, miR-4673, miR-6779-5p, miR-4706, miR-1268b, miR-4632-5p, miR-3197, miR-6798-5p, miR-711, miR-6840-3p, miR-6763-5p, miR-6727-5p, miR-371a-5p, miR-6824-5p, miR-4648, miR-1227-5p, miR-564, miR-3679-3p, miR-2861, miR-6737-5p, miR-4725-3p, miR-6716-5p, miR-4675, miR-1915-3p, miR-671-5p, miR-3656, miR-6722-3p, miR-4707-5p, miR-4449, miR-1202, miR-4649-5p, miR-744-5p, miR-642a-3p, miR-451a, miR-6870-5p, miR-4443, miR-6808-5p, miR-4728-5p, miR-937-5p, miR-135a-3p, miR-663b, miR-1343-5p, miR-6822-5p, miR-6803-5p, miR-6805-3p, miR-128-2-5p, miR-4640-5p, miR-1469, miR-92a-2-5p, miR-3940-5p, miR-4281, miR-1260b, miR-4758-5p, miR-1915-5p, miR-5001-5p, miR-4286, miR-6126, miR-6789-5p, miR-4459, miR-1268a, miR-6752-5p, miR-6131, miR-6800-5p, miR-4532, miR-6872-3p, miR-718, miR-6769a-5p, miR-4707-3p, miR-6765-5p, miR-4739, miR-4525, miR-4270, miR-4534, miR-6785-5p, miR-6850-5p, miR-4697-5p, miR-1260a, miR-4486, miR-6880-5p, miR-6802-5p, miR-6861-5p, miR-92b-5p, miR-1238-5p, miR-6851-5p, miR-7704, miR-149-3p, miR-4689, miR-4688, miR-125a-3p, miR-23b-3p, miR-614, miR-1913, miR-16-5p, miR-6717-5p, miR-3648, miR-3162-5p, miR-1909-3p, miR-8073, miR-6769b-5p, miR-6836-3p, miR-4484, miR-6819-5p, and miR-6794-5p, and/or miR-575, miR-24-3p, miR-675-5p, miR-486-3p, miR-6777-5p, miR-4497, miR-296-3p, miR-6738-5p, miR-4731-5p, miR-6889-5p, miR-6786-5p, miR-92a-3p, miR-4294, miR-4763-3p, miR-6076, miR-663a, miR-760, miR-4667-5p, miR-6090, miR-4730, miR-7106-5p, miR-3196, miR-5698, miR-6087, miR-4665-5p, miR-8059, and miR-6879-5p.

\* \* \* \* \*

SEQUENCE LISTING

```
<160> NUMBER OF SEQ ID NOS: 700

<210> SEQ ID NO 1
<211> LENGTH: 21
<212> TYPE: RNA
<213> ORGANISM: Homo sapiens

<400> SEQUENCE: 1
gcugggaagg caaagggacg u                                                 21

<210> SEQ ID NO 2
<211> LENGTH: 24
<212> TYPE: RNA
<213> ORGANISM: Homo sapiens

<400> SEQUENCE: 2
ccccgggaac gucgagacug gagc                                              24

<210> SEQ ID NO 3
<211> LENGTH: 21
<212> TYPE: RNA
<213> ORGANISM: Homo sapiens

<400> SEQUENCE: 3
ugagggaccc aggacaggag a                                                 21

<210> SEQ ID NO 4
<211> LENGTH: 22
<212> TYPE: RNA
<213> ORGANISM: Homo sapiens

<400> SEQUENCE: 4
uuggggauug ggucaggcca gu                                                22

<210> SEQ ID NO 5
<211> LENGTH: 21
<212> TYPE: RNA
<213> ORGANISM: Homo sapiens

<400> SEQUENCE: 5
cgggagcugg ggucugcagg u                                                 21

<210> SEQ ID NO 6
<211> LENGTH: 23
<212> TYPE: RNA
<213> ORGANISM: Homo sapiens

<400> SEQUENCE: 6
agaggcuuug ugcggauacg ggg                                               23
```

```
<210> SEQ ID NO 7
<211> LENGTH: 23
<212> TYPE: RNA
<213> ORGANISM: Homo sapiens

<400> SEQUENCE: 7
ggaugguugg gggcggucgg cgu                                              23

<210> SEQ ID NO 8
<211> LENGTH: 18
<212> TYPE: RNA
<213> ORGANISM: Homo sapiens

<400> SEQUENCE: 8
ccagaggugg ggacugag                                                    18

<210> SEQ ID NO 9
<211> LENGTH: 22
<212> TYPE: RNA
<213> ORGANISM: Homo sapiens

<400> SEQUENCE: 9
cuccuggggc ccgcacucuc gc                                               22

<210> SEQ ID NO 10
<211> LENGTH: 21
<212> TYPE: RNA
<213> ORGANISM: Homo sapiens

<400> SEQUENCE: 10
guguggccgg caggcgggug g                                                21

<210> SEQ ID NO 11
<211> LENGTH: 22
<212> TYPE: RNA
<213> ORGANISM: Homo sapiens

<400> SEQUENCE: 11
uggggaggug uggagucagc au                                               22

<210> SEQ ID NO 12
<211> LENGTH: 19
<212> TYPE: RNA
<213> ORGANISM: Homo sapiens

<400> SEQUENCE: 12
uugaucucgg aagcuaagc                                                   19

<210> SEQ ID NO 13
<211> LENGTH: 23
<212> TYPE: RNA
<213> ORGANISM: Homo sapiens

<400> SEQUENCE: 13
agaagaaggc ggucggucug cgg                                              23

<210> SEQ ID NO 14
<211> LENGTH: 21
<212> TYPE: RNA
<213> ORGANISM: Homo sapiens

<400> SEQUENCE: 14
agcggugcuc cugcgggccg a                                                21
```

```
<210> SEQ ID NO 15
<211> LENGTH: 22
<212> TYPE: RNA
<213> ORGANISM: Homo sapiens

<400> SEQUENCE: 15 ccccugggc ugggcaggcg ga                                            22

<210> SEQ ID NO 16
<211> LENGTH: 21
<212> TYPE: RNA
<213> ORGANISM: Homo sapiens

<400> SEQUENCE: 16
caggcaggug uaggguggag c                                            21

<210> SEQ ID NO 17
<211> LENGTH: 21
<212> TYPE: RNA
<213> ORGANISM: Homo sapiens

<400> SEQUENCE: 17 caggagugggg ggugggacg u                                            21

<210> SEQ ID NO 18
<211> LENGTH: 22
<212> TYPE: RNA
<213> ORGANISM: Homo sapiens

<400> SEQUENCE: 18
ggcuggagcg agugcagugg ug                                           22

<210> SEQ ID NO 19
<211> LENGTH: 21
<212> TYPE: RNA
<213> ORGANISM: Homo sapiens

<400> SEQUENCE: 19
cgggccggag gucaagggcg u                                            21

<210> SEQ ID NO 20
<211> LENGTH: 21
<212> TYPE: RNA
<213> ORGANISM: Homo sapiens

<400> SEQUENCE: 20
cggcggggac ggcgauuggu c                                            21

<210> SEQ ID NO 21
<211> LENGTH: 18
<212> TYPE: RNA
<213> ORGANISM: Homo sapiens

<400> SEQUENCE: 21
cggugagcgc ucgcuggc                                                18

<210> SEQ ID NO 22
<211> LENGTH: 21
<212> TYPE: RNA
<213> ORGANISM: Homo sapiens

<400> SEQUENCE: 22
aagggacagg gagggucgug g                                            21
```

```
<210> SEQ ID NO 23
<211> LENGTH: 18
<212> TYPE: RNA
<213> ORGANISM: Homo sapiens

<400> SEQUENCE: 23 gguggcuuc ccggaggg                                                    18

<210> SEQ ID NO 24
<211> LENGTH: 24
<212> TYPE: RNA
<213> ORGANISM: Homo sapiens

<400> SEQUENCE: 24
ugaggggccu cagaccgagc uuuu                                            24

<210> SEQ ID NO 25
<211> LENGTH: 22
<212> TYPE: RNA
<213> ORGANISM: Homo sapiens

<400> SEQUENCE: 25
guggguacgg cccagugggg gg                                              22

<210> SEQ ID NO 26
<211> LENGTH: 20
<212> TYPE: RNA
<213> ORGANISM: Homo sapiens

<400> SEQUENCE: 26
gugucugggc ggacagcugc                                                 20

<210> SEQ ID NO 27
<211> LENGTH: 22
<212> TYPE: RNA
<213> ORGANISM: Homo sapiens

<400> SEQUENCE: 27 ugagcccug ugccgccccc ag                                               22

<210> SEQ ID NO 28
<211> LENGTH: 22
<212> TYPE: RNA
<213> ORGANISM: Homo sapiens

<400> SEQUENCE: 28
cugguacagg ccugggggac ag                                              22

<210> SEQ ID NO 29
<211> LENGTH: 21
<212> TYPE: RNA
<213> ORGANISM: Homo sapiens

<400> SEQUENCE: 29
acaggagugg ggugggaca u                                                21

<210> SEQ ID NO 30
<211> LENGTH: 20
<212> TYPE: RNA
<213> ORGANISM: Homo sapiens

<400> SEQUENCE: 30
```

```
gcggaaggcg gagcggcgga                                                     20

<210> SEQ ID NO 31
<211> LENGTH: 22
<212> TYPE: RNA
<213> ORGANISM: Homo sapiens

<400> SEQUENCE: 31
agacugacgg cuggaggccc au                                                  22

<210> SEQ ID NO 32
<211> LENGTH: 22
<212> TYPE: RNA
<213> ORGANISM: Homo sapiens

<400> SEQUENCE: 32 uggcggggu agagcuggcu gc                                                   22

<210> SEQ ID NO 33
<211> LENGTH: 20
<212> TYPE: RNA
<213> ORGANISM: Homo sapiens

<400> SEQUENCE: 33
gccggggcuu ugggugaggg                                                     20

<210> SEQ ID NO 34
<211> LENGTH: 22
<212> TYPE: RNA
<213> ORGANISM: Homo sapiens

<400> SEQUENCE: 34
gggggucccc ggugcucgga uc                                                  22

<210> SEQ ID NO 35
<211> LENGTH: 21
<212> TYPE: RNA
<213> ORGANISM: Homo sapiens

<400> SEQUENCE: 35
ucaccuggcu ggcccgccca g                                                   21

<210> SEQ ID NO 36
<211> LENGTH: 21
<212> TYPE: RNA
<213> ORGANISM: Homo sapiens

<400> SEQUENCE: 36 guugggugc aggggucugc u                                                    21

<210> SEQ ID NO 37
<211> LENGTH: 22
<212> TYPE: RNA
<213> ORGANISM: Homo sapiens

<400> SEQUENCE: 37
uggggguggu cucuagccaa gg                                                  22

<210> SEQ ID NO 38
<211> LENGTH: 22
<212> TYPE: RNA
<213> ORGANISM: Homo sapiens

<400> SEQUENCE: 38
```

```
ucaaaaucag gagucggggc uu                                               22

<210> SEQ ID NO 39
<211> LENGTH: 23
<212> TYPE: RNA
<213> ORGANISM: Homo sapiens

<400> SEQUENCE: 39
uggggaaggc uuggcaggga aga                                              23

<210> SEQ ID NO 40
<211> LENGTH: 22
<212> TYPE: RNA
<213> ORGANISM: Homo sapiens

<400> SEQUENCE: 40
ggcuacaaca caggacccgg gc                                               22

<210> SEQ ID NO 41
<211> LENGTH: 23
<212> TYPE: RNA
<213> ORGANISM: Homo sapiens

<400> SEQUENCE: 41
cggggccgua gcacugucug aga                                              23

<210> SEQ ID NO 42
<211> LENGTH: 22
<212> TYPE: RNA
<213> ORGANISM: Homo sapiens

<400> SEQUENCE: 42
ugggcgaggg cggcugagcg gc                                               22

<210> SEQ ID NO 43
<211> LENGTH: 22
<212> TYPE: RNA
<213> ORGANISM: Homo sapiens

<400> SEQUENCE: 43
gugggugcug gugggagccg ug                                               22

<210> SEQ ID NO 44
<211> LENGTH: 22
<212> TYPE: RNA
<213> ORGANISM: Homo sapiens

<400> SEQUENCE: 44
uagggauggg aggccaggau ga                                               22

<210> SEQ ID NO 45
<211> LENGTH: 21
<212> TYPE: RNA
<213> ORGANISM: Homo sapiens

<400> SEQUENCE: 45
uggggguguG gggagagaga g                                                21

<210> SEQ ID NO 46
<211> LENGTH: 18
<212> TYPE: RNA
<213> ORGANISM: Homo sapiens
```

```
<400> SEQUENCE: 46
auccuaguca cggcacca                                              18

<210> SEQ ID NO 47
<211> LENGTH: 22
<212> TYPE: RNA
<213> ORGANISM: Homo sapiens

<400> SEQUENCE: 47 aguggaggc cagggcacgg ca                                          22

<210> SEQ ID NO 48
<211> LENGTH: 19
<212> TYPE: RNA
<213> ORGANISM: Homo sapiens

<400> SEQUENCE: 48
cggggccaga gcagagagc                                             19

<210> SEQ ID NO 49
<211> LENGTH: 23
<212> TYPE: RNA
<213> ORGANISM: Homo sapiens

<400> SEQUENCE: 49
acaggcggcu guagcaaugg ggg                                        23

<210> SEQ ID NO 50
<211> LENGTH: 22
<212> TYPE: RNA
<213> ORGANISM: Homo sapiens

<400> SEQUENCE: 50
uggcggcggu aguuaugggc uu                                         22

<210> SEQ ID NO 51
<211> LENGTH: 21
<212> TYPE: RNA
<213> ORGANISM: Homo sapiens

<400> SEQUENCE: 51
cuggggggag gagacccugc u                                          21

<210> SEQ ID NO 52
<211> LENGTH: 20
<212> TYPE: RNA
<213> ORGANISM: Homo sapiens

<400> SEQUENCE: 52
agagaugaag cggggggggcg                                           20

<210> SEQ ID NO 53
<211> LENGTH: 25
<212> TYPE: RNA
<213> ORGANISM: Homo sapiens

<400> SEQUENCE: 53 uaggggugggg ggaauucagg ggugu                                     25

<210> SEQ ID NO 54
<211> LENGTH: 21
<212> TYPE: RNA
<213> ORGANISM: Homo sapiens
```

```
<400> SEQUENCE: 54
auccaguucu cugaggggc u                                              21

<210> SEQ ID NO 55
<211> LENGTH: 20
<212> TYPE: RNA
<213> ORGANISM: Homo sapiens

<400> SEQUENCE: 55
ggauccgagu cacggcacca                                               20

<210> SEQ ID NO 56
<211> LENGTH: 23
<212> TYPE: RNA
<213> ORGANISM: Homo sapiens

<400> SEQUENCE: 56
cugggcccgc ggcgggcgug ggg                                           23

<210> SEQ ID NO 57
<211> LENGTH: 20
<212> TYPE: RNA
<213> ORGANISM: Homo sapiens

<400> SEQUENCE: 57
ggcggcgggg agguaggcag                                               20

<210> SEQ ID NO 58
<211> LENGTH: 17
<212> TYPE: RNA
<213> ORGANISM: Homo sapiens

<400> SEQUENCE: 58
gggagaaggg ucggggc                                                  17

<210> SEQ ID NO 59
<211> LENGTH: 23
<212> TYPE: RNA
<213> ORGANISM: Homo sapiens

<400> SEQUENCE: 59 aggugggc uggagguggg gcu                                             23

<210> SEQ ID NO 60
<211> LENGTH: 26
<212> TYPE: RNA
<213> ORGANISM: Homo sapiens

<400> SEQUENCE: 60
cucggccgcg gcgcguagcc cccgcc                                        26

<210> SEQ ID NO 61
<211> LENGTH: 23
<212> TYPE: RNA
<213> ORGANISM: Homo sapiens

<400> SEQUENCE: 61
ucaauaggaa agagguggga ccu                                           23

<210> SEQ ID NO 62
<211> LENGTH: 19
<212> TYPE: RNA
```

```
<213> ORGANISM: Homo sapiens

<400> SEQUENCE: 62
ugcggcagag cugggguca                                                  19

<210> SEQ ID NO 63
<211> LENGTH: 23
<212> TYPE: RNA
<213> ORGANISM: Homo sapiens

<400> SEQUENCE: 63 ugggggaca gauggagagg aca                                              23

<210> SEQ ID NO 64
<211> LENGTH: 23
<212> TYPE: RNA
<213> ORGANISM: Homo sapiens

<400> SEQUENCE: 64
ugaggauaug gcagggaagg gga                                             23

<210> SEQ ID NO 65
<211> LENGTH: 21
<212> TYPE: RNA
<213> ORGANISM: Homo sapiens

<400> SEQUENCE: 65
cguggaggac gaggaggagg c                                               21

<210> SEQ ID NO 66
<211> LENGTH: 23
<212> TYPE: RNA
<213> ORGANISM: Homo sapiens

<400> SEQUENCE: 66
ugggcagggg cuuauuguag gag                                             23

<210> SEQ ID NO 67
<211> LENGTH: 22
<212> TYPE: RNA
<213> ORGANISM: Homo sapiens

<400> SEQUENCE: 67
caggcacggg agcucaggug ag                                              22

<210> SEQ ID NO 68
<211> LENGTH: 24
<212> TYPE: RNA
<213> ORGANISM: Homo sapiens

<400> SEQUENCE: 68
uggggagcug aggcucuggg ggug                                            24

<210> SEQ ID NO 69
<211> LENGTH: 23
<212> TYPE: RNA
<213> ORGANISM: Homo sapiens

<400> SEQUENCE: 69
gacacgggcg acagcugcgg ccc                                             23

<210> SEQ ID NO 70
<211> LENGTH: 18
```

```
<212> TYPE: RNA
<213> ORGANISM: Homo sapiens

<400> SEQUENCE: 70
uucccagcca acgcacca                                               18

<210> SEQ ID NO 71
<211> LENGTH: 22
<212> TYPE: RNA
<213> ORGANISM: Homo sapiens

<400> SEQUENCE: 71
ucgggccugg gguuggggga gc                                          22

<210> SEQ ID NO 72
<211> LENGTH: 22
<212> TYPE: RNA
<213> ORGANISM: Homo sapiens

<400> SEQUENCE: 72
ggaggggucc cgcacuggga gg                                          22

<210> SEQ ID NO 73
<211> LENGTH: 20
<212> TYPE: RNA
<213> ORGANISM: Homo sapiens

<400> SEQUENCE: 73
cggggugggu gaggucgggc                                             20

<210> SEQ ID NO 74
<211> LENGTH: 22
<212> TYPE: RNA
<213> ORGANISM: Homo sapiens

<400> SEQUENCE: 74
caggaggcag ugggcgagca gg                                          22

<210> SEQ ID NO 75
<211> LENGTH: 23
<212> TYPE: RNA
<213> ORGANISM: Homo sapiens

<400> SEQUENCE: 75 uggggcugg gaugggccau ggu                                          23

<210> SEQ ID NO 76
<211> LENGTH: 20
<212> TYPE: RNA
<213> ORGANISM: Homo sapiens

<400> SEQUENCE: 76
ucacaccugc cucgccccccc                                            20

<210> SEQ ID NO 77
<211> LENGTH: 22
<212> TYPE: RNA
<213> ORGANISM: Homo sapiens

<400> SEQUENCE: 77
agacacauuu ggagagggac cc                                          22

<210> SEQ ID NO 78
```

-continued

```
<211> LENGTH: 22
<212> TYPE: RNA
<213> ORGANISM: Homo sapiens

<400> SEQUENCE: 78
ccgggagaag gagguggccu gg                                              22

<210> SEQ ID NO 79
<211> LENGTH: 22
<212> TYPE: RNA
<213> ORGANISM: Homo sapiens

<400> SEQUENCE: 79
gugggcuggg cugggcuggg cc                                              22

<210> SEQ ID NO 80
<211> LENGTH: 23
<212> TYPE: RNA
<213> ORGANISM: Homo sapiens

<400> SEQUENCE: 80
ucgaggacug guggaagggc cuu                                             23

<210> SEQ ID NO 81
<211> LENGTH: 20
<212> TYPE: RNA
<213> ORGANISM: Homo sapiens

<400> SEQUENCE: 81 uaggggugg caggcuggcc                                                  20

<210> SEQ ID NO 82
<211> LENGTH: 23
<212> TYPE: RNA
<213> ORGANISM: Homo sapiens

<400> SEQUENCE: 82
ccucccugcc cgccucucug cag                                             23

<210> SEQ ID NO 83
<211> LENGTH: 21
<212> TYPE: RNA
<213> ORGANISM: Homo sapiens

<400> SEQUENCE: 83
aucacauugc cagggauuuc c                                               21

<210> SEQ ID NO 84
<211> LENGTH: 22
<212> TYPE: RNA
<213> ORGANISM: Homo sapiens

<400> SEQUENCE: 84
cagaagggga guugggagca ga                                              22

<210> SEQ ID NO 85
<211> LENGTH: 24
<212> TYPE: RNA
<213> ORGANISM: Homo sapiens

<400> SEQUENCE: 85 uggggagcc augagauaag agca                                             24
```

```
<210> SEQ ID NO 86
<211> LENGTH: 23
<212> TYPE: RNA
<213> ORGANISM: Homo sapiens

<400> SEQUENCE: 86
ugagcaccac acaggccggg cgc                                               23

<210> SEQ ID NO 87
<211> LENGTH: 22
<212> TYPE: RNA
<213> ORGANISM: Homo sapiens

<400> SEQUENCE: 87
gcugcgggcu gcggucaggg cg                                                22

<210> SEQ ID NO 88
<211> LENGTH: 21
<212> TYPE: RNA
<213> ORGANISM: Homo sapiens

<400> SEQUENCE: 88
uggggcgggg caggucccug c                                                 21

<210> SEQ ID NO 89
<211> LENGTH: 17
<212> TYPE: RNA
<213> ORGANISM: Homo sapiens

<400> SEQUENCE: 89
gccggacaag agggagg                                                      17

<210> SEQ ID NO 90
<211> LENGTH: 22
<212> TYPE: RNA
<213> ORGANISM: Homo sapiens

<400> SEQUENCE: 90
caggaaggau uuagggacag gc                                                22

<210> SEQ ID NO 91
<211> LENGTH: 23
<212> TYPE: RNA
<213> ORGANISM: Homo sapiens

<400> SEQUENCE: 91
ugaggggcag agagcgagac uuu                                               23

<210> SEQ ID NO 92
<211> LENGTH: 22
<212> TYPE: RNA
<213> ORGANISM: Homo sapiens

<400> SEQUENCE: 92
acgcccuucc cccccuucuu ca                                                22

<210> SEQ ID NO 93
<211> LENGTH: 20
<212> TYPE: RNA
<213> ORGANISM: Homo sapiens

<400> SEQUENCE: 93
ucucuucauc uaccccccag                                                   20
```

```
<210> SEQ ID NO 94
<211> LENGTH: 22
<212> TYPE: RNA
<213> ORGANISM: Homo sapiens

<400> SEQUENCE: 94
gugaacgggc gccaucccga gg                                              22

<210> SEQ ID NO 95
<211> LENGTH: 23
<212> TYPE: RNA
<213> ORGANISM: Homo sapiens

<400> SEQUENCE: 95
cgggcugucc ggaggggucg gcu                                             23

<210> SEQ ID NO 96
<211> LENGTH: 22
<212> TYPE: RNA
<213> ORGANISM: Homo sapiens

<400> SEQUENCE: 96
ugauugucuu cccccacccu ca                                              22

<210> SEQ ID NO 97
<211> LENGTH: 22
<212> TYPE: RNA
<213> ORGANISM: Homo sapiens

<400> SEQUENCE: 97
uccaggcagg agccggacug ga                                              22

<210> SEQ ID NO 98
<211> LENGTH: 21
<212> TYPE: RNA
<213> ORGANISM: Homo sapiens

<400> SEQUENCE: 98 cuggagggg cuggguuugg c                                                21

<210> SEQ ID NO 99
<211> LENGTH: 25
<212> TYPE: RNA
<213> ORGANISM: Homo sapiens

<400> SEQUENCE: 99
agcggggagg aagugggcgc ugcuu                                           25

<210> SEQ ID NO 100
<211> LENGTH: 20
<212> TYPE: RNA
<213> ORGANISM: Homo sapiens

<400> SEQUENCE: 100
cgggcguggu gguggggug                                                  20

<210> SEQ ID NO 101
<211> LENGTH: 23
<212> TYPE: RNA
<213> ORGANISM: Homo sapiens

<400> SEQUENCE: 101
gagggcagcg uggguguggc gga                                             23
```

```
<210> SEQ ID NO 102
<211> LENGTH: 23
<212> TYPE: RNA
<213> ORGANISM: Homo sapiens

<400> SEQUENCE: 102
ggaggcgcag gcucggaaag gcg                                          23

<210> SEQ ID NO 103
<211> LENGTH: 23
<212> TYPE: RNA
<213> ORGANISM: Homo sapiens

<400> SEQUENCE: 103 ccaggggau gggcgagcuu ggg                                           23

<210> SEQ ID NO 104
<211> LENGTH: 22
<212> TYPE: RNA
<213> ORGANISM: Homo sapiens

<400> SEQUENCE: 104
gggacccagg gagagacgua ag                                           22

<210> SEQ ID NO 105
<211> LENGTH: 22
<212> TYPE: RNA
<213> ORGANISM: Homo sapiens

<400> SEQUENCE: 105
gcccaggacu uugugcgggg ug                                           22

<210> SEQ ID NO 106
<211> LENGTH: 19
<212> TYPE: RNA
<213> ORGANISM: Homo sapiens

<400> SEQUENCE: 106
cuggggagug gcuggggag                                               19

<210> SEQ ID NO 107
<211> LENGTH: 23
<212> TYPE: RNA
<213> ORGANISM: Homo sapiens

<400> SEQUENCE: 107
cucggggcag gcggcuggga gcg                                          23

<210> SEQ ID NO 108
<211> LENGTH: 20
<212> TYPE: RNA
<213> ORGANISM: Homo sapiens

<400> SEQUENCE: 108
acucaaacug uggggcacu                                               20

<210> SEQ ID NO 109
<211> LENGTH: 22
<212> TYPE: RNA
<213> ORGANISM: Homo sapiens

<400> SEQUENCE: 109
```

-continued guaggggagg uugggccagg ga                                        22

<210> SEQ ID NO 110
<211> LENGTH: 20
<212> TYPE: RNA
<213> ORGANISM: Homo sapiens

<400> SEQUENCE: 110
ugugggacug caaaugggag                                           20

<210> SEQ ID NO 111
<211> LENGTH: 17
<212> TYPE: RNA
<213> ORGANISM: Homo sapiens

<400> SEQUENCE: 111 gugggggccag gcggugg                                             17

<210> SEQ ID NO 112
<211> LENGTH: 19
<212> TYPE: RNA
<213> ORGANISM: Homo sapiens

<400> SEQUENCE: 112
aggcacggug ucagcaggc                                            19

<210> SEQ ID NO 113
<211> LENGTH: 22
<212> TYPE: RNA
<213> ORGANISM: Homo sapiens

<400> SEQUENCE: 113
cuucccccca guaaucuuca uc                                        22

<210> SEQ ID NO 114
<211> LENGTH: 19
<212> TYPE: RNA
<213> ORGANISM: Homo sapiens

<400> SEQUENCE: 114
ggggccuggc gguggggcgg                                           19

<210> SEQ ID NO 115
<211> LENGTH: 21
<212> TYPE: RNA
<213> ORGANISM: Homo sapiens

<400> SEQUENCE: 115
uugggguggu cggcccugga g                                         21

<210> SEQ ID NO 116
<211> LENGTH: 19
<212> TYPE: RNA
<213> ORGANISM: Homo sapiens

<400> SEQUENCE: 116
gagccaguug gacaggagc                                            19

<210> SEQ ID NO 117
<211> LENGTH: 22
<212> TYPE: RNA
<213> ORGANISM: Homo sapiens

<400> SEQUENCE: 117 ugggggaaggc gucagugucg gg				22

<210> SEQ ID NO 118
<211> LENGTH: 20
<212> TYPE: RNA
<213> ORGANISM: Homo sapiens

<400> SEQUENCE: 118 ugggaaugggg gguaagggcc				20

<210> SEQ ID NO 119
<211> LENGTH: 22
<212> TYPE: RNA
<213> ORGANISM: Homo sapiens

<400> SEQUENCE: 119
ggggcuguga uugaccagca gg			22

<210> SEQ ID NO 120
<211> LENGTH: 20
<212> TYPE: RNA
<213> ORGANISM: Homo sapiens

<400> SEQUENCE: 120
ccccagggcg acgcggcggg				20

<210> SEQ ID NO 121
<211> LENGTH: 23
<212> TYPE: RNA
<213> ORGANISM: Homo sapiens

<400> SEQUENCE: 121
aggaagcccu ggaggggcug gag			23

<210> SEQ ID NO 122
<211> LENGTH: 17
<212> TYPE: RNA
<213> ORGANISM: Homo sapiens

<400> SEQUENCE: 122
ggcgggugcg ggggugg				17

<210> SEQ ID NO 123
<211> LENGTH: 22
<212> TYPE: RNA
<213> ORGANISM: Homo sapiens

<400> SEQUENCE: 123 ugcaggggguc ggugggcca gg			22

<210> SEQ ID NO 124
<211> LENGTH: 23
<212> TYPE: RNA
<213> ORGANISM: Homo sapiens

<400> SEQUENCE: 124
gccccggcgc gggcggguuc ugg			23

<210> SEQ ID NO 125
<211> LENGTH: 22
<212> TYPE: RNA
<213> ORGANISM: Homo sapiens

```
<400> SEQUENCE: 125
cgucccgggg cugcgcgagg ca                                        22

<210> SEQ ID NO 126
<211> LENGTH: 21
<212> TYPE: RNA
<213> ORGANISM: Homo sapiens

<400> SEQUENCE: 126
gugccagcug caguggggga g                                         21

<210> SEQ ID NO 127
<211> LENGTH: 24
<212> TYPE: RNA
<213> ORGANISM: Homo sapiens

<400> SEQUENCE: 127
ugggcgaggg gugggcucuc agag                                      24

<210> SEQ ID NO 128
<211> LENGTH: 22
<212> TYPE: RNA
<213> ORGANISM: Homo sapiens

<400> SEQUENCE: 128
ugcggggcua gggcuaacag ca                                        22

<210> SEQ ID NO 129
<211> LENGTH: 22
<212> TYPE: RNA
<213> ORGANISM: Homo sapiens

<400> SEQUENCE: 129
agacacauuu ggagagggaa cc                                        22

<210> SEQ ID NO 130
<211> LENGTH: 22
<212> TYPE: RNA
<213> ORGANISM: Homo sapiens

<400> SEQUENCE: 130
aaaccguuac cauuacugag uu                                        22

<210> SEQ ID NO 131
<211> LENGTH: 19
<212> TYPE: RNA
<213> ORGANISM: Homo sapiens

<400> SEQUENCE: 131 uggggagau gggggguuga                                            19

<210> SEQ ID NO 132
<211> LENGTH: 17
<212> TYPE: RNA
<213> ORGANISM: Homo sapiens

<400> SEQUENCE: 132
uuggaggcgu ggguuuu                                              17

<210> SEQ ID NO 133
<211> LENGTH: 22
<212> TYPE: RNA
<213> ORGANISM: Homo sapiens
```

```
<400> SEQUENCE: 133
caggcaggga ggugggacca ug                                              22

<210> SEQ ID NO 134
<211> LENGTH: 23
<212> TYPE: RNA
<213> ORGANISM: Homo sapiens

<400> SEQUENCE: 134 ugggaggga gaggcagcaa gca                                              23

<210> SEQ ID NO 135
<211> LENGTH: 20
<212> TYPE: RNA
<213> ORGANISM: Homo sapiens

<400> SEQUENCE: 135
gugagucagg gugggcugg                                                  20

<210> SEQ ID NO 136
<211> LENGTH: 22
<212> TYPE: RNA
<213> ORGANISM: Homo sapiens

<400> SEQUENCE: 136
uauagggauu ggagccgugg cg                                              22

<210> SEQ ID NO 137
<211> LENGTH: 22
<212> TYPE: RNA
<213> ORGANISM: Homo sapiens

<400> SEQUENCE: 137
gguggcccgg ccgugccuga gg                                              22

<210> SEQ ID NO 138
<211> LENGTH: 22
<212> TYPE: RNA
<213> ORGANISM: Homo sapiens

<400> SEQUENCE: 138
uggggagcgg cccccgggug gg                                              22

<210> SEQ ID NO 139
<211> LENGTH: 20
<212> TYPE: RNA
<213> ORGANISM: Homo sapiens

<400> SEQUENCE: 139
cagggaacca guugggcuu                                                  20

<210> SEQ ID NO 140
<211> LENGTH: 22
<212> TYPE: RNA
<213> ORGANISM: Homo sapiens

<400> SEQUENCE: 140 cuggggugg gggcugggc gu                                                22

<210> SEQ ID NO 141
<211> LENGTH: 23
<212> TYPE: RNA
```

<213> ORGANISM: Homo sapiens

<400> SEQUENCE: 141
uugcucugcu ccccgcccc cag                                           23

<210> SEQ ID NO 142
<211> LENGTH: 23
<212> TYPE: RNA
<213> ORGANISM: Homo sapiens

<400> SEQUENCE: 142
gggggccgau acacuguacg aga                                          23

<210> SEQ ID NO 143
<211> LENGTH: 23
<212> TYPE: RNA
<213> ORGANISM: Homo sapiens

<400> SEQUENCE: 143
ugggccaggg agcagcuggu ggg                                          23

<210> SEQ ID NO 144
<211> LENGTH: 22
<212> TYPE: RNA
<213> ORGANISM: Homo sapiens

<400> SEQUENCE: 144
cucggcgcgg ggcgcgggcu cc                                           22

<210> SEQ ID NO 145
<211> LENGTH: 22
<212> TYPE: RNA
<213> ORGANISM: Homo sapiens

<400> SEQUENCE: 145 gggugggggau uuguugcauu ac                                          22

<210> SEQ ID NO 146
<211> LENGTH: 20
<212> TYPE: RNA
<213> ORGANISM: Homo sapiens

<400> SEQUENCE: 146 gugggguuggg gcgggcucug                                             20

<210> SEQ ID NO 147
<211> LENGTH: 18
<212> TYPE: RNA
<213> ORGANISM: Homo sapiens

<400> SEQUENCE: 147
ggguccnggg gaggggggg                                               18

<210> SEQ ID NO 148
<211> LENGTH: 19
<212> TYPE: RNA
<213> ORGANISM: Homo sapiens

<400> SEQUENCE: 148
aucccaccac ugccaccau                                               19

<210> SEQ ID NO 149
<211> LENGTH: 23

```
<212> TYPE: RNA
<213> ORGANISM: Homo sapiens

<400> SEQUENCE: 149
gugaguggga gccgguggggg cug                                           23

<210> SEQ ID NO 150
<211> LENGTH: 22
<212> TYPE: RNA
<213> ORGANISM: Homo sapiens

<400> SEQUENCE: 150
accuugccuu gcugcccggg cc                                             22

<210> SEQ ID NO 151
<211> LENGTH: 24
<212> TYPE: RNA
<213> ORGANISM: Homo sapiens

<400> SEQUENCE: 151
agggcuggac ucagcggcgg agcu                                           24

<210> SEQ ID NO 152
<211> LENGTH: 17
<212> TYPE: RNA
<213> ORGANISM: Homo sapiens

<400> SEQUENCE: 152
accccacucc ugguacc                                                   17

<210> SEQ ID NO 153
<211> LENGTH: 18
<212> TYPE: RNA
<213> ORGANISM: Homo sapiens

<400> SEQUENCE: 153
gugaaggccc ggcggaga                                                  18

<210> SEQ ID NO 154
<211> LENGTH: 24
<212> TYPE: RNA
<213> ORGANISM: Homo sapiens

<400> SEQUENCE: 154
guaggggcgu cccgggcgcg cggg                                           24

<210> SEQ ID NO 155
<211> LENGTH: 22
<212> TYPE: RNA
<213> ORGANISM: Homo sapiens

<400> SEQUENCE: 155
ccaggaggcg gaggaggugg ag                                             22

<210> SEQ ID NO 156
<211> LENGTH: 18
<212> TYPE: RNA
<213> ORGANISM: Homo sapiens

<400> SEQUENCE: 156
cgggcguggu ggugggggg                                                 18

<210> SEQ ID NO 157
```

```
<211> LENGTH: 22
<212> TYPE: RNA
<213> ORGANISM: Homo sapiens

<400> SEQUENCE: 157 gggggguguug gagccagggg gc                                              22

<210> SEQ ID NO 158
<211> LENGTH: 19
<212> TYPE: RNA
<213> ORGANISM: Homo sapiens

<400> SEQUENCE: 158
ggcuggucag augggagug                                                   19

<210> SEQ ID NO 159
<211> LENGTH: 21
<212> TYPE: RNA
<213> ORGANISM: Homo sapiens

<400> SEQUENCE: 159
guaggugaca gucaggggcg g                                                21

<210> SEQ ID NO 160
<211> LENGTH: 17
<212> TYPE: RNA
<213> ORGANISM: Homo sapiens

<400> SEQUENCE: 160
ccccggggag cccggcg                                                     17

<210> SEQ ID NO 161
<211> LENGTH: 21
<212> TYPE: RNA
<213> ORGANISM: Homo sapiens

<400> SEQUENCE: 161
cccaugccuc cugccgcggu c                                                21

<210> SEQ ID NO 162
<211> LENGTH: 21
<212> TYPE: RNA
<213> ORGANISM: Homo sapiens

<400> SEQUENCE: 162
cuuccgcccc gccgggcguc g                                                21

<210> SEQ ID NO 163
<211> LENGTH: 21
<212> TYPE: RNA
<213> ORGANISM: Homo sapiens

<400> SEQUENCE: 163 aggugggguau ggaggagccc u                                               21

<210> SEQ ID NO 164
<211> LENGTH: 22
<212> TYPE: RNA
<213> ORGANISM: Homo sapiens

<400> SEQUENCE: 164
agcccgcccc agccgagguu cu                                               22
```

```
<210> SEQ ID NO 165
<211> LENGTH: 25
<212> TYPE: RNA
<213> ORGANISM: Homo sapiens

<400> SEQUENCE: 165
gugaggcggg gccaggaggg ugugu                                          25

<210> SEQ ID NO 166
<211> LENGTH: 25
<212> TYPE: RNA
<213> ORGANISM: Homo sapiens

<400> SEQUENCE: 166
aagggaggag gagcggaggg gcccu                                          25

<210> SEQ ID NO 167
<211> LENGTH: 21
<212> TYPE: RNA
<213> ORGANISM: Homo sapiens

<400> SEQUENCE: 167 gggggggaugu gcaugcuggu u                                             21

<210> SEQ ID NO 168
<211> LENGTH: 20
<212> TYPE: RNA
<213> ORGANISM: Homo sapiens

<400> SEQUENCE: 168
ucagggaguc aggggagggc                                                20

<210> SEQ ID NO 169
<211> LENGTH: 17
<212> TYPE: RNA
<213> ORGANISM: Homo sapiens

<400> SEQUENCE: 169
ggauggagga gggguucu                                                  17

<210> SEQ ID NO 170
<211> LENGTH: 22
<212> TYPE: RNA
<213> ORGANISM: Homo sapiens

<400> SEQUENCE: 170
ugggagggcg uggaugaugg ug                                             22

<210> SEQ ID NO 171
<211> LENGTH: 22
<212> TYPE: RNA
<213> ORGANISM: Homo sapiens

<400> SEQUENCE: 171
gugcggaacg cuggccgggg cg                                             22

<210> SEQ ID NO 172
<211> LENGTH: 22
<212> TYPE: RNA
<213> ORGANISM: Homo sapiens

<400> SEQUENCE: 172 aggggggcgca gucacugacg ug                                            22
```

<210> SEQ ID NO 173
<211> LENGTH: 18
<212> TYPE: RNA
<213> ORGANISM: Homo sapiens

<400> SEQUENCE: 173
aucccaccuc ugccacca                                              18

<210> SEQ ID NO 174
<211> LENGTH: 17
<212> TYPE: RNA
<213> ORGANISM: Homo sapiens

<400> SEQUENCE: 174
gcugggcgag gcuggca                                               17

<210> SEQ ID NO 175
<211> LENGTH: 22
<212> TYPE: RNA
<213> ORGANISM: Homo sapiens

<400> SEQUENCE: 175
ugguggagga agagggcagc uc                                         22

<210> SEQ ID NO 176
<211> LENGTH: 20
<212> TYPE: RNA
<213> ORGANISM: Homo sapiens

<400> SEQUENCE: 176
cuaggugggg ggcuugaagc                                            20

<210> SEQ ID NO 177
<211> LENGTH: 22
<212> TYPE: RNA
<213> ORGANISM: Homo sapiens

<400> SEQUENCE: 177 acugguagg uggggcucca gg                                          22

<210> SEQ ID NO 178
<211> LENGTH: 22
<212> TYPE: RNA
<213> ORGANISM: Homo sapiens

<400> SEQUENCE: 178
agggacggga cgcggugcag ug                                         22

<210> SEQ ID NO 179
<211> LENGTH: 23
<212> TYPE: RNA
<213> ORGANISM: Homo sapiens

<400> SEQUENCE: 179
gugaguggga gccccagugu gug                                        23

<210> SEQ ID NO 180
<211> LENGTH: 23
<212> TYPE: RNA
<213> ORGANISM: Homo sapiens

<400> SEQUENCE: 180
aggagguggu acuagggcc agc                                         23

```
<210> SEQ ID NO 181
<211> LENGTH: 19
<212> TYPE: RNA
<213> ORGANISM: Homo sapiens

<400> SEQUENCE: 181
cggggucggc ggcgacgug                                               19

<210> SEQ ID NO 182
<211> LENGTH: 21
<212> TYPE: RNA
<213> ORGANISM: Homo sapiens

<400> SEQUENCE: 182
agggagggac gggggcugug c                                            21

<210> SEQ ID NO 183
<211> LENGTH: 22
<212> TYPE: RNA
<213> ORGANISM: Homo sapiens

<400> SEQUENCE: 183
uugaggagac auggugggg cc                                            22

<210> SEQ ID NO 184
<211> LENGTH: 22
<212> TYPE: RNA
<213> ORGANISM: Homo sapiens

<400> SEQUENCE: 184
uaggggcagc agaggaccug gg                                           22

<210> SEQ ID NO 185
<211> LENGTH: 22
<212> TYPE: RNA
<213> ORGANISM: Homo sapiens

<400> SEQUENCE: 185
acaggugagg uucuugggag cc                                           22

<210> SEQ ID NO 186
<211> LENGTH: 21
<212> TYPE: RNA
<213> ORGANISM: Homo sapiens

<400> SEQUENCE: 186
aucacauugc cagggauuac c                                            21

<210> SEQ ID NO 187
<211> LENGTH: 23
<212> TYPE: RNA
<213> ORGANISM: Homo sapiens

<400> SEQUENCE: 187
gaacgccugu ucuugccagg ugg                                          23

<210> SEQ ID NO 188
<211> LENGTH: 22
<212> TYPE: RNA
<213> ORGANISM: Homo sapiens

<400> SEQUENCE: 188
``` ucugccccu ccgcugcugc ca                                               22

<210> SEQ ID NO 189
<211> LENGTH: 22
<212> TYPE: RNA
<213> ORGANISM: Homo sapiens

<400> SEQUENCE: 189
uagcagcacg uaaauauugg cg                                              22

<210> SEQ ID NO 190
<211> LENGTH: 23
<212> TYPE: RNA
<213> ORGANISM: Homo sapiens

<400> SEQUENCE: 190
uggugcggag agggcccaca gug                                             23

<210> SEQ ID NO 191
<211> LENGTH: 21
<212> TYPE: RNA
<213> ORGANISM: Homo sapiens

<400> SEQUENCE: 191
cggggcagcu caguacagga u                                               21

<210> SEQ ID NO 192
<211> LENGTH: 23
<212> TYPE: RNA
<213> ORGANISM: Homo sapiens

<400> SEQUENCE: 192
acggggaguc aggcaguggu gga                                             23

<210> SEQ ID NO 193
<211> LENGTH: 17
<212> TYPE: RNA
<213> ORGANISM: Homo sapiens

<400> SEQUENCE: 193
cuccgggacg gcugggc                                                    17

<210> SEQ ID NO 194
<211> LENGTH: 22
<212> TYPE: RNA
<213> ORGANISM: Homo sapiens

<400> SEQUENCE: 194
gaggguuggg uggaggcucu cc                                              22

<210> SEQ ID NO 195
<211> LENGTH: 23
<212> TYPE: RNA
<213> ORGANISM: Homo sapiens

<400> SEQUENCE: 195 cgaggguag aagagcacag ggg                                              23

<210> SEQ ID NO 196
<211> LENGTH: 22
<212> TYPE: RNA
<213> ORGANISM: Homo sapiens

<400> SEQUENCE: 196 ugcuggggc cacaugagug ug                                        22

<210> SEQ ID NO 197
<211> LENGTH: 23
<212> TYPE: RNA
<213> ORGANISM: Homo sapiens

<400> SEQUENCE: 197
ucggggaguc uggggccgg aau                                       23

<210> SEQ ID NO 198
<211> LENGTH: 21
<212> TYPE: RNA
<213> ORGANISM: Homo sapiens

<400> SEQUENCE: 198
gcgguggggc cggaggggcg u                                        21

<210> SEQ ID NO 199
<211> LENGTH: 22
<212> TYPE: RNA
<213> ORGANISM: Homo sapiens

<400> SEQUENCE: 199
uauugcacuu gucccggccu gu                                       22

<210> SEQ ID NO 200
<211> LENGTH: 17
<212> TYPE: RNA
<213> ORGANISM: Homo sapiens

<400> SEQUENCE: 200
gggagucuac agcaggg                                             17

<210> SEQ ID NO 201
<211> LENGTH: 24
<212> TYPE: RNA
<213> ORGANISM: Homo sapiens

<400> SEQUENCE: 201
aggcaggggc uggugcuggg cggg                                     24

<210> SEQ ID NO 202
<211> LENGTH: 21
<212> TYPE: RNA
<213> ORGANISM: Homo sapiens

<400> SEQUENCE: 202
agcaugacag aggagaggug g                                        21

<210> SEQ ID NO 203
<211> LENGTH: 22
<212> TYPE: RNA
<213> ORGANISM: Homo sapiens

<400> SEQUENCE: 203
aggcggggcg ccgcgggacc gc                                       22

<210> SEQ ID NO 204
<211> LENGTH: 20
<212> TYPE: RNA
<213> ORGANISM: Homo sapiens

```
<400> SEQUENCE: 204
cggcucuggg ucugugggga                                               20

<210> SEQ ID NO 205
<211> LENGTH: 22
<212> TYPE: RNA
<213> ORGANISM: Homo sapiens

<400> SEQUENCE: 205 acugggagc agaaggagaa cc                                             22

<210> SEQ ID NO 206
<211> LENGTH: 19
<212> TYPE: RNA
<213> ORGANISM: Homo sapiens

<400> SEQUENCE: 206
ggggagcgag gggcggggc                                                19

<210> SEQ ID NO 207
<211> LENGTH: 23
<212> TYPE: RNA
<213> ORGANISM: Homo sapiens

<400> SEQUENCE: 207
cuggcggagc ccauuccaug cca                                           23

<210> SEQ ID NO 208
<211> LENGTH: 20
<212> TYPE: RNA
<213> ORGANISM: Homo sapiens

<400> SEQUENCE: 208
ugggaggagg ggaucuuggg                                               20

<210> SEQ ID NO 209
<211> LENGTH: 18
<212> TYPE: RNA
<213> ORGANISM: Homo sapiens

<400> SEQUENCE: 209
cggggcggca ggggccuc                                                 18

<210> SEQ ID NO 210
<211> LENGTH: 22
<212> TYPE: RNA
<213> ORGANISM: Homo sapiens

<400> SEQUENCE: 210 uggggagug cagugauugu gg                                             22

<210> SEQ ID NO 211
<211> LENGTH: 18
<212> TYPE: RNA
<213> ORGANISM: Homo sapiens

<400> SEQUENCE: 211
ugaggcgggg gggcgagc                                                 18

<210> SEQ ID NO 212
<211> LENGTH: 23
<212> TYPE: RNA
<213> ORGANISM: Homo sapiens
```

```
<400> SEQUENCE: 212 cuggggacg cgugagcgcg agc                                               23

<210> SEQ ID NO 213
<211> LENGTH: 22
<212> TYPE: RNA
<213> ORGANISM: Homo sapiens

<400> SEQUENCE: 213
ggggaacugu agaugaaaag gc                                               22

<210> SEQ ID NO 214
<211> LENGTH: 22
<212> TYPE: RNA
<213> ORGANISM: Homo sapiens

<400> SEQUENCE: 214
cagggcaggg aaggugggag ag                                               22

<210> SEQ ID NO 215
<211> LENGTH: 110
<212> TYPE: RNA
<213> ORGANISM: Homo sapiens

<400> SEQUENCE: 215
ggcuacaguc uuucuucaug ugacucgugg acuucccuuu gucauccuau gccugagaau      60
auaugaagga ggcugggaag gcaaagggac guucaauugu caucacuggc                110

<210> SEQ ID NO 216
<211> LENGTH: 136
<212> TYPE: RNA
<213> ORGANISM: Homo sapiens

<400> SEQUENCE: 216
ccgcuugccu cgcccagcgc agccccggcc gcugggcgca cccguccogu ucgucccgg      60 acguugcucu cuaccccggg aacgucgaga cuggagcgcc cgaacugagc caccuucgcg     120
gaccccgaga gcggcg                                                    136

<210> SEQ ID NO 217
<211> LENGTH: 72
<212> TYPE: RNA
<213> ORGANISM: Homo sapiens

<400> SEQUENCE: 217
gagucugagg gacccaggac aggagaaggc cuauggugau uugcauucuu ccugcccugg     60
cuccauccuc ag                                                        72

<210> SEQ ID NO 218
<211> LENGTH: 93
<212> TYPE: RNA
<213> ORGANISM: Homo sapiens

<400> SEQUENCE: 218
gcuuguuggg gauugggguca ggccagguguu caagggcccc uccucuagua cucccuguuu   60
guguucugcc acugacugag cuucucccca cag                                  93

<210> SEQ ID NO 219
<211> LENGTH: 61
<212> TYPE: RNA
```

```
<213> ORGANISM: Homo sapiens

<400> SEQUENCE: 219
gggggcggga gcuggggucu gcagguucgc acugaugccu gcucgcccug ucucccgcua      60
g                                                                     61

<210> SEQ ID NO 220
<211> LENGTH: 85
<212> TYPE: RNA
<213> ORGANISM: Homo sapiens

<400> SEQUENCE: 220
ggcgccuccu gcucugcugu gccgccaggg ccuccccuag cgcgccuucu ggagaggcuu      60
ugugcggaua cggggcugga ggccu                                           85

<210> SEQ ID NO 221
<211> LENGTH: 86
<212> TYPE: RNA
<213> ORGANISM: Homo sapiens

<400> SEQUENCE: 221
cgccugagcg ugcagcagga caucuuccug accugguaau aauuagguga gaaggauggu      60 uggggcggu cggcguaacu caggga                                           86

<210> SEQ ID NO 222
<211> LENGTH: 86
<212> TYPE: RNA
<213> ORGANISM: Homo sapiens

<400> SEQUENCE: 222
ggcuuagaaa caguccuag guaggauuug gggaggagcu aagaagcccc uacagggccc       60
agaggugggg acugagccuu aguugg                                          86

<210> SEQ ID NO 223
<211> LENGTH: 84
<212> TYPE: RNA
<213> ORGANISM: Homo sapiens

<400> SEQUENCE: 223
gcuggcgucg gugcugggga gcggcccccg gguggccuc ugcucuggcc ccuccugggg       60
cccgcacucu cgcucugggc ccgc                                            84

<210> SEQ ID NO 224
<211> LENGTH: 87
<212> TYPE: RNA
<213> ORGANISM: Homo sapiens

<400> SEQUENCE: 224
guguggccgg caggcgggug ggcggggggcg gccgguggga accccgcccc gccccgcgcc     60
cgcacucacc cgcccgucuc cccacag                                         87

<210> SEQ ID NO 225
<211> LENGTH: 66
<212> TYPE: RNA
<213> ORGANISM: Homo sapiens

<400> SEQUENCE: 225
gggcaugggg aggugggag ucagcauggg gcuaggaggc cccgcgcuga cccgccuucu       60
ccgcag                                                                66
```

<210> SEQ ID NO 226
<211> LENGTH: 61
<212> TYPE: RNA
<213> ORGANISM: Homo sapiens

<400> SEQUENCE: 226
ucucguuuga ucucggaagc uaagcagggu ugggccuggu uaguacuugg augggaaacu    60
u                                                                   61

<210> SEQ ID NO 227
<211> LENGTH: 53
<212> TYPE: RNA
<213> ORGANISM: Homo sapiens

<400> SEQUENCE: 227
guuugaucuc ggaagcuaag caggucnggg ccugguuagu acuuggaugg gag           53

<210> SEQ ID NO 228
<211> LENGTH: 68
<212> TYPE: RNA
<213> ORGANISM: Homo sapiens

<400> SEQUENCE: 228
gaauggaaga agaaggcggu cggucugcgg gagccaggcc gcagagccau ccgccuucug    60
uccauguc                                                            68

<210> SEQ ID NO 229
<211> LENGTH: 71
<212> TYPE: RNA
<213> ORGANISM: Homo sapiens

<400> SEQUENCE: 229
gugucugugc cggucccagg agaaccugca gaggcaucgg gucagcggug cuccugcggg    60
ccgacacuca c                                                        71

<210> SEQ ID NO 230
<211> LENGTH: 67
<212> TYPE: RNA
<213> ORGANISM: Homo sapiens

<400> SEQUENCE: 230
ccagaccccu ggggcugggc aggcggaaag aggucugaac ugccucugcc uccuuggucu    60
ccggcag                                                             67

<210> SEQ ID NO 231
<211> LENGTH: 69
<212> TYPE: RNA
<213> ORGANISM: Homo sapiens

<400> SEQUENCE: 231
ccgggcaggc agguguaggg uggagcccac uguggcuccu gacucagccc ugcugccuuc    60
accugccag                                                           69

<210> SEQ ID NO 232
<211> LENGTH: 102
<212> TYPE: RNA
<213> ORGANISM: Homo sapiens

<400> SEQUENCE: 232

```
uguguuccccu auccuccuua ugucccaccc ccacuccugu uugaauauuu caccagaaac    60
aggagugggg gguggggacgu aaggaggaug ggggaaagaa ca                      102
```

<210> SEQ ID NO 233
<211> LENGTH: 68
<212> TYPE: RNA
<213> ORGANISM: Homo sapiens

<400> SEQUENCE: 233

```
ugcccaggcu ggagcgagug caguggugca gucagucuua gcucacugca gccucgaacu    60
ccugggcu                                                             68
```

<210> SEQ ID NO 234
<211> LENGTH: 64
<212> TYPE: RNA
<213> ORGANISM: Homo sapiens

<400> SEQUENCE: 234

```
aaccccgggc cggaggucaa gggcgucgcu ucucccuaau guugccucuu uuccacggcc    60
ucag                                                                 64
```

<210> SEQ ID NO 235
<211> LENGTH: 80
<212> TYPE: RNA
<213> ORGANISM: Homo sapiens

<400> SEQUENCE: 235

```
cgggaaugcc gcggcgggga cggcgauugg uccguaugug uggugccacc ggccgccggc    60
uccgccccgg ccccgcccc                                                 80
```

<210> SEQ ID NO 236
<211> LENGTH: 74
<212> TYPE: RNA
<213> ORGANISM: Homo sapiens

<400> SEQUENCE: 236

```
gcagcccggu gagcgcucgc uggccuggca gugcgucgga agaacagggc ggguggggcc    60
gcgcacaucu cugc                                                      74
```

<210> SEQ ID NO 237
<211> LENGTH: 99
<212> TYPE: RNA
<213> ORGANISM: Homo sapiens

<400> SEQUENCE: 237

```
gcaagggaca gggagggucg uggcgacacu cgcgccagcu cccgggacgg cugggcucgg    60
gcuggucgcc gaccuccgac ccuccacuag augccuggc                           99
```

<210> SEQ ID NO 238
<211> LENGTH: 73
<212> TYPE: RNA
<213> ORGANISM: Homo sapiens

<400> SEQUENCE: 238

```
gaaaacaacc agguggggcuu cccggagggc ggaacacccca gccccagcau ccagggcuca  60
ccuaccacgu uug                                                       73
```

<210> SEQ ID NO 239
<211> LENGTH: 75

```
<212> TYPE: RNA
<213> ORGANISM: Homo sapiens

<400> SEQUENCE: 239
aagcaagacu gaggggccuc agaccgagcu uuuggaaaau agaaaagucu cgcucucugc    60
cccucagccu aacuu                                                    75

<210> SEQ ID NO 240
<211> LENGTH: 90
<212> TYPE: RNA
<213> ORGANISM: Homo sapiens

<400> SEQUENCE: 240
guggguacgg cccagugggg gggagaggga cacgcccugg gcucugccca gggugcagcc    60
ggacugacug agccccugug ccgccccag                                     90

<210> SEQ ID NO 241
<211> LENGTH: 92
<212> TYPE: RNA
<213> ORGANISM: Homo sapiens

<400> SEQUENCE: 241
gucagugucu gggcggacag cugcaggaaa gggaagacca aggcuugcug ucuguccagu    60
cugccacccu acccugucug uucuugccac ag                                 92

<210> SEQ ID NO 242
<211> LENGTH: 84
<212> TYPE: RNA
<213> ORGANISM: Homo sapiens

<400> SEQUENCE: 242
cuccccaugg cccugucucc caacccuugu accagugcug ggcucagacc cugguacagg    60 ccuggggac agggaccugg ggac                                           84

<210> SEQ ID NO 243
<211> LENGTH: 81
<212> TYPE: RNA
<213> ORGANISM: Homo sapiens

<400> SEQUENCE: 243
cauccuccuu acgucccacc ccccacuccu guuucuggug aaauauucaa acaggagugg    60
gggugggaca uaaggaggau a                                             81

<210> SEQ ID NO 244
<211> LENGTH: 96
<212> TYPE: RNA
<213> ORGANISM: Homo sapiens

<400> SEQUENCE: 244
gcucuggggc gugccgccgc cgucgcugcc accuccccua ccgcuagugg aagaaugg      60 cggaaggcgg agcggcggau cuggacaccc agcggu                             96

<210> SEQ ID NO 245
<211> LENGTH: 86
<212> TYPE: RNA
<213> ORGANISM: Homo sapiens

<400> SEQUENCE: 245
auucuaggug gggagacuga cggcuggagg cccauaagcu gucuaaaacu ucggccccca    60
```
gauuucuggu cuccccacuu cagaac                                   86

<210> SEQ ID NO 246
<211> LENGTH: 61
<212> TYPE: RNA
<213> ORGANISM: Homo sapiens

<400> SEQUENCE: 246
ucggcuggcg gggguagagc uggcugcagg cccggccccu cucagcugcu gcccucuuca  60
g                                                              61

<210> SEQ ID NO 247
<211> LENGTH: 67
<212> TYPE: RNA
<213> ORGANISM: Homo sapiens

<400> SEQUENCE: 247
uacaggccgg ggcuuugggu gagggacccc cggagucugu cacggucuca ccccaacucu  60
gccccag                                                        67

<210> SEQ ID NO 248
<211> LENGTH: 96
<212> TYPE: RNA
<213> ORGANISM: Homo sapiens

<400> SEQUENCE: 248
cucgggaggg gcgggagggg ggucccccggu gcucggaucu cgagggugcu uauuguucgg  60
uccgagccug ggucucccuc uuccccccaa cccccc                        96

<210> SEQ ID NO 249
<211> LENGTH: 87
<212> TYPE: RNA
<213> ORGANISM: Homo sapiens

<400> SEQUENCE: 249
gugaggcggg gccaggaggg uguguggcgu gggugcugcg gggccgucag ggugccugcg  60
ggacgcucac cuggcuggcc cgcccag                                  87

<210> SEQ ID NO 250
<211> LENGTH: 137
<212> TYPE: RNA
<213> ORGANISM: Homo sapiens

<400> SEQUENCE: 250
agccagacaa gagggucaug gggagucacu gucaacccag agcaggcacu gccccugcga  60
ccagccuggg gcaucgguug ggugcaggg gucugcuggu gaugcuuucc aucucuuugc  120
uuuguccuga uuguagc                                             137

<210> SEQ ID NO 251
<211> LENGTH: 65
<212> TYPE: RNA
<213> ORGANISM: Homo sapiens

<400> SEQUENCE: 251
agcccugggg guggucucua gccaaggcuc uggggucuca cccuuggcug gucucugcuc  60
cgcag                                                          65

<210> SEQ ID NO 252
<211> LENGTH: 81

```
<212> TYPE: RNA
<213> ORGANISM: Homo sapiens

<400> SEQUENCE: 252
uagaggcagu ucaacagau guguagacuu uugauaugag aaauugguuu caaaaucagg       60
agucggggcu uuacugcuuu u                                               81

<210> SEQ ID NO 253
<211> LENGTH: 79
<212> TYPE: RNA
<213> ORGANISM: Homo sapiens

<400> SEQUENCE: 253
cagccugggg aaggcuuggc agggaagaca caugagcagu gccuccacuu cacgccucuc     60
ccuugucucc uuucccuag                                                  79

<210> SEQ ID NO 254
<211> LENGTH: 109
<212> TYPE: RNA
<213> ORGANISM: Homo sapiens

<400> SEQUENCE: 254
ggucgggcuc accaugacac agugugagac cucgggcuac aacacaggac ccgggcgcug     60
cucugacccc ucgugucuug guugcagcc ggagggacgc agguccgca                 109

<210> SEQ ID NO 255
<211> LENGTH: 82
<212> TYPE: RNA
<213> ORGANISM: Homo sapiens

<400> SEQUENCE: 255
ugagcuguug gauucggggc cguagcacug ucugagaggu uuacauuucu cacagugaac     60
cggucucuuu uucagcugcu uc                                              82

<210> SEQ ID NO 256
<211> LENGTH: 65
<212> TYPE: RNA
<213> ORGANISM: Homo sapiens

<400> SEQUENCE: 256
gagggugggc gagggcggcu gagcggcucc auccccggc cugcucaucc cccucgcccu      60
cucag                                                                 65

<210> SEQ ID NO 257
<211> LENGTH: 63
<212> TYPE: RNA
<213> ORGANISM: Homo sapiens

<400> SEQUENCE: 257
aauggugggg ugcuggugggg agccgugccc uggccacuca uucggcucuc ucccucaccc    60
uag                                                                   63

<210> SEQ ID NO 258
<211> LENGTH: 69
<212> TYPE: RNA
<213> ORGANISM: Homo sapiens

<400> SEQUENCE: 258
gggcuuaggg augggaggcc aggaugaaga uuaaucccua aucccaaca cuggccuugc     60
```

| | |
|---|---|
| uaucccag | 69 |

<210> SEQ ID NO 259
<211> LENGTH: 86
<212> TYPE: RNA
<213> ORGANISM: Homo sapiens

<400> SEQUENCE: 259

| | |
|---|---|
| ggggcugggg gugugggag agagagugca cagccagcuc agggauuaaa gcucuuucuc | 60 |
| ucucucucuc ucccacuucc cugcag | 86 |

<210> SEQ ID NO 260
<211> LENGTH: 68
<212> TYPE: RNA
<213> ORGANISM: Homo sapiens

<400> SEQUENCE: 260

| | |
|---|---|
| gugcaaagag caggaggaca ggggauuuau cucccaaggg aggucccug auccaguca | 60 |
| cggcacca | 68 |

<210> SEQ ID NO 261
<211> LENGTH: 82
<212> TYPE: RNA
<213> ORGANISM: Homo sapiens

<400> SEQUENCE: 261

| | |
|---|---|
| gugaguggga ggccagggca cggcaggggg agcugcaggg cuagggagg ggccccagcg | 60 |
| ucugagcccu guccucccgc ag | 82 |

<210> SEQ ID NO 262
<211> LENGTH: 82
<212> TYPE: RNA
<213> ORGANISM: Homo sapiens

<400> SEQUENCE: 262

| | |
|---|---|
| gugaguggga ggccagggca cggcaggggg agcugcaggg cuagggagg ggccccagcg | 60 |
| ucugagcccu guccucccgc ag | 82 |

<210> SEQ ID NO 263
<211> LENGTH: 61
<212> TYPE: RNA
<213> ORGANISM: Homo sapiens

<400> SEQUENCE: 263

| | |
|---|---|
| aacugcgggg ccagagcaga gagcccuugc acaccaccag ccucucccuc cugugcccca | 60 |
| g | 61 |

<210> SEQ ID NO 264
<211> LENGTH: 106
<212> TYPE: RNA
<213> ORGANISM: Homo sapiens

<400> SEQUENCE: 264

| | |
|---|---|
| agaagaaugc ccaaccagcc cucaguugcu acagucccu guuguuucag cucgacaaca | 60 |
| acaggcggcu uagcaauugg ggggcuggau gggcaucuca augugc | 106 |

<210> SEQ ID NO 265
<211> LENGTH: 63
<212> TYPE: RNA
<213> ORGANISM: Homo sapiens

```
<400> SEQUENCE: 265
ugguggcggc gguaguuaug ggcuucucuu ucucaccagc agccccuggg ccgccgccuc    60
ccu                                                                 63

<210> SEQ ID NO 266
<211> LENGTH: 65
<212> TYPE: RNA
<213> ORGANISM: Homo sapiens

<400> SEQUENCE: 266
gucuccuggg gggaggagac ccugcucucc cuggcagcaa gccucccug cccuuccaga    60 uuagc                                                               65

<210> SEQ ID NO 267
<211> LENGTH: 51
<212> TYPE: RNA
<213> ORGANISM: Homo sapiens

<400> SEQUENCE: 267
agagaugaag cgggggggcg gggucuugcu cuauugccua cgcugaucuc a            51

<210> SEQ ID NO 268
<211> LENGTH: 69
<212> TYPE: RNA
<213> ORGANISM: Homo sapiens

<400> SEQUENCE: 268
uggguagggg gugggggaau ucaggggugu cgaacucaug gcugccaccu uuguccccc    60 auccugcag                                                           69

<210> SEQ ID NO 269
<211> LENGTH: 115
<212> TYPE: RNA
<213> ORGANISM: Homo sapiens

<400> SEQUENCE: 269
gagcaaaaac cagagaacaa caugggagcg uuccuaaccc cuaaggcaac uggaugggag    60
accugaccca uccaguucuc ugaggggcu cuugugguu cuacaagguu guuca          115

<210> SEQ ID NO 270
<211> LENGTH: 55
<212> TYPE: RNA
<213> ORGANISM: Homo sapiens

<400> SEQUENCE: 270
ccggauccga gucacggcac caaauuucau gcguguccgu gugaagagac cacca         55

<210> SEQ ID NO 271
<211> LENGTH: 92
<212> TYPE: RNA
<213> ORGANISM: Homo sapiens

<400> SEQUENCE: 271
cgcugcgcuu cugggcccgc ggcgggcgug gggcugcccg ggccggucga ccagcgcgcc    60
guagcucccg aggcccgagc cgcgaccccgc gg                                92

<210> SEQ ID NO 272
<211> LENGTH: 80
<212> TYPE: RNA
```

```
<213> ORGANISM: Homo sapiens

<400> SEQUENCE: 272
gcgucaagau ggcggcgggg agguaggcag agcaggacgc cgcugcugcc gccgccaccg    60
ccgccuccgc uccagucgcc                                                80

<210> SEQ ID NO 273
<211> LENGTH: 86
<212> TYPE: RNA
<213> ORGANISM: Homo sapiens

<400> SEQUENCE: 273
agggagaagg gucggggcag ggagggcagg gcaggcucug ggguggggg ucugugaguc     60 agccacggcu cugcccacgu cuccc                                          86

<210> SEQ ID NO 274
<211> LENGTH: 63
<212> TYPE: RNA
<213> ORGANISM: Homo sapiens

<400> SEQUENCE: 274
acccuagggu ggggcuggag gugggggcuga ggcugagucu uccucccuu ccucccugcc    60 cag                                                                  63

<210> SEQ ID NO 275
<211> LENGTH: 79
<212> TYPE: RNA
<213> ORGANISM: Homo sapiens

<400> SEQUENCE: 275
cucgaggugc uggggggacgc gugagcgcga gccgcuuccu cacggcucgg ccgcggcgcg   60
uagcccccgc cacaucggg                                                 79

<210> SEQ ID NO 276
<211> LENGTH: 98
<212> TYPE: RNA
<213> ORGANISM: Homo sapiens

<400> SEQUENCE: 276
cuuggucaau aggaaagagg ugggaccucc uggcuuuucc ucugcagcau ggcucggacc    60
uagugcaaug uuuaagcucc ccucucuuuc cuguucag                            98

<210> SEQ ID NO 277
<211> LENGTH: 62
<212> TYPE: RNA
<213> ORGANISM: Homo sapiens

<400> SEQUENCE: 277
ccuucugcgg cagagcuggg gucaccagcc cucauguacu ugugacuucu ccccugccac    60
ag                                                                   62

<210> SEQ ID NO 278
<211> LENGTH: 65
<212> TYPE: RNA
<213> ORGANISM: Homo sapiens

<400> SEQUENCE: 278
gagaaugggg ggacagaugg agaggacaca ggcuggcacu gaggucccu ccacuuuccu     60 ccuag                                                                65
```

<210> SEQ ID NO 279
<211> LENGTH: 68
<212> TYPE: RNA
<213> ORGANISM: Homo sapiens

<400> SEQUENCE: 279
cguggugagg auauggcagg gaaggggagu ucccucuau uccuucccc ccaguaaucu      60 ucaucaug                                                             68

<210> SEQ ID NO 280
<211> LENGTH: 103
<212> TYPE: RNA
<213> ORGANISM: Homo sapiens

<400> SEQUENCE: 280
gugucggcug uggcgugacu gucccucugu gucccccacu aggcccacug cucaguggag    60
cguggaggac gaggaggagg ccguccacga gcaaugccag cau                     103

<210> SEQ ID NO 281
<211> LENGTH: 87
<212> TYPE: RNA
<213> ORGANISM: Homo sapiens

<400> SEQUENCE: 281
cccucaucuc ugggcagggg cuuauuguag gagucucuga agagagcugu ggacugaccu    60
gcuuuaaccc uuccccaggu ucccauu                                        87

<210> SEQ ID NO 282
<211> LENGTH: 83
<212> TYPE: RNA
<213> ORGANISM: Homo sapiens

<400> SEQUENCE: 282
aauagagggu gcacaggcac gggagcucag gugaggcagg gagcugagcu caccugaccu    60
cccaugccug ugcacccucu auu                                            83

<210> SEQ ID NO 283
<211> LENGTH: 82
<212> TYPE: RNA
<213> ORGANISM: Homo sapiens

<400> SEQUENCE: 283
ugugggcagg gcccuggga gcugaggcuc uggggguggc cggggcugac ccugggccuc     60
ugcuccccag ugucugaccg cg                                             82

<210> SEQ ID NO 284
<211> LENGTH: 98
<212> TYPE: RNA
<213> ORGANISM: Homo sapiens

<400> SEQUENCE: 284 uucucaccc cgccugacac gggcgacagc ugcggcccgc uguuucacu cgggccgagu      60 gcgucuccug ucaggcaagg gagagcagag ccccccug                            98

<210> SEQ ID NO 285
<211> LENGTH: 49
<212> TYPE: RNA
<213> ORGANISM: Homo sapiens

```
<400> SEQUENCE: 285
uucccagcca acgcaccaaa aaugauaugg gucuguuguc uggagaaac      49

<210> SEQ ID NO 286
<211> LENGTH: 69
<212> TYPE: RNA
<213> ORGANISM: Homo sapiens

<400> SEQUENCE: 286
ggcccucggg ccuggggbuug ggggagcucu guccugucuc acucauugcu ccuccccugc  60
cuggcccag                                                          69

<210> SEQ ID NO 287
<211> LENGTH: 80
<212> TYPE: RNA
<213> ORGANISM: Homo sapiens

<400> SEQUENCE: 287
cgugugagcc cgcccugugc ccggcccacu ucugcuuccu cuuagcgcag gaggggvccc  60
gcacugggag gggcccucac                                              80

<210> SEQ ID NO 288
<211> LENGTH: 73
<212> TYPE: RNA
<213> ORGANISM: Homo sapiens

<400> SEQUENCE: 288
cggcgacggc ggggugggug aggucgggcc ccaagacucg ggguuugccg ggcgccucag  60
uucaccgcgg ccg                                                     73

<210> SEQ ID NO 289
<211> LENGTH: 74
<212> TYPE: RNA
<213> ORGANISM: Homo sapiens

<400> SEQUENCE: 289
ccugcaggag gcagugggcg agcaggcggg gcagcccaau gccaugggcc ugaucucacc  60
gcugccuccu uccc                                                    74

<210> SEQ ID NO 290
<211> LENGTH: 70
<212> TYPE: RNA
<213> ORGANISM: Homo sapiens

<400> SEQUENCE: 290
gucccugggg gcugggaugg gccaugguigu gcucugaucc cccugugguc ucuuggcccc  60
caggaacucc                                                         70

<210> SEQ ID NO 291
<211> LENGTH: 73
<212> TYPE: RNA
<213> ORGANISM: Homo sapiens

<400> SEQUENCE: 291
gugggcgggg gcaggugugu ggugggluggu ggccugcggu gagcagggcc cucacaccug  60
ccucgccccc cag                                                     73

<210> SEQ ID NO 292
<211> LENGTH: 77
```

-continued

```
<212> TYPE: RNA
<213> ORGANISM: Homo sapiens

<400> SEQUENCE: 292
gaguugggag guucccucuc caaauguguc uugauccccc accccaagac acauuuggag      60
agggacccuc ccaacuc                                                    77

<210> SEQ ID NO 293
<211> LENGTH: 63
<212> TYPE: RNA
<213> ORGANISM: Homo sapiens

<400> SEQUENCE: 293
cuugcccggg agaaggaggu ggccuggaga gcugcugucu ccagccgccg ccugucucca      60
cag                                                                   63

<210> SEQ ID NO 294
<211> LENGTH: 79
<212> TYPE: RNA
<213> ORGANISM: Homo sapiens

<400> SEQUENCE: 294 gugaggsuggg ggccagcagg gagugggcug ggcugggcug ggccaaggua caaggccuca     60
```
(Note: reading as)
```
gugaggsuggg ggccagcagg gagugggcug ggcugggcug ggccaaggua caaggccuca     60
cccugcaucc cgcacccag                                                  79

<210> SEQ ID NO 295
<211> LENGTH: 63
<212> TYPE: RNA
<213> ORGANISM: Homo sapiens

<400> SEQUENCE: 295
gagucgagga cugguggaag ggccuuuccc cucagaccaa ggcccuggcc ccagcuucuu      60
cuc                                                                   63

<210> SEQ ID NO 296
<211> LENGTH: 60
<212> TYPE: RNA
<213> ORGANISM: Homo sapiens

<400> SEQUENCE: 296
aggccuaggg gguggcaggc uggccaucag ugugggcuaa cccuguccuc ucccucccag      60

<210> SEQ ID NO 297
<211> LENGTH: 59
<212> TYPE: RNA
<213> ORGANISM: Homo sapiens

<400> SEQUENCE: 297
cuccagggag acagugugug aggccucuug ccauggccuc ccugcccgcc ucucugcag       59

<210> SEQ ID NO 298
<211> LENGTH: 73
<212> TYPE: RNA
<213> ORGANISM: Homo sapiens

<400> SEQUENCE: 298
ggccggcugg gguuccuggg gaugggauuu gcuuccuguc acaaaucaca uugccaggga      60
uuuccaaccg acc                                                        73

<210> SEQ ID NO 299
```

```
<211> LENGTH: 84
<212> TYPE: RNA
<213> ORGANISM: Homo sapiens

<400> SEQUENCE: 299
ggcccctccu ucucagcccc agcucccgcu caccccugcc acgucaaagg aggcagaagg      60
ggaguuggga gcagagaggg gacc                                            84

<210> SEQ ID NO 300
<211> LENGTH: 81
<212> TYPE: RNA
<213> ORGANISM: Homo sapiens

<400> SEQUENCE: 300
aguuggugag ggagccauga gauaagagca ccuccuagag aauguugaac uaaaggugcc      60
cucucuggcu ccuccccaaa g                                               81

<210> SEQ ID NO 301
<211> LENGTH: 97
<212> TYPE: RNA
<213> ORGANISM: Homo sapiens

<400> SEQUENCE: 301
cccgggaccu ugguccaggc gcuggucugc guggugcucg gguggauaag ucgaucuga       60 gcaccacaca ggccgggcgc cgggaccaag ggggcuc                              97

<210> SEQ ID NO 302
<211> LENGTH: 70
<212> TYPE: RNA
<213> ORGANISM: Homo sapiens

<400> SEQUENCE: 302
cucgggcccg accgcgccgg cccgcaccuc ccggcccgga gcugcgggcu gcggucaggg      60
cgaucccggg                                                            70

<210> SEQ ID NO 303
<211> LENGTH: 66
<212> TYPE: RNA
<213> ORGANISM: Homo sapiens

<400> SEQUENCE: 303 ccgaguggg cggggcaggu cccugcaggg acugugacac ugaaggaccu gcaccuucgc       60
ccacag                                                                66

<210> SEQ ID NO 304
<211> LENGTH: 67
<212> TYPE: RNA
<213> ORGANISM: Homo sapiens

<400> SEQUENCE: 304
gcgcccuccc ucucucccg gugugcaaau gugugugugc ggguguaugc cggacaagag       60
ggaggug                                                               67

<210> SEQ ID NO 305
<211> LENGTH: 70
<212> TYPE: RNA
<213> ORGANISM: Homo sapiens

<400> SEQUENCE: 305
aaaagccugu cccuaaguce cucccagccu uccagaguug gugccaggaa ggauuuaggg      60
```

```
acaggcuuug                                                      70

<210> SEQ ID NO 306
<211> LENGTH: 94
<212> TYPE: RNA
<213> ORGANISM: Homo sapiens

<400> SEQUENCE: 306
auaaaggaag uuaggcugag gggcagagag cgagacuuuu cuauuuccca aaagcucggu    60
cugaggcccc ucagucuugc uuccuaaccc gcgc                               94

<210> SEQ ID NO 307
<211> LENGTH: 66
<212> TYPE: RNA
<213> ORGANISM: Homo sapiens

<400> SEQUENCE: 307
gggaggaggg aggagauggg ccaaguuccc ucuggcugga acgcccuucc cccccuucuu    60
caccug                                                              66

<210> SEQ ID NO 308
<211> LENGTH: 57
<212> TYPE: RNA
<213> ORGANISM: Homo sapiens

<400> SEQUENCE: 308
cauuggaggg uguggaagac aucugggcca acucugaucu cuucaucuac cccccag       57

<210> SEQ ID NO 309
<211> LENGTH: 79
<212> TYPE: RNA
<213> ORGANISM: Homo sapiens

<400> SEQUENCE: 309
gugcagaucc uugggagccc uguuagacuc uggauuuuac acuuggagug aacgggcgcc    60
aucccgaggc uuugcacag                                                79

<210> SEQ ID NO 310
<211> LENGTH: 90
<212> TYPE: RNA
<213> ORGANISM: Homo sapiens

<400> SEQUENCE: 310 cgggcgggc ggguccggcc gccuccgagc ccggccggca gccccggcc uuaaagcgcg      60 ggcuguccgg aggggucggc uuucccaccg                                    90

<210> SEQ ID NO 311
<211> LENGTH: 72
<212> TYPE: RNA
<213> ORGANISM: Homo sapiens

<400> SEQUENCE: 311
augagcgggu gggagcagau cuuauugaga guuccuucuc cugcuccuga uugucuuccc    60
ccacccucac ag                                                       72

<210> SEQ ID NO 312
<211> LENGTH: 59
<212> TYPE: RNA
<213> ORGANISM: Homo sapiens
```

<400> SEQUENCE: 312
guccaggcag gagccggacu ggaccucagg gaagaggcug acccggcccc ucuugcggc    59

<210> SEQ ID NO 313
<211> LENGTH: 64
<212> TYPE: RNA
<213> ORGANISM: Homo sapiens

<400> SEQUENCE: 313
gagcucuggg aggggcuggg uuuggcagga caguuccaa gcccugucuc ucccaucuu    60 ccag                                                               64

<210> SEQ ID NO 314
<211> LENGTH: 82
<212> TYPE: RNA
<213> ORGANISM: Homo sapiens

<400> SEQUENCE: 314
gcuacgggga gcggggagga agugggcgcu gcuucugcgu uaucuggaag gagcagccca   60
cuccuguccu gggcucugug gu                                            82

<210> SEQ ID NO 315
<211> LENGTH: 50
<212> TYPE: RNA
<213> ORGANISM: Homo sapiens

<400> SEQUENCE: 315
acccgggcgu ggugguggg gugggugccu guaauuccag cuaguuggga              50

<210> SEQ ID NO 316
<211> LENGTH: 61
<212> TYPE: RNA
<213> ORGANISM: Homo sapiens

<400> SEQUENCE: 316
gagggcagcg uggguguggc ggaggcaggc gugaccguuu gccgcccucu cgcugcucua   60
g                                                                  61

<210> SEQ ID NO 317
<211> LENGTH: 73
<212> TYPE: RNA
<213> ORGANISM: Homo sapiens

<400> SEQUENCE: 317
ggcgagggga ggcgcaggcu cggaaaggcg cgcgaggcuc caggcuccuu cccgauccac   60
cgcucuccuc gcu                                                     73

<210> SEQ ID NO 318
<211> LENGTH: 67
<212> TYPE: RNA
<213> ORGANISM: Homo sapiens

<400> SEQUENCE: 318
ggcagccagg gggaugggcg agcuugggcc cauuccuuuc cuuacccuac cccccauccc   60
ccuguag                                                            67

<210> SEQ ID NO 319
<211> LENGTH: 76
<212> TYPE: RNA
<213> ORGANISM: Homo sapiens

<400> SEQUENCE: 319
acugacuuug agucucuccu cagggugcug caggcaaagc uggggaccca gggagagacg    60
uaagugaggg gagaug                                                    76

<210> SEQ ID NO 320
<211> LENGTH: 71
<212> TYPE: RNA
<213> ORGANISM: Homo sapiens

<400> SEQUENCE: 320
ugaccacccc cgggcaaaga ccugcagauc cccuguuaga gacgggccca ggacuuugug    60
cggggugccc a                                                         71

<210> SEQ ID NO 321
<211> LENGTH: 65
<212> TYPE: RNA
<213> ORGANISM: Homo sapiens

<400> SEQUENCE: 321
uucuccuggg gaguggcugg ggagcagaca gacccaaccu caugcucccc ggccucugcc    60
cccag                                                                65

<210> SEQ ID NO 322
<211> LENGTH: 65
<212> TYPE: RNA
<213> ORGANISM: Homo sapiens

<400> SEQUENCE: 322
gggugcucgg ggcaggcggc ugggagcggc ccucacauug auggcuccug ccaccuccuc    60
cgcag                                                                65

<210> SEQ ID NO 323
<211> LENGTH: 67
<212> TYPE: RNA
<213> ORGANISM: Homo sapiens

<400> SEQUENCE: 323
guggcacuca aacugugggg gcacuuucug cucucuggug aaagugccgc caucuuuga    60 guguuac                                                              67

<210> SEQ ID NO 324
<211> LENGTH: 63
<212> TYPE: RNA
<213> ORGANISM: Homo sapiens

<400> SEQUENCE: 324
gagguguagg ggagguuggg ccagggaugc cuucacugug ucucucuggu cuugccaccc    60
cag                                                                  63

<210> SEQ ID NO 325
<211> LENGTH: 72
<212> TYPE: RNA
<213> ORGANISM: Homo sapiens

<400> SEQUENCE: 325
ugugggacug caaaugggag cucagcaccu gccugccacc cacgcagacc agcccugcu    60 cuguucccac ag                                                        72

```
<210> SEQ ID NO 326
<211> LENGTH: 88
<212> TYPE: RNA
<213> ORGANISM: Homo sapiens

<400> SEQUENCE: 326 gugggccag gcggugguug gcacugcugg ggugggcaca gcagccaugc agagcgggca    60
uuugaccccg ugccacccuu uuccccag                                      88

<210> SEQ ID NO 327
<211> LENGTH: 94
<212> TYPE: RNA
<213> ORGANISM: Homo sapiens

<400> SEQUENCE: 327
cgggcagcgg gugccaggca cggugucagc aggcaacaug gccgagaggc cggggccucc    60
gggcggcgcc guguccgcga ccgcguaccc ugac                                94

<210> SEQ ID NO 328
<211> LENGTH: 90
<212> TYPE: RNA
<213> ORGANISM: Homo sapiens

<400> SEQUENCE: 328
ggcgccucug cagcuccggc uccccuggc cucucgggaa cuacaagucc caggggccu      60 ggcggugggc ggcgggcgga agaggcgggg                                     90

<210> SEQ ID NO 329
<211> LENGTH: 70
<212> TYPE: RNA
<213> ORGANISM: Homo sapiens

<400> SEQUENCE: 329 uugguuggg gugucggcc cuggaggggg uuuguuugcu uauucccuc ugugcuucac       60 cccuacccag                                                           70

<210> SEQ ID NO 330
<211> LENGTH: 94
<212> TYPE: RNA
<213> ORGANISM: Homo sapiens

<400> SEQUENCE: 330
aauucagccc ugccacuggc uuaugucaug accuugggcu acucaggcug ucugcacaau    60
gagccaguug gacaggagca gugccacuca acuc                                94

<210> SEQ ID NO 331
<211> LENGTH: 90
<212> TYPE: RNA
<213> ORGANISM: Homo sapiens

<400> SEQUENCE: 331
gugucucucu ggagacccug cagccuuccc acccaccagg gagcuuucca ugggcugugg    60
ggaaggcguc agugucgggu gagggaacac                                     90

<210> SEQ ID NO 332
<211> LENGTH: 80
<212> TYPE: RNA
<213> ORGANISM: Homo sapiens

<400> SEQUENCE: 332
```
gagaggccaa gaccuuggga auggggguaa gggccuucug agcccagguc cgaacucucc    60
auuccucugc agagcgcucu                                                80

<210> SEQ ID NO 333
<211> LENGTH: 77
<212> TYPE: RNA
<213> ORGANISM: Homo sapiens

<400> SEQUENCE: 333
caugagaaau ccugcugguc aaccauagcc cuggucagac ucccggggc ugugauugac     60 cagcaggacu ucucaug                                                   77

<210> SEQ ID NO 334
<211> LENGTH: 80
<212> TYPE: RNA
<213> ORGANISM: Homo sapiens

<400> SEQUENCE: 334
ugagaggccg caccuugccu ugcugcccgg gccgugcacc cgugggcccc agggcgacgc    60 ggcggggcg gcccuagcga                                                 80

<210> SEQ ID NO 335
<211> LENGTH: 118
<212> TYPE: RNA
<213> ORGANISM: Homo sapiens

<400> SEQUENCE: 335
gcaggugaac uggcaggcca ggaagaggag gaagcccugg aggggcugga ggugauggau    60
guuuuccucc gguucucagg gcuccaccuc uuucgggccg uagagccagg gcuggugc     118

<210> SEQ ID NO 336
<211> LENGTH: 69
<212> TYPE: RNA
<213> ORGANISM: Homo sapiens

<400> SEQUENCE: 336
cuuucggcca gcgggacggc auccgaggug ggcuaggcuc gggcccgugg cgggugcggg    60
ggugggagg                                                            69

<210> SEQ ID NO 337
<211> LENGTH: 78
<212> TYPE: RNA
<213> ORGANISM: Homo sapiens

<400> SEQUENCE: 337
ggccucaggc aggcgcaccc gaccacaugc auggcuggug gcggcugca ggggucgggu     60 gggccaggcu gugggcg                                                   78

<210> SEQ ID NO 338
<211> LENGTH: 80
<212> TYPE: RNA
<213> ORGANISM: Homo sapiens

<400> SEQUENCE: 338 gguccggag ccccggcgcg ggcgggguucu gggguguaga cgcugcuggc cagcccgccc    60
cagccgaggu ucucggcacc                                                80

<210> SEQ ID NO 339

```
<211> LENGTH: 66
<212> TYPE: RNA
<213> ORGANISM: Homo sapiens

<400> SEQUENCE: 339
agcagcccuc ggcggcccgg ggggcgggcg gcggugcccg ucccggggcu gcgcgaggca    60
caggcg                                                              66

<210> SEQ ID NO 340
<211> LENGTH: 83
<212> TYPE: RNA
<213> ORGANISM: Homo sapiens

<400> SEQUENCE: 340
ccugcugcag aggugccagc ugcagugggg gaggcacugc cagggcugcc cacucugcuu    60
agccagcagg ugccaagaac agg                                           83

<210> SEQ ID NO 341
<211> LENGTH: 64
<212> TYPE: RNA
<213> ORGANISM: Homo sapiens

<400> SEQUENCE: 341
ucugggcgag ggugggcuc ucagagggc uggcaguacu gcucugaggc cugccucucc     60
ccag                                                                64

<210> SEQ ID NO 342
<211> LENGTH: 98
<212> TYPE: RNA
<213> ORGANISM: Homo sapiens

<400> SEQUENCE: 342
uugggcaagg ugcggggcua gggcuaacag cagucuuacu gaagguuucc uggaaaccac    60
gcacaugcug uugccacuaa ccucaaccuu acucgguc                           98

<210> SEQ ID NO 343
<211> LENGTH: 97
<212> TYPE: RNA
<213> ORGANISM: Homo sapiens

<400> SEQUENCE: 343
aucugaguug ggagggucccc ucccaaaug ugucuugggg uggggauca agacacauuu    60 ggagagggaa ccucccaacu cggccucugc caucauu                            97

<210> SEQ ID NO 344
<211> LENGTH: 72
<212> TYPE: RNA
<213> ORGANISM: Homo sapiens

<400> SEQUENCE: 344
cuugggaaug gcaaggaaac cguuaccauu acugaguuua guaaugguaa ugguucucuu    60
gcuauaccca ga                                                       72

<210> SEQ ID NO 345
<211> LENGTH: 60
<212> TYPE: RNA
<213> ORGANISM: Homo sapiens

<400> SEQUENCE: 345
caaggugggg gagaugggggg uugaacuuca uuucucaugc ucauccccau cuccuuucag   60
```

<210> SEQ ID NO 346
<211> LENGTH: 53
<212> TYPE: RNA
<213> ORGANISM: Homo sapiens

<400> SEQUENCE: 346 ggugggguu ggaggcgugg guuuuagaac cuaucccuuu cuagcccuga gca        53

<210> SEQ ID NO 347
<211> LENGTH: 59
<212> TYPE: RNA
<213> ORGANISM: Homo sapiens

<400> SEQUENCE: 347
ggggccaggc agggaggugg gaccauggg gccuugcugu gugaccaccg uuccugcag   59

<210> SEQ ID NO 348
<211> LENGTH: 67
<212> TYPE: RNA
<213> ORGANISM: Homo sapiens

<400> SEQUENCE: 348
gugggagggg agaggcagca agcacacagg gccugggacu agcaugcuga ccucccuccu   60
gccccag                                                              67

<210> SEQ ID NO 349
<211> LENGTH: 86
<212> TYPE: RNA
<213> ORGANISM: Homo sapiens

<400> SEQUENCE: 349
agcacugccc ccggugaguc agggugggc uggccccug cuucgugccc auccgcgcuc      60
ugacucucug cccaccugca ggagcu                                         86

<210> SEQ ID NO 350
<211> LENGTH: 90
<212> TYPE: RNA
<213> ORGANISM: Homo sapiens

<400> SEQUENCE: 350
aggccucgcu guucucuaug gcuuuuauu ccuaugugau ucuacugcuc acucauauag     60
ggauuggagc cguggcgcac ggcggggaca                                     90

<210> SEQ ID NO 351
<211> LENGTH: 115
<212> TYPE: RNA
<213> ORGANISM: Homo sapiens

<400> SEQUENCE: 351
ggugccgagg gccguccggc auccuaggcg ggucgcugcg guaccucccu ccugucugug    60
gcggugggau cccguggccg uguuuccug guggcccggc cgugccugag guuuc         115

<210> SEQ ID NO 352
<211> LENGTH: 61
<212> TYPE: RNA
<213> ORGANISM: Homo sapiens

<400> SEQUENCE: 352
uggcccaggg aaccaguugg ggcuuccgcu cugcagaggc ucuaacuggc uuucccugca    60
g                                                                         61

<210> SEQ ID NO 353
<211> LENGTH: 65
<212> TYPE: RNA
<213> ORGANISM: Homo sapiens

<400> SEQUENCE: 353
cuccucuggg ggugggggc ugggcguggu ggacagcgau gcaucccucg ccuucucacc          60
cucag                                                                    65

<210> SEQ ID NO 354
<211> LENGTH: 62
<212> TYPE: RNA
<213> ORGANISM: Homo sapiens

<400> SEQUENCE: 354
uggccuaggg ggcggcuugu ggaguguaug ggcugagccu ugcucugcuc ccccgccccc        60
ag                                                                       62

<210> SEQ ID NO 355
<211> LENGTH: 84
<212> TYPE: RNA
<213> ORGANISM: Homo sapiens

<400> SEQUENCE: 355
ugugcagugg aagggggc cgauacacug uacgagagug aguagcaggu cucacaguga          60
accggucucu uucccuacug uguc                                               84

<210> SEQ ID NO 356
<211> LENGTH: 90
<212> TYPE: RNA
<213> ORGANISM: Homo sapiens

<400> SEQUENCE: 356
cugugggcug ggccagggag cagcuggugg gugggaagua agaucugacc uggacuccau        60
cccacccacc cccuguuucc uggcccacag                                         90

<210> SEQ ID NO 357
<211> LENGTH: 47
<212> TYPE: RNA
<213> ORGANISM: Homo sapiens

<400> SEQUENCE: 357
cucggcgcgg ggcgcgggcu ccggguuggg gcgagccaac gccgggg                      47

<210> SEQ ID NO 358
<211> LENGTH: 75
<212> TYPE: RNA
<213> ORGANISM: Homo sapiens

<400> SEQUENCE: 358
ucaucccugg gugggauuu guugcauuac uuguguucua uauaaaguau ugcacuugc          60 ccggccugug gaaga                                                         75

<210> SEQ ID NO 359
<211> LENGTH: 102
<212> TYPE: RNA
<213> ORGANISM: Homo sapiens

<400> SEQUENCE: 359
gcuuaucgag gaaaagaucg aggugggung gggcgggcuc uggggauuug gucucacagc    60
ccggauccca gcccacuuac cuugguuacu cuccuuccuu cu    102

<210> SEQ ID NO 360
<211> LENGTH: 62
<212> TYPE: RNA
<213> ORGANISM: Homo sapiens

<400> SEQUENCE: 360
gcuggggguc ccccgacagu guggagcugg ggccgggucc cggggagggg gguucgggc    60 ag    62

<210> SEQ ID NO 361
<211> LENGTH: 89
<212> TYPE: RNA
<213> ORGANISM: Homo sapiens

<400> SEQUENCE: 361
ucuccguuua ucccaccacu gccaccauua uugcuacugu ucagcaggug cugcuggugg    60
ugauggugau agucuggugg gggcggugg    89

<210> SEQ ID NO 362
<211> LENGTH: 71
<212> TYPE: RNA
<213> ORGANISM: Homo sapiens

<400> SEQUENCE: 362 ggugagugg agccggugggg gcuggaguaa gggcacgccc ggggcugccc caccugcuga    60
ccacccuccc c    71

<210> SEQ ID NO 363
<211> LENGTH: 100
<212> TYPE: RNA
<213> ORGANISM: Homo sapiens

<400> SEQUENCE: 363
agcucagggc ggcugcgcag agggcuggac ucagcggcgg agcuggcugc uggccucagu    60
ucugccucug uccagguccu ugugacccgc ccgcucuccu    100

<210> SEQ ID NO 364
<211> LENGTH: 93
<212> TYPE: RNA
<213> ORGANISM: Homo sapiens

<400> SEQUENCE: 364
uacuuauggc accccacucc ugguaccaua gucauaaguu aggagauguu agagcuguga    60
guaccaugac uuaagugugg uggcuuaaac aug    93

<210> SEQ ID NO 365
<211> LENGTH: 89
<212> TYPE: RNA
<213> ORGANISM: Homo sapiens

<400> SEQUENCE: 365
agccugnggg aaagagaaga gcagggcagg gugaaggccc ggcggagaca cucugcccac    60
cccacacccu gccuaugggc cacacagcu    89

<210> SEQ ID NO 366

```
<211> LENGTH: 98
<212> TYPE: RNA
<213> ORGANISM: Homo sapiens

<400> SEQUENCE: 366
cgagguaggg gcguccuggg cgcgcgggcg ggucccaggc ugggcccuc ggaggccggg    60 ugcucacugc cccguccugg cgcccguguc uccuccag                          98

<210> SEQ ID NO 367
<211> LENGTH: 66
<212> TYPE: RNA
<213> ORGANISM: Homo sapiens

<400> SEQUENCE: 367
acccaggagg cggaggaggu ggagguugca gugagccaag aucguggcac ugacuccagc    60
cugggg                                                               66

<210> SEQ ID NO 368
<211> LENGTH: 52
<212> TYPE: RNA
<213> ORGANISM: Homo sapiens

<400> SEQUENCE: 368
uagccgggcg ugguggugg ggccuguggu cccagcuacu uuggaggcug ag             52

<210> SEQ ID NO 369
<211> LENGTH: 71
<212> TYPE: RNA
<213> ORGANISM: Homo sapiens

<400> SEQUENCE: 369 auggagggg guguggagcc aggggggccca ggucuacagc uucuccccgc ucccugcccc    60
cauacuccca g                                                         71

<210> SEQ ID NO 370
<211> LENGTH: 109
<212> TYPE: RNA
<213> ORGANISM: Homo sapiens

<400> SEQUENCE: 370
ucccgcauuc ccucugcuuu ggucaggugg ugcccuccuu ccauggguag agccagagau    60
gguggguucu ggcuggucag augggagugg acagagaccc ggggucuc                109

<210> SEQ ID NO 371
<211> LENGTH: 82
<212> TYPE: RNA
<213> ORGANISM: Homo sapiens

<400> SEQUENCE: 371
accuguaggu gacagucagg ggcgggugu ggugggcug ggcuggccc ccuccucaca      60 ccucuccugg caucgccccc ag                                             82

<210> SEQ ID NO 372
<211> LENGTH: 51
<212> TYPE: RNA
<213> ORGANISM: Homo sapiens

<400> SEQUENCE: 372
acagaccccg gggagcccgg cggugaagcu ccugguaucc ugggugucug a              51
```

```
<210> SEQ ID NO 373
<211> LENGTH: 62
<212> TYPE: RNA
<213> ORGANISM: Homo sapiens

<400> SEQUENCE: 373
gugggucucg caucaggagg caaggccagg acccgcugac ccaugccucc ugccgcgguc    60
ag                                                                  62

<210> SEQ ID NO 374
<211> LENGTH: 70
<212> TYPE: RNA
<213> ORGANISM: Homo sapiens

<400> SEQUENCE: 374
ggccgcggcg cgcaagaugg cggcgggccc gggcaccgcc ccuuccgccc gccgggcgu     60 cgcacgaggc                                                          70

<210> SEQ ID NO 375
<211> LENGTH: 73
<212> TYPE: RNA
<213> ORGANISM: Homo sapiens

<400> SEQUENCE: 375
aggccaggug gguauggagg agcccucaua uggcaguugg cgagggccca gugagccccu    60
cucugcucuc cag                                                      73

<210> SEQ ID NO 376
<211> LENGTH: 74
<212> TYPE: RNA
<213> ORGANISM: Homo sapiens

<400> SEQUENCE: 376
gggaggaaga agggaggagg agcggagggg cccuugucuu cccagagccu cucccuuccu    60
ccccuccccc uccc                                                     74

<210> SEQ ID NO 377
<211> LENGTH: 75
<212> TYPE: RNA
<213> ORGANISM: Homo sapiens

<400> SEQUENCE: 377
gucagagggg ggaugugcau gcugguuggg gugggcugcc uguggaccaa ucagcgugca    60
cuuccccacc cugaa                                                    75

<210> SEQ ID NO 378
<211> LENGTH: 70
<212> TYPE: RNA
<213> ORGANISM: Homo sapiens

<400> SEQUENCE: 378
acaaauagcu ucagggaguc agggggaggc agaaauagau ggccuucccc ugcugggaag    60 aaagugggguc                                                         70

<210> SEQ ID NO 379
<211> LENGTH: 60
<212> TYPE: RNA
<213> ORGANISM: Homo sapiens

<400> SEQUENCE: 379
```
ugugaaugac cccuuccag agccaaaauc accagggaug gaggagggu cuugguacu                60

<210> SEQ ID NO 380
<211> LENGTH: 81
<212> TYPE: RNA
<213> ORGANISM: Homo sapiens

<400> SEQUENCE: 380
cucccuggga gggcguggau gaugguggga gaggagcccc acuggaag ucgaccccc                60 acaucgcccc accuucccca g                                                       81

<210> SEQ ID NO 381
<211> LENGTH: 61
<212> TYPE: RNA
<213> ORGANISM: Homo sapiens

<400> SEQUENCE: 381
gugcggaacg cuggccgggg cgggagggga agggacgccc ggccggaacg ccgcacucac              60
g                                                                             61

<210> SEQ ID NO 382
<211> LENGTH: 78
<212> TYPE: RNA
<213> ORGANISM: Homo sapiens

<400> SEQUENCE: 382
gggcccagaa gggggcgcag ucacugacgu gaagggacca caucccgcuu caugucagug             60
acuccugccc cuuggucu                                                           78

<210> SEQ ID NO 383
<211> LENGTH: 73
<212> TYPE: RNA
<213> ORGANISM: Homo sapiens

<400> SEQUENCE: 383 accuuccag cucaucccac cucugccacc aaaacacuca ucgcggguc agagggagug                60 ccaaaaaagg uaa                                                                73

<210> SEQ ID NO 384
<211> LENGTH: 63
<212> TYPE: RNA
<213> ORGANISM: Homo sapiens

<400> SEQUENCE: 384
gcaugcuggg cgaggcuggc aucuagcaca ggcgguagau gcuugcucuu gccauugcaa             60
uga                                                                           63

<210> SEQ ID NO 385
<211> LENGTH: 62
<212> TYPE: RNA
<213> ORGANISM: Homo sapiens

<400> SEQUENCE: 385
gaggguggug gaggaagagg gcagcuccca ugacugccug accgccuucu cuccuccccc             60
ag                                                                            62

<210> SEQ ID NO 386
<211> LENGTH: 65
<212> TYPE: RNA
<213> ORGANISM: Homo sapiens

<400> SEQUENCE: 386
gagggcuagg uggggggcuu aagccccga gaugccucac gucuuccccc cucucaccua    60
agcag    65

<210> SEQ ID NO 387
<211> LENGTH: 64
<212> TYPE: RNA
<213> ORGANISM: Homo sapiens

<400> SEQUENCE: 387
gaggcacugg uaggugggg cuccagggcu ccugacaccu ggaccucucc ucccaggcc    60 caca    64

<210> SEQ ID NO 388
<211> LENGTH: 96
<212> TYPE: RNA
<213> ORGANISM: Homo sapiens

<400> SEQUENCE: 388
cgggccccgg gcgggcggga gggacgggac gcggugcagu guuguuuuuu ccccgccaa    60 uauugcacuc gucccggccu ccggccccc cggccc    96

<210> SEQ ID NO 389
<211> LENGTH: 83
<212> TYPE: RNA
<213> ORGANISM: Homo sapiens

<400> SEQUENCE: 389
gugaguggga gccccagugu guggguggg ccauggcggg uggcagccc agccucugag    60 ccuuccucgu cugucugccc cag    83

<210> SEQ ID NO 390
<211> LENGTH: 67
<212> TYPE: RNA
<213> ORGANISM: Homo sapiens

<400> SEQUENCE: 390
cagggaggag gugguacuag gggccagcaa ccugauuacc ccucuuuggc ccuuuguacc    60
ccuccag    67

<210> SEQ ID NO 391
<211> LENGTH: 59
<212> TYPE: RNA
<213> ORGANISM: Homo sapiens

<400> SEQUENCE: 391
cggggucggc ggcgacgugc ucagcuuggc acccaaguuc ugccgcuccg acgcccggc    59

<210> SEQ ID NO 392
<211> LENGTH: 89
<212> TYPE: RNA
<213> ORGANISM: Homo sapiens

<400> SEQUENCE: 392
gccggcgccc gagcucuggc uccgugucuu cacucccgug cuuguccgag gagggaggga    60
gggacggggg cugugcuggg gcagcugga    89

<210> SEQ ID NO 393

```
<211> LENGTH: 70
<212> TYPE: RNA
<213> ORGANISM: Homo sapiens

<400> SEQUENCE: 393
gguuucuccu ugaggagaca uggugggggc cggucaggca gcccaugcca uguguccuca      60
uggagaggcc                                                            70

<210> SEQ ID NO 394
<211> LENGTH: 83
<212> TYPE: RNA
<213> ORGANISM: Homo sapiens

<400> SEQUENCE: 394
gucuacuccc agggugccaa gcuguuucgu guucccuccc uaggggauccc cagguagggg     60 cagcagagga ccugggccug gac                                             83

<210> SEQ ID NO 395
<211> LENGTH: 86
<212> TYPE: RNA
<213> ORGANISM: Homo sapiens

<400> SEQUENCE: 395
ugccagucuc uagguccccug agacccuuua accugugagg acauccaggg ucacagguga    60
gguucuuggg agccuggcgu cuggcc                                          86

<210> SEQ ID NO 396
<211> LENGTH: 97
<212> TYPE: RNA
<213> ORGANISM: Homo sapiens

<400> SEQUENCE: 396
cucaggugcu cuggcugcuu ggguuccugg caugcugauu ugugacuuaa gauuaaaauc     60
acauugccag ggauuaccac gcaaccacga ccuuggc                              97

<210> SEQ ID NO 397
<211> LENGTH: 90
<212> TYPE: RNA
<213> ORGANISM: Homo sapiens

<400> SEQUENCE: 397
ucuaagaaac gcagguggucu cugaagccug caggggcagg ccagcccugc acugaacgcc    60
uguucuugcc aggugggcaga agguugcugc                                     90

<210> SEQ ID NO 398
<211> LENGTH: 80
<212> TYPE: RNA
<213> ORGANISM: Homo sapiens

<400> SEQUENCE: 398
accucuaccu cccggcagag gaggcugcag aggcuggcuu uccaaaacuc ugcccccucc     60
gcugcugcca aguggcuggu                                                 80

<210> SEQ ID NO 399
<211> LENGTH: 89
<212> TYPE: RNA
<213> ORGANISM: Homo sapiens

<400> SEQUENCE: 399
gucagcagug ccuuagcagc acguaaauau uggcguuaag auucuaaaau uaucuccagu     60
```

```
auuaacugug cugcugaagu aagguugac                              89

<210> SEQ ID NO 400
<211> LENGTH: 81
<212> TYPE: RNA
<213> ORGANISM: Homo sapiens

<400> SEQUENCE: 400
guuccacucu agcagcacgu aaauauuggc guagugaaau auauauuaaa caccaauauu    60 acugcugc uuuaguguga c                                        81

<210> SEQ ID NO 401
<211> LENGTH: 73
<212> TYPE: RNA
<213> ORGANISM: Homo sapiens

<400> SEQUENCE: 401 cccaggucu ggugcggaga gggcccacag uggacuuggu gacgcuguau gcccucaccg    60 cucagcccu ggg                                                73

<210> SEQ ID NO 402
<211> LENGTH: 68
<212> TYPE: RNA
<213> ORGANISM: Homo sapiens

<400> SEQUENCE: 402
gcauccugua cugagcugcc ccgaggcccu ucaugcugcc cagcucgggg cagcucagua    60
caggauac                                                     68

<210> SEQ ID NO 403
<211> LENGTH: 64
<212> TYPE: RNA
<213> ORGANISM: Homo sapiens

<400> SEQUENCE: 403
uccuguacug agcugccccg agcugggcag caugaagggc cucggggcag cucaguacag    60
gaug                                                         64

<210> SEQ ID NO 404
<211> LENGTH: 66
<212> TYPE: RNA
<213> ORGANISM: Homo sapiens

<400> SEQUENCE: 404
ucaagacggg gagucaggca guguggaga uggagagccc ugagccucca cucuccuggc    60
ccccag                                                       66

<210> SEQ ID NO 405
<211> LENGTH: 89
<212> TYPE: RNA
<213> ORGANISM: Homo sapiens

<400> SEQUENCE: 405
accuccggga cggcugggcg ccggcggccg ggagauccgc gcuuccugaa ucccggccgg    60
cccgcccggc gcccguccgc ccgcggguc                              89

<210> SEQ ID NO 406
<211> LENGTH: 80
<212> TYPE: RNA
```

<213> ORGANISM: Homo sapiens

<400> SEQUENCE: 406
aggacccuuc cagagggccc ccccucaauc cuguuguucc uaauucagag gguugggugg    60
aggcucuccu gaagggcucu    80

<210> SEQ ID NO 407
<211> LENGTH: 64
<212> TYPE: RNA
<213> ORGANISM: Homo sapiens

<400> SEQUENCE: 407
gaaggcgagg gguagaagag cacaggggu cugauaaacc cuucugccug cauucuacuc    60
ccag    64

<210> SEQ ID NO 408
<211> LENGTH: 70
<212> TYPE: RNA
<213> ORGANISM: Homo sapiens

<400> SEQUENCE: 408
cccugccagu gcuggggcc acaugagugu gcagucaucc acacacaagu ggccccaac    60 acuggcaggg    70

<210> SEQ ID NO 409
<211> LENGTH: 59
<212> TYPE: RNA
<213> ORGANISM: Homo sapiens

<400> SEQUENCE: 409
cugugucggg gagucugggg uccggaauuc uccagagccu cugugcccu acuucccag    59

<210> SEQ ID NO 410
<211> LENGTH: 113
<212> TYPE: RNA
<213> ORGANISM: Homo sapiens

<400> SEQUENCE: 410 gccgggugggg gcgggcggc cucaggaggg gcccagcucc ccuggaugug cugcggugggg    60 gccggagggg cgucacgugc acccaaguga cgccccuucu gauucugccu cag    113

<210> SEQ ID NO 411
<211> LENGTH: 78
<212> TYPE: RNA
<213> ORGANISM: Homo sapiens

<400> SEQUENCE: 411 cuucuacac agguugggau cgguugcaau gcuguguuuc uguauggau ugcacuuguc    60 ccggccuguu gaguuugg    78

<210> SEQ ID NO 412
<211> LENGTH: 76
<212> TYPE: RNA
<213> ORGANISM: Homo sapiens

<400> SEQUENCE: 412
ccgaugccuc gggagucuac agcagggcca ugucugugag ggcccaaggg ugcaugugc    60 ucccagguuu cggugc    76

```
<210> SEQ ID NO 413
<211> LENGTH: 92
<212> TYPE: RNA
<213> ORGANISM: Homo sapiens

<400> SEQUENCE: 413
ccugucccuc cugcccugcg ccugcccagc ccuccugcuc uggugacuga ggaccgccag      60
gcaggggcug gugcugggcg gggggcggcg gg                                   92

<210> SEQ ID NO 414
<211> LENGTH: 113
<212> TYPE: RNA
<213> ORGANISM: Homo sapiens

<400> SEQUENCE: 414
agcaugacag aggagaggug gagguaggcg agaguaauau aauuucucca ggagaacauc      60
ugagagggga aguugcuuuc cugcccuggc ccuuucaccc uccugaguuu ggg            113

<210> SEQ ID NO 415
<211> LENGTH: 93
<212> TYPE: RNA
<213> ORGANISM: Homo sapiens

<400> SEQUENCE: 415
ccuuccggcg ucccaggcgg ggcgccgcgg gaccgcccuc gugucugugg cgugggauc       60 ccgcggccgu guuuuccugg uggcccggcc aug                                  93

<210> SEQ ID NO 416
<211> LENGTH: 80
<212> TYPE: RNA
<213> ORGANISM: Homo sapiens

<400> SEQUENCE: 416
ggcgcgucgc cccccucagu ccaccagagc ccggauaccu cagaaauucg gcucggguc       60 uguggggagc gaaaugcaac                                                 80

<210> SEQ ID NO 417
<211> LENGTH: 66
<212> TYPE: RNA
<213> ORGANISM: Homo sapiens

<400> SEQUENCE: 417
ugacugggga gcagaaggag aacccaagaa aagcugacuu ggaggucccu ccuucugucc      60
ccacag                                                                66

<210> SEQ ID NO 418
<211> LENGTH: 60
<212> TYPE: RNA
<213> ORGANISM: Homo sapiens

<400> SEQUENCE: 418
cgcugggucc gcgcgcccug ggccgggcga uguccgcuug ggggagcgag gggcggggcg      60

<210> SEQ ID NO 419
<211> LENGTH: 76
<212> TYPE: RNA
<213> ORGANISM: Homo sapiens

<400> SEQUENCE: 419
cgcaggccuc uggcggagcc cauuccaugc cagaugcuga gcgauggcug gugugugcug      60
```
cuccacaggc cuggug                                                76

<210> SEQ ID NO 420
<211> LENGTH: 65
<212> TYPE: RNA
<213> ORGANISM: Homo sapiens

<400> SEQUENCE: 420
gcuucuggga ggaggggauc uugggaguga ucccaacagc ugagcucccu gaaucccugu    60
cccag                                                                65

<210> SEQ ID NO 421
<211> LENGTH: 64
<212> TYPE: RNA
<213> ORGANISM: Homo sapiens

<400> SEQUENCE: 421 ggguggggc ggggcggcag gggccucccc cagugccagg ccccauucug cuucucuccc    60
agcu                                                                 64

<210> SEQ ID NO 422
<211> LENGTH: 72
<212> TYPE: RNA
<213> ORGANISM: Homo sapiens

<400> SEQUENCE: 422
cugugcaccu gggggagugc agugauugug gaaugcaaag ucccacaauc acguacucc    60 ccaggugcac ag                                                        72

<210> SEQ ID NO 423
<211> LENGTH: 49
<212> TYPE: RNA
<213> ORGANISM: Homo sapiens

<400> SEQUENCE: 423
ggugaggcgg gggggcgagc ccugaggggc ucucgcuucu ggcgccaag                49

<210> SEQ ID NO 424
<211> LENGTH: 81
<212> TYPE: RNA
<213> ORGANISM: Homo sapiens

<400> SEQUENCE: 424
uacaggugca ggggaacugu agaugaaaag gcuuggcacu ugagggaaag ccucaguuca    60
uucucauuuu gcucaccugu u                                              81

<210> SEQ ID NO 425
<211> LENGTH: 66
<212> TYPE: RNA
<213> ORGANISM: Homo sapiens

<400> SEQUENCE: 425
cagagcaggg cagggaaggu gggagagggg cccagcugac ccuccuguca cccgcuccuu    60
gcccag                                                               66

<210> SEQ ID NO 426
<211> LENGTH: 24
<212> TYPE: RNA
<213> ORGANISM: Homo sapiens

<400> SEQUENCE: 426
gaggcuggga aggcaaaggg acgu                                          24

<210> SEQ ID NO 427
<211> LENGTH: 15
<212> TYPE: RNA
<213> ORGANISM: Homo sapiens

<400> SEQUENCE: 427
gaaggaggcu gggaa                                                    15

<210> SEQ ID NO 428
<211> LENGTH: 22
<212> TYPE: RNA
<213> ORGANISM: Homo sapiens

<400> SEQUENCE: 428
ccgggaacgu cgagacugga gc                                            22

<210> SEQ ID NO 429
<211> LENGTH: 15
<212> TYPE: RNA
<213> ORGANISM: Homo sapiens

<400> SEQUENCE: 429
cgggaacguc gagac                                                    15

<210> SEQ ID NO 430
<211> LENGTH: 26
<212> TYPE: RNA
<213> ORGANISM: Homo sapiens

<400> SEQUENCE: 430
ccuucuggag aggcuuugug cggaua                                        26

<210> SEQ ID NO 431
<211> LENGTH: 15
<212> TYPE: RNA
<213> ORGANISM: Homo sapiens

<400> SEQUENCE: 431
ccuucuggag aggcu                                                    15

<210> SEQ ID NO 432
<211> LENGTH: 23
<212> TYPE: RNA
<213> ORGANISM: Homo sapiens

<400> SEQUENCE: 432
cuccuggggc ccgcacucuc gcu                                           23

<210> SEQ ID NO 433
<211> LENGTH: 18
<212> TYPE: RNA
<213> ORGANISM: Homo sapiens

<400> SEQUENCE: 433
cuccuggggc ccgcacuc                                                 18

<210> SEQ ID NO 434
<211> LENGTH: 23
<212> TYPE: RNA
<213> ORGANISM: Homo sapiens

```
<400> SEQUENCE: 434
agaagaaggc ggucggucug cgg                                    23

<210> SEQ ID NO 435
<211> LENGTH: 21
<212> TYPE: RNA
<213> ORGANISM: Homo sapiens

<400> SEQUENCE: 435
aagaaggcgg ucggucugcg g                                      21

<210> SEQ ID NO 436
<211> LENGTH: 21
<212> TYPE: RNA
<213> ORGANISM: Homo sapiens

<400> SEQUENCE: 436
cccaggcugg agcgagugca g                                      21

<210> SEQ ID NO 437
<211> LENGTH: 15
<212> TYPE: RNA
<213> ORGANISM: Homo sapiens

<400> SEQUENCE: 437
agcucacugc agccu                                             15

<210> SEQ ID NO 438
<211> LENGTH: 22
<212> TYPE: RNA
<213> ORGANISM: Homo sapiens

<400> SEQUENCE: 438
cgcggcgggg acggcgauug gu                                     22

<210> SEQ ID NO 439
<211> LENGTH: 17
<212> TYPE: RNA
<213> ORGANISM: Homo sapiens

<400> SEQUENCE: 439
cggcggggac ggcgauu                                           17

<210> SEQ ID NO 440
<211> LENGTH: 17
<212> TYPE: RNA
<213> ORGANISM: Homo sapiens

<400> SEQUENCE: 440
ggugagcgcu cgcuggc                                           17

<210> SEQ ID NO 441
<211> LENGTH: 15
<212> TYPE: RNA
<213> ORGANISM: Homo sapiens

<400> SEQUENCE: 441
cggugagcgc ucgcu                                             15

<210> SEQ ID NO 442
<211> LENGTH: 18
<212> TYPE: RNA
<213> ORGANISM: Homo sapiens
```

```
<400> SEQUENCE: 442 gguggggcuuc ccggaggg                                              18

<210> SEQ ID NO 443
<211> LENGTH: 15
<212> TYPE: RNA
<213> ORGANISM: Homo sapiens

<400> SEQUENCE: 443 gguggggcuuc ccgga                                                 15

<210> SEQ ID NO 444
<211> LENGTH: 24
<212> TYPE: RNA
<213> ORGANISM: Homo sapiens

<400> SEQUENCE: 444
cugguacagg ccuggggac aggg                                         24

<210> SEQ ID NO 445
<211> LENGTH: 18
<212> TYPE: RNA
<213> ORGANISM: Homo sapiens

<400> SEQUENCE: 445
cugguacagg ccuggggg                                               18

<210> SEQ ID NO 446
<211> LENGTH: 23
<212> TYPE: RNA
<213> ORGANISM: Homo sapiens

<400> SEQUENCE: 446
acaggagugg ggugggaca uaa                                          23

<210> SEQ ID NO 447
<211> LENGTH: 20
<212> TYPE: RNA
<213> ORGANISM: Homo sapiens

<400> SEQUENCE: 447
acaggagugg ggugggaca                                              20

<210> SEQ ID NO 448
<211> LENGTH: 23
<212> TYPE: RNA
<213> ORGANISM: Homo sapiens

<400> SEQUENCE: 448
cuaguggaag aagauggcgg aag                                         23

<210> SEQ ID NO 449
<211> LENGTH: 15
<212> TYPE: RNA
<213> ORGANISM: Homo sapiens

<400> SEQUENCE: 449
uaguggaaga agaug                                                  15

<210> SEQ ID NO 450
<211> LENGTH: 18
<212> TYPE: RNA
```

```
<213> ORGANISM: Homo sapiens

<400> SEQUENCE: 450
ucuagguggg gagacuga                                              18

<210> SEQ ID NO 451
<211> LENGTH: 16
<212> TYPE: RNA
<213> ORGANISM: Homo sapiens

<400> SEQUENCE: 451 gugggagac ugacgg                                                 16

<210> SEQ ID NO 452
<211> LENGTH: 23
<212> TYPE: RNA
<213> ORGANISM: Homo sapiens

<400> SEQUENCE: 452
gggggucccc ggugcucgga ucu                                        23

<210> SEQ ID NO 453
<211> LENGTH: 16
<212> TYPE: RNA
<213> ORGANISM: Homo sapiens

<400> SEQUENCE: 453
ucgggagggg cgggag                                                16

<210> SEQ ID NO 454
<211> LENGTH: 16
<212> TYPE: RNA
<213> ORGANISM: Homo sapiens

<400> SEQUENCE: 454
ugcuggugau gcuuuc                                                16

<210> SEQ ID NO 455
<211> LENGTH: 16
<212> TYPE: RNA
<213> ORGANISM: Homo sapiens

<400> SEQUENCE: 455
ugcuggugau gcuuuc                                                16

<210> SEQ ID NO 456
<211> LENGTH: 23
<212> TYPE: RNA
<213> ORGANISM: Homo sapiens

<400> SEQUENCE: 456
ggcuacaaca caggacccgg gcg                                        23

<210> SEQ ID NO 457
<211> LENGTH: 21
<212> TYPE: RNA
<213> ORGANISM: Homo sapiens

<400> SEQUENCE: 457
ggcuacaaca caggacccgg g                                          21

<210> SEQ ID NO 458
<211> LENGTH: 23
```

<212> TYPE: RNA
<213> ORGANISM: Homo sapiens

<400> SEQUENCE: 458
cggggccgua gcacugucug aga                                       23

<210> SEQ ID NO 459
<211> LENGTH: 20
<212> TYPE: RNA
<213> ORGANISM: Homo sapiens

<400> SEQUENCE: 459
cggggccgua gcacugucug                                           20

<210> SEQ ID NO 460
<211> LENGTH: 17
<212> TYPE: RNA
<213> ORGANISM: Homo sapiens

<400> SEQUENCE: 460
uccuagucac ggcacca                                              17

<210> SEQ ID NO 461
<211> LENGTH: 17
<212> TYPE: RNA
<213> ORGANISM: Homo sapiens

<400> SEQUENCE: 461
uccuagucac ggcacca                                              17

<210> SEQ ID NO 462
<211> LENGTH: 19
<212> TYPE: RNA
<213> ORGANISM: Homo sapiens

<400> SEQUENCE: 462
agugggaggc cagggcacg                                            19

<210> SEQ ID NO 463
<211> LENGTH: 15
<212> TYPE: RNA
<213> ORGANISM: Homo sapiens

<400> SEQUENCE: 463 aggggagcu gcagg                                                 15

<210> SEQ ID NO 464
<211> LENGTH: 25
<212> TYPE: RNA
<213> ORGANISM: Homo sapiens

<400> SEQUENCE: 464
uggcggcggu aguuaugggc uucuc                                     25

<210> SEQ ID NO 465
<211> LENGTH: 25
<212> TYPE: RNA
<213> ORGANISM: Homo sapiens

<400> SEQUENCE: 465
uggcggcggu aguuaugggc uucuc                                     25

<210> SEQ ID NO 466

```
<211> LENGTH: 15
<212> TYPE: RNA
<213> ORGANISM: Homo sapiens

<400> SEQUENCE: 466
ugaagcgggg gggcg                                                    15

<210> SEQ ID NO 467
<211> LENGTH: 15
<212> TYPE: RNA
<213> ORGANISM: Homo sapiens

<400> SEQUENCE: 467
ugaagcgggg gggcg                                                    15

<210> SEQ ID NO 468
<211> LENGTH: 21
<212> TYPE: RNA
<213> ORGANISM: Homo sapiens

<400> SEQUENCE: 468
auccaguucu cugaggggc u                                              21

<210> SEQ ID NO 469
<211> LENGTH: 21
<212> TYPE: RNA
<213> ORGANISM: Homo sapiens

<400> SEQUENCE: 469
auccaguucu cugaggggc u                                              21

<210> SEQ ID NO 470
<211> LENGTH: 21
<212> TYPE: RNA
<213> ORGANISM: Homo sapiens

<400> SEQUENCE: 470
cggauccgag ucacggcacc a                                             21

<210> SEQ ID NO 471
<211> LENGTH: 15
<212> TYPE: RNA
<213> ORGANISM: Homo sapiens

<400> SEQUENCE: 471
ggauccgagu cacgg                                                    15

<210> SEQ ID NO 472
<211> LENGTH: 25
<212> TYPE: RNA
<213> ORGANISM: Homo sapiens

<400> SEQUENCE: 472
uucugggccc gcggcgggcg ugggg                                         25

<210> SEQ ID NO 473
<211> LENGTH: 15
<212> TYPE: RNA
<213> ORGANISM: Homo sapiens

<400> SEQUENCE: 473
cgcggcgggc guggg                                                    15
```

```
<210> SEQ ID NO 474
<211> LENGTH: 23
<212> TYPE: RNA
<213> ORGANISM: Homo sapiens

<400> SEQUENCE: 474
agggucgggg cagggagggc agg                                              23

<210> SEQ ID NO 475
<211> LENGTH: 15
<212> TYPE: RNA
<213> ORGANISM: Homo sapiens

<400> SEQUENCE: 475
gggagaaggg ucggg                                                       15

<210> SEQ ID NO 476
<211> LENGTH: 23
<212> TYPE: RNA
<213> ORGANISM: Homo sapiens

<400> SEQUENCE: 476
ugaggauaug gcagggaagg gga                                              23

<210> SEQ ID NO 477
<211> LENGTH: 19
<212> TYPE: RNA
<213> ORGANISM: Homo sapiens

<400> SEQUENCE: 477
ugaggauaug gcagggaag                                                   19

<210> SEQ ID NO 478
<211> LENGTH: 25
<212> TYPE: RNA
<213> ORGANISM: Homo sapiens

<400> SEQUENCE: 478
ugggcagggg cuuauuguag gaguc                                            25

<210> SEQ ID NO 479
<211> LENGTH: 19
<212> TYPE: RNA
<213> ORGANISM: Homo sapiens

<400> SEQUENCE: 479
ugggcagggg cuuauugua                                                   19

<210> SEQ ID NO 480
<211> LENGTH: 22
<212> TYPE: RNA
<213> ORGANISM: Homo sapiens

<400> SEQUENCE: 480
caggcacggg agcucaggug ag                                               22

<210> SEQ ID NO 481
<211> LENGTH: 17
<212> TYPE: RNA
<213> ORGANISM: Homo sapiens

<400> SEQUENCE: 481
caggcacggg agcucag                                                     17
```

```
<210> SEQ ID NO 482
<211> LENGTH: 24
<212> TYPE: RNA
<213> ORGANISM: Homo sapiens

<400> SEQUENCE: 482 ugggggagcug aggcucuggg ggug                                          24

<210> SEQ ID NO 483
<211> LENGTH: 15
<212> TYPE: RNA
<213> ORGANISM: Homo sapiens

<400> SEQUENCE: 483
ggcccugggg agcug                                                     15

<210> SEQ ID NO 484
<211> LENGTH: 23
<212> TYPE: RNA
<213> ORGANISM: Homo sapiens

<400> SEQUENCE: 484 aggaggggguc ccgcacuggg agg                                           23

<210> SEQ ID NO 485
<211> LENGTH: 15
<212> TYPE: RNA
<213> ORGANISM: Homo sapiens

<400> SEQUENCE: 485
ugggaggggc ccuca                                                     15

<210> SEQ ID NO 486
<211> LENGTH: 23
<212> TYPE: RNA
<213> ORGANISM: Homo sapiens

<400> SEQUENCE: 486
ggugggugag gucgggcccc aag                                            23

<210> SEQ ID NO 487
<211> LENGTH: 20
<212> TYPE: RNA
<213> ORGANISM: Homo sapiens

<400> SEQUENCE: 487
cggggugggu gaggucgggc                                                20

<210> SEQ ID NO 488
<211> LENGTH: 21
<212> TYPE: RNA
<213> ORGANISM: Homo sapiens

<400> SEQUENCE: 488
aggaggcagu gggcgagcag g                                              21

<210> SEQ ID NO 489
<211> LENGTH: 21
<212> TYPE: RNA
<213> ORGANISM: Homo sapiens

<400> SEQUENCE: 489
aggaggcagu gggcgagcag g                                              21
```

```
<210> SEQ ID NO 490
<211> LENGTH: 22
<212> TYPE: RNA
<213> ORGANISM: Homo sapiens

<400> SEQUENCE: 490
ccucacaccu gccucgcccc cc                                            22

<210> SEQ ID NO 491
<211> LENGTH: 15
<212> TYPE: RNA
<213> ORGANISM: Homo sapiens

<400> SEQUENCE: 491
ucacaccugc cucgc                                                    15

<210> SEQ ID NO 492
<211> LENGTH: 20
<212> TYPE: RNA
<213> ORGANISM: Homo sapiens

<400> SEQUENCE: 492
aagacacauu uggagaggga                                               20

<210> SEQ ID NO 493
<211> LENGTH: 16
<212> TYPE: RNA
<213> ORGANISM: Homo sapiens

<400> SEQUENCE: 493
agacacauuu ggagag                                                   16

<210> SEQ ID NO 494
<211> LENGTH: 23
<212> TYPE: RNA
<213> ORGANISM: Homo sapiens

<400> SEQUENCE: 494
gugggcuggg cugggcuggg cca                                           23

<210> SEQ ID NO 495
<211> LENGTH: 15
<212> TYPE: RNA
<213> ORGANISM: Homo sapiens

<400> SEQUENCE: 495
gggcugggcu gggcu                                                    15

<210> SEQ ID NO 496
<211> LENGTH: 24
<212> TYPE: RNA
<213> ORGANISM: Homo sapiens

<400> SEQUENCE: 496
ucgaggacug guggaagggc cuuu                                          24

<210> SEQ ID NO 497
<211> LENGTH: 16
<212> TYPE: RNA
<213> ORGANISM: Homo sapiens

<400> SEQUENCE: 497
```
ucgaggacug guggaa                                                  16

<210> SEQ ID NO 498
<211> LENGTH: 27
<212> TYPE: RNA
<213> ORGANISM: Homo sapiens

<400> SEQUENCE: 498
aucacauugc cagggauuuc caaccga                                      27

<210> SEQ ID NO 499
<211> LENGTH: 15
<212> TYPE: RNA
<213> ORGANISM: Homo sapiens

<400> SEQUENCE: 499
aaucacauug ccagg                                                   15

<210> SEQ ID NO 500
<211> LENGTH: 22
<212> TYPE: RNA
<213> ORGANISM: Homo sapiens

<400> SEQUENCE: 500
cagaagggga guugggagca ga                                           22

<210> SEQ ID NO 501
<211> LENGTH: 16
<212> TYPE: RNA
<213> ORGANISM: Homo sapiens

<400> SEQUENCE: 501 gaagggagu ugggag                                                   16

<210> SEQ ID NO 502
<211> LENGTH: 25
<212> TYPE: RNA
<213> ORGANISM: Homo sapiens

<400> SEQUENCE: 502
gggggagcca ugagauaaga gcacc                                        25

<210> SEQ ID NO 503
<211> LENGTH: 20
<212> TYPE: RNA
<213> ORGANISM: Homo sapiens

<400> SEQUENCE: 503 uggggagcc augagauaag                                               20

<210> SEQ ID NO 504
<211> LENGTH: 24
<212> TYPE: RNA
<213> ORGANISM: Homo sapiens

<400> SEQUENCE: 504
gcugcgggcu gcggucaggg cgau                                         24

<210> SEQ ID NO 505
<211> LENGTH: 20
<212> TYPE: RNA
<213> ORGANISM: Homo sapiens

<400> SEQUENCE: 505

```
gcugcgggcu gcggucaggg                                              20

<210> SEQ ID NO 506
<211> LENGTH: 20
<212> TYPE: RNA
<213> ORGANISM: Homo sapiens

<400> SEQUENCE: 506
cuccccggug ugcaaaugug                                              20

<210> SEQ ID NO 507
<211> LENGTH: 15
<212> TYPE: RNA
<213> ORGANISM: Homo sapiens

<400> SEQUENCE: 507
gugugcggug uuaug                                                   15

<210> SEQ ID NO 508
<211> LENGTH: 25
<212> TYPE: RNA
<213> ORGANISM: Homo sapiens

<400> SEQUENCE: 508
caggaaggau uuagggacag gcuuu                                        25

<210> SEQ ID NO 509
<211> LENGTH: 19
<212> TYPE: RNA
<213> ORGANISM: Homo sapiens

<400> SEQUENCE: 509
caggaaggau uuagggaca                                               19

<210> SEQ ID NO 510
<211> LENGTH: 30
<212> TYPE: RNA
<213> ORGANISM: Homo sapiens

<400> SEQUENCE: 510
ugaggggcag agagcgagac uuuucuauuu                                   30

<210> SEQ ID NO 511
<211> LENGTH: 15
<212> TYPE: RNA
<213> ORGANISM: Homo sapiens

<400> SEQUENCE: 511
ugaggggcag agagc                                                   15

<210> SEQ ID NO 512
<211> LENGTH: 26
<212> TYPE: RNA
<213> ORGANISM: Homo sapiens

<400> SEQUENCE: 512
aggagggagg agaugggcca aguucc                                       26

<210> SEQ ID NO 513
<211> LENGTH: 15
<212> TYPE: RNA
<213> ORGANISM: Homo sapiens
```

<400> SEQUENCE: 513
gggaggaggg aggag                                                    15

<210> SEQ ID NO 514
<211> LENGTH: 21
<212> TYPE: RNA
<213> ORGANISM: Homo sapiens

<400> SEQUENCE: 514
caacucugau cucuucaucu a                                             21

<210> SEQ ID NO 515
<211> LENGTH: 20
<212> TYPE: RNA
<213> ORGANISM: Homo sapiens

<400> SEQUENCE: 515
ucucuucauc uaccccccag                                               20

<210> SEQ ID NO 516
<211> LENGTH: 27
<212> TYPE: RNA
<213> ORGANISM: Homo sapiens

<400> SEQUENCE: 516
gugaacgggc gccaucccga ggcuuug                                       27

<210> SEQ ID NO 517
<211> LENGTH: 16
<212> TYPE: RNA
<213> ORGANISM: Homo sapiens

<400> SEQUENCE: 517
gugaacgggc gccauc                                                   16

<210> SEQ ID NO 518
<211> LENGTH: 26
<212> TYPE: RNA
<213> ORGANISM: Homo sapiens

<400> SEQUENCE: 518
gcgggcuguc cggaggggguc ggcuuu                                       26

<210> SEQ ID NO 519
<211> LENGTH: 16
<212> TYPE: RNA
<213> ORGANISM: Homo sapiens

<400> SEQUENCE: 519 gcguccgga gggguc                                                    16

<210> SEQ ID NO 520
<211> LENGTH: 24
<212> TYPE: RNA
<213> ORGANISM: Homo sapiens

<400> SEQUENCE: 520
caggcaggag ccggacugga ccuc                                          24

<210> SEQ ID NO 521
<211> LENGTH: 21
<212> TYPE: RNA
<213> ORGANISM: Homo sapiens

<400> SEQUENCE: 521
uccaggcagg agccggacug g                                              21

<210> SEQ ID NO 522
<211> LENGTH: 25
<212> TYPE: RNA
<213> ORGANISM: Homo sapiens

<400> SEQUENCE: 522
agcggggagg aagugggcgc ugcuu                                          25

<210> SEQ ID NO 523
<211> LENGTH: 21
<212> TYPE: RNA
<213> ORGANISM: Homo sapiens

<400> SEQUENCE: 523
agcggggagg aagugggcgc u                                              21

<210> SEQ ID NO 524
<211> LENGTH: 24
<212> TYPE: RNA
<213> ORGANISM: Homo sapiens

<400> SEQUENCE: 524
cgggcguggu gguggggug ggug                                            24

<210> SEQ ID NO 525
<211> LENGTH: 15
<212> TYPE: RNA
<213> ORGANISM: Homo sapiens

<400> SEQUENCE: 525
cgggcguggu ggugg                                                     15

<210> SEQ ID NO 526
<211> LENGTH: 21
<212> TYPE: RNA
<213> ORGANISM: Homo sapiens

<400> SEQUENCE: 526
gagggcagcg ugggugggc g                                               21

<210> SEQ ID NO 527
<211> LENGTH: 21
<212> TYPE: RNA
<213> ORGANISM: Homo sapiens

<400> SEQUENCE: 527
gagggcagcg ugggugggc g                                               21

<210> SEQ ID NO 528
<211> LENGTH: 23
<212> TYPE: RNA
<213> ORGANISM: Homo sapiens

<400> SEQUENCE: 528
ggaggcgcag gcucggaaag gcg                                            23

<210> SEQ ID NO 529
<211> LENGTH: 15
<212> TYPE: RNA

```
<213> ORGANISM: Homo sapiens

<400> SEQUENCE: 529
gcaggcucgg aaagg                                                     15

<210> SEQ ID NO 530
<211> LENGTH: 16
<212> TYPE: RNA
<213> ORGANISM: Homo sapiens

<400> SEQUENCE: 530
ggacccaggg agagac                                                    16

<210> SEQ ID NO 531
<211> LENGTH: 16
<212> TYPE: RNA
<213> ORGANISM: Homo sapiens

<400> SEQUENCE: 531
ggacccaggg agagac                                                    16

<210> SEQ ID NO 532
<211> LENGTH: 22
<212> TYPE: RNA
<213> ORGANISM: Homo sapiens

<400> SEQUENCE: 532
acucaaacug uggggggcacu uu                                            22

<210> SEQ ID NO 533
<211> LENGTH: 19
<212> TYPE: RNA
<213> ORGANISM: Homo sapiens

<400> SEQUENCE: 533
acucaaacug uggggggcac                                                19

<210> SEQ ID NO 534
<211> LENGTH: 22
<212> TYPE: RNA
<213> ORGANISM: Homo sapiens

<400> SEQUENCE: 534
ugugggacug caaaugggag cu                                             22

<210> SEQ ID NO 535
<211> LENGTH: 22
<212> TYPE: RNA
<213> ORGANISM: Homo sapiens

<400> SEQUENCE: 535
ugugggacug caaaugggag cu                                             22

<210> SEQ ID NO 536
<211> LENGTH: 18
<212> TYPE: RNA
<213> ORGANISM: Homo sapiens

<400> SEQUENCE: 536
cuccgggcgg cgccgugu                                                  18

<210> SEQ ID NO 537
<211> LENGTH: 18
```

```
<212> TYPE: RNA
<213> ORGANISM: Homo sapiens

<400> SEQUENCE: 537
cuccgggcgg cgccgugu                                                 18

<210> SEQ ID NO 538
<211> LENGTH: 21
<212> TYPE: RNA
<213> ORGANISM: Homo sapiens

<400> SEQUENCE: 538 cuuccccca guaaucuuca u                                              21

<210> SEQ ID NO 539
<211> LENGTH: 21
<212> TYPE: RNA
<213> ORGANISM: Homo sapiens

<400> SEQUENCE: 539 cuuccccca guaaucuuca u                                              21

<210> SEQ ID NO 540
<211> LENGTH: 16
<212> TYPE: RNA
<213> ORGANISM: Homo sapiens

<400> SEQUENCE: 540
ggcggugggc ggcggg                                                   16

<210> SEQ ID NO 541
<211> LENGTH: 15
<212> TYPE: RNA
<213> ORGANISM: Homo sapiens

<400> SEQUENCE: 541
ggccucucgg gaacu                                                    15

<210> SEQ ID NO 542
<211> LENGTH: 23
<212> TYPE: RNA
<213> ORGANISM: Homo sapiens

<400> SEQUENCE: 542
uggggaaggc gucagugucg ggu                                           23

<210> SEQ ID NO 543
<211> LENGTH: 16
<212> TYPE: RNA
<213> ORGANISM: Homo sapiens

<400> SEQUENCE: 543
uggggaaggc gucagu                                                   16

<210> SEQ ID NO 544
<211> LENGTH: 21
<212> TYPE: RNA
<213> ORGANISM: Homo sapiens

<400> SEQUENCE: 544
ugggaauggg gguaagggcc u                                             21

<210> SEQ ID NO 545
```

-continued

```
<211> LENGTH: 15
<212> TYPE: RNA
<213> ORGANISM: Homo sapiens

<400> SEQUENCE: 545
cuucugagcc caggu                                                      15

<210> SEQ ID NO 546
<211> LENGTH: 20
<212> TYPE: RNA
<213> ORGANISM: Homo sapiens

<400> SEQUENCE: 546
ccccagggcg acgcggcggg                                                 20

<210> SEQ ID NO 547
<211> LENGTH: 15
<212> TYPE: RNA
<213> ORGANISM: Homo sapiens

<400> SEQUENCE: 547
cgcggcgggg gcggc                                                      15

<210> SEQ ID NO 548
<211> LENGTH: 25
<212> TYPE: RNA
<213> ORGANISM: Homo sapiens

<400> SEQUENCE: 548
aggaagcccu ggaggggcug gaggu                                           25

<210> SEQ ID NO 549
<211> LENGTH: 15
<212> TYPE: RNA
<213> ORGANISM: Homo sapiens

<400> SEQUENCE: 549
aggaagagga ggaag                                                      15

<210> SEQ ID NO 550
<211> LENGTH: 19
<212> TYPE: RNA
<213> ORGANISM: Homo sapiens

<400> SEQUENCE: 550
uggcgggugc ggggguggg                                                  19

<210> SEQ ID NO 551
<211> LENGTH: 15
<212> TYPE: RNA
<213> ORGANISM: Homo sapiens

<400> SEQUENCE: 551
uggcgggugc ggggg                                                      15

<210> SEQ ID NO 552
<211> LENGTH: 23
<212> TYPE: RNA
<213> ORGANISM: Homo sapiens

<400> SEQUENCE: 552
gccccggcgc gggcggguuc ugg                                             23
```

-continued

```
<210> SEQ ID NO 553
<211> LENGTH: 16
<212> TYPE: RNA
<213> ORGANISM: Homo sapiens

<400> SEQUENCE: 553
ggagccccgg cgcggg                                                    16

<210> SEQ ID NO 554
<211> LENGTH: 26
<212> TYPE: RNA
<213> ORGANISM: Homo sapiens

<400> SEQUENCE: 554
gucccggggc ugcgcgaggc acaggc                                         26

<210> SEQ ID NO 555
<211> LENGTH: 15
<212> TYPE: RNA
<213> ORGANISM: Homo sapiens

<400> SEQUENCE: 555
ggcccggggg gcggg                                                     15

<210> SEQ ID NO 556
<211> LENGTH: 16
<212> TYPE: RNA
<213> ORGANISM: Homo sapiens

<400> SEQUENCE: 556
agcugcagug ggggag                                                    16

<210> SEQ ID NO 557
<211> LENGTH: 15
<212> TYPE: RNA
<213> ORGANISM: Homo sapiens

<400> SEQUENCE: 557
gcugcagugg gggag                                                     15

<210> SEQ ID NO 558
<211> LENGTH: 15
<212> TYPE: RNA
<213> ORGANISM: Homo sapiens

<400> SEQUENCE: 558
ucugggcgag gggug                                                     15

<210> SEQ ID NO 559
<211> LENGTH: 15
<212> TYPE: RNA
<213> ORGANISM: Homo sapiens

<400> SEQUENCE: 559
ucugggcgag gggug                                                     15

<210> SEQ ID NO 560
<211> LENGTH: 25
<212> TYPE: RNA
<213> ORGANISM: Homo sapiens

<400> SEQUENCE: 560
ugcggggcua gggcuaacag caguc                                          25
```

```
<210> SEQ ID NO 561
<211> LENGTH: 15
<212> TYPE: RNA
<213> ORGANISM: Homo sapiens

<400> SEQUENCE: 561
ugcggggcua gggcu                                                15

<210> SEQ ID NO 562
<211> LENGTH: 24
<212> TYPE: RNA
<213> ORGANISM: Homo sapiens

<400> SEQUENCE: 562
agacacauuu ggagagggaa ccuc                                      24

<210> SEQ ID NO 563
<211> LENGTH: 16
<212> TYPE: RNA
<213> ORGANISM: Homo sapiens

<400> SEQUENCE: 563
agacacauuu ggagag                                               16

<210> SEQ ID NO 564
<211> LENGTH: 27
<212> TYPE: RNA
<213> ORGANISM: Homo sapiens

<400> SEQUENCE: 564
aaaccguuac cauuacugag uuuagua                                   27

<210> SEQ ID NO 565
<211> LENGTH: 15
<212> TYPE: RNA
<213> ORGANISM: Homo sapiens

<400> SEQUENCE: 565
gaaaccguua ccauu                                                15

<210> SEQ ID NO 566
<211> LENGTH: 21
<212> TYPE: RNA
<213> ORGANISM: Homo sapiens

<400> SEQUENCE: 566
guuggaggcg uggguuuuag a                                         21

<210> SEQ ID NO 567
<211> LENGTH: 15
<212> TYPE: RNA
<213> ORGANISM: Homo sapiens

<400> SEQUENCE: 567
guuggaggcg ugggu                                                15

<210> SEQ ID NO 568
<211> LENGTH: 22
<212> TYPE: RNA
<213> ORGANISM: Homo sapiens

<400> SEQUENCE: 568 ugggaggggga gaggcagcaa gc                                       22
```

```
<210> SEQ ID NO 569
<211> LENGTH: 22
<212> TYPE: RNA
<213> ORGANISM: Homo sapiens

<400> SEQUENCE: 569 ugggaggga gaggcagcaa gc                                          22

<210> SEQ ID NO 570
<211> LENGTH: 21
<212> TYPE: RNA
<213> ORGANISM: Homo sapiens

<400> SEQUENCE: 570
gugagucagg gugggcugg c                                           21

<210> SEQ ID NO 571
<211> LENGTH: 21
<212> TYPE: RNA
<213> ORGANISM: Homo sapiens

<400> SEQUENCE: 571
gugagucagg gugggcugg c                                           21

<210> SEQ ID NO 572
<211> LENGTH: 22
<212> TYPE: RNA
<213> ORGANISM: Homo sapiens

<400> SEQUENCE: 572
auauagggau uggagccgug gc                                         22

<210> SEQ ID NO 573
<211> LENGTH: 20
<212> TYPE: RNA
<213> ORGANISM: Homo sapiens

<400> SEQUENCE: 573
auauagggau uggagccgug                                            20

<210> SEQ ID NO 574
<211> LENGTH: 23
<212> TYPE: RNA
<213> ORGANISM: Homo sapiens

<400> SEQUENCE: 574
ggcccggccg ugccugaggu uuc                                        23

<210> SEQ ID NO 575
<211> LENGTH: 15
<212> TYPE: RNA
<213> ORGANISM: Homo sapiens

<400> SEQUENCE: 575
ggcgguggga ucccg                                                 15

<210> SEQ ID NO 576
<211> LENGTH: 23
<212> TYPE: RNA
<213> ORGANISM: Homo sapiens

<400> SEQUENCE: 576
```

| | |
|---|---|
| gggggccgau acacuguacg aga | 23 |

<210> SEQ ID NO 577
<211> LENGTH: 20
<212> TYPE: RNA
<213> ORGANISM: Homo sapiens

<400> SEQUENCE: 577

| | |
|---|---|
| gggggccgau acacuguacg | 20 |

<210> SEQ ID NO 578
<211> LENGTH: 25
<212> TYPE: RNA
<213> ORGANISM: Homo sapiens

<400> SEQUENCE: 578

| | |
|---|---|
| cugggccagg gagcagcugg ugggu | 25 |

<210> SEQ ID NO 579
<211> LENGTH: 20
<212> TYPE: RNA
<213> ORGANISM: Homo sapiens

<400> SEQUENCE: 579

| | |
|---|---|
| ugggccaggg agcagcuggu | 20 |

<210> SEQ ID NO 580
<211> LENGTH: 25
<212> TYPE: RNA
<213> ORGANISM: Homo sapiens

<400> SEQUENCE: 580

| | |
|---|---|
| ggguggggau uuguugcauu acuug | 25 |

<210> SEQ ID NO 581
<211> LENGTH: 20
<212> TYPE: RNA
<213> ORGANISM: Homo sapiens

<400> SEQUENCE: 581

| | |
|---|---|
| ggguggggau uuguugcauu | 20 |

<210> SEQ ID NO 582
<211> LENGTH: 19
<212> TYPE: RNA
<213> ORGANISM: Homo sapiens

<400> SEQUENCE: 582

| | |
|---|---|
| guggguuggg gcgggcucu | 19 |

<210> SEQ ID NO 583
<211> LENGTH: 19
<212> TYPE: RNA
<213> ORGANISM: Homo sapiens

<400> SEQUENCE: 583

| | |
|---|---|
| guggguuggg gcgggcucu | 19 |

<210> SEQ ID NO 584
<211> LENGTH: 16
<212> TYPE: RNA
<213> ORGANISM: Homo sapiens

<400> SEQUENCE: 584

```
cuggggguee cccgac                                                    16

<210> SEQ ID NO 585
<211> LENGTH: 15
<212> TYPE: RNA
<213> ORGANISM: Homo sapiens

<400> SEQUENCE: 585
guguggagcu ggggc                                                     15

<210> SEQ ID NO 586
<211> LENGTH: 20
<212> TYPE: RNA
<213> ORGANISM: Homo sapiens

<400> SEQUENCE: 586
aucccaccac ugccaccauu                                                20

<210> SEQ ID NO 587
<211> LENGTH: 15
<212> TYPE: RNA
<213> ORGANISM: Homo sapiens

<400> SEQUENCE: 587
aucccaccac ugcca                                                     15

<210> SEQ ID NO 588
<211> LENGTH: 24
<212> TYPE: RNA
<213> ORGANISM: Homo sapiens

<400> SEQUENCE: 588
gugaguggga gccgguggg cugg                                            24

<210> SEQ ID NO 589
<211> LENGTH: 15
<212> TYPE: RNA
<213> ORGANISM: Homo sapiens

<400> SEQUENCE: 589
ggggcuggag uaagg                                                     15

<210> SEQ ID NO 590
<211> LENGTH: 23
<212> TYPE: RNA
<213> ORGANISM: Homo sapiens

<400> SEQUENCE: 590
caccuugccu ugcugcccgg gcc                                            23

<210> SEQ ID NO 591
<211> LENGTH: 22
<212> TYPE: RNA
<213> ORGANISM: Homo sapiens

<400> SEQUENCE: 591
caccuugccu ugcugcccgg gc                                             22

<210> SEQ ID NO 592
<211> LENGTH: 26
<212> TYPE: RNA
<213> ORGANISM: Homo sapiens
```

```
<400> SEQUENCE: 592
agggcuggac ucagcggcgg agcugg                                          26

<210> SEQ ID NO 593
<211> LENGTH: 17
<212> TYPE: RNA
<213> ORGANISM: Homo sapiens

<400> SEQUENCE: 593
gcggcggagc uggcugc                                                    17

<210> SEQ ID NO 594
<211> LENGTH: 22
<212> TYPE: RNA
<213> ORGANISM: Homo sapiens

<400> SEQUENCE: 594
accccacucc ugguaccaua gu                                              22

<210> SEQ ID NO 595
<211> LENGTH: 15
<212> TYPE: RNA
<213> ORGANISM: Homo sapiens

<400> SEQUENCE: 595
accccacucc uggua                                                      15

<210> SEQ ID NO 596
<211> LENGTH: 16
<212> TYPE: RNA
<213> ORGANISM: Homo sapiens

<400> SEQUENCE: 596
gugaaggccc ggcgga                                                     16

<210> SEQ ID NO 597
<211> LENGTH: 15
<212> TYPE: RNA
<213> ORGANISM: Homo sapiens

<400> SEQUENCE: 597
gugaaggccc ggcgg                                                      15

<210> SEQ ID NO 598
<211> LENGTH: 23
<212> TYPE: RNA
<213> ORGANISM: Homo sapiens

<400> SEQUENCE: 598
ccaggaggcg gaggaggugg agg                                             23

<210> SEQ ID NO 599
<211> LENGTH: 15
<212> TYPE: RNA
<213> ORGANISM: Homo sapiens

<400> SEQUENCE: 599
acccaggagg cggag                                                      15

<210> SEQ ID NO 600
<211> LENGTH: 21
<212> TYPE: RNA
<213> ORGANISM: Homo sapiens
```

```
<400> SEQUENCE: 600
gccgggcgug guggugggg c                                              21

<210> SEQ ID NO 601
<211> LENGTH: 15
<212> TYPE: RNA
<213> ORGANISM: Homo sapiens

<400> SEQUENCE: 601
uagccgggcg uggug                                                    15

<210> SEQ ID NO 602
<211> LENGTH: 20
<212> TYPE: RNA
<213> ORGANISM: Homo sapiens

<400> SEQUENCE: 602
ggcuggucag augggagugg                                               20

<210> SEQ ID NO 603
<211> LENGTH: 20
<212> TYPE: RNA
<213> ORGANISM: Homo sapiens

<400> SEQUENCE: 603
ggcuggucag augggagugg                                               20

<210> SEQ ID NO 604
<211> LENGTH: 20
<212> TYPE: RNA
<213> ORGANISM: Homo sapiens

<400> SEQUENCE: 604
ccccggggag cccggcggug                                               20

<210> SEQ ID NO 605
<211> LENGTH: 15
<212> TYPE: RNA
<213> ORGANISM: Homo sapiens

<400> SEQUENCE: 605
accccgggga gcccg                                                    15

<210> SEQ ID NO 606
<211> LENGTH: 15
<212> TYPE: RNA
<213> ORGANISM: Homo sapiens

<400> SEQUENCE: 606
ggcggcgggc ccggg                                                    15

<210> SEQ ID NO 607
<211> LENGTH: 15
<212> TYPE: RNA
<213> ORGANISM: Homo sapiens

<400> SEQUENCE: 607
ggcggcgggc ccggg                                                    15

<210> SEQ ID NO 608
<211> LENGTH: 23
<212> TYPE: RNA
```

<213> ORGANISM: Homo sapiens

<400> SEQUENCE: 608
cagcccgccc cagccgaggu ucu                                          23

<210> SEQ ID NO 609
<211> LENGTH: 17
<212> TYPE: RNA
<213> ORGANISM: Homo sapiens

<400> SEQUENCE: 609
agcccgcccc agccgag                                                 17

<210> SEQ ID NO 610
<211> LENGTH: 23
<212> TYPE: RNA
<213> ORGANISM: Homo sapiens

<400> SEQUENCE: 610
aagggaggag gagcggaggg gcc                                          23

<210> SEQ ID NO 611
<211> LENGTH: 15
<212> TYPE: RNA
<213> ORGANISM: Homo sapiens

<400> SEQUENCE: 611
gggaggagga gcgga                                                   15

<210> SEQ ID NO 612
<211> LENGTH: 23
<212> TYPE: RNA
<213> ORGANISM: Homo sapiens

<400> SEQUENCE: 612 gggggggaugu gcaugcuggu ugg                                         23

<210> SEQ ID NO 613
<211> LENGTH: 15
<212> TYPE: RNA
<213> ORGANISM: Homo sapiens

<400> SEQUENCE: 613
aucagcgugc acuuc                                                   15

<210> SEQ ID NO 614
<211> LENGTH: 20
<212> TYPE: RNA
<213> ORGANISM: Homo sapiens

<400> SEQUENCE: 614
aucccaccuc ugccaccaaa                                              20

<210> SEQ ID NO 615
<211> LENGTH: 15
<212> TYPE: RNA
<213> ORGANISM: Homo sapiens

<400> SEQUENCE: 615
aucccaccuc ugcca                                                   15

<210> SEQ ID NO 616
<211> LENGTH: 19

```
<212> TYPE: RNA
<213> ORGANISM: Homo sapiens

<400> SEQUENCE: 616
gcugggcgag gcuggcauc                                               19

<210> SEQ ID NO 617
<211> LENGTH: 17
<212> TYPE: RNA
<213> ORGANISM: Homo sapiens

<400> SEQUENCE: 617
gcugggcgag gcuggca                                                 17

<210> SEQ ID NO 618
<211> LENGTH: 26
<212> TYPE: RNA
<213> ORGANISM: Homo sapiens

<400> SEQUENCE: 618
agggacggga cgcggugcag uguugu                                       26

<210> SEQ ID NO 619
<211> LENGTH: 15
<212> TYPE: RNA
<213> ORGANISM: Homo sapiens

<400> SEQUENCE: 619
ggcgggcggg aggga                                                   15

<210> SEQ ID NO 620
<211> LENGTH: 23
<212> TYPE: RNA
<213> ORGANISM: Homo sapiens

<400> SEQUENCE: 620
gagggaggga cggggcugu gcu                                           23

<210> SEQ ID NO 621
<211> LENGTH: 15
<212> TYPE: RNA
<213> ORGANISM: Homo sapiens

<400> SEQUENCE: 621
gaggagggag ggagg                                                   15

<210> SEQ ID NO 622
<211> LENGTH: 21
<212> TYPE: RNA
<213> ORGANISM: Homo sapiens

<400> SEQUENCE: 622
uugaggagac auggugggg c                                             21

<210> SEQ ID NO 623
<211> LENGTH: 15
<212> TYPE: RNA
<213> ORGANISM: Homo sapiens

<400> SEQUENCE: 623
uugaggagac auggu                                                   15

<210> SEQ ID NO 624
```

```
<211> LENGTH: 23
<212> TYPE: RNA
<213> ORGANISM: Homo sapiens

<400> SEQUENCE: 624 uagggggcagc agaggaccug ggc                                              23

<210> SEQ ID NO 625
<211> LENGTH: 20
<212> TYPE: RNA
<213> ORGANISM: Homo sapiens

<400> SEQUENCE: 625 uagggggcagc agaggaccug                                                  20

<210> SEQ ID NO 626
<211> LENGTH: 23
<212> TYPE: RNA
<213> ORGANISM: Homo sapiens

<400> SEQUENCE: 626
cacaggugag guucuuggga gcc                                               23

<210> SEQ ID NO 627
<211> LENGTH: 15
<212> TYPE: RNA
<213> ORGANISM: Homo sapiens

<400> SEQUENCE: 627
acaggugagg uucuu                                                        15

<210> SEQ ID NO 628
<211> LENGTH: 26
<212> TYPE: RNA
<213> ORGANISM: Homo sapiens

<400> SEQUENCE: 628
aaaaucacau ugccagggau uaccac                                            26

<210> SEQ ID NO 629
<211> LENGTH: 15
<212> TYPE: RNA
<213> ORGANISM: Homo sapiens

<400> SEQUENCE: 629
aaucacauug ccagg                                                        15

<210> SEQ ID NO 630
<211> LENGTH: 17
<212> TYPE: RNA
<213> ORGANISM: Homo sapiens

<400> SEQUENCE: 630
ugcaggggca ggccagc                                                      17

<210> SEQ ID NO 631
<211> LENGTH: 17
<212> TYPE: RNA
<213> ORGANISM: Homo sapiens

<400> SEQUENCE: 631
ugcaggggca ggccagc                                                      17
```

```
<210> SEQ ID NO 632
<211> LENGTH: 22
<212> TYPE: RNA
<213> ORGANISM: Homo sapiens

<400> SEQUENCE: 632
ccggcagagg aggcugcaga gg                                            22

<210> SEQ ID NO 633
<211> LENGTH: 19
<212> TYPE: RNA
<213> ORGANISM: Homo sapiens

<400> SEQUENCE: 633
ccggcagagg aggcugcag                                                19

<210> SEQ ID NO 634
<211> LENGTH: 27
<212> TYPE: RNA
<213> ORGANISM: Homo sapiens

<400> SEQUENCE: 634
uagcagcacg uaaauauugg cguuaag                                       27

<210> SEQ ID NO 635
<211> LENGTH: 15
<212> TYPE: RNA
<213> ORGANISM: Homo sapiens

<400> SEQUENCE: 635
uagcagcacg uaaau                                                    15

<210> SEQ ID NO 636
<211> LENGTH: 23
<212> TYPE: RNA
<213> ORGANISM: Homo sapiens

<400> SEQUENCE: 636
uggugcggag agggcccaca gug                                           23

<210> SEQ ID NO 637
<211> LENGTH: 15
<212> TYPE: RNA
<213> ORGANISM: Homo sapiens

<400> SEQUENCE: 637
gggucuggug cggag                                                    15

<210> SEQ ID NO 638
<211> LENGTH: 23
<212> TYPE: RNA
<213> ORGANISM: Homo sapiens

<400> SEQUENCE: 638
cggggcagcu caguacagga uac                                           23

<210> SEQ ID NO 639
<211> LENGTH: 15
<212> TYPE: RNA
<213> ORGANISM: Homo sapiens

<400> SEQUENCE: 639
agcucaguac aggau                                                    15
```

```
<210> SEQ ID NO 640
<211> LENGTH: 17
<212> TYPE: RNA
<213> ORGANISM: Homo sapiens

<400> SEQUENCE: 640
ccuccgggac ggcuggg                                                17

<210> SEQ ID NO 641
<211> LENGTH: 15
<212> TYPE: RNA
<213> ORGANISM: Homo sapiens

<400> SEQUENCE: 641
cuccgggacg gcugg                                                  15

<210> SEQ ID NO 642
<211> LENGTH: 22
<212> TYPE: RNA
<213> ORGANISM: Homo sapiens

<400> SEQUENCE: 642
gaggguuggg uggaggcucu cc                                          22

<210> SEQ ID NO 643
<211> LENGTH: 15
<212> TYPE: RNA
<213> ORGANISM: Homo sapiens

<400> SEQUENCE: 643
gaggguuggg uggag                                                  15

<210> SEQ ID NO 644
<211> LENGTH: 21
<212> TYPE: RNA
<213> ORGANISM: Homo sapiens

<400> SEQUENCE: 644 ugcuggggc cacaugagug u                                            21

<210> SEQ ID NO 645
<211> LENGTH: 20
<212> TYPE: RNA
<213> ORGANISM: Homo sapiens

<400> SEQUENCE: 645 gcuggggcc acaugagugu                                              20

<210> SEQ ID NO 646
<211> LENGTH: 28
<212> TYPE: RNA
<213> ORGANISM: Homo sapiens

<400> SEQUENCE: 646
guauggauuu gcacuugucc cggccugu                                    28

<210> SEQ ID NO 647
<211> LENGTH: 15
<212> TYPE: RNA
<213> ORGANISM: Homo sapiens

<400> SEQUENCE: 647
uauugcacuu guccc                                                  15
```

```
<210> SEQ ID NO 648
<211> LENGTH: 24
<212> TYPE: RNA
<213> ORGANISM: Homo sapiens

<400> SEQUENCE: 648
aggcaggggc uggugcuggg cggg                                          24

<210> SEQ ID NO 649
<211> LENGTH: 15
<212> TYPE: RNA
<213> ORGANISM: Homo sapiens

<400> SEQUENCE: 649 gggcggggggg cggcg                                                   15

<210> SEQ ID NO 650
<211> LENGTH: 26
<212> TYPE: RNA
<213> ORGANISM: Homo sapiens

<400> SEQUENCE: 650 cgugggauc ccgcggccgu guuuuc                                         26

<210> SEQ ID NO 651
<211> LENGTH: 15
<212> TYPE: RNA
<213> ORGANISM: Homo sapiens

<400> SEQUENCE: 651
ggggcgccgc gggac                                                    15

<210> SEQ ID NO 652
<211> LENGTH: 23
<212> TYPE: RNA
<213> ORGANISM: Homo sapiens

<400> SEQUENCE: 652
ucggcucugg gucugugggg agc                                           23

<210> SEQ ID NO 653
<211> LENGTH: 15
<212> TYPE: RNA
<213> ORGANISM: Homo sapiens

<400> SEQUENCE: 653
gcccggauac cucag                                                    15

<210> SEQ ID NO 654
<211> LENGTH: 24
<212> TYPE: RNA
<213> ORGANISM: Homo sapiens

<400> SEQUENCE: 654 ugacuggggga gcagaaggag aacc                                         24

<210> SEQ ID NO 655
<211> LENGTH: 15
<212> TYPE: RNA
<213> ORGANISM: Homo sapiens

<400> SEQUENCE: 655
```

```
gacuggggag cagaa                                                    15

<210> SEQ ID NO 656
<211> LENGTH: 22
<212> TYPE: RNA
<213> ORGANISM: Homo sapiens

<400> SEQUENCE: 656
uggcggagcc cauuccaugc ca                                            22

<210> SEQ ID NO 657
<211> LENGTH: 21
<212> TYPE: RNA
<213> ORGANISM: Homo sapiens

<400> SEQUENCE: 657
cuggcggagc ccauuccaug c                                             21

<210> SEQ ID NO 658
<211> LENGTH: 17
<212> TYPE: RNA
<213> ORGANISM: Homo sapiens

<400> SEQUENCE: 658
gcggggcggc aggggcc                                                  17

<210> SEQ ID NO 659
<211> LENGTH: 15
<212> TYPE: RNA
<213> ORGANISM: Homo sapiens

<400> SEQUENCE: 659
gggggcgggg cggca                                                    15

<210> SEQ ID NO 660
<211> LENGTH: 24
<212> TYPE: RNA
<213> ORGANISM: Homo sapiens

<400> SEQUENCE: 660 uggggagug cagugauugu ggaa                                           24

<210> SEQ ID NO 661
<211> LENGTH: 19
<212> TYPE: RNA
<213> ORGANISM: Homo sapiens

<400> SEQUENCE: 661 uggggagug cagugauug                                                 19

<210> SEQ ID NO 662
<211> LENGTH: 26
<212> TYPE: RNA
<213> ORGANISM: Homo sapiens

<400> SEQUENCE: 662
gaggggcucu cgcuucuggc gccaag                                        26

<210> SEQ ID NO 663
<211> LENGTH: 15
<212> TYPE: RNA
<213> ORGANISM: Homo sapiens

<400> SEQUENCE: 663
```

```
ggugaggcgg ggggg                                                        15

<210> SEQ ID NO 664
<211> LENGTH: 23
<212> TYPE: RNA
<213> ORGANISM: Homo sapiens

<400> SEQUENCE: 664 cuggggacg cgugagcgcg agc                                                23

<210> SEQ ID NO 665
<211> LENGTH: 21
<212> TYPE: RNA
<213> ORGANISM: Homo sapiens

<400> SEQUENCE: 665 cuggggacg cgugagcgcg a                                                  21

<210> SEQ ID NO 666
<211> LENGTH: 22
<212> TYPE: RNA
<213> ORGANISM: Homo sapiens

<400> SEQUENCE: 666
aggcgaugug gggauguaga ga                                                22

<210> SEQ ID NO 667
<211> LENGTH: 21
<212> TYPE: RNA
<213> ORGANISM: Homo sapiens

<400> SEQUENCE: 667
agccgcgggg aucgccgagg g                                                 21

<210> SEQ ID NO 668
<211> LENGTH: 23
<212> TYPE: RNA
<213> ORGANISM: Homo sapiens

<400> SEQUENCE: 668
uuagggagua gaagguggg gag                                                23

<210> SEQ ID NO 669
<211> LENGTH: 22
<212> TYPE: RNA
<213> ORGANISM: Homo sapiens

<400> SEQUENCE: 669
cgcaggggcc gggugcucac cg                                                22

<210> SEQ ID NO 670
<211> LENGTH: 22
<212> TYPE: RNA
<213> ORGANISM: Homo sapiens

<400> SEQUENCE: 670
accuggcagc agggagcguc gu                                                22

<210> SEQ ID NO 671
<211> LENGTH: 23
<212> TYPE: RNA
<213> ORGANISM: Homo sapiens
```

```
<400> SEQUENCE: 671
uggugggugg ggaggagaaag ugc                                          23

<210> SEQ ID NO 672
<211> LENGTH: 21
<212> TYPE: RNA
<213> ORGANISM: Homo sapiens

<400> SEQUENCE: 672
augccucccc cggccccgca g                                             21

<210> SEQ ID NO 673
<211> LENGTH: 20
<212> TYPE: RNA
<213> ORGANISM: Homo sapiens

<400> SEQUENCE: 673
aaaaggcggg agaagcccca                                               20

<210> SEQ ID NO 674
<211> LENGTH: 22
<212> TYPE: RNA
<213> ORGANISM: Homo sapiens

<400> SEQUENCE: 674
uuggggugga gggccaagga gc                                            22

<210> SEQ ID NO 675
<211> LENGTH: 20
<212> TYPE: RNA
<213> ORGANISM: Homo sapiens

<400> SEQUENCE: 675 caggggggacu gggggugagc                                              20

<210> SEQ ID NO 676
<211> LENGTH: 22
<212> TYPE: RNA
<213> ORGANISM: Homo sapiens

<400> SEQUENCE: 676
uggcucaguu cagcaggaac ag                                            22

<210> SEQ ID NO 677
<211> LENGTH: 73
<212> TYPE: RNA
<213> ORGANISM: Homo sapiens

<400> SEQUENCE: 677
cugguguuug aggcgaugug gggaugauaga gacaacuucc cagucucauu uccucauccu    60
gccaggccac cau                                                      73

<210> SEQ ID NO 678
<211> LENGTH: 180
<212> TYPE: RNA
<213> ORGANISM: Homo sapiens

<400> SEQUENCE: 678
cgcgacugcg gcggcggugg uggggggagc cgcggggauc gccgagggcc ggucggccgc    60
cccgggugcc gcgcggugcc gccggcggcg gugaggcccc gcgcgugugu cccgcugcg    120 gucggccgcg cucgaggggu ccccguggcg ucccuucccc cgccggccgc cuuucucgcg    180
```

<210> SEQ ID NO 679
<211> LENGTH: 82
<212> TYPE: RNA
<213> ORGANISM: Homo sapiens

<400> SEQUENCE: 679
cugacuuuuu uagggaguag aaggguggggg agcaugaaca auguuucuca cucccuaccc    60
cuccacuccc caaaaaaguc ag                                             82

<210> SEQ ID NO 680
<211> LENGTH: 80
<212> TYPE: RNA
<213> ORGANISM: Homo sapiens

<400> SEQUENCE: 680
cauccaggac aauggugagu gccggugccu gcccuggggc cgucccugcg caggggccgg    60
gugcucaccg caucugcccc                                                80

<210> SEQ ID NO 681
<211> LENGTH: 72
<212> TYPE: RNA
<213> ORGANISM: Homo sapiens

<400> SEQUENCE: 681
gauuucagug accuggcagc agggagcguc gucaguguuu gacuguuuau gguaugucag    60
ggagcugguu cc                                                        72

<210> SEQ ID NO 682
<211> LENGTH: 62
<212> TYPE: RNA
<213> ORGANISM: Homo sapiens

<400> SEQUENCE: 682
cuuccuggug ggugggggagg agaagugccg uccucaugag ccccucucug ucccacccau    60
ag                                                                   62

<210> SEQ ID NO 683
<211> LENGTH: 63
<212> TYPE: RNA
<213> ORGANISM: Homo sapiens

<400> SEQUENCE: 683
ggcuccgcag ggcccuggcg caggcaucca dacagcgggc gaaugccucc cccggcccccg    60 cag                                                                  63

<210> SEQ ID NO 684
<211> LENGTH: 83
<212> TYPE: RNA
<213> ORGANISM: Homo sapiens

<400> SEQUENCE: 684
ggguuuccuc ugccuuuuuu uccaaugaaa auaacgaaac cuguuauuuc ccauugaggg    60
ggaaaaaggc gggagaagcc cca                                            83

<210> SEQ ID NO 685
<211> LENGTH: 61
<212> TYPE: RNA
<213> ORGANISM: Homo sapiens

```
<400> SEQUENCE: 685
gaggguuggg guggagggcc aaggagcugg gugggugcc aagccucugu cccaccccca       60
g                                                                    61

<210> SEQ ID NO 686
<211> LENGTH: 68
<212> TYPE: RNA
<213> ORGANISM: Homo sapiens

<400> SEQUENCE: 686
gggcgcaggg ggacuggggg ugagcaggcc cagaacccag cucgugcuca cucucagucc      60
cucccuag                                                             68

<210> SEQ ID NO 687
<211> LENGTH: 68
<212> TYPE: RNA
<213> ORGANISM: Homo sapiens

<400> SEQUENCE: 687
cuccggugcc uacugagcug auaucaguuc ucauuuuaca cacuggcuca guucagcagg      60
aacaggag                                                             68

<210> SEQ ID NO 688
<211> LENGTH: 73
<212> TYPE: RNA
<213> ORGANISM: Homo sapiens

<400> SEQUENCE: 688
cucugccucc cgugccuacu gagcugaaac acaguugguu uguguacacu ggcucaguuc      60
agcaggaaca ggg                                                       73

<210> SEQ ID NO 689
<211> LENGTH: 21
<212> TYPE: RNA
<213> ORGANISM: Homo sapiens

<400> SEQUENCE: 689
gaggcgaugu ggggauguag a                                              21

<210> SEQ ID NO 690
<211> LENGTH: 20
<212> TYPE: RNA
<213> ORGANISM: Homo sapiens

<400> SEQUENCE: 690
cccagucuca uuuccucauc                                                20

<210> SEQ ID NO 691
<211> LENGTH: 29
<212> TYPE: RNA
<213> ORGANISM: Homo sapiens

<400> SEQUENCE: 691
gggagccgcg gggaucgccg agggccggu                                      29

<210> SEQ ID NO 692
<211> LENGTH: 15
<212> TYPE: RNA
<213> ORGANISM: Homo sapiens

<400> SEQUENCE: 692
```

```
ggcggcggug guggg                                                     15

<210> SEQ ID NO 693
<211> LENGTH: 23
<212> TYPE: RNA
<213> ORGANISM: Homo sapiens

<400> SEQUENCE: 693
agggaguaga aggguggga gca                                             23

<210> SEQ ID NO 694
<211> LENGTH: 16
<212> TYPE: RNA
<213> ORGANISM: Homo sapiens

<400> SEQUENCE: 694
uagggaguag aagggu                                                    16

<210> SEQ ID NO 695
<211> LENGTH: 23
<212> TYPE: RNA
<213> ORGANISM: Homo sapiens

<400> SEQUENCE: 695
ugcgcagggg ccggguggcuc acc                                           23

<210> SEQ ID NO 696
<211> LENGTH: 19
<212> TYPE: RNA
<213> ORGANISM: Homo sapiens

<400> SEQUENCE: 696
cgcaggggcc gggugcuca                                                 19

<210> SEQ ID NO 697
<211> LENGTH: 22
<212> TYPE: RNA
<213> ORGANISM: Homo sapiens

<400> SEQUENCE: 697
gaaaaaggcg ggagaagccc ca                                             22

<210> SEQ ID NO 698
<211> LENGTH: 15
<212> TYPE: RNA
<213> ORGANISM: Homo sapiens

<400> SEQUENCE: 698
gaaaaaggcg ggaga                                                     15

<210> SEQ ID NO 699
<211> LENGTH: 24
<212> TYPE: RNA
<213> ORGANISM: Homo sapiens
```

```
<400> SEQUENCE: 699
acuggcucag uucagcagga acag                                          24

<210> SEQ ID NO 700
<211> LENGTH: 15
<212> TYPE: RNA
<213> ORGANISM: Homo sapiens

<400> SEQUENCE: 700
uggcucaguu cagca                                                    15
```